(12) United States Patent
Ruben et al.

US006924356B2

(10) Patent No.: US 6,924,356 B2
(45) Date of Patent: Aug. 2, 2005

(54) HUMAN PROTEIN HHEPU32

(75) Inventors: Steven M. Ruben, Olney, MD (US); Craig A. Rosen, Laytonsville, MD (US); Hla Kyaw, Frederick, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 113 days.

(21) Appl. No.: 10/062,548

(22) Filed: Feb. 5, 2002

(65) Prior Publication Data

US 2003/0096982 A1 May 22, 2003

Related U.S. Application Data

(63) Continuation of application No. 09/369,247, filed as application No. PCT/US99/02293 on Feb. 4, 1999, now Pat. No. 6,569,992.
(60) Provisional application No. 60/074,118, filed on Feb. 9, 1998, provisional application No. 60/074,157, filed on Feb. 9, 1998, provisional application No. 60/074,037, filed on Feb. 9, 1998, provisional application No. 60/074,141, filed on Feb. 9, 1998, and provisional application No. 60/074,341, filed on Feb. 9, 1998.

(51) Int. Cl.[7] .......................... C07K 1/00; C12P 21/06; C12P 21/04; A61K 38/00; C07H 21/02
(52) U.S. Cl. .................. 530/350; 435/69.1; 435/70.1; 530/300; 536/23.1
(58) Field of Search ........................ 435/69.1, 70.1, 435/6; 530/300, 350; 536/23.1, 24.3

(56) References Cited

U.S. PATENT DOCUMENTS

| | | | |
|---|---|---|---|
| 5,536,637 A | | 7/1996 | Jacobs |
| 2003/0073129 A1 | * | 4/2003 | Baker et al. .................. 435/7.1 |

FOREIGN PATENT DOCUMENTS

| | | |
|---|---|---|
| EP | 0 607054 A2 | 7/1994 |
| EP | 1130094 A2 | 9/2001 |
| WO | WO 97/07198 A2 | 2/1997 |
| WO | WO 99/40100 | 8/1999 |
| WO | WO 00/00610 A2 | 1/2000 |
| WO | WO 00/12708 A2 | 3/2000 |
| WO | WO 01/53312 A1 | 7/2001 |
| WO | WO 01/53486 A1 | 7/2001 |
| WO | WO 01/77290 | 10/2001 |

OTHER PUBLICATIONS

Genback Accession No. HS665135 (Mar. 4, 2000).
Genback Accession No. HSAA99406 (Mar. 3, 2000).
Genback Accession No. HS697134 (Mar. 4, 2000).
Genback Accession No. HSAA99467 (Mar. 3, 2000).
Genback Accession No. AI761909 (Jun. 24, 1999).
Genback Accession No. AI283077 (Jan. 29, 1999).
Genback Accession No. R71665 (created Jun. 5, 1995; updated Mar. 4, 2000).
Genback Accession No. AA099406 (created Oct. 29, 1996; updated Mar. 3, 2000).
Genback Accession No. R71697 (created Jun. 5, 1995; updated Mar. 4, 2000).
Genback Accession No. AA099467 (created Oct. 29, 1996; updated Mar. 3, 2000).
Genback Accession No. AA910871 (Apr. 13, 1998).
Genback Accession No. AA179892 (Dec. 31, 1996).
Genback Accession No. A1751270 (Jun. 22, 1999).
Genbank Accession No. AA180424 (Dec. 31, 1996).
Genbank Accession No. AA169699 (Dec. 20, 1996).
Genbank Accession No. AA282527 (Aug. 13, 1997).
Genbank Accession No. AA169226 (Dec. 20, 1996).
Genbank Accession No. AA744012 (Jan. 23, 1998).
Genbank Accession No. AA630387 (Mar. 6, 1998).
Genbank Accession No. AA806038 (Feb. 19, 1998).
Genbank Accession No. AI185702 (Oct. 29, 1998).
Genbank Accession No. R69144 (Jun. 1, 1995).
Genbank Accession No. R69260 (Aug. 4, 1997).
Genbank Accession No. AA332623 (Apr. 21, 1997).
Genbank Accession No. AA744320 (Jan. 23, 1998).
Genbank Accession No. AA282635 (Aug. 13, 1997).
Genbank Accession No. AI625888 (Apr. 22, 1999).
Genbank Accession No. AA968997 (Jul. 7, 1998).
Genbank Accession No. AA196702 (Jan. 22, 1997).
Genbank Accession No. AI847620 (Jul. 15, 1999).
Genbank Accession No. AA248976 (Mar. 11, 1997).
Genbank Accession No. AA463820 (Jun. 10, 1997).
Genbank Accession No. AA442426 (Jun. 2, 1997).
Genbank Accession No. AA555076 (Sep. 5, 1997).
Genbank Accession No. AA642074 (Oct. 27, 1997).
Genbank Accession No. N71600 (Arp. 2, 1996).
Genbank Accession No. N32595 (Jan. 10, 1996).
Genbank Accession No. AA442570 (Jun. 2, 1997).
Genbank Accession No. AA639694 (Oct. 23, 1997).
Genbank Accession No. AA338949 (Apr. 21, 1997).
Genbank Accession No. AA552323 (Sep. 5, 1997).
Genbank Accession No. AA0445888 (May 11, 1997).

* cited by examiner

Primary Examiner—Kenneth R. Horlick
Assistant Examiner—Young J. Kim
(74) Attorney, Agent, or Firm—Human Genome Sciences, Inc.

(57) ABSTRACT

The present invention relates to novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating disorders related to these novel human secreted proteins.

17 Claims, No Drawings

US 6,924,356 B2

HUMAN PROTEIN HHEPU32

This Application is a continuation of, and claims priority under 35 U.S.C. §120 to, U.S. application Ser. No. 09/369,247 (filed on Aug. 5, 1999), now U.S. Pat. No. 6,569,992, which is a continuation-in-part of, and claims priority under 35 U.S.C. §120 to, international application PCT/US/99/02293 (filed on Feb. 4, 1999), which is a non-provisional of, and claims benefit under 35 U.S.C. §119(e) to, U.S. Provisional Applications 60/074,118; 60/074,157; 60/074,037; 60/074,141; and, 60/074,341 (each filed on Feb. 9, 1998). Each of the above referenced applications is hereby incorporated by reference in its entirety herein.

FIELD OF THE INVENTION

This invention relates to newly identified polynucleotides and the polypeptides encoded by these polynucleotides, uses of such polynucleotides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical disorders by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant methods for producing the polypeptides and polynucleotides. Also provided are diagnostic methods for detecting disorders related to the polypeptides, and therapeutic methods for treating such disorders. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of the coding sequence, but do not comprise all or a portion of any intron. In another embodiment, the nucleic acid comprising the coding sequence does not contain coding sequences of a genomic flanking gene (i.e., 5' or 3' to the gene in the genome).

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Polynucleotides and Polypeptides of the Invention
Features of Protein Encoded by Gene No: 1

The translation product of this gene shares sequence homology with tapasin and poliovirus receptor, which are thought to be important in the assembly and function of multimeric MHC class I-TAP complexes or poliovirus infection.

Preferred polypeptides of the invention comprise the following amino acid sequence: VKVKEKSAAEGTGKKP-KGCRLPGVLGEPPSSAGPRKQR-RTVEKGGGQGGNSRAAS (SEQ ID NO:109). Polynucleotides encoding these polypeptides are also provided.

This gene is expressed primarily in early stage human liver, placental tissues, a breast cancer cell line treated with 0.3 nM R1881 compound as well as breast tissue, and to a lesser extent in many other tissues in an ubiquitous manner.

Therefore, polynucleotides and polypeptides of the invention are useful as reagents for differential identification of the tissue(s) or cell type(s) present in a biological sample and for diagnosis of diseases and conditions which include, but are not limited to, immune, reproductive, and hepatic disorders and diseases, and infection, e.g., enteroviral (poliovirus or other picornaviruses), and proper placental function. Similarly, polypeptides and antibodies directed to these polypeptides are useful in providing immunological probes for differential identification of the tissue(s) or cell type(s). For a number of disorders of the above tissues or cells, particularly of the immune system and placenta, expression of this gene at significantly higher or lower levels is routinely detected in certain tissues or cell types (e.g., immune, placental, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO:60 as residues: Ala-19 to Gln-29. Polynucleotides encoding said polypeptides are also provided.

The tissue distribution in human liver, combined with the homology to tapasin, poliovirus receptor, and other immunoglobulin molecules indicates that polynucleotides and polypeptides corresponding to this gene are useful for the diagnosis and/or intervention of immune related disorders or viral infections. The utility includes immune modulation, tissue/organ transplantation, tumor immunity, allergy treatment, and autoimmmune diseases. Expression within embryonic (placental) tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus, this protein may also be involved in apoptosis or tissue differentiation and could again be useful in cancer therapy. Furthermore, the tissue distribution in breast cancer tissue indicates that the translation product of this gene is useful for the diagnosis and/or treatment of breast cancers, as well as cancers of other tissues where expression has been observed. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1796 of SEQ ID NO:11, b is an integer of 15 to 1810, where both a and b correspond to the positions of nucleotide residues shown in SEQ ID NO:11, and where b is greater than or equal to a+14.

Features of Protein Encoded by Gene No: 2

The translation product of this gene shares sequence homology with lysyl hydroxylase, which is thought to be important in the post-translational biosynthesis of collagen; specifically, the formation of hydroxylysine in collagens.

When tested against fibroblast cell lines, supernatants removed from cells containing this gene activated the EGR1 assay. Thus, it is likely that this gene activates fibroblast cells, and to a lesser extent other musculo-skeletal cells, through a signal transduction pathway. Early growth response 1 (EGR1) is a promoter associated with certain genes that induces various tissues and cell types upon activation, leading the cells to undergo differentiation and proliferation.

The gene encoding the disclosed cDNA is thought to reside on chromosome 9. Accordingly, polynucleotides related to this invention are useful as a marker in linkage analysis for chromosome 9.

This gene is expressed primarily in placental and breast tissues, as well as a variety of other tissues and cell types.

Therefore, polynucleotides and polypeptides of the invention are useful as reagents for differential identification of the tissue(s) or cell type(s) present in a biological sample and for diagnosis of diseases and conditions which include, but are not limited to, osteogenesis imperfecta, chondrodysplasias, osteoporosis, osteoarthritis, Alport syndrome, Ehlers-Danlos syndrome as well as other connective tissue disorders. Similarly, polypeptides and antibodies directed to these polypeptides are useful in providing immunological probes for differential identification of the tissue(s) or cell type(s). For a number of disorders of the above tissues or cells, particularly of the connective tissue, expression of this gene at significantly higher or lower levels is routinely detected in certain tissues or cell types (e.g., connective, reproductive, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in placenta and the homology to lysyl hydroxylase, in conjunction with the biological activity data, indicates that polynucleotides and polypeptides corresponding to this gene are useful for the treatment and/or diagnosis of conditions related to vascular or reproductive disorders, and potentially in the biosynthesis of collagen. The collagen superfamily of proteins now contains at least 19 proteins formally defined as collagens and an additional ten proteins that have collagen-like domains. The most abundant collagens form extracellular fibrils or network-like structures, but the others fulfill a variety of biological functions. There are at least eight highly specific post-translational enzymes involved in collagen biosynthesis. The protein product of this gene is quite likely another. Over 400 mutations in 6 different collagens cause a variety of human diseases that include osteogenesis imperfecta, chondrodysplasias, some forms of osteoporosis, some forms of osteoarthritis, and the renal disease known as the Alport syndrome. Many of the disease phenotypes have been produced in transgenic mice with mutated collagen genes. There has been increasing interest in the possibility that the unique post-translational enzymes involved in collagen biosynthesis, such as the protein product of this gene, offer attractive targets for specifically inhibiting excessive fibrotic reactions in a number of diseases. Moreover, the protein is useful in the detection, treatment, and/or prevention of a variety of vascular disorders and conditions, which include, but are not limited to miscrovascular disease, vascular leak syndrome, aneurysm, stroke, embolism, thrombosis, and/or atherosclerosis. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2339 of SEQ ID NO:12, b is an integer of 15 to 2353, where both a and b correspond to the positions of nucleotide residues shown in SEQ ID NO:12, and where b is greater than or equal to a+14.

Features of Protein Encoded by Gene No: 3

The translation product of this gene shares sequence homology with a murine G-protein coupled receptor, which is thought to be important in signal transduction for extracellular signals (See Genbank Accession No.: AF027955).

Preferred polypeptides of the invention comprise the following amino acid sequence: EEHRYFKANDTLGF (SEQ ID NO: 110). Polynucleotides encoding these polypeptides are also provided.

This gene is expressed primarily in brain tissues, such as cerebellum and fetal dura mater tissues, and in fetal tissues or early stage lung.

Therefore, polynucleotides and polypeptides of the invention are useful as reagents for differential identification of the tissue(s) or cell type(s) present in a biological sample and for diagnosis of diseases and conditions which include, but are not limited to, neurological and/or psychological disorders, or lung diseases. Similarly, polypeptides and antibodies directed to these polypeptides are useful in providing immunological probes for differential identification of the tissue(s) or cell type(s). For a number of disorders of the above tissues or cells, particularly of the central nervous system and respiratory system, expression of this gene at significantly higher or lower levels is routinely detected in certain tissues or cell types (e.g., neural, pulmonary, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 62 as residues: Val-89 to Leu-95, Pro-175 to Tyr-181. Polynucleotides encoding said polypeptides are also provided.

The tissue distribution in fetal lung and brain tissues such as cerebellum and fetal dura mater, and the homology to a murine G-protein coupled receptor, indicates that polynucleotides and polypeptides corresponding to this gene are useful for the diagnosis and/or intervention of neurological, psychological and respiratory diseases. The G-protein coupled receptor can be used as a reagent for ligand screening, antagonist and agonist identification and development, or for the blocking of receptor mediated viral infection. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 914 of SEQ ID NO:13, b is an integer of 15 to 928, where both a and b correspond to the positions of nucleotide residues shown in SEQ ID NO:13, and where b is greater than or equal to a+14.

Features of Protein Encoded by Gene No: 4

The translation product of this gene shares some sequence homology with various chains of the T-cell receptor, which are important in signalling between different cells of the immune system.

The gene encoding the disclosed cDNA is thought to reside on the X chromosome. Accordingly, polynucleotides related to this invention are useful as a marker in linkage analysis for the X chromosome.

This gene is expressed primarily in placental tissue, and to a lesser extent in activated monocytes and dendritic cells.

Therefore, polynucleotides and polypeptides of the invention are useful as reagents for differential identification of the tissue(s) or cell type(s) present in a biological sample and for diagnosis of diseases and conditions which include, but are not limited to, immune disorders and reproductive disorders, particularly pregnancy-associated disorders. Similarly, polypeptides and antibodies directed to these polypeptides are useful in providing immunological probes for differential identification of the tissue(s) or cell type(s). For a number of disorders of the above tissues or cells, particularly of the immune system and female reproductive system, expression of this gene at significantly higher or lower levels is routinely detected in certain tissues or cell types (e.g., immune, reproductive, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 63 as residues: Val-29 to Val-37, Asp-71 to His-76, Gln-78 to Gly-84, Met-105 to His-110, Trp-117 to Gly-122, Gln-136 to Lys-141, Leu-143 to Ala-149, Thr-162 to Asp-174, Ser-181 to Lys-186, Arg-214 to Glu-220, Glu-232 to Glu-238, Cys-249 to Asp-265. Polynucleotides encoding said polypeptides are also provided.

The tissue distribution in dendritic cells, activated monocytes and placental tissue (a tissue rich in hematopoeitic cells), and its homology to the T-cell receptor, indicates that polynucleotides and polypeptides corresponding to this gene are useful in the treatment, prophylaxis and/or diagnosis of immune and autoimmune diseases, such as lupus, transplant rejection, allergic reactions, arthritis, asthma, immunodeficiency diseases, leukemia, and AIDS. Its expression predominantly in hematopoietic cells also indicates that the gene could be important for the treatment and/or detection of hematopoietic disorders such as graft versus host reaction, graft versus host disease, transplant rejection, myelogenous leukemia, bone marrow fibrosis, and myeloproliferative disease. The protein could also be used to enhance or protect the proliferation, differentiation, and functional activation of hematopoietic progenitor cells such as bone marrow cells, which could be useful for cancer patients undergoing chemotherapy or patients undergoing bone marrow transplantation.

The protein may also be useful as a means to increase the proliferation of peripheral blood leukocytes, which could be useful in the combat of a range of hematopoietic disorders including immnmunodeficiency diseases, leukemia, and septicemia. In addition, expression in placenta indicates the gene or the protein encoded by this gene could be useful in the treatment, prophylaxis and/or diagnosis of placentitis, placenta previa, pregnancy disease, and miscarriage. Specific expression within the placenta indicates that this gene product may play a role in the proper establishment and maintenance of placental function. Alternately, this gene product is produced by the placenta and then transported to the embryo, where it may play a crucial role in the development and/or survival of the developing embryo or fetus. Expression of this gene product in a vascular-rich tissue such as the placenta also indicates that this gene product is produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1576 of SEQ ID NO:14, b is an integer of 15 to 1590, where both a and b correspond to the positions of nucleotide residues shown in SEQ ID NO:14, and where b is greater than or equal to a+14.

Features of Protein Encoded by Gene No: 5

Preferred polypeptides of the invention comprise the following amino acid sequence: GTSGTSGTRWNVHF (SEQ ID NO: 111). Polynucleotides encoding these polypeptides are also provided.

The gene encoding the disclosed cDNA is thought to reside on chromosome 11. Accordingly, polynucleotides related to this invention are useful as a marker in linkage analysis for chromosome 11.

This gene is expressed primarily in infant brain tissue.

Therefore, polynucleotides and polypeptides of the invention are useful as reagents for differential identification of the tissue(s) or cell type(s) present in a biological sample and for diagnosis of diseases and conditions which include, but are not limited to, developmental, neurodegenerative and behavioral diseases of the brain such as schizophrenia, Alzheimer's Disease, Parkinson's Disease, Huntington's Disease, transmissible spongiform encephalopathies (TSE), Creutzfeldt-Jakob disease (CJD), specific brain tumors, aphasia, mania, depression, dementia, paranoia, addictive behavior and sleep disorders. Similarly, polypeptides and antibodies directed to these polypeptides are useful in providing immunological probes for differential identification of the tissue(s) or cell type(s). For a number of disorders of the above tissues or cells, particularly of the brain, expression of this gene at significantly higher or lower levels is routinely detected in certain tissues or cell types (e.g., neural, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in infant brain tissue indicates that polynucleotides and polypeptides corresponding to this gene are useful for the treatment and/or diagnosis of developmental, degenerative and behavioral diseases and conditions of the brain such as schizophrenia, Alzheimer's Disease, Parkinson's Disease, Huntington's Disease, transmissible spongiform encephalopathy (TSE), Creutzfeldt-Jakob disease (CJD), aphasia, depression, specific brain tumors, mania, dementia, paranoia, addictive behavior and sleep disorders. Furthermore, this gene product is involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's. The expression within infant tissue indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:15 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 801 of SEQ ID NO:15, b is an integer of 15 to 815, where both a and b correspond to the positions of nucleotide residues shown in SEQ ID NO:15, and where b is greater than or equal to a+14.

Features of Protein Encoded by Gene No: 6

This gene is expressed primarily in hepatocellular tumor tissue.

Therefore, polynucleotides and polypeptides of the invention are useful as reagents for differential identification of the tissue(s) or cell type(s) present in a biological sample and for diagnosis of diseases and conditions which include, but are not limited to, hepatocellular tumors, hepatoblastoma, liver metabolic diseases and conditions that are attributable to the differentiation of hepatocyte progenitor cells. Similarly, polypeptides and antibodies directed to these polypeptides are useful in providing immunological probes for differential identification of the tissue(s) or cell type(s). For a number of disorders of the above tissues or cells, particularly of the liver, expression of this gene at significantly higher or lower levels is routinely detected in certain tissues or cell types (e.g., liver, and cancerous and wounded tissues) or bodily fluids (e.g., lymph, serum, plasma, bile, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in hepatocellular tumor tissue indicates that polynucleotides and polypeptides corresponding to this gene are useful for the detection and/or treatment of liver cancers and conditions such as hepatocellular tumors, hepatoblastoma, jaundice, hepatitis, liver metabolic diseases, and other disorders that are attributable to the differentiation of hepatocyte progenitor cells. Furthermore, the tissue distribution indicates that the translation product of this gene is useful for the diagnosis and/or treatment of cancers of other tissues where expression has been observed. Protein, as well as, antibodies directed against the protein may show utility as a tumor marker and immunotherapy targets for the above listed tumors and tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 976 of SEQ ID NO:16, b is an integer of 15 to 990, where both a and b correspond to the positions of nucleotide residues shown in SEQ ID NO:16, and where b is greater than or equal to a+14.

Features of Protein Encoded by Gene No: 7

Preferred polypeptides of the invention comprise the following amino acid sequence:

(SEQ ID NO:112)
DGAGAFRAPWEPGVPASPQPPEPGQLLRRRQGRRGGVGSPRTPAGGSRGR

RLPATKRGTSGRRARGSSGRINASQT, (SEQ ID NO:113)
QHGLQIILQRDGVPGGDAGEPHGQXRGLHAQQLEPVGSVDLWIFRVDAAG

SGPXVXXGLLRHLQGLPGTVGKPRTMDETGPPAVGEPRSGPSAGSAGPTA

AASPRPAATSPTGRHIAGRCSQPTADDXPEEVCLKTLLLCLRMGEMRSEA

PGAAXEKNNFYRDARDSRGSGXGTGGNAACAQSPLPRTSKIRSKLRGRGW

GCRGGDSEPPVRKQ, (SEQ ID NO:114)
QHGLQILLQRDGVPGGDAGEPHGQXRGLHAQQLHRPVGSVDLWIFRVDA, (SEQ ID NO:115)
AGSGPXVXXGNELRHLQGLPGTVGHPRTMDETGPPAVGEPRSGPSAGS, (SEQ ID NO:116)
AGPTAAASPRPAATSPTGRAAHIAGRCSQPTADDXPEFVCLKTLLLCLR, (SEQ ID NO:117)
MGEMRSEAPGAAXEKNNEYRDARDSRGSGXGTGGNAACAQSPLPRTSK, (SEQ ID NO:118)
and/or IRSKLRGRGWGCRGGDSEPPVRKQ.

Polynucleotides encoding these polypeptides are also provided.

This gene is expressed primarily in osteoblasts.

Therefore, polynucleotides and polypeptides of the invention are useful as reagents for differential identification of the tissue(s) or cell type(s) present in a biological sample and for diagnosis of diseases and conditions which include, but are not limited to: skeletal disorders and diseases, particularly osteoporosis, osteosarcoma, osteonecrosis, arthritis, tendonitis, chrondomalacia and inflammation. Similarly, polypeptides and antibodies directed to these polypeptides are useful in providing immunological probes for differential identification of the tissue(s) or cell type(s). For a number of disorders of the above tissues or cells, particularly of bone, expression of this gene at significantly higher or lower levels is routinely detected in certain tissues or cell types (e.g., skeletal, osteoblasts, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 66 as residues: Pro-33 to Phe-43, Pro-48 to Lys-54, His-61 to Val-66. Polynucleotides encoding said polypeptides are also provided.

The tissue distribution in osteoblasts indicates that polynucleotides and polypeptides corresponding to this gene are useful for the treatment and/or diagnosis of osteoporosis, fractures, osteosarcoma, ossification, osteonecrosis, trauma, arthritis, tendonitis, chrondomalacia and inflammation. Furthermore, elevated levels of expression of this gene product in osteoblasts indicates that it may play a role in the survival, proliferation, and/or growth of osteoblasts. Therefore, it is useful in influencing bone mass in such conditions as osteoporosis. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1174 of SEQ ID NO:17, b is an integer of 15 to 1188, where both a and b correspond to the positions of nucleotide residues shown in SEQ ID NO:17, and where b is greater than or equal to a+14.

Features of Protein Encoded by Gene No: 8

This gene is expressed primarily in brain and infant brain tissues, such as in the frontal cortex.

Therefore, polynucleotides and polypeptides of the invention are useful as reagents for differential identification of the tissue(s) or cell type(s) present in a biological sample and for diagnosis of diseases and conditions which include, but are not limited to, developmental, degenerative and behavioral diseases of the brain such as schizophrenia, Alzheimer's Disease, Parkinson's Disease, Huntington's Disease, transmissible spongiform encephalopathies (TSE), Creutzfeldt-Jakob disease (CJD), specific brain tumors, aphasia, mania, depression, dementia, paranoia, addictive behavior and sleep disorders. Similarly, polypeptides and antibodies directed to these polypeptides are useful in providing immunological probes for differential identification of the tissue(s) or cell type(s). For a number of disorders of the above tissues or cells, particularly of the brain, expression of this gene at significantly higher or lower levels is routinely detected in certain tissues or cell types (e.g., brain, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in infant and adult brain tissues such as the frontal cortex indicates that polynucleotides and polypeptides corresponding to this gene are useful for the treatment and/or diagnosis of developmental, degenerative and behavioral diseases and conditions of the brain such as schizophrenia, Alzheimer's Disease, Parkinson's Disease, Huntington's Disease, transmissible spongiform encephalopathy (TSE), Creutzfeldt-Jakob disease (CJD), aphasia, depression, specific brain tumors, mania, dementia, paranoia, addictive behavior and sleep disorders. Furthermore, elevated expression of this gene product within the frontal cortex of the brain indicates that it is involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's. Moreover, the expression within infant tissue indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. Protein, as well as, antibodies directed against the protein may show utility as a tumor marker and/or immunotherapy targets for the above listed tissues. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:18 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1591 of SEQ ID NO:18, b is an integer of 15 to 1605, where both a and b correspond to the positions of nucleotide residues shown in SEQ ID NO:18, and where b is greater than or equal to a+14.

Features of Protein Encoded by Gene No: 9

The translation product of this gene shares sequence homology with a *C. elegans* protein which is involved in development (See GenBank Accession No.: AF038611).

Preferred polypeptides of the invention comprise the following amino acid sequence: GTSPEAYVGPGGPECP (SEQ ID NO: 119). Polynucleotides encoding these polypeptides are also provided.

The gene encoding the disclosed cDNA is thought to reside on chromosome 10. Accordingly, polynucleotides related to this invention are useful as a marker in linkage analysis for chromosome 10.

This gene is expressed primarily in adipocytes, early development stage tissues such as 8-week old embryonic tissues, immune tissues such as fetal liver/spleen, and cancerous tissues such as testes tumors, and to a lesser extent in some other tissues, such as prostate and testes.

Therefore, polynucleotides and polypeptides of the invention are useful as reagents for differential identification of the tissue(s) or cell type(s) present in a biological sample and for diagnosis of diseases and conditions which include, but are not limited to, developmental disorders, and particularly obesity, diabetes, growth disorders, and immune diseases or disorders. Similarly, polypeptides and antibodies directed to these polypeptides are useful in providing immunological probes for differential identification of the tissue(s) or cell type(s). For a number of disorders of the above tissues or cells, particularly of the adipocytes, early development stage tissues, immune tissues, and cancer tissues, expression of this gene at significantly higher or lower levels is routinely detected in certain tissues or cell types (e.g., metabolic, developmental, immune, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 68 as residues: Gly-19 to Ser-27, Gln-39 to Gly-45, Gln-48 to Ala-55, Ala-75 to Thr-80, Thr-198 to Gly-211. Polynucleotides encoding said polypeptides are also provided.

The tissue distribution in developmental, immune, metabolic, and cancerous tissues indicates that polynucleotides and polypeptides corresponding to this gene are useful for the diagnosis and/or treatment of obesity, diabetes, growth disorders, and immune diseases. The tissue distribution in testes, and tumor tissue thereof, indicates that polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that is expressed, particularly at low levels, in other tissues of the body.

Therefore, this gene product is expressed in other specific tissues or organs where it may play related functional roles in other processes, such as hematopoiesis, inflammation, bone formation, and kidney function, to name a few possible target indications. Moreover, expression within 8-week old embryonic tissues and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus, this protein may also be involved in apoptosis or tissue differentiation and could again be useful in cancer therapy. Additionally, expression of this gene product in fetal liver/spleen tissue indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2075 of SEQ ID NO:19, b is an integer of 15 to 2089, where both a and b correspond to the positions of nucleotide residues shown in SEQ ID NO:19, and where b is greater than or equal to a+14.

Features of Protein Encoded by Gene No: 10

This gene is expressed primarily in retinal tissue, and to a lesser extent in the amygdala of the brain.

Therefore, polynucleotides and polypeptides of the invention are useful as reagents for differential identification of the tissue(s) or cell type(s) present in a biological sample and for diagnosis of diseases and conditions which include, but are not limited to, eye defects, neurological and behavioral disorders and diseases. Similarly, polypeptides and antibodies directed to these polypeptides are useful in providing immunological probes for differential identification of the tissue(s) or cell type(s). For a number of disorders of the above tissues or cells, particularly of the occular and nervous systems, expression of this gene at significantly higher or lower levels is routinely detected in certain tissues or cell types (e.g., retinal, brain, and cancerous and wounded tissues) or bodily fluids (e.g., lymph, serum, plasma, vitreous and aqueous humors, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 69 as residues: Ser-39 to Ser-46, Gly-60 to Gln-71. Polynucleotides encoding said polypeptides are also provided.

The tissue distribution predominantly in retinal tissue indicates a role for this gene product in the treatment, prophylaxis and/or diagnosis of eye disorders including blindness, color blindness, short-sightedness, long-sightedness, retinitis pigmentosa, retinitis proliferans, retinablastoma, retinochoroiditis, retinopathy and retinoschisis. Expression in amygdala tissue in the brain indicates a role in the detection, treatment and/or prophylaxis of neurodegenerative disease states and behavioural disorders such as Alzheimer's Disease, Parkinson's Disease, Huntinton's Disease, schizophrenia, mania, dementia, paranoia, obsessive compulsive disorder and panic disorder. Furthermore, the amygdala processes sensory information and relays this to other areas of the brain, including the endocrine and autonomic domains of the hypothalamus and the brain stem. Therefore, the translation product of this gene is likely to be involved in the processing of sensory information, for example, from the eyes. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1267 of SEQ ID NO:20, b is an integer of 15 to 1281, where both a and b correspond to the positions of nucleotide residues shown in SEQ ID NO:20, and where b is greater than or equal to a+14.

Features of Protein Encoded by Gene No: 11

Preferred polypeptides of the invention comprise the following amino acid sequence: SCIHTGDVMIXPV-LSCFTRF (SEQ ID NO: 120). Polynucleotides encoding these polypeptides are also provided.

When tested against U937 myeloid cell lines, supernatants removed from cells containing this gene activated the GAS assay. Thus, it is likely that this gene activates myeloid cells, and to a lesser extent other immune cells, through the JAK-STAT signal transduction pathway. The gamma activating sequence (GAS) is a promoter element found upstream of many genes which are involved in the JAK-STAT pathway. The JAK-STAT pathway is a large, signal transduction pathway involved in the differentiation and proliferation of cells. Therefore, activation of the JAK-STAT pathway, reflected by the binding of the GAS element, can be used to indicate proteins involved in the proliferation and differentiation of cells.

The gene encoding the disclosed cDNA is thought to reside on chromosome 16. Accordingly, polynucleotides related to this invention are useful as a marker in linkage analysis for chromosome 16.

This gene is expressed primarily in frontal cortex brain tissue from a schizophrenia patient and teratocarcinoma tissue, and to a lesser extent in placenta, osteoblast and embryonic tissues.

Therefore, polynucleotides and polypeptides of the invention are useful as reagents for differential identification of the tissue(s) or cell type(s) present in a biological sample and for diagnosis of diseases and conditions which include, but are not limited to, developmental or vascular disorders or defects. Similarly, polypeptides and antibodies directed to these polypeptides are useful in providing immunological probes for differential identification of the tissue(s) or cell type(s). For a number of disorders of the above tissues or cells, particularly of the nervous system and embryonic systems, expression of this gene at significantly higher or lower levels is routinely detected in certain tissues or cell types (e.g., nervous, embryonic, vascular, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 70 as residues: Thr-21 to Leu-26. Polynucleotides encoding said polypeptides are also provided.

The tissue distribution in early development tissues (i.e., placental, embryonic) indicates that polynucleotides and polypeptides corresponding to this gene are useful for the diagnosis and/or intervention of developmental disorders, including the defects in nervous system and bone morphogenesis. Furthermore, the tissue distribution indicates that polynucleotides and polypeptides corresponding to this gene are useful for the diagnosis and/or treatment of disorders of the placenta. Specific expression within the placenta indicates that this gene product may play a role in the proper establishment and maintenance of placental function. Alternately, this gene product is produced by the placenta and then transported to the embryo, where it may play a crucial role in the development and/or survival of the developing embryo or fetus. Expression of this gene product in a vascular-rich tissue such as the placenta also indicates that this gene product is produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1747 of SEQ ID NO:21, b is an integer of 15 to 1761, where both a and b correspond to the positions of nucleotide residues shown in SEQ ID NO:21, and where b is greater than or equal to a+14.

Features of Protein Encoded by Gene No: 12

The translation product of this gene shares sequence homology with smaller hepatocellular oncoprotein (hhcm) gene product, which is thought to be important in the tumorigenesis of hepatocellular carcinoma.

Preferred polypeptides of the invention comprise the following amino acid sequence: GRHLVASQKRVL-RDRRVQTGIWSDQLYSQRPWAPVTWPDH-WGVCVCVYVC (SEQ ID NO: 121). Polynucleotides encoding these polypeptides are also provided.

This gene is expressed primarily in pancreas islet cell tumor.

Therefore, polynucleotides and polypeptides of the invention are useful as reagents for differential identification of the tissue(s) or cell type(s) present in a biological sample and for diagnosis of diseases and conditions which include, but are not limited to, endocrine or hepatic disorders, particularly pancreas islet cell tumors. Similarly, polypeptides and antibodies directed to these polypeptides are useful in providing immunological probes for differential identification of the tissue(s) or cell type(s). For a number of disorders of the above tissues or cells, particularly of the pancreas, expression of this gene at significantly higher or lower levels is routinely detected in certain tissues or cell types (e.g., pancreas, hepatic, and cancerous and wounded tissues) or bodily fluids (e.g., lymph, serum, plasma, urine, bile, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 71 as residues: Gly-26 to Lys-33, Lys-47 to His-52. Polynucleotides encoding said polypeptides are also provided.

The tissue distribution in pancreas islet cell tumors, and the homology to the smaller hepatocellular oncoprotein (hhcm) gene product, indicates that polynucleotides and polypeptides corresponding to this gene are useful for the diagnosis and/or intervention of pancreas islet cell tumors and hepatocellular carcinomas, as well as preneoplastic or pathological conditions of the liver. Furthermore, the translation product of this gene is useful for the detection and/or treatment of cancers of other tissues where expression has been observed. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1175 of SEQ ID NO:22, b is an integer of 15 to 1189, where both a and b correspond to the positions of nucleotide residues shown in SEQ ID NO:22, and where b is greater than or equal to a+14.

Features of Protein Encoded by Gene No: 13

The translation product of this gene shares sequence homology with actinin, which is thought to be important in actin gelation. Recently another group has published a human gene which shares homology with this gene, calling it smoothelin (See Genbank Accession No.: gnl|PID|e1284289).

The gene encoding the disclosed cDNA is thought to reside on chromosome 22. Accordingly, polynucleotides related to this invention are useful as a marker in linkage analysis for chromosome 22.

Preferred polypeptides of the invention comprise the following amino acid sequence:

(SEQ ID NO:122)
AFPHSIPCQVMAVPSPQLLLERPXLPVSFMFLTSHPPPRLVCP;

(SEQ ID NO:123)
LPTLHSLSSYGCPLTPAAPREALXTCVIHVSNKPPSTPSCVPHAPVINLC

CVGVGGPFAHAWGIPCPDQRDKERERRLQEARGRPGEGRGNTATETTTRH

SQRAADGSAVSTVTKTERLVHSNDGTRTARTTTVESSFVRRSENGSGSTM

MQTKTFSSSSSSKXMGSIFDREDQASPRAGSLAALEKRQAEKKKELMKAQ

SLPKTSASQARKAMIEKLEKEGAAGSPGGPRAAVQRSTSEGVPNANSIKQ

MLLDWCRAKTRGYEHYDIQNTSSSWSDGMAFCALVHNFFPEAFDYGQLSP

QNRRQNFEVAFSSAETHADCPQLLDTEDMVRLREPDWKCVYTYIQEFYRC

LVQKGLVKTKKS, (SEQ ID NO:124)
LPTLHSLSSYGCPLTPAAPREALXTCVIHVSNKPPSTPSCVPHAPV, (SEQ ID NO:125)
HLCCVGVGGPFAHAWGIPCPDQRDKERERRLQEARGRPGEGRGNTA, (SEQ ID NO:126)
TETTTRHSQRAADGSAVSTVTKTERLVHSNDGTRTARTTTVESSFV, (SEQ ID NO:127)
RRSENGSGSTMMQTKTFSSSSSSKIKMGSIFDREDQASPRAGSLAAL, (SEQ ID NO:128)
EKRQAEKKKELMKAQSLPKTSASQARKAMTEKLEKEGAAGSPGGPRA, (SEQ ID NO:129)
AVQRSTSFGVPNANSIKQMLLDWCRAKTRGYEHVDIQNESSSWSDGM, (SEQ ID NO:130)
AFCALVHNFFPEAEDYGQLSPQNRRQNFEVAFSSAETHADCPQLLDTED, (SEQ ID NO:131)
and/or MVRLREPDWKCVYTYIQEEYRCLVQKGLVKTKKS.

Polynucleotides encoding these polypeptides are also provided.

This gene is expressed primarily in kidney cortex, skeletal muscle, prostate and to a lesser extent in many other tissues.

Therefore, polynucleotides and polypeptides of the invention are useful as reagents for differential identification of the tissue(s) or cell type(s) present in a biological sample and for diagnosis of diseases and conditions which include, but are not limited to, skeletal muscle diseases or kidney diseases. Similarly, polypeptides and antibodies directed to these polypeptides are useful in providing immunological probes for differential identification of the tissue(s) or cell type(s). For a number of disorders of the above tissues or cells, particularly of the skeletal muscle or kidney, expression of this gene at significantly higher or lower levels is routinely detected in certain tissues or cell types (e.g., musculo-skeletal, kidney, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 72 as residues: Ala-23 to Arg-36, His-38 to Ala-46, Pro-50 to Gly-56, Arg-85 to Val-94. Polynucleotides encoding said polypeptides are also provided.

The tissue distribution in skeletal muscle tissue, and the homology to actinin and smoothelin, indicates that polynucleotides and polypeptides corresponding to this gene are useful for the diagnosis and/or treatment of skeletal muscle diseases, including muscular dystrophy, kidney diseases and prostate ailments. Additionally, the gene product can be used as a target for anti-tumor agent development. Furthermore, the tissue distribution in skeletal muscle tissue indicates that the protein product of this gene is useful for the diagnosis and treatment of conditions and pathologies of the cardiovascular system, such as heart disease, restenosis, atherosclerosis, stoke, angina, thrombosis, and wound healing. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1478 of SEQ ID NO:23, b is an integer of 15 to 1492, where both a and b correspond to the positions of nucleotide residues shown in SEQ ID NO:23, and where b is greater than or equal to a+14.

Features of Protein Encoded by Gene No: 14

The gene encoding the disclosed cDNA is thought to reside on chromosome 12. Accordingly, polynucleotides related to this invention are useful as a marker in linkage analysis for chromosome 12.

This gene is expressed primarily in hematopoietic tissues and cell types such as T cells, bone marrow, spleen, and lymphocytic leukemia, and to a lesser extent in testes and other tissues.

Therefore, polynucleotides and polypeptides of the invention are useful as reagents for differential identification of the tissue(s) or cell type(s) present in a biological sample and for diagnosis of diseases and conditions which include, but are not limited to, hematopoietic, immune, and inflammatory disorders. Similarly, polypeptides and antibodies directed to these polypeptides are useful in providing immunological probes for differential identification of the tissue(s) or cell type(s). For a number of disorders of the above tissues or cells, particularly of the hematopoietic and immune tissues, expression of this gene at significantly higher or lower levels is routinely detected in certain tissues or cell types (e.g., immune, reproductive, and cancerous and wounded tissues) or bodily fluids (e.g., lymph, serum, plasma, urine, seminal fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 73 as residues: Tyr-22 to His-27, Ile-54 to Gln-60. Polynucleotides encoding said polypeptides are also provided.

The tissue distribution in a wide variety of immune tissues indicates that polynucleotides and polypeptides corresponding to this gene are useful for the diagnosis and/or treatment of hematopoietic, immune, and inflammatory disorders. Furthermore, the tissue distribution in a wide variety of immune tissues indicates that polynucleotides and polypeptides corresponding to this gene are useful for the diagnosis and treatment of a variety of immune system disorders. Expression of this gene product in T-cells, bone marrow, and spleen tissue indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1594 of SEQ ID NO:24, b is an integer of 15 to 1608, where both a and b correspond to the positions of nucleotide residues shown in SEQ ID NO:24, and where b is greater than or equal to a+14.

Features of Protein Encoded by Gene No: 15

The translation product of this gene shares sequence homology with a putative transmembrane protein from Helicobacter pylori (GeneSeq Accession No.: W20765).

Preferred polypeptides of the invention comprise the following amino acid sequence:

(SEQ ID NO:132)
KMEWLADPTAWLGLLTLIVLXLVLGIDNLVFIXIXAXKLPPEQRDRARLI

GLSLALLMRLGLLASISWLVTLTQPLEEVFDKSFSGRDLIMLFGGVFLLF

KATMELHERLEGHVAQRTGNVAYAMFWPIVAQIVVLDAVFSLDAVITAVG

MVDELAVMMIAXIISIGLMIVASKPLTRFVNAHPTVIMLCLGFLMMIGFA

LTAEGLGFHIPKGYLYAAIGFSILIELENQLARSRRKKSAQGTLPRRER

TAHAVMRLLGGRNLAVEEVGEEVADLLDNPDANGGPLFDRRERVMISGVL

QLAERPIRTLMTPRAKVDSIDLSDDPXTIRLKLXIRLTRACP, (SEQ ID NO:133)
KMEWLADPTAWLGLLTLIVLXLVLGIDNLVFIXIXAXKLPPEQRDRAR, (SEQ ID NO:134)
LIGLSLALLMRLGLLASISWLVTLTQPLFEVEDKSFSGRDLIMLFGGVF,

-continued
(SEQ ID NO:135)
LLFKATMELHERLEGHVAQRTGNVAYAMFWPIVAQIVVLDAVFSLDA, (SEQ ID NO:136)
VITAVGMVDELAVMMIAXIISIGLMIVASKPLTRFVNAHPTVIMLCLGF, (SEQ ID NO:137)
LMMIGFALTAEGLGFHIPKGYLYAAIGFSILTELFNQIARSRRKKSAQGT, (SEQ ID NO:138)
LPRRERTAHAVNIRLLGGRNLAVEEVGEEVADLLDNPDANGGPLFDRRE, and/or (SEQ ID NO:139)
RVMISGVLQLAERPIRTLMTPRAKVDSIDLSDDPXTIRLKLXIRLTRACP.

Polynucleotides encoding these polypeptides are also provided.

This gene is expressed primarily in CD34 positive cord blood cells.

Therefore, polynucleotides and polypeptides of the invention are useful as reagents for differential identification of the tissue(s) or cell type(s) present in a biological sample and for diagnosis of diseases and conditions which include, but are not limited to, hematopoiesis or developmental disorders and diseases. Similarly, polypeptides and antibodies directed to these polypeptides are useful in providing immunological probes for differential identification of the tissue(s) or cell type(s). For a number of disorders of the above tissues or cells, particularly of CD34 positive cells, expression of this gene at significantly higher or lower levels is routinely detected in certain tissues or cell types (e.g., immune, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 74 as residues: Asp-34 to Pro-46. Polynucleotides encoding said polypeptides are also provided.

The tissue distribution in CD34 positive cord blood cells indicates that polynucleotides and polypeptides corresponding to this gene are useful for the diagnosis and/or treatment of hematopoiesis disorders. Expression of this gene product in CD34 positive cord blood cells indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1950 of SEQ ID NO:25, b is an integer of 15 to 1964, where both a and b correspond to the positions of nucleotide residues shown in SEQ ID NO:25, and where b is greater than or equal to a+14.

Features of Protein Encoded by Gene No: 16

The translation product of this gene shares sequence homology with atrophin-1, which is thought to be important in dentatorubral and pallidoluylsian atrophy (DRPLA), a progressive neurological disorder characterized by neuronal degeneration.

This gene is expressed primarily in fetal brain.

Therefore, polynucleotides and polypeptides of the invention are useful as reagents for differential identification of the tissue(s) or cell type(s) present in a biological sample and for diagnosis of diseases and conditions which include, but are not limited to, neural or developmental disorders and diseases, particularly neurodegenerative conditions. Similarly, polypeptides and antibodies directed to these polypeptides are useful in providing immunological probes for differential identification of the tissue(s) or cell type(s). For a number of disorders of the above tissues or cells, particularly of the nervous system, expression of this gene at significantly higher or lower levels is routinely detected in certain tissues or cell types (e.g., neural, developmental, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 75 as residues: Asn-20 to Gly-27, Ser-49 to Trp-54, Leu-95 to Thr-101, Ala-140 to Pro-148. Polynucleotides encoding said polypeptides are also provided.

The tissue distribution in fetal brain tissue, and the homology to atrophin-1, indicates that polynucleotides and polypeptides corresponding to this gene are useful for the diagnosis and intervention of neurodegenerative diseases, including dentatorubral and pallidoluylsian atrophy (DRPLA), and Huntington's Disease. Additionally, the tissue distribution indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 919 of SEQ ID NO:26, b is an integer of 15 to 933, where both a and b correspond to the positions of nucleotide residues shown in SEQ ID NO:26, and where b is greater than or equal to a+14.

Features of Protein Encoded by Gene No: 17

The translation product of this gene shares sequence homology with a *C. elegans* protein F25H2.12 which is involved in development (See GenBank Accession No.: gnl|PID|e264283).

Preferred polypeptides of the invention comprise the following amino acid sequence: LLTSPVSWHSTVPSW (SEQ ID NO: 140). Polynucleotides encoding these polypeptides are also provided.

This gene is expressed primarily in tumors, such as lung tumors, in immune tissues and cell types such as fetal liver/spleen tissues, and in brain tissue such as infant brain tissue, and to a lesser extent in other tissues.

Therefore, polynucleotides and polypeptides of the invention are useful as reagents for differential identification of the tissue(s) or cell type(s) present in a biological sample and for diagnosis of diseases and conditions which include, but are not limited to, developmental disorders and diseases, tumorigenesis, immune and inflammatory disorders, and neural diseases. Similarly, polypeptides and antibodies directed to these polypeptides are useful in providing immunological probes for differential identification of the tissue(s) or cell type(s). For a number of disorders of the above tissues or cells, particularly of the tumor, immune tissues and cell types, and brain, expression of this gene at significantly higher or lower levels is routinely detected in certain tissues or cell types (e.g., neural, developmental, immune, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 76 as residues: Thr-3 to Ser-8, Pro-30 to Pro-35, Asn-41 to Arg-47, Val-56 to His-62, Val-71 to Asp-76. Polynucleotides encoding said polypeptides are also provided.

The tissue distribution in immune, neural, and cancerous tissues indicates that polynucleotides and polypeptides corresponding to this gene are useful for the diagnosis and/or treatment of tumors, immune and inflammatory disorders, and neural diseases. The tissue distribution in brain tissue indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Alternatively, the expression of this gene product in fetal liver/spleen tissue indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Additionally, the tissue distribution in cancerous tissues, such as cancerous lung tissue, indicates that the translation product of this gene is useful for the diagnosis and/or treatment of lung cancers, as well as cancers of other tissues where expression has been observed. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1223 of SEQ ID NO:27, b is an integer of 15 to 1237, where both a and b correspond to the positions of nucleotide residues shown in SEQ ID NO:27, and where b is greater than or equal to a+14.

Features of Protein Encoded by Gene No: 18

Preferred polypeptides of the invention comprise the following amino acid sequence: SALSISNHQGFF (SEQ ID NO: 141). Polynucleotides encoding these polypeptides are also provided.

This gene is expressed primarily in activated T-cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders and diseases. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 77 as residues: His-16 to Asn-24, Trp-36 to Ala-43, His-59 to Leu-66, Glu-82 to Gly-90, Ser-113 to Trp-123, Pro-145 to Thr-154, Ala-164 to Pro-176. Polynucleotides encoding said polypeptides are also provided.

The tissue distribution of this gene primarily in activated T-cells indicates that polynucleotides and polypeptides corresponding to this gene are useful for the treatment, prophylaxis and/or diagnosis of immune and autoimmune diseases, such as lupus, transplant rejection, allergic reactions, arthritis, asthma, immunodeficiency diseases, leukemia, AIDS and that it may also play a role in the treatment, prophlaxis and detection of thymus disorders such as Grave's Disease, lymphocytic thyroiditis, hyperthyroidism and hypothyroidism. Expression of this gene product in T-cells indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in T cells also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 946 of SEQ ID NO:28, b is an integer of 15 to 960, where both a and b correspond to the positions of nucleotide residues shown in SEQ ID NO:28, and where b is greater than or equal to a+14.

Features of Protein Encoded by Gene No: 19

When tested against fibroblast cell lines, supernatants removed from cells containing this gene activated the EGR1 assay. Thus, it is likely that this gene activates fibroblast cells, and to a lesser extent other musculo-skeletal cells, through a signal transduction pathway. Early growth response 1 (EGR1) is a promoter associated with certain genes that induces various tissues and cell types upon activation, leading the cells to undergo differentiation and proliferation.

This gene is expressed primarily in testes tissue.

Therefore, polynucleotides and polypeptides of the invention are useful as reagents for differential identification of the tissue(s) or cell type(s) present in a biological sample and for diagnosis of diseases and conditions which include, but are not limited to, male reproductive and endocrine disorders, as well as testicular cancer. Similarly, polypeptides and antibodies directed to these polypeptides are useful in providing immunological probes for differential identification of the tissue(s) or cell type(s). For a number of disorders of the above tissues or cells, particularly of the male reproductive system, expression of this gene at significantly higher or lower levels is routinely detected in certain tissues or cell types (e.g., testes, reproductive, and cancerous and wounded tissues) or bodily fluids (e.g., lymph, serum, plasma, urine, seminal fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 78 as residues: Gly-33 to Ser-44. Polynucleotides encoding said polypeptides are also provided.

The tissue distribution in testes tissue indicates that polynucleotides and polypeptides corresponding to this gene are useful for the diagnosis and/or treatment of male reproductive and endocrine disorders. It may also prove to be valuable in the diagnosis and treatment of testicular cancer, as well as cancers of other tissues where expression has been observed. Furthermore, the tissue distribution indicates that polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that is expressed, particularly at low levels, in other tissues of the body. Therefore, this gene product is expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1053 of SEQ ID NO:29, b is an integer of 15 to 1067, where both a and b correspond to the positions of nucleotide residues shown in SEQ ID NO:29, and where b is greater than or equal to a+14.

Features of Protein Encoded by Gene No: 20

This gene is expressed primarily in T-cells.

Therefore, polynucleotides and polypeptides of the invention are useful as reagents for differential identification of the tissue(s) or cell type(s) present in a biological sample and for diagnosis of diseases and conditions which include, but are not limited to, immune and hematopoietic diseases and disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution of this gene in T-cells indicates that polynucleotides and polypeptides corresponding to this gene are useful for the treatment, prophylaxis and diagnosis of immune and autoimmune diseases, such as lupus, transplant rejection, allergic reactions, arthritis, asthma, immunodeficiency diseases, leukemia, and AIDS. The gene or gene product may also play a role in the treatment, prophlaxis and/or detection of thymus disorders such as Grave's Disease, lymphocytic thyroiditis, hyperthyroidism and hypothyroidism. Expression of this gene product in T cells also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1049 of SEQ ID NO:30, b is an integer of 15 to 1063, where both a and b correspond to the positions of nucleotide residues shown in SEQ ID NO:30, and where b is greater than or equal to a+14.

Features of Protein Encoded by Gene No: 21

This gene is expressed primarily in tonsils.

Therefore, polynucleotides and polypeptides of the invention are useful as reagents for differential identification of the tissue(s) or cell type(s) present in a biological sample and for diagnosis of diseases and conditions which include, but are not limited to, tonsilitis and immune disorders and diseases. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 80 as residues: Pro-35 to Ser-40. Polynucleotides encoding said polypeptides are also provided.

The tissue distribution of this gene in tonsils, a lymphoid tissue, indicates that polynucleotides and polypeptides corresponding to this gene are useful for the treatment, prophylaxis and/or diagnosis of immune and autoimmune diseases, in addition to tonsilitis and tonsilopharyngitis. Expression of this gene product indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1416 of SEQ ID NO:31, b is an integer of 15 to 1430, where both a and b correspond to the positions of nucleotide residues shown in SEQ ID NO:31, and where b is greater than or equal to a+14.

Features of Protein Encoded by Gene No: 22

The gene encoding the disclosed cDNA is believed to reside on chromosome 10. Accordingly, polynucleotides related to this invention are useful as a marker in linkage analysis for chromosome 10.

This gene is expressed primarily in the corpus striatum (of patient suffering from depression), as well as in bone marrow tissue.

Therefore, polynucleotides and polypeptides of the invention are useful as reagents for differential identification of the tissue(s) or cell type(s) present in a biological sample and for diagnosis of diseases and conditions which include, but are not limited to, neural disorders and diseases, particularly behavioral disorders (e.g.depression) and hematopoeitic disorders (e.g. anemias and immune deficiencies). Similarly, polypeptides and antibodies directed to these polypeptides are useful in providing immunological probes for differential identification of the tissue(s) or cell type(s). For a number of disorders of the above tissues or cells, particularly of the brain and immune system, expression of this gene at significantly higher or lower levels is routinely detected in certain tissues or cell types (e.g., brain, immune, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 81 as residues: His-29 to Asn-34. Polynucleotides encoding said polypeptides are also provided.

The tissue distribution in corpus striatum tissue of the brain and in bone marrow tissue indicates that polynucleotides and polypeptides corresponding to this gene are useful for the treatment and/or diagnosis of patients suffering from depression, but also perhaps other brain disorders and conditions such as schizophrenia, Alzheimer's Disease, Parkinson's Disease, Huntington's Disease, transmissible spongiform encephalopathy (TSE), Creutzfeldt-Jakob disease (CJD), aphasia, specific brain tumors, mania, dementia, paranoia, addictive behavior and sleep disorders. In addition, the expression in bone marrow tissue indicates a role for the protein product of this gene in immune deficiencies, anemias and other hematopoeitic conditions. Furthermore, the tissue distribution in bone marrow indicates that polynucleotides and polypeptides corresponding to this gene are useful for the treatment and diagnosis of hematopoietic related disorders such as anemia, pancytopenia, leukopenia, thrombocytopenia or leukemia. The uses include bone marrow cell ex vivo culture, bone marrow transplantation, bone marrow reconstitution, radiotherapy or chemotherapy of neoplasia.

The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1368 of SEQ ID NO:32, b is an integer of 15 to 1382, where both a and b correspond to the positions of nucleotide residues shown in SEQ ID NO:32, and where b is greater than or equal to a+14.

Features of Protein Encoded by Gene No: 23

When tested against fibroblast cell lines, supernatants removed from cells containing this gene activated the EGR1 assay. Thus, it is likely that this gene activates fibroblast cells, or more generally, integumentary cells, in addition to other cells and cell types, through a signal transduction pathway. Early growth response 1 (EGR1) is a promoter associated with certain genes that induces various tissues and cell types upon activation, leading the cells to undergo differentiation and proliferation.

The gene encoding the disclosed cDNA is thought to reside on chromosome 20. Accordingly, polynucleotides related to this invention are useful as a marker in linkage analysis for chromosome 20.

This gene is expressed primarily in placental tissue, endometrial cells and breast tissue, and to a lesser extent in a variety of other tissues and cell types.

Therefore, polynucleotides and polypeptides of the invention are useful as reagents for differential identification of the tissue(s) or cell type(s) present in a biological sample and for diagnosis of diseases and conditions which include, but are not limited to, developmental anomalies, fetal deficiencies, endometrial cancers and reproductive disorders. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels is routinely detected in certain tissues or cell types (e.g., reproductive, developmental, placental, and cancerous and wounded tissues) or bodily fluids (e.g., lymph, serum, plasma, urine, amniotic fluid,synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in placental tissue, endometrial tissue, and breast tissue indicates that polynucleotides and polypeptides corresponding to this gene are useful for the treatment and/or diagnosis of developmental abnormalities, fetal deficiencies, reproductive disorders and ovarian or other endometrial cancers, as well as cancers of other tissues where expression has been observed. Furthermore, the tissue distribution indicates that polynucleotides and polypeptides corresponding to this gene are useful for the diagnosis and/or treatment of disorders of the placenta. Specific expression within the placenta indicates that this gene product may play a role in the proper establishment and maintenance of placental function. Alternately, this gene product is produced by the placenta and then transported to the embryo, where it may play a crucial role in the development and/or survival of the developing embryo or fetus. Expression of this gene product in a vascular-rich tissue such as the placenta also indicates that this gene product is produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body. Additionally, expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus, this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1488 of SEQ ID NO:33, b is an integer of 15 to 1502, where both a and b correspond to the positions of nucleotide residues shown in SEQ ID NO:33, and where b is greater than or equal to a+14.

Features of Protein Encoded by Gene No: 24

Preferred polypeptides of the invention comprise the following amino acid sequence: HKGSGRPPTKEAMEP-MELMEEMLGLWVSADTP (SEQ ID NO: 142). Polynucleotides encoding these polypeptides are also provided.

This gene is expressed primarily in fast growing tissues and cell types such as early developmental stage tissues (12-week old embryonic tissues), immune tissues such as T-cells and bone marrow, and tumor tissues such as skin tumors, and to a lesser extent in other tissues.

Therefore, polynucleotides and polypeptides of the invention are useful as reagents for differential identification of the tissue(s) or cell type(s) present in a biological sample and for diagnosis of diseases and conditions which include, but are not limited to, developmental disorders, immune diseases, and tumorigenesis. Similarly, polypeptides and antibodies directed to these polypeptides are useful in providing immunological probes for differential identification of the tissue(s) or cell type(s). For a number of disorders of the above tissues or cells, particularly of the fast growing tissues and cell types such as early stage developmental tissues, immune tissues, and tumor tissues, expression of this gene at significantly higher or lower levels is routinely detected in certain tissues or cell types (e.g., developmental, immune, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 83 as residues: Asp-26 to Asn-31, Ser-37 to His-49, Ala-65 to Ser-73. Polynucleotides encoding said polypeptides are also provided.

The tissue distribution in immune, developing, and cancerous tissues indicates that the protein product of this gene is useful for the diagnosis and/or treatment of developmental disorders, immune diseases, and tumors. The tissue distribution indicates that polynucleotides and polypeptides corresponding to this gene are useful for the diagnosis and/or treatment of a variety of immune system disorders. Expression of this gene product in T-cells and bone marrow indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Alternatively, the tissue distribution in skin tumors indicates that the translation product of this gene is useful for the disgnosis and/or treatment of skin tumors, as well as tumors of other tissues where expression has been observed.

Moreover, expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus, this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 713 of SEQ ID NO:34, b is an integer of 15 to 727, where both a and b correspond to the positions of nucleotide residues shown in SEQ ID NO:34, and where b is greater than or equal to a+14.

Features of Protein Encoded by Gene No: 25

The translation product of this gene shares sequence homology with a number of glycoprotein proteases (including a zinc metallopeptidase Genbank Accession number Z99271) from parasites such as Leishmania and Trypanosomes and the nematode *Caenorhabditis elegans*. In addition, a zinc protease domain has been identified as TVKHEVIHAL (SEQ ID NO: 143).

Preferred polypeptides of the invention comprise the following sequence (sequence A), or a fragment thereof which retains the biological activity of a polypeptide comprising the entire sequence. Protease activities are the preferred biological activity. Assays for determining protease activity are known in the art.

Preferred polypeptides of the invention comprise the following amino acid sequence:

(SEQ ID NO:144)
EXLLPEKKNLVKNKLLXXAISYLEKTFQVRRPAGTILLSRQCATNQYLRK

ENDPHRYCTGECAAHTKCGPVIVPEEHLQQCRVYRGGKWPHGAVGVPDQE

GISDADFVLYVGALATERCSHENIISYAAYCQQEANMDRPIAGYANLCPN

MISTQPQEFVGMLSTVKHEVIHALGFSAGLFAFYHDKDGNPLTSRFADGL

PPFNYSLGLYQWSDKVVRKVXRLWDVRDNKIVRHTVYLLVTPRVVEEARK

HFDCPVLEGMELENQGGVGTELNHWEKRLLENEAMTGSHTQNRVLSRITL

ALMEDTGWYKANYSMAEKLDWGRGMGCDFVRKSCKFWIDQQRQKRQMLSP

YCDTLRSNPLQLTCRQDQRAVAVCNLQKFPKPLPQEYQYEDELSGIPAED

LPYYGGSVEIADYXPFSQEFSWHLSGEYQRSSDCRILENQPEIFKNYGAE

KYGPHSVCLIQKSAFVMEKCERKLSYPDWGSGCYQVSCSPQGLKVWVQDT

-continued
SYLCSRAGQVLPVSIQMNGWIHDGNLLCPSCWDFCELCPPETDPPATNLT

RALPLDLCSCSS, (SEQ ID NO:145)
EXLLPEKKNLVKNKLLXXAISYLEKTFQVRRPAGTILLSRQCATNQY, (SEQ ID NO:146)
LRKENDPHRYCTGECAAHTKCGPVIVPEEHLQQCRVYRGGKWPHG, (SEQ ID NO:147)
AVGVPDQEGISDADFVLYVGALATERCSHEMISYAAYCQQEANM, (SEQ ID NO:148)
DRPIAGYANLCPNMISTQPQEFVGMLSTVKHEVIHALGFSAGLFAF, (SEQ ID NO:149)
YHDKDGNPLTSRFADGLPPFNYSLGLYQWSDKVVRKVXRLWDVRD, (SEQ ID NO:150)
NKIVRHTVYLLVTPRVVEEARKHEDCPVLEGMELENQGGVGTELNH, (SEQ ID NO:151)
WEKRLLENEAMTGSHTQNRVLSRITLALMEDTGWYKANYSMAEKL, (SEQ ID NO:152)
DWGRGMGCDFVRKSCKFWIDQQRQKRQMLSPYCDTLRSNPLQLTC, (SEQ ID NO:153)
RQDQRAVAVCNLQKFPKPLPQEYQYFDELSGIPAEDLPYYGGSVEIA, (SEQ ID NO:154)
DYXPFSQEFSWKLSGEYQRSSDCRILENQPEIFIKNYGAEKYGPHSVCL, (SEQ ID NO:155)
IQKSAFVMIEKCERKLSYPDWGSGCYQVSCSPQGLKVWVQDTSYLCS, and/or (SEQ ID NO:156)
RAGQVLPVSIQMNGWIHDGNLLCPSCWDFCELCPPETDPPATNLTRALPL
DLCSCSS.

Polynucleotides encoding these polypeptides are also provided.

This gene is expressed primarily in testes tissue and T-cells.

Therefore, polynucleotides and polypeptides of the invention are useful as reagents for differential identification of the tissue(s) or cell type(s) present in a biological sample and for diagnosis of diseases and conditions which include, but are not limited to, immune disorders and/or male infertility. Similarly, polypeptides and antibodies directed to these polypeptides are useful in providing immunological probes for differential identification of the tissue(s) or cell type(s). For a number of disorders of the above tissues or cells, particularly of the immune system and male reproductive system, expression of this gene at significantly higher or lower levels is routinely detected in certain tissues or cell types (e.g., immune, reproductive, and cancerous and wounded tissues) or bodily fluids (e.g., lymph, serum, plasma, urine, seminal fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 84 as residues: Met-1 to Gly-6, Arg-11 to Gly-21. Polynucleotides encoding said polypeptides are also provided.

The tissue distribution in testes tissue and T-cells, and the homology to a cell surface marker, indicates that polynucleotides and polypeptides corresponding to this gene are useful for the treatment, prophylaxis and/or detection of male infertility, in addition to immune and autoimmune diseases, such as lupus, transplant rejection, allergic reactions, arthritis, asthma, immunodeficiency diseases, leukemia, and AIDS.

The translation product of this gene may also play a role in the treatment, prophlaxis and/or detection of thymus disorders such as Grave's Disease, lymphocytic thyroiditis, hyperthyroidism and hypothyroidism. Expression of this gene product in T-cells indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in T cells strongly indicates a role for this protein in immune function and immune surveillance. Furthermore, the tissue distribution in testes tissue indicates that polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that is expressed, particularly at low levels, in other tissues of the body. Therefore, this gene product is expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1977 of SEQ ID NO:35, b is an integer of 15 to 1991, where both a and b correspond to the positions of nucleotide residues shown in SEQ ID NO:35, and where b is greater than or equal to a+14.

Features of Protein Encoded by Gene No: 26

Preferred polypeptides of the invention comprise the following amino acid sequence: IKEKLHVHG (SEQ ID NO: 157). Polynucleotides encoding these polypeptides are also provided.

This gene is expressed primarily in brain tissue, such as the amygdala.

Therefore, polynucleotides and polypeptides of the invention are useful as reagents for differential identification of the tissue(s) or cell type(s) present in a biological sample and for diagnosis of diseases and conditions which include, but are not limited to, neurological and behavioural disorders. Similarly, polypeptides and antibodies directed to these polypeptides are useful in providing immunological probes for differential identification of the tissue(s) or cell type(s). For a number of disorders of the above tissues or cells, particularly of the nervous system expression of this gene at significantly higher or lower levels is routinely detected in certain tissues or cell types (e.g., neural, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 85 as residues: Arg-30 to Tyr-39. Polynucleotides encoding said polypeptides are also provided.

The tissue distribution exclusively in brain tissues such as the amygdala indicates that polynucleotides and polypeptides corresponding to this gene are useful for the detection and/or treatment of neurodegenerative disease states and behavioural disorders such as Alzheimer's Disease, Parkinson's Disease, Huntington's Disease, schizophrenia, mania, dementia, paranoia, obsessive compulsive disorder and panic disorder. The amygdala processes sensory information and relays this to other areas of the brain including the endocrine and autonomic domains of the hypothalamus and the brain stem. Therefore, the translation product of this gene is involved in neuronal survival; synapse formation; conductance; neural differentiation, etc. Such involvement may impact many processes, such as learning and cognition. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2307 of SEQ ID NO:36, b is an integer of 15 to 2321, where both a and b correspond to the positions of nucleotide residues shown in SEQ ID NO:36, and where b is greater than or equal to a+14.

Features of Protein Encoded by Gene No: 27

Preferred polypeptides of the invention comprise the following amino acid sequence: GFGVYILYA (SEQ ID NO: 158). Polynucleotides encoding these polypeptides are also provided.

When tested against U937 Myeloid cell lines, supernatants removed from cells containing this gene activated the GAS assay. Thus, it is likely that this gene activates myeloid cells, and to a lesser extent other immune system cells, through the JAK-STAT signal transduction pathway. The gamma activating sequence (GAS) is a promoter element found upstream of many genes which are involved in the JAK-STAT pathway. The JAK-STAT pathway is a large, signal transduction pathway involved in the differentiation and proliferation of cells. Therefore, activation of the JAK-STAT pathway, reflected by the binding of the GAS element, can be used to indicate proteins-involved in the proliferation and differentiation of cells.

This gene is expressed primarily in early development stage tissues and anergic T cells.

Therefore, polynucleotides and polypeptides of the invention are useful as reagents for differential identification of the tissue(s) or cell type(s) present in a biological sample and for diagnosis of diseases and conditions which include, but are not limited to, growth and developmental disorders and immune and inflammatory diseases. Similarly, polypeptides and antibodies directed to these polypeptides are useful in providing immunological probes for differential identification of the tissue(s) or cell type(s). For a number of disorders of the above tissues or cells, particularly of the early development stage tissues and anergic T cells, expression of this gene at significantly higher or lower levels is routinely detected in certain tissues or cell types (e.g., developing, immune, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in embryonic and immune tissues indicates that polynucleotides and polypeptides corresponding to this gene are useful for the detection and/or treatment of growth and developmental disorders and immune and inflammatory diseases. The tissue distribution in T-cells indicates that polynucleotides and polypeptides corresponding to this gene are useful for the diagnosis and treatment of a variety of immune system disorders. Expression of this gene product in T-cells indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Furthermore, expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus, this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1544 of SEQ ID NO:37, b is an integer of 15 to 1558, where both a and b correspond to the positions of nucleotide residues shown in SEQ ID NO:37, and where b is greater than or equal to a+14.

Features of Protein Encoded by Gene No: 28

Preferred polypeptides of the invention comprise the following amino acid sequence: KPSGTVYTLFSLNSGTL (SEQ ID NO: 159). Polynucleotides encoding these polypeptides are also provided.

This gene is expressed primarily in some activated peripheral blood cells and disease tissues such as melanoma, multiple sclerosis, and osteosarcoma, and to a lesser extent in some other tissues such as gall bladder tissue.

Therefore, polynucleotides and polypeptides of the invention are useful as reagents for differential identification of the tissue(s) or cell type(s) present in a biological sample and for diagnosis of diseases and conditions which include, but are not limited to, immune and inflammatory disorders and various diseases such as melanoma, multiple sclerosis, and osteosarcoma. Similarly, polypeptides and antibodies directed to these polypeptides are useful in providing immunological probes for differential identification of the tissue(s) or cell type(s). For a number of disorders of the above tissues or cells, particularly of the peripheral blood cells and tissues affected by disease such as melanoma, multiple sclerosis, and osteosarcoma, expression of this gene at significantly higher or lower levels is routinely detected in certain tissues or cell types (e.g., peripheral blood cells, and cancerous and wounded tissues) or bodily fluids (e.g., lymph, serum, plasma, bile, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution peripheral blood cells, melanoma tissue, multiple sclerosis tissue, and osteosarcoma tissue indicates that polynucleotides and polypeptides corresponding to this gene are useful for the diagnosis and/or treatment of immune and inflammatory disorders, and multiple sclerosis. Furthermore, the tissue distribution indicates that the translation product of this gene is useful for the treatment and/or diagnosis of various cancers, such as melanomas and osteosarcomas, as well as cancers of other tissues where expression has been observed. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1687 of SEQ ID NO:38, b is an integer of 15 to 1701, where both a and b correspond to the positions of nucleotide residues shown in SEQ ID NO:38, and where b is greater than or equal to a+14.

Features of Protein Encoded by Gene No: 29

This gene is expressed primarily in adipose tissue and dendritic cells.

Therefore, polynucleotides and polypeptides of the invention are useful as reagents for differential identification of the tissue(s) or cell type(s) present in a biological sample and for diagnosis of diseases and conditions which include, but are not limited to, metabolic and immune disorders or diseases, particularly obesity. Similarly, polypeptides and antibodies directed to these polypeptides are useful in providing immunological probes for differential identification of the tissue(s) or cell type(s). For a number of disorders of the above tissues or cells, particularly of the immune, metabolic and digestive systems, expression of this gene at significantly higher or lower levels is routinely detected in certain tissues or cell types (e.g., immune, metabolic, digestive, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 88 as residues: Ile-40 to Glu-45, Cys-63 to Val-69, Glu-83 to Asn-94, Pro-107 to Cys-115, Phe-137 to Ser-143, Ser-159 to Thr-167, Glu-200 to Tyr-210. Polynucleotides encoding said polypeptides are also provided.

The tissue distribution in primarily adipose tissue indicates that polynucleotides and polypeptides corresponding to this gene are useful for the treatment, diagnosis and/or prophylaxis of obesity related disorders. In addition, expression in dendritic cells indicates a potential role in the treatment, diagnosis and/or prophylaxis of immune and autoimmune disorders such as lupus, transplant rejection, allergic reactions, arthritis, asthma, immunodeficiency diseases, leukemia, and AIDS. The tissue distribution in adipose tissue indicates that polynucleotides and polypeptides corresponding to this gene are useful for the treatment of obesity and other metabolic and endocrine conditions or disorders. Furthermore, the protein product of this gene may show utility in ameliorating conditions which occur secondary to aberrant fatty-acid metabolism (e.g. aberrant myelin sheath development), either directly or indirectly. Expression of this gene product in dendritic cells indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in dendritic cells also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1889 of SEQ ID NO:39, b is an integer of 15 to 1903, where both a and b correspond to the positions of nucleotide residues shown in SEQ ID NO:39, and where b is greater than or equal to a+14.

Features of Protein Encoded by Gene No: 30

The translation product of this gene shares sequence homology with ATP-dependent RNA helicases, which are thought to be important in RNA binding and nucleic acid metabolism.

Preferred polypeptides of the invention comprise the following amino acid sequence: ADLTAVCSAWKPGAK-PVGL (SEQ ID NO: 160). Polynucleotides encoding these polypeptides are also provided.

The gene encoding the disclosed cDNA is thought to reside on chromosome 22. Accordingly, polynucleotides related to this invention are useful as a marker in linkage analysis for chromosome 22.

This gene is expressed primarily in ovary tumor, infant adrenal gland and white fat tissues, and to a lesser extent in many other tissues including bladder, endometrial stromal cells, Jurkat cells, pineal gland, and infant brain tissues.

Therefore, polynucleotides and polypeptides of the invention are useful as reagents for differential identification of the tissue(s) or cell type(s) present in a biological sample and for diagnosis of diseases and conditions which include, but are not limited to, disorders of the ovary or adrenal gland. Similarly, polypeptides and antibodies directed to these polypeptides are useful in providing immunological probes for differential identification of the tissue(s) or cell type(s). For a number of disorders of the above tissues or cells, particularly of the endocrine systems, expression of this gene at significantly higher or lower levels is routinely detected in certain tissues or cell types (e.g., endocrine, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 89 as residues: Gln-66 to Cys-71, Thr-76 to Gly-81, His-87 to Asp-92. Polynucleotides encoding said polypeptides are also provided.

The tissue distribution in the ovary and adrenal gland tissues, and the homology to ATP-dependent RNA helicases, indicates that polynucleotides and polypeptides corresponding to this gene are useful as a hormone and/or endocrine with either systemic or reproductive functions, as growth factors for germ cell maintenance and in vitro culture, and as a tool for fertility control. Furthermore, the translation product of this gene is useful for the detection and/or treatment of sexual dysfunction or sex development disorders as well as ovarian tumors, such as serous adenocarcinoma, dysgerminoma, embryonal carcinoma, choriocarcinoma, and teratoma, for example. The tissue distribution of the gene product may also indicate its function as a hormone. Additionally, the homology to ATP-dependent RNA helicases indicates that the translation product of this gene is utilized for the intervention of RNA viral infections. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:40 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1266 of SEQ ID NO:40, b is an integer of 15 to 1280, where both a and b correspond to the positions of nucleotide residues shown in SEQ ID NO:40, and where b is greater than or equal to a+14.

Features of Protein Encoded by Gene No: 31

The translation product of this gene shares limited sequence homology with urokinase inhibitor, which is thought to be important in the inhibition of urokinase enzymatic activity.

This gene is expressed primarily in frontal cortex tissue of the brain.

Therefore, polynucleotides and polypeptides of the invention are useful as reagents for differential identification of the tissue(s) or cell type(s) present in a biological sample and for diagnosis of diseases and conditions which include, but are not limited to, neurodegenerative and cardiovascular disorders and diseases. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels is routinely detected in certain tissues or cell types (e.g., neural, cardiovascular, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 90 as residues: Pro-31 to Pro-37. Polynucleotides encoding said polypeptides are also provided.

The tissue distribution in frontal cortex tissue of the brain, and the homology to urokinase inhibitor, indicates that polynucleotides and polypeptides corresponding to this gene are useful for the diagnosis and/or intervention of neurodegenerative diseases, in preventing tumour metastasis, in ovulation and uterine ovum implantation, and as anti-neoplastic agents. Representative uses are described in the "Regeneration" and "Hyperproliferative Disorders" sections below, in Example 11, 15, and 18, and elsewhere herein. Furthermore, elevated expression of this gene product within the frontal cortex of the brain indicates that it is involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's. The protein is useful for the detection, treatment, and/or prevention of cardiovascular diseases. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:41 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1904 of SEQ ID NO:41, b is an integer of 15 to 1918, where both a and b correspond to the positions of nucleotide residues shown in SEQ ID NO:41, and where b is greater than or equal to a+14.

Features of Protein Encoded by Gene No: 32

When tested against sensory neuronal cell lines, supernatants removed from cells containing this gene activated the EGR1 assay. Thus, it is likely that this gene activates sensory neuron cells, and to a lesser extent other neuronal cells, in addition to other cells or cell types, through a signal transduction pathway. Early growth response 1 (EGR1) is a promoter associated with certain genes that induces various tissues and cell types upon activation, leading the cells to undergo differentiation and proliferation.

This gene is expressed primarily in frontal cortex tissue of the brain.

Therefore, polynucleotides and polypeptides of the invention are useful as reagents for differential identification of the tissue(s) or cell type(s) present in a biological sample and for diagnosis of diseases and conditions which include, but are not limited to, neural disorders and diseases. Similarly, polypeptides and antibodies directed to these polypeptides are useful in providing immunological probes for differential identification of the tissue(s) or cell type(s). For a number of disorders of the above tissues or cells, particularly of the brain, expression of this gene at significantly higher or lower levels is routinely detected in certain tissues or cell types (e.g., brain, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in frontal cortex tissue of the brain, in conjunction with the biological activity data, indicates that polynucleotides and polypeptides corresponding to this gene are useful for the diagnosis and/or treatment of neural disorders. Representative uses are described in the "Regeneration" and "Hyperproliferative Disorders" sections below, in Example 11, 15, and 18, and elsewhere herein. Elevated expression of this gene product within the frontal cortex of the brain indicates that it is involved in neuronal survival; synapse formation; conductance; neural differentiation, etc.

Such involvement may impact many processes, such as learning and cognition. It may also be useful in the treatment of such neurodegenerative disorders as schizophrenia; ALS; or Alzheimer's. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:42 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1254 of SEQ ID NO:42, b is an integer of 15 to 1268, where both a and b correspond to the positions of nucleotide residues shown in SEQ ID NO:42, and where b is greater than or equal to a+14.

Features of Protein Encoded by Gene No: 33

The gene encoding the disclosed cDNA is thought to reside on chromosome 3. Accordingly, polynucleotides related to this invention are useful as a marker in linkage analysis for chromosome 3.

In another embodiment, polypeptides comprising the amino acid sequence of the open reading frame upstream of the predicted signal peptide are contemplated by the present invention. Specifically, polypeptides of the invention comprise the following amino acid sequence:

(SEQ ID NO:162)
GSNKLINHLEQCSIGWIFVCLFVCCYSECVMFCIQQKWLFSELFYEVGLM

GTDSLRKKYNCKSVEVFPSQDVKCQRSDSCGRMGSKLYKSLEMNEVRQLS

LRQKTM.

Polynucleotides encoding these polypeptides are also provided.

This gene is expressed primarily in synovial membrane and adipose tissues, as well as in T-cells.

Therefore, polynucleotides and polypeptides of the invention are useful as reagents for differential identification of the tissue(s) or cell type(s) present in a biological sample and for diagnosis of diseases and conditions which include, but are not limited to, skeletal disorders, synovioma, synovitis, obesity, and immune disorders and diseases. Similarly, polypeptides and antibodies directed to these polypeptides are useful in providing immunological probes for differential identification of the tissue(s) or cell type(s). For a number of disorders of the above tissues or cells, particularly of the immune and metabolic systems, and the body's connective tissue, expression of this gene at significantly higher or lower levels is routinely detected in certain tissues or cell types (e.g., musculo-skeletal, immune, metabolic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 92 as residues: Ser-24 to Cys-31, Gln-40 to Gly-51, Leu-71 to Met-76. Polynucleotides encoding said polypeptides are also provided.

The tissue distribution of this gene primarily in synovial fluid, in adipose tissue, and in T-cells indicates that polynucleotides and polypeptides corresponding to this gene are useful for the treatment, detection and/or prophlaxis of disease states associated with these cell types including synovioma, synovitis, obesity, immune and autoimmune diseases, such as lupus, transplant rejection, allergic reactions, arthritis, asthma, immunodeficiency diseases, leukemia, and AIDS. Representative uses are described in the "Immune Activity" and "infectious disease" sections below, in Example 11, 13, 14, 16, 18, 19, 20, and 27, and elsewhere herein. The distribution in adipose tissue indicates that polynucleotides and polypeptides corresponding to this gene are useful for the treatment of obesity and other metabolic and endocrine conditions or disorders. Furthermore, the protein product of this gene may show utility in ameliorating conditions which occur secondary to aberrant fatty-acid metabolism (e.g. aberrant myelin sheath development), either directly or indirectly. In addition, the expression of this gene product in synovium indicates a role in the detection and treatment of disorders and conditions affecting the skeletal system, in particular osteoporosis as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial arthritis, Atelosteogenesis type II, metaphyseal chondrodysplasia type Schmid). Expression of this gene product in T-cells indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in T cells also strongly indicates a role for this protein in immune function and immune surveillance. Protein is useful in modulating the immune response, particularly to proliferating or abberrant cells or cell-types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:43 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1187 of SEQ ID NO:43, b is an integer of 15 to 1201, where both a and b correspond to the positions of nucleotide residues shown in SEQ ID NO:43, and where b is greater than or equal to a+14.

Features of Protein Encoded by Gene No: 34

This gene is expressed primarily in brain and pancreas tumor tissues.

Therefore, polynucleotides and polypeptides of the invention are useful as reagents for differential identification of the tissue(s) or cell type(s) present in a biological sample and for diagnosis of diseases and conditions which include, but are not limited to, neural diseases and tumors, particularly of the pancreas. Similarly, polypeptides and antibodies directed to these polypeptides are useful in providing immunological probes for differential identification of the tissue(s) or cell type(s). For a number of disorders of the above tissues or cells, particularly of the brain tissue and pancreas tumor, expression of this gene at significantly higher or lower levels is routinely detected in certain tissues or cell types (e.g., neural, metabolic, pancreas, and cancerous and wounded tissues) or bodily fluids (e.g., lymph, serum, plasma, urine, bile, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 93 as residues: Thr-50 to Phe-55. Polynucleotides encoding said polypeptides are also provided.

The tissue distribution in brain tissue and pancreatic tumor tissue indicates that polynucleotides and polypeptides corresponding to this gene are useful for the diagnosis and/or treatment of neural diseases and tumors, particularly pancreatic tumors. Representative uses are described in the "Regeneration" and "Hyperproliferative Disorders" sections below, in Example 11, 15, and 18, and elsewhere herein. The distribution in brain tissue indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Alternatively, the tissue distribution in pancreatic tumor tissue indicates that the translation product of this gene is useful for the detection and/or treatment of pancreatic tumors, as well as tumors of other tissues where expression has been observed. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:44 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 805 of SEQ ID NO:44, b is an integer of 15 to 819, where both a and b correspond to the positions of nucleotide residues shown in SEQ ID NO:44, and where b is greater than or equal to a+14.

Features of Protein Encoded by Gene No: 35

Preferred polypeptides of the invention comprise the following amino acid sequence:

(SEQ ID NO:163)
TTWATSSVVARXTIThLFPPHSGISVNIQDLAPSCAGFLFGVANTAGALA

GVVGVCLGGYL

Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence:

(SEQ ID NO:164)
TTWATSSVVARXTHHLFPPHSGISVNIQDLAPSCAGFLFGVANTAGALAG

VVGVCLGGYLMIETTGSWTCLFNLVAIISNLGLCTFLVFGQAQRVDLSST

HEDL

Polynucleotides encoding these polypeptides are also provided.

This gene is expressed primarily in fetal liver/spleen tissue, and to a lesser extent in a variety of other tissues.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders and diseases, including leukemias, lymphomas, arthritis and asthma. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., immune, hematopoietic, and cancerous and wounded tissues) or bodily fluids (e.g., lymph, serum, plasma, amniotic fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 94 as residues: Met-1 to Ser-6, Ser-38 to Leu-43. Polynucleotides encoding said polypeptides are also provided.

The tissue distribution in fetal liver/spleen tissue indicates that polynucleotides and polypeptides corresponding to this gene are useful for the diagnosis and/or treatment of immune disorders including: leukemias, lymphomas, autoimmunities, immunodeficiencies(e.g. AIDS), immunosupressive conditions (e.g.transplantation) and hematopoeitic disorders. Representative uses are described in the "Immune Activity" and "infectious disease" sections below, in Example 11, 13, 14, 16, 18, 19, 20, and 27, and elsewhere herein. In addition this gene product is applicable in conditions of general microbial infection, inflammation or cancer. Furthermore, expression of this gene product in fetal liver/spleen tissues indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:45 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1552 of SEQ ID NO:45, b is an integer of 15 to 1566, where both a and b correspond to the positions of nucleotide residues shown in SEQ ID NO:45, and where b is greater than or equal to a+14.

Features of Protein Encoded by Gene No: 36

This gene is expressed primarily in infant brain tissues.

Therefore, polynucleotides and polypeptides of the invention are useful as reagents for differential identification of the tissue(s) or cell type(s) present in a biological sample and for diagnosis of diseases and conditions which include, but are not limited to, neural and/or developmental disorders and diseases. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels is routinely detected in certain tissues or cell types (e.g., brain, developmental, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in infant brain tissue indicates that the product of this gene is useful for the diagnosis and/or treatment of central nervous system and neurodegenerative disorders. Representative uses are described in the "Regeneration" and "Hyperproliferative Disorders" section elsewhere herein. Representative uses are described in the "Regeneration" and "Hyperproliferative Disorders" sections below, in Example 11, 15, and 18, and elsewhere herein. Polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Moreover, the expression within infant tissue indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. Furthermore, the protein may also be used to determine biological activity, to raise antibodies, as tissue markers, to isolate cognate ligands or receptors, to identify agents that modulate their interactions, in addition to its use as a nutritional supplement.

Many polynucleotide sequences, such as EST sequences, are publicly available and accessible through sequence databases. Some of these sequences are related to SEQ ID NO:46 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2080 of SEQ ID NO:46, b is an integer of 15 to 2094, where both a and b correspond to the positions of nucleotide residues shown in SEQ ID NO:46, and where b is greater than or equal to a+14.

Features of Protein Encoded by Gene No: 37

This gene is expressed primarily in apoptotic T-cells and T-cell lymphoma.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders and diseases, particularly those relating to T-cell disorders, such as immunodeficiencies. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 96 as residues: Cys-32 to Asn-37. Polynucleotides encoding said polypeptides are also provided.

The tissue distribution in T-cells and T-cell lymphoma indicates that polynucleotides and polypeptides corresponding to this gene are useful for the diagnosis and/or treatment of immune system disorders. Representative uses are described in the "Immune Activity" and "infectious disease" sections below, in Example 11, 13, 14, 16, 18, 19, 20, and 27, and elsewhere herein. Expression of this gene product in T-cells indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in T cells also strongly indicates a role for this protein in immune function and immune surveillance. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:47 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 942 of SEQ ID NO:47, b is an integer of 15 to 956, where both a and b correspond to the positions of nucleotide residues shown in SEQ ID NO:47, and where b is greater than or equal to a+14.

Features of Protein Encoded by Gene No: 38

The polypeptide of this gene has been determined to have eleven potential transmembrane domains at about amino acid position 2–18, 77–93, 128–144, 180–196, 201–217, 258–274, 279–295, 314–330, 343–359, 380–396, and/or 414–430 of the amino acid sequence referenced in Table 1 for this gene. Based upon these characteristics, it is believed that the protein product of this gene shares structural features to type IIIb membrane proteins.

In another embodiment, polypeptides comprising the amino acid sequence of the open reading frame upstream of the predicted signal peptide are contemplated by the present invention. Specifically, polypeptides of the invention comprise the following amino acid sequence:

(SEQ ID NO:167)
GGGQRXARLPEAGCEGRERCWNPSRSRSHSGEGGLAAWSRTCPGRPRRPG

QQVVRGPTMLVTAYLAFVGLLASCLGLELSRCRAKPPGRACSNPSFLREQ

LDFYQVYFLALAADWLQAPYLYKLYQHYYELEGQIAILYVCGLASTVLFG

LVASSLVDWLGRKNSCVLFSLTYSLCCLTKLSQDYFVLLVGRALGGLSTA

LLFSAFEAWY

IHEHVERHDFPAEWIPATFARAAEWNHVLAVVAGVAAEAVASWIGLGPVA

PFVAAIPLLALAGALALRNWGENYDRQRAFSRTCAGGLRCLLSDRRVLLL

GTIQALFESVIFIFVFLWTPVLDPHGAPLGIIFSSEMAASLLGSSLYRIA

TSKRYHLQPMHLLSLAVLIVVFSLFMLTESTSPGQESPVESFIAFLLIEL

ACGLYFPSMSFLRRKVIPETEQAGVLNWFRVPLHSLACLGLLVLHDSDRK

TGTRNMFSICSAVMVMALLAVVGLFTVVRHDAELRVPSPTEEPYAPEL

Polynucleotides encoding these polypeptides are also provided.

Preferred polypeptides of the invention comprise the following amino acid sequence: DSPLTVLPEDGYGSD-SHLSSQVVRGPT (SEQ ID NO: 165). Polynucleotides encoding these polypeptides are also provided.

A preferred polypeptide fragment of the invention comprises the following amino acid sequence:

(SEQ ID NO:166)
MLVTAYLAEVGLLASCLGLELSRCRAKPGRACSNPSFQLDFYQVYFLA

LAADWLQAPYLYKLYQHYYFLEQIAILYVCGLASTVLFGLVASSLVDWLG

RKNSCVLFSLTYSLCCLTKLSQDYFVLLVGRALGGLSTAALLSLRGLVYP

Polynucleotides encoding these polypeptides are also provided.

This gene is expressed primarily in activated T-cells and human testes tumor.

Therefore, polynucleotides and polypeptides of the invention are useful as reagents for differential identification of the tissue(s) or cell type(s) present in a biological sample and for diagnosis of diseases and conditions which include, but are not limited to, disorders relating to the immune system, and T-cells in particular, as well as male reproductive diseases. Similarly, polypeptides and antibodies directed to these polypeptides are useful in providing immunological probes for differential identification of the tissue(s) or cell type(s). For a number of disorders of the above tissues or cells, particularly of the immune system and male reproductive system, expression of this gene at significantly higher or lower levels is routinely detected in certain tissues or cell types (e.g., immune, reproductive, and cancerous and wounded tissues) or bodily fluids (e.g., lymph, serum, plasma, urine, seminal fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 97 as residues: Arg-23 to Ser-34, Asn-221 to Phe-232, Thr-303 to His-308, Ser-334 to Pro-340, Asp-398 to Asn-407, Pro-439 to Ala-447. Polynucleotides encoding said polypeptides are also provided.

The tissue distribution in testes tumor tissue and T-cells indicates that polynucleotides and polypeptides corresponding to this gene are useful for the diagnosis and/or treatment of immune and male reproductive disorders. Representative uses are described in the "Immune Activity" and "infectious disease" sections below, in Example 11, 13, 14, 16, 18, 19, 20, and 27, and elsewhere herein. Expression of this gene product in T-cells indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in T cells also strongly indicates a role for this protein in immune function and immune surveillance. Furthermore, the tissue distribution indicates that polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence.

This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that is expressed, particularly at low levels, in other tissues of the body. Therefore, this gene product is expressed in other specific tissues or organs where it may play related functional roles in other processes, such as hematopoiesis, inflammation, bone formation, and kidney function, to name a few possible target indications. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:48 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1845 of SEQ ID NO:48, b is an integer of 15 to 1859, where both a and b correspond to the positions of nucleotide residues shown in SEQ ID NO:48, and where b is greater than or equal to a+14.

Features of Protein Encoded by Gene No: 39

The translation product of this gene shares sequence homology with the human PEX gene (See Genbank Accession No.: Y10196).

Preferred polypeptides of the invention comprise the following amino acid sequence: VEAIFSELVIVLNKMSH-CVLSGT (SEQ ID NO: 168). Polynucleotides encoding these polypeptides are also provided.

The polypeptide of this gene has been determined to have a transmembrane domain at about amino acid position 13–29 of the amino acid sequence referenced in Table 1 for this gene. Based upon these characteristics, it is believed that the protein product of this gene shares structural features to type II membrane proteins.

In another embodiment, polypeptides comprising the amino acid sequence of the open reading frame upstream of the predicted signal peptide are contemplated by the present invention. Specifically, polypeptides of the invention comprise the following amino acid sequence:

```
                                          (SEQ ID NO:169)
VEAIFSELVIVLNKMSHCVLSGTMQAHPIFIYHKRVFFLLKFIFYIIFCF

FFLDISTLYCSLSTFCKK
```

Polynucleotides encoding these polypeptides are also provided.

This gene is expressed primarily in amniotic cells, ovarian cancer, and fetal heart tissue.

Therefore, polynucleotides and polypeptides of the invention are useful as reagents for differential identification of the tissue(s) or cell type(s) present in a biological sample and for diagnosis of diseases and conditions which include, but are not limited to, reproductive and developmental diseases or disorders and diseases of the circulatory system. Similarly, polypeptides and antibodies directed to these polypeptides are useful in providing immunological probes for differential identification of the tissue(s) or cell type(s). For a number of disorders of the above tissues or cells, particularly of the central nervous system, reproductive and circulatory systems, expression of this gene at significantly higher or lower levels is routinely detected in certain tissues or cell types (e.g., central nervous system, reproductive, circulatory, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in fetal heart, ovarian cancer, and amniotic cells, and the homology to human PEX gene, indicates that polynucleotides and polypeptides corresponding to this gene are useful for the diagnosis and/or treatment of diseases of the central nervous system, reproductive and circulatory systems. Representative uses are described in the "Chemotaxis" and "Binding Activity" sections below, in Examples 11, 12, 13, 14, 15, 16, 18, 19, and 20, and elsewhere herein. The tissue distribution in fetal heart tissue indicates that the protein product of this gene is useful for the diagnosis and treatment of conditions and pathologies of the cardiovascular system, such as heart disease, restenosis, atherosclerosis, stoke, angina, thrombosis, and wound healing. Furthermore, the tissue distribution in ovarian cancer tissue indicates that the translation product of this gene is useful for the diagnosis and/or treatment of ovarian cancer, as well as cancers of other tissues where expression has been observed. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:49 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1447 of SEQ ID NO:49, b is an integer of 15 to 1461, where both a and b correspond to the positions of nucleotide residues shown in SEQ ID NO:49, and where b is greater than or equal to a+14.

Features of Protein Encoded by Gene No: 40

Preferred polypeptides of the invention comprise the following amino acid sequence: KPTKMPLL-WVWALIAAVSQPELWYRE (SEQ ID NO: 170). Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence:

(SEQ ID NO:171)
KPTKMPLLWVWALIAAVSQPELWYREMGVLLLFSFFFPNGSFSPVVLPSY

FPNSSSYFVFCTSFWRPLSFQKG

Polynucleotides encoding these polypeptides are also provided.

The gene encoding the disclosed cDNA is thought to reside on chromosome 1. Accordingly, polynucleotides related to this invention are useful as a marker in linkage analysis for chromosome 1.

This gene is expressed primarily in ovarian tumor, tissue affected by multiple sclerosis, and bladder tissue from a female.

Therefore, polynucleotides and polypeptides of the invention are useful as reagents for differential identification of the tissue(s) or cell type(s) present in a biological sample and for diagnosis of diseases and conditions which include, but are not limited to, disorders in female reproductive and urinary systems, and nervous system disorders. Similarly, polypeptides and antibodies directed to these polypeptides are useful in providing immunological probes for differential identification of the tissue(s) or cell type(s). For a number of disorders of the above tissues or cells, particularly of the reproductive, urinary, and central nervous systems, expression of this gene at significantly higher or lower levels is routinely detected in certain tissues or cell types (e.g., reproductive, neural, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 99 as residues: Phe-25 to Ser-30. Polynucleotides encoding said polypeptides are also provided.

The tissue distribution in ovarian tumor tissue, bladder and multiple sclerosis tissues indicates that polynucleotides and polypeptides corresponding to this gene are useful for the diagnosis and/or treatment of reproductive, urinary, and central nervous systems disorders. Representative uses are described in the "Hyperproliferative Disorders" and "Regeneration" sections below and elsewhere herein. The tissue distribution in ovarian cancer tissue indicates that the translation product of this gene is useful for the detection and/or treatment of ovarian cancer, as well as cancers of other tissues where expression has been observed. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:50 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1224 of SEQ ID NO:50, b is an integer of 15 to 1238, where both a and b correspond to the positions of nucleotide residues shown in SEQ ID NO:50, and where b is greater than or equal to a+14.

Features of Protein Encoded by Gene No: 41

The polypeptide of this gene has been determined to have a transmembrane domain at about amino acid position 5–21 of the amino acid sequence referenced in Table 1 for this gene. Moreover, a cytoplasmic tail encompassing amino acids 22 to 50 of this protein has also been determined. Based upon these characteristics, it is believed that the protein product of this gene shares structural features to type Ib membrane proteins.

The gene encoding the disclosed cDNA is thought to reside on chromosome 5. Accordingly, polynucleotides related to this invention are useful as a marker in linkage analysis for chromosome 5.

This gene is expressed primarily in stromal cells, and was found in a cDNA library derived from fetal liver and spleen.

Therefore, polynucleotides and polypeptides of the invention are useful as reagents for differential identification of the tissue(s) or cell type(s) present in a biological sample and for diagnosis of diseases and conditions which include, but are not limited to, disorders in connective tissue, and the immune and hematopoietic systems. Similarly, polypeptides and antibodies directed to these polypeptides are useful in providing immunological probes for differential identification of the tissue(s) or cell type(s). For a number of disorders of the above tissues or cells, particularly of the muscular and skeletal system, and immune system, expression of this gene at significantly higher or lower levels is routinely detected in certain tissues or cell types (e.g., immune, hematopoietic, musculo-skeletal, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO:100 as residues: Pro-28 to Ser-37. Polynucleotides encoding said polypeptides are also provided.

The tissue distribution in stromal cells indicates that polynucleotides and polypeptides corresponding to this gene are useful for the diagnosis and/or treatment of connective tissue and immune system disorders. Representative uses are described in the "Immune Activity" and "infectious disease" sections below, in Example 11, 13, 14, 16, 18, 19, 20, and 27, and elsewhere herein. The tissue distribution indicates that polynucleotides and polypeptides corresponding to this gene are useful for the treatment and diagnosis of hematopoietic related disorders such as anemia, pancytopenia, leukopenia, thrombocytopenia or leukemia, since stromal cells are important in the production of cells of hematopoietic lineages. The uses include bone marrow cell ex vivo culture, bone marrow transplantation, bone marrow reconstitution, radiotherapy or chemotherapy of neoplasia.

The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:51 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2567 of SEQ ID NO:51, b is an integer of 15 to 2581, where both a and b correspond to the positions of nucleotide residues shown in SEQ ID NO:51, and where b is greater than or equal to a+14.
Features of Protein Encoded by Gene No: 42

This gene is expressed primarily in infant brain and ovarian cancer, and to a lesser extent in adrenal gland tumor tissue.

Therefore, polynucleotides and polypeptides of the invention are useful as reagents for differential identification of the tissue(s) or cell type(s) present in a biological sample and for diagnosis of diseases and conditions which include, but are not limited to, disorders in the nervous system and female reproductive system, as well as cancers. Similarly, polypeptides and antibodies directed to these polypeptides are useful in providing immunological probes for differential identification of the tissue(s) or cell type(s). For a number of disorders of the above tissues or cells, particularly of the central nervous system, endocrine, and female reproductive system, expression of this gene at significantly higher or lower levels is routinely detected in certain tissues or cell types (e.g., neural, reproductive, endocrine, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 101 as residues: Leu-24 to Ser-29. Polynucleotides encoding said polypeptides are also provided.

The tissue distribution in infant brain tissue and cancerous tissues of ovarian and adrenal gland nature indicates that polynucleotides and polypeptides corresponding to this gene are useful for the diagnosis and/or treatment of central nervous system and female reproductive system disorders. Representative uses are described in the "Hyperproliferative Disorders" and "Regeneration" sections below and elsewhere herein. The tissue distribution in cancerous tissues of the ovaries and adrenal glands indicates that the translation product of this gene is useful for the detection and/or treatment of cancers of the endocrine (adrenal glands) and female reproductive (ovaries) systems, as well as cancers of other tissues and systems where expression has been observed.

Alternatively, the tissue distribution in infant brain tissue indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:52 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 977 of SEQ ID NO:52, b is an integer of 15 to 991, where both a and b correspond to the positions of nucleotide residues shown in SEQ ID NO:52, and where b is greater than or equal to a+14.

Features of Protein Encoded by Gene No: 43

In another embodiment, polypeptides comprising the amino acid sequence of the open reading frame upstream of the predicted signal peptide are contemplated by the present invention. Specifically, polypeptides of the invention comprise the following amino acid sequence:

(SEQ ID NO:172)
CFTHWNVEPRLWMTSFLMERVQEGWKTPGFKLSIPHMGFSIIFRPEAARP

EVRLHLSALFVLLLATLGFLLGTMCGCGMCEQKGG.

Polynucleotides encoding these polypeptides are also provided.

This gene is expressed primarily in fetal liver/spleen tissue, and to a lesser extent in placental tissue.

Therefore, polynucleotides and polypeptides of the invention are useful as reagents for differential identification of the tissue(s) or cell type(s) present in a biological sample and for diagnosis of diseases and conditions which include, but are not limited to, immune and hematopoiesis disorders, and proper placental maintanence. Similarly, polypeptides and antibodies directed to these polypeptides are useful in providing immunological probes for differential identification of the tissue(s) or cell type(s). For a number of disorders of the above tissues or cells, particularly of the immune and developing systems, expression of this gene at significantly higher or lower levels is routinely detected in certain tissues or cell types (e.g., immune, placental, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 102 as residues: Cys-44 to Gly-49. Polynucleotides encoding said polypeptides are also provided.

The tissue distribution in fetal liver/spleen and placental tissues indicates that polynucleotides and polypeptides corresponding to this gene are useful for the diagnosis and/or treatment of immune disorders. Representative uses are described in the "Immune Activity" and "infectious disease" sections below, in Example 11, 13, 14, 16, 18, 19, 20, and 27, and elsewhere herein. The tissue distribution in placental tissue indicates that polynucleotides and polypeptides corresponding to this gene are useful for the diagnosis and/or treatment of disorders of the placenta. Specific expression within the placenta indicates that this gene product may play a role in the proper establishment and maintenance of placental function.

Alternately, this gene product is produced by the placenta and then transported to the embryo, where it may play a crucial role in the development and/or survival of the developing embryo or fetus. Expression of this gene product in a vascular-rich tissue such as the placenta also indicates that this gene product is produced more generally in endothelial cells or within the circulation. In such instances, it may play more generalized roles in vascular function, such as angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body. Furthermore, the tissue distribution indicates that polynucleotides and polypeptides corresponding to this gene are useful for the diagnosis and treatment of a variety of immune system disorders. Expression of this gene product in fetal liver/spleen tissue indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:53 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2408 of SEQ ID NO:53, b is an integer of 15 to 2422, where both a and b correspond to the positions of nucleotide residues shown in SEQ ID NO:53, and where b is greater than or equal to a+14.

Features of Protein Encoded by Gene No: 44

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, neutropenia and neutrophilia. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., immune, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the diagnosis and/or treatment of immune system disorders. Representative uses are described in the "Immune Activity" and "infectious disease" sections below, in Example 11, 13, 14, 16, 18, 19, 20, and 27, and elsewhere herein. Expression of this gene product in neutrophils indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in neutrophils also strongly indicates a role for this protein in immune function and immune surveillance. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:54 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 971 of SEQ ID NO:54, b is an integer of 15 to 985, where both a and b correspond to the positions of nucleotide residues shown in SEQ ID NO:54, and where b is greater than or equal to a+14.

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 1 | HDPOW86 | 209603 Jan. 29, 1998 | pCMVSport 3.0 | 11 | 1810 | 58 | 1810 | 192 | 192 | 60 | 1 | 18 | 19 | 307 |
| 2 | HSYAG26 | 209603 Jan. 29, 1998 | pCMVSport 3.0 | 12 | 2353 | 31 | 1721 | 39 | 39 | 61 | 1 | 22 | 23 | 578 |
| 3 | HLHCH40 | 209603 Jan. 29, 1998 | Uni-ZAP XR | 13 | 928 | 1 | 928 | 43 | 43 | 62 | 1 | 13 | 14 | 184 |
| 3 | HLHCH40 | 209603 Jan. 29, 1998 | Uni-ZAP XR | 55 | 932 | 13 | 932 | 53 | 53 | 104 | 1 | 16 | 17 | 122 |
| 4 | HSDEK49 | 209603 Jan. 29, 1998 | Uni-ZAP XR | 14 | 1590 | 96 | 1590 | 126 | 126 | 63 | 1 | 21 | 22 | 305 |
| 5 | HLMBO76 | 209603 Jan. 29, 1998 | Lambda ZAP II | 15 | 815 | 1 | 795 | 43 | 43 | 64 | 1 | 43 | 44 | 107 |
| 6 | HLQDR48 | 209603 Jan. 29, 1998 | Lambda ZAP II | 16 | 990 | 1 | 990 | 3 | 3 | 65 | 1 | 21 | 22 | 190 |
| 7 | HOHBY12 | 209603 Jan. 29, 1998 | pCMVSport 2.0 | 17 | 1188 | 1 | 1188 | 232 | 232 | 66 | 1 | 25 | 26 | 199 |
| 8 | HOSEK86 | 209603 Jan. 29, 1998 | Uni-ZAP XR | 18 | 1605 | 1 | 1605 | 81 | 81 | 67 | 1 | 35 | 36 | 61 |
| 9 | HAJBZ75 | 209603 Jan. 29, 1998 | pCMVSport 3.0 | 19 | 2089 | 10 | 2085 | 49 | 49 | 68 | 1 | 22 | 23 | 607 |
| 10 | HAGCH75 | 209603 Jan. 29, 1998 | Uni-ZAP XR | 20 | 1281 | 1 | 1281 | 80 | 80 | 69 | 1 | 17 | 18 | 89 |
| 11 | HE8MH91 | 209603 Jan. 29, 1998 | Uni-ZAP XR | 21 | 1761 | 1 | 1761 | 63 | 63 | 70 | 1 | 23 | 24 | 116 |
| 12 | HISCJ55 | 209603 Jan. 29, 1998 | pSport1 | 22 | 1189 | 1 | 1189 | 151 | 151 | 71 | 1 | 21 | 22 | 139 |
| 13 | HKISB57 | 209603 Jan. 29, 1998 | pBluescript | 23 | 1492 | 1 | 1439 | 130 | 130 | 72 | 1 | 20 | 21 | 95 |
| 14 | HTEBJ71 | 209603 Jan. 29, 1998 | Uni-ZAP XR | 24 | 1608 | 1 | 1608 | 51 | 51 | 73 | 1 | 20 | 21 | 77 |
| 15 | HCWKR01 | 209603 Jan. 29, 1998 | ZAP Express | 25 | 1964 | 1 | 1964 | 65 | 65 | 74 | 1 | 28 | 29 | 54 |
| 16 | HFCEW05 | 209603 Jan. 29, 1998 | Uni-ZAP XR | 26 | 933 | 1 | 933 | 34 | 34 | 75 | 1 | 18 | 19 | 209 |
| 17 | HCEPF19 | 209603 Jan. 29, 1998 | Uni-ZAP XR | 27 | 1237 | 51 | 1224 | 292 | 292 | 76 | 1 | 25 | 26 | 104 |
| 18 | HTACZ01 | 209603 Jan. 29, 1998 | Uni-ZAP XR | 28 | 960 | 1 | 960 | 60 | 60 | 77 | 1 | 17 | 18 | 176 |
| 18 | HTACZ01 | 209603 Jan. 29, 1998 | Uni-ZAP XR | 56 | 957 | 1 | 957 | 53 | 53 | 105 | 1 | 17 | 18 | 55 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 19 | HUDAM89 | 209603 Jan. 29, 1998 | ZAP Express | 29 | 1067 | 1 | 1067 | 15 | 15 | 78 | 1 | 20 | 21 | 44 |
| 20 | HSAXF60 | 209603 Jan. 29, 1998 | Uni-ZAP XR | 30 | 1063 | 1 | 1063 | 198 | 198 | 79 | 1 | 21 | 22 | 70 |
| 21 | HTOGR42 | 209603 Jan. 29, 1998 | Uni-ZAP XR | 31 | 1430 | 1 | 1430 | 14 | 14 | 80 | 1 | 18 | 19 | 56 |
| 21 | HTOGR42 | 209603 Jan. 29, 1998 | Uni-ZAP XR | 57 | 1433 | 1 | 1433 | 13 | 13 | 106 | 1 | 18 | 19 | 60 |
| 22 | HMVBN46 | 209603 Jan. 29, 1998 | pSport1 | 32 | 1382 | 1 | 1382 | 10 | 10 | 81 | 1 | 19 | 20 | 48 |
| 23 | HUVEB53 | 209603 Jan. 29, 1998 | Uni-ZAP XR | 33 | 1502 | 1 | 1502 | 14 | 14 | 82 | 1 | 20 | 21 | 45 |
| 24 | HSVBU91 | 209603 Jan. 29, 1998 | Uni-ZAP XR | 34 | 727 | 1 | 727 | 256 | 256 | 83 | 1 | 18 | 19 | 90 |
| 25 | HTXFL30 | 209603 Jan. 29, 1998 | Uni-ZAP XR | 35 | 1991 | 1 | 1991 | 30 | 30 | 84 | 1 | 39 | 40 | 102 |
| 26 | HAGAM64 | 209603 Jan. 29, 1998 | Uni-ZAP XR | 36 | 2321 | 1 | 2321 | 57 | 57 | 85 | 1 | 31 | 32 | 44 |
| 27 | HE2PH36 | 209603 Jan. 29, 1998 | Uni-ZAP XR | 37 | 1558 | 1 | 1558 | 28 | 28 | 86 | 1 | 21 | 22 | 66 |
| 28 | HGBDY06 | 209603 Jan. 29, 1998 | Uni-ZAP XR | 38 | 1701 | 48 | 1701 | 196 | 196 | 87 | 1 | 23 | 24 | 71 |
| 29 | HWBAO62 | 209603 Jan. 29, 1998 | pCMVSport 3.0 | 39 | 1903 | 1 | 1903 | 52 | 52 | 88 | 1 | 30 | 31 | 212 |
| 29 | HWBAO62 | 209603 Jan. 29, 1998 | pCMVSport 3.0 | 58 | 1940 | 1 | 1940 | 81 | 81 | 107 | 1 | 30 | 31 | 101 |
| 30 | HBAFJ33 | 209603 Jan. 29, 1998 | pSport1 | 40 | 1280 | 1 | 1252 | 60 | 60 | 89 | 1 | 15 | 16 | 110 |
| 31 | HFXDJ75 | 209603 Jan. 29, 1998 | Lambda ZAP II | 41 | 1918 | 1 | 1914 | 44 | 44 | 90 | 1 | 26 | 27 | 41 |
| 32 | HFPCY04 | 209603 Jan. 29, 1998 | Uni-ZAP XR | 42 | 1268 | 1 | 1268 | 201 | 201 | 91 | 1 | 32 | 33 | 58 |
| 33 | HSNBG78 | 209603 Jan. 29, 1998 | Uni-ZAP XR | 43 | 1201 | 247 | 1188 | 291 | 291 | 92 | 1 | 21 | 22 | 76 |
| 34 | HBQAB27 | 209603 Jan. 29, 1998 | Lambda ZAP II | 44 | 819 | 1 | 819 | 119 | 119 | 93 | 1 | 21 | 22 | 68 |
| 35 | HTOJY21 | 209603 Jan. 29, 1998 | Uni-ZAP XR | 45 | 1566 | 205 | 1566 | 317 | 317 | 94 | 1 | 31 | 32 | 43 |
| 36 | HHTMM30 | 209603 Jan. 29, 1998 | ZAP Express | 46 | 2094 | 1 | 2094 | 71 | 71 | 95 | 1 | 18 | 19 | 46 |
| 37 | HLTAF58 | 209603 Jan. 29, 1998 | Uni-ZAP XR | 47 | 956 | 1 | 956 | 103 | 103 | 96 | 1 | 30 | 31 | 47 |
| 38 | HHEPU32 | 209603 Jan. 29, 1998 | pCMVSport 3.0 | 48 | 1859 | 315 | 1859 | 176 | 176 | 97 | 1 | 18 | 19 | 450 |
| 38 | HHEPU32 | 209603 Jan. 29, 1998 | pCMVSport 3.0 | 59 | 1715 | 1 | 1715 | 124 | 124 | 108 | 1 | 18 | 19 | 153 |
| 39 | HHFDM48 | 209603 Jan. 29, 1998 | Uni-ZAP XR | 49 | 1461 | 1 | 1461 | 139 | 139 | 98 | 1 | 34 | 35 | 45 |
| 40 | HKABI84 | 209603 Jan. 29, 1998 | pCMVSport 2.0 | 50 | 1238 | 45 | 1238 | 274 | 274 | 99 | 1 | 16 | 17 | 47 |
| 41 | HMVAX72 | 209603 Jan. 29, 1998 | pSport1 | 51 | 2581 | 1 | 2581 | 23 | 23 | 100 | 1 | 29 | 30 | 50 |
| 42 | HODDN60 | 209603 Jan. 29, 1998 | Uni-ZAP XR | 52 | 991 | 1 | 991 | 34 | 34 | 101 | 1 | 19 | 20 | 40 |
| 43 | HPMEI44 | 209603 Jan. 29, 1998 | Uni-ZAP XR | 53 | 2422 | 563 | 2422 | 578 | 578 | 102 | 1 | 39 | 40 | 49 |
| 44 | HNGJP69 | 209603 Jan. 29, 1998 | Uni-ZAP XR | 54 | 985 | 1 | 985 | 321 | 321 | 103 | 1 | 14 | 15 | 74 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X and the translated SEQ ID NO:Y are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used to generate antibodies which bind specifically to the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs. Species homologs may be isolated and identified by making suitable probes or primers from the sequences provided herein and screening a suitable nucleic acid source for the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, prosequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified by the one-step method described in Smith and Johnson, Gene 67:31–40 (1988). Polypeptides of the invention also can be purified from natural or recombinant sources using antibodies of the invention raised against the secreted protein in methods which are well known in the art.

Signal Sequences

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1–6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., + or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. These polypeptides, and the polynucleotides encoding such polypeptides, are contemplated by the present invention.

Polynucleotide and Polypeptide Variants

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragement specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignement of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

In the present invention, a "polynucleotide fragment" refers to a short polynucleotide having a nucleic acid sequence contained in the deposited clone or shown in SEQ ID NO:X. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the deposited clone or the nucleotide sequence shown in SEQ ID NO:X. These nucleotide fragments are useful as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:Y or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotide fragments encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotide fragments encoding these domains are also contemplated.

Other preferred fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Epitopes & Antibodies

In the present invention, "epitopes" refer to polypeptide fragments having antigenic or immunogenic activity in an animal, especially in a human. A preferred embodiment of the present invention relates to a polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., Proc. Natl. Acad. Sci. USA 81:3998–4002 (1983).)

Fragments which function as epitopes may be produced by any conventional means. (See, e.g, Houghten, R. A., Proc. Natl. Acad. Sci. USA 82:5131–5135 (1985) further described in U.S. Pat. No. 4,631,211.)

In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope. (See, for instance, Wilson et al., Cell 37:767–778 (1984); Sutcliffe, J. G. et al., Science 219:660–666 (1983).)

Similarly, immunogenic epitopes can be used to induce antibodies according to methods well known in the art. (See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316–325 (1983).) Thus, these fragments are preferred, as well as the products of a FAB or other immunoglobulin expression library. Moreover, antibodies of the present invention include chimeric, single chain, and humanized antibodies.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

In addition to the foregoing, a polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell . Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder.

Moreover, polypeptides of the present invention can be used to treat disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to a polypeptide of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Biological Activities

The polynucleotides and polypeptides of the present invention can be used in assays to test for one or more biological activities. If these polynucleotides and polypeptides do exhibit activity in a particular assay, it is likely that these molecules may be involved in the diseases associated with the biological activity. Thus, the polynucleotides and polypeptides could be used to treat the associated disease.

Immune Activity

A polypeptide or polynucleotide of the present invention may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, a polynucleotide or polypeptide of the present invention can be used as a marker or detector of a particular immune system disease or disorder.

A polynucleotide or polypeptide of the present invention may be useful in treating or detecting deficiencies or disorders of hematopoietic cells. A polypeptide or polynucleotide of the present invention could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polypeptide or polynucleotide of the present invention could also be used to modulate hemostatic (the stopping of bleeding) or thrombolytic activity (clot formation). For example, by increasing hemostatic or thrombolytic activity, a polynucleotide or polypeptide of the present invention could be used to treat blood coagulation disorders (e.g., afibrinogenemia, factor deficiencies), blood platelet disorders (e.g. thrombocytopenia), or wounds resulting from trauma, surgery, or other causes. Alternatively, a polynucleotide or polypeptide of the present invention that can decrease hemostatic or thrombolytic activity could be used to inhibit or dissolve clotting. These molecules could be important in the treatment of heart attacks (infarction), strokes, or scarring.

A polynucleotide or polypeptide of the present invention may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of a polypeptide or polynucleotide of the present invention that inhibits an immune response, particularly the proliferation, differentiation, or chemotaxis of T-cells, may be an effective therapy in preventing autoimmune disorders.

Examples of autoimmune disorders that can be treated or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

Similarly, allergic reactions and conditions, such as asthma (particularly allergic asthma) or other respiratory problems, may also be treated by a polypeptide or polynucleotide of the present invention. Moreover, these molecules can be used to treat anaphylaxis, hypersensitivity to an antigenic molecule, or blood group incompatibility.

A polynucleotide or polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polypeptide or polynucleotide of the present invention that inhibits an immune response, particularly the proliferation, differentiation, or chemotaxis of T-cells, may be an effective therapy in preventing organ rejection or GVHD.

Similarly, a polypeptide or polynucleotide of the present invention may also be used to modulate inflammation. For example, the polypeptide or polynucleotide may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polypeptide or polynucleotide can be used to treat or detect hyperproliferative disorders, including neoplasms. A polypeptide or polynucleotide of the present invention may inhibit the proliferation of the disorder through direct or indirect interactions. Alternatively, a polypeptide or polynucleotide of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotide or polypeptide of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotide or polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

A polypeptide or polynucleotide of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, the polypeptide or polynucleotide of the present invention may also directly inhibit the infectious agent, without necessarily eliciting an immune response.

Viruses are one example of an infectious agent that can cause disease or symptoms that can be treated or detected by a polynucleotide or polypeptide of the present invention. Examples of viruses, include, but are not limited to the following DNA and RNA viral families: *Arbovirus, Adenoviridae, Arenaviridae, Arterivirus, Birnaviridae, Bunyaviridae, Caliciviridae, Circoviridae, Coronaviridae, Flaviviridae, Hepadnaviridae* (Hepatitis), *Herpesviridae* (such as, Cytomegalovirus, Herpes Simplex, Herpes Zoster), *Mononegavirus* (e.g., *Paramyxoviridae, Morbillivirus, Rhabdoviridae*), *Orthomyxoviridae* (e.g., Influenza), *Papovaviridae, Parvoviridae, Picornaviridae, Poxviridae* (such as Smallpox or Vaccinia), *Reoviridae* (e.g., *Rotavirus*), *Retroviridae* (HTLV-I, HTLV-II, Lentivirus), and *Togaviridae* (e.g., *Rubivirus*). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. A polypeptide or polynucleotide of the present invention can be used to treat or detect any of these symptoms or diseases.

Similarly, bacterial or fungal agents that can cause disease or symptoms and that can be treated or detected by a polynucleotide or polypeptide of the present invention include, but not limited to, the following Gram-Negative and Gram-positive bacterial families and fungi: *Actinomycetales* (e.g., *Corynebacterium, Mycobacterium, Norcardia*), *Aspergillosis, Bacillaceae* (e.g., *Anthrax, Clostridium*), *Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae* (*Klebsiella, Salmonella, Serratia, Yersinia*), *Erysipelothrix, Helicobacter, Legionellosis, Leptospirosis, Listeria, Mycoplasmatales, Neisseriaceae* (e.g., *Acinetobacter, Gonorrhea, Menigococcal*), *Pasteurellacea Infections* (e.g., *Actinobacillus, Heamophilus, Pasteurella*), *Pseudomonas, Rickettsiaceae, Chlamydiaceae, Syphilis, and Staphylococcal*. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. A polypeptide or polynucleotide of the present invention can be used to treat or detect any of these symptoms or diseases.

Moreover, parasitic agents causing disease or symptoms that can be treated or detected by a polynucleotide or polypeptide of the present invention include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A polypeptide or polynucleotide of the present invention can be used to treat or detect any of these symptoms or diseases.

Preferably, treatment using a polypeptide or polynucleotide of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide of the present invention may increase regeneration of tissues difficult to heal. For example, increased tendon/ligament regeneration would quicken recovery time after damage. A polynucleotide or polypeptide of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide of the present invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotide or polypeptide of the present invention.

Chemotaxis

A polynucleotide or polypeptide of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide of the present invention may inhibit chemotactic activity. These molecules could also be used to treat disorders. Thus, a polynucleotide or polypeptide of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or E. coli. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptide from suitably manipulated cells or tissues.

Therefore, the invention includes a method of identifying compounds which bind to a polypeptide of the invention comprising the steps of: (a) incubating a candidate binding compound with a polypeptide of the invention; and (b) determining if binding has occurred. Moreover, the invention includes a method of identifying agonists/antagonists comprising the steps of: (a) incubating a candidate compound with a polypeptide of the invention, (b) assaying a biological activity , and (b) determining if a biological activity of the polypeptide has been altered.

Other Activities

A polypeptide or polynucleotide of the present invention may also increase or decrease the differentiation or proliferation of embryonic stem cells, besides, as discussed above, hematopoietic lineage.

A polypeptide or polynucleotide of the present invention may also be used to modulate mammalian characteristics, such as body height, weight, hair color, eye color, skin, percentage of adipose tissue, pigmentation, size, and shape (e.g., cosmetic surgery). Similarly, a polypeptide or polynucleotide of the present invention may be used to modulate mammalian metabolism affecting catabolism, anabolism, processing, utilization, and storage of energy.

A polypeptide or polynucleotide of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide or polynucleotide of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95%,identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

EXAMPLES

Example 1

Isolation of a Selected cDNA Clone From the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library | Corresponding Deposited Plasmid |
| --- | --- |
| Lambda Zap | pBluescript (pBS) |
| Uni-Zap XR | pBluescript (pBS) |
| Zap Express | pBK |
| lafmid BA | plafmid BA |
| pSport 1 | pSport 1 |
| pCMVSport 2.0 | pCMVSport 2.0 |
| pCMVSport 3.0 | pCMVSport 3.0 |
| pCR ®2.1 | pCR ®2.1 |

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into E. coli strain XL-1 Blue, also available from Stratagene. pBS comes in 4 forms SK+, SK−, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into E. coli strain DH10B, also available from Life Technologies. (See, for instance, Gruber, C. E., et al., Focus 15:59 (1993).) Vector lafmid BA (Bento Soares, Columbia University, N.Y.) contains an ampicillin resistance gene and can be transformed into E. coli strain XL-1 Blue. Vector pCR®2.1, which is available from Invitrogen, 1600 Faraday Avenue, Carlsbad, Calif. 92008, contains an ampicillin resistance gene and may be transformed into E. coli strain DH10B, available from Life Technologies. (See, for instance, Clark, J. M., Nuc. Acids Res. 16:9677–9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 μl of reaction mixture with 0.5 ug of the above cDNA template. A convenient reaction mixture is 1.5–5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3" "RACE" protocols which are well known in the art. For instance, a method similar to 5' RACE is available for generating the missing 5' end of a desired full-length transcript. (Fromont-Racine et al., Nucleic Acids Res. 21(7) :1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT 1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70° C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an E. coli origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in E. coli when it is present in the form of inclusion bodies. Unless otherwise specified, all of the following steps are conducted at 4–10° C.

Upon completion of the production phase of the E. coli fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 μg of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five μg of a plasmid containing the polynucleotide is co-transfected with 1.0 μg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One μg of BaculoGold™ virus DNA and 5 μg of the plasmid are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 μCi of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five μg of the expression plasmid pC6 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc Region

```
                                              (SEQ ID NO:1)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAAC

CACAGGTGTACACCCTGCCCCCATCCCGGGATGAGCTGACCAAGAACCAG

GTCAGCCTGACCTGCCTGGTCAAAGGCTTCTATCCAAGCGACATCGCCGT

GGAGTGGGAGAGCAATGGGCAGCCGGAGAACAACTACAAGACCACGCCT

CCCGTGCTGGACTCCGACGGCTCCTTCTTCCTCTACAGCAAGCTCACCGT

GGACAAGAGCAGGTGGCAGCAGGGGAACGTCTTCTCATGCTCCGTGATGC

ATGAGGCTCTGCACAACCACTACACGCAGAAGAGCCTCTCCCTGTCTCCG

GGTAAATGAGTGCGACGGCCGCGACTCTAGAGGAT
```

Example 10

Production of an Antibody from a Polypeptide

The antibodies of the present invention can be prepared by a variety of methods. (See, Current Protocols, Chapter 2.) For example, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Production of Secreted Protein for High-throughput Screening Assays

The following protocol produces a supernatant containing a polypeptide to be tested. This supernatant can then be used in the Screening Assays described in Examples 13–20.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2 \times 10^5$ cells/well in 0.5 ml DMEM(Dulbecco's Modified Eagle Medium)(with 4.5 G/L glucose and L-glutamine (12-604F Biowhittaker))/10% heat inactivated FBS(14-503F Biowhittaker)/1×Penstrep(17-602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37° C. for 6 hours.

While cells are incubating, prepare appropriate media, either 1% BSA in DMEM with 1×penstrep, or CHO-5 media (116.6 mg/L of CaCl2 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$-$H_2O$; 71.02 mg/L of $Na_2HPO4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/L of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-$2H_2O$; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1×penstrep. (BSA (81-068-3 Bayer) 100 gm dissolved in 1 L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37° C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13–20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| Ligand | JAKs | | | | STATS | GAS (elements) or ISRE |
| --- | --- | --- | --- | --- | --- | --- |
| | tyk2 | Jak1 | Jak2 | Jak3 | | |
| IFN family | | | | | | |
| IFN-a/B | + | + | − | − | 1,2,3 | ISRE |
| IFN-g | | + | + | − | 1 | GAS (IRF1 > Lys6 > IFP) |
| Il-10 | + | ? | ? | − | 1,3 | |
| gp130 family | | | | | | |
| IL-6 (Pleiotropic) | + | + | + | ? | 1,3 | GAS (IRF1 > Lys6 > IFP) |
| Il-11 (Pleiotropic) | ? | + | ? | ? | 1,3 | |
| OnM (Pleiotropic) | ? | + | + | ? | 1,3 | |
| LIF (Pleiotropic) | ? | + | + | ? | 1,3 | |
| CNTF (Pleiotropic) | −/+ | + | + | ? | 1,3 | |
| G-CSF (Pleiotropic) | ? | + | ? | ? | 1,3 | |
| IL-12 (Pleiotropic) | + | − | + | + | 1,3 | |
| g-C family | | | | | | |
| IL-2 (lymphocytes) | − | + | − | + | 1,3,5 | GAS |
| IL-4 (lymph/myeloid) | − | + | − | + | 6 | GAS (IRF1 = IFP >> Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1,3,5 | |
| EPO | ? | − | + | − | 5 | GAS (B-CAS > IRF1 = IFP >> Ly6) |
| Receptor Tyrosine Kinases | | | | | | |
| EGF | ? | + | + | − | 1,3 | GAS (IRF1) |
| PDGF | ? | + | + | − | 1,3 | |
| CSF-1 | ? | + | + | − | 1,3 | GAS (not IRF1) |

To construct a synthetic GAS containing promoter element, which is used in the Biological Assays described in Examples 13–14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is:

(SEQ ID NO:3)
5':GCGCCTCGAGATTTCCCCGAAATCTAGATTTCCCCGAAATGATTTCC

CCGAAATGATTTCCCCGAAATATCTGCCATCTCAATTAG:3'

The downstream primer is complementary to the SV40 promoter and is flanked with a Hind III site: 5':GCG-GCAAGCTTTTTGCAAAGCCTAGGC:3' (SEQ ID NO:4)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

(SEQ ID NO:5)
5':CTCGAGATCCCCGAAATCTAGATTTCCCCGAAATGATLTTCCCCGAA
ATGATTTCCCCGAAATATCTGCCATCTCAATTAGTCAGCAACCATAGTCC
CGCCCCTAACTCCGCCCATCCCGCCCCTAACTCCGCCCAGTTCCGCCCAT
TCTCCGCCCCATGGCTGACTAATTTTTTTTATGCAGAGGCCGAGGCCGCC
TCGGCCTCTGAGCTATTCCAGAAGTAGTGAGGAGGCTTTTTTGGAGGCCT
AGGCTTTTGCAAAAAGCTT:3'

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13–14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, II-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 13

High-throughput Screening Assay for T-cell Activity

The following protocol is used to assess T-cell activity by identifying factors, such as growth factors and cytokines, that may proliferate or differentiate T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1%Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1\times10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing a polypeptide as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20° C. until SEAP assays are performed according to Example 17. The plates containing the remaining treated cells are placed at 4° C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 14

High-throughput Screening Assay Identifying Myeloid Activity

The following protocol is used to assess myeloid activity by identifying factors, such as growth factors and cytokines, that may proliferate or differentiate myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259–265) is used. First, harvest $2 \times 10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37° C. for 45 min.

Wash the cells with RPMI 1640 medium containing 10% FBS and then resuspend in 10 ml complete medium and incubate at 37° C for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1 \times 10^8$ cells (this is enough for ten 96-well plates assay) and wash with PBS. Suspend the cells in 200 ml above described growth medium, with a final density of $5 \times 10^5$ cells/ml. Plate 200 ul cells per well in the 96-well plate (or $1 \times 10^5$ cells/well).

Add 50 ul of the supernatant prepared by the protocol described in Example 11. Incubate at 37° C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15

High-throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

```
                                       (SEQ ID NO:6)
5'GCGCTCGAGGGATGACAGCGATAGAACCCCGG-
3'

5'GCGAAGCTTCGCGACTCCCCGGATCCGCCTC-3' (SEQ ID NO:7)
```

Using the GAS:SEAP/Neo vector produced in Example 12, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. # 12449-78P), 5% heat-inactivated fetal bovine serum (EBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5 \times 10^5$ cells/ml.

Add 200 ul of the cell suspension to each well of 96-well plate (equivalent to $1 \times 10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16

High-throughput Screening Assay for T-cell Activity

NF-κB (Nuclear Factor κB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-κB regulates the expression of genes involved in immune cell activation, control of apoptosis (NF-κB appears to shield cells from apoptosis), B and T-cell development, anti-viral and antimicrobial responses, and multiple stress responses.

In non-stimulated conditions, NF-κB is retained in the cytoplasm with I-κB (Inhibitor κB). However, upon stimulation, I-κB is phosphorylated and degraded, causing NF-κB to shuttle to the nucleus, thereby activating transcription of target genes. Target genes activated by NF-κB include IL-2, IL-6, GM-CSF, ICAM-1 and class 1 MHC.

Due to its central role and ability to respond to a range of stimuli, reporter constructs utilizing the NF-κB promoter element are used to screen the supernatants produced in Example 11. Activators or inhibitors of NF-κB would be useful in treating diseases. For example, inhibitors of NF-κB could be used to treat those diseases related to the acute or chronic activation of NF-κB, such as rheumatoid arthritis.

To construct a vector containing the NF-κB promoter element, a PCR based strategy is employed. The upstream primer contains four tandem copies of the NF-κB binding site (GGGGACTTTCCC) (SEQ ID NO:8), 18 bp of sequence complementary to the 5' end of the SV40 early promoter sequence, and is flanked with an XhoI site:

```
                                              (SEQ ID NO:9)
5':GCGGCCTCGAGGGGACTTTCCCGGGGACTTTCCGGGGACTTTCCGGG

ACTTTCCATCCTGCCATCTCAATTAG:3'
```

The downstream primer is complementary to the 3' end of the SV40 promoter and is flanked with a Hind III site:

5':GCGGCAAGCTTTTTGCAAAGCCTAGGC:3' (SEQ ID NO:4)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

```
                                              (SEQ ID NO:10)
5':CTCGAGGGGACTTTCCCCGGGGACTTTCCGGGGACTTTCCGGGACTT

TCCATCTGCCATCTCAATFfAGTCAGCAACCATAGTCCCGCCCCTAACTC

CGCCCATCCCGCCCCTAACTCCGCCCAGTTCCGCCCACTTCTCCGCCCCA

TGGCTGACTAATTTTTTTATTTATGCAGAGGCCGAGGCCGCCTCGGCCTC

TGAGCTATTCCAGAAGTAGTGAGGAGGCTTTTTTGGAGGCCTAGGCTTTT

GCAAAAAGCTT:3'
```

Next, replace the SV40 minimal promoter element present in the pSEAP2-promoter plasmid (Clontech) with this NF-κB/SV40 fragment using XhoI and HindIII. However, this vector does not contain a neomycin resistance gene, and therefore, is not preferred for mammalian expression systems.

In order to generate stable mammalian cell lines, the NF-κB/SV40/SEAP cassette is removed from the above NF-κB/SEAP vector using restriction enzymes SalI and NotI, and inserted into a vector containing neomycin resistance. Particularly, the NF-κB/SV40/SEAP cassette was inserted into pGFP-1 (Clontech), replacing the GFP gene, after restricting pGFP-1 with SalI and NotI.

Once NF-κB/SV40/SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1,1, 10 ng) is added to wells H9, H10, and H11, with a 5–10 fold activation typically observed.

Example 17

Assay for SEAP Activity

As a reporter molecule for the assays described in Examples 13–16, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5×Dilution Buffer and dispense 15 μl of 2.5×dilution buffer into Optiplates containing 35 μl of a supernatant. Seal the plates with a plastic sealer and incubate at 65° C. for 30 min. Separate the Optiplates to avoid uneven heating.

Cool the samples to room temperature for 15 minutes. Empty the dispenser and prime with the Assay Buffer. Add 50 μl Assay Buffer and incubate at room temperature 5 min. Empty the dispenser and prime with the Reaction Buffer (see the table below). Add 50 μl Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| Reaction Buffer Formulation: | | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |

-continued

Reaction Buffer Formulation:

| # of plates | Rxn buffer diluent (ml) | CSPD (ml) |
|---|---|---|
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol desribes an assay for calcium, this protocol can easily be modified to detect changes in potassium, sodium, pH, membrane potential, or any other small molecule which is dectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo4 is added to each well. The plate is incubated at 37° C. in a $CO_2$ incubator for 60 min. The plate is washed four times in the Biotek washer with HBSS leaving 100 ul of buffer.

For non-adherent cells, the cells are spun down from culture media. Cells are re-suspended to $2–5\times10^6$ cells/ml with HBSS in a 50-ml conical tube. 4 ul of 1 mg/ml fluo-4 solution in 10% pluronic acid DMSO is added to each ml of cell suspension. The tube is then placed in a 37° C. water bath for 30–60 min. The cells are washed twice with HBSS, resuspended to $1\times10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular $Ca^{++}$ concentration.

Example 19

High-throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4° C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (# 1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4° C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg$_{2+}$ (5 mM ATP/50 mM MgCl$_2$), then 10 ul of 5×Assay Buffer (40 mM imidazole hydrochloride, pH7.3, 40 mM beta-glycerophosphate, 1 mM EGTA, 100 mM MgCl$_2$, 5 mM MnCl$_2$, 0.5 mg/ml BSA), then 5 ul of Sodium Vanadate(1 mM), and then 5 ul of water. Mix the components gently and preincubate the reaction mix at 30° C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37° C. for 20 min. This allows the streptavadin coated 96 well plate to associate with the biotinylated peptide. Wash the MTP module with 300 ul/well of PBS four times. Next add 75 ul of anti-phosphotyrosine antibody conjugated to horse radish peroxidase(anti-P-Tyr-POD(0.5 u/ml)) to each well and incubate at 37° C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4° C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21

Method of Determining Alterations in a Gene Corresponding to a Polynucleotide RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95° C. for 30 seconds; 60–120 seconds at 52–58° C.; and 60–120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton, T. A. and Graham, M. W., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22

Method of Detecting Abnormal Levels of a Polypeptide in a Biological Sample A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The secreted polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(−)-3-hydroxybutyric acid (EP 133,988). Sustained-release compositions also include liposomally entrapped polypeptides. Liposomes containing the secreted polypeptide are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 24

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB 101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 27

Method of Treatment Using Gene Therapy—in vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 28

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (N.Y.) 11:1263–1270 (1993); Wright et al., Biotechnology (N.Y.) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al.; Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 29

Knock-out Animals

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated protein comprising the amino acid sequence of the secreted portion of the polypeptide encoded by the HHEPU32 cDNA contained in ATCC Deposit No. 209603.

2. The isolated protein of claim 1 which comprises the amino acid sequence of the complete polypeptide encoded by the HHEPU32 cDNA contained in ATCC Deposit No. 209603, excepting the N-terminal methionine.

3. The isolated protein of claim 1 which comprises the amino acid sequence of the complete polypeptide encoded by the HHEPU32 cDNA contained in ATCC Deposit No. 209603.

4. The protein of claim 1 which further comprises a polypeptide sequence heterologous to the polypeptide encoded by the HHEPU32 cDNA contained in ATCG Deposit No. 209603.

5. A composition comprising the protein of claim 1 and an acceptable carrier.

6. An isolated protein produced by the method comprising:
(a) expressing the protein of claim 1 by a cell; and
(b) recovering said protein.

7. An isolated protein comprising amino acid residues 19 to 153 of SEQ ID NO: 108.

8. The isolated protein of claim 7 which comprises amino acid residues 2 to 153 of SEQ ID NO: 108.

9. The isolated protein of claim 7 which comprises amino acid residues 1 to 153 of SEQ ID NO: 108.

10. The protein of claim 7 which further comprises a polypeptide sequence heterologous to SEQ ID NO: 108.

11. A composition comprising the protein of claim 7 and an acceptable carrier.

12. An isolated protein produced by the method comprising:
(a) expressing the protein of claim 7 by a cell; and
(b) recovering said protein.

13. An isolated protein consisting of a fragment of SEQ ID NO: 108, wherein said fragment is at least 30 contiguous amino acid residues in length.

14. The isolated protein of claim 13, wherein said fragment is at least 50 contiguous amino acid residues in length.

15. The protein of claim 13 which further comprises a polypeptide sequence heterologous to SEQ ID NO: 108.

16. A composition comprising the protein of claim 13 and an acceptable carrier.

17. An isolated protein produced by the method comprising:
(a) expressing the protein of claim 13 by a cell; and
(b) recovering said protein.

\* \* \* \* \*

UNITED STATES PATENT AND TRADEMARK OFFICE
CERTIFICATE OF CORRECTION

PATENT NO. : 6,924,356 B2
DATED : August 2, 2005
INVENTOR(S) : Ruben et al.

It is certified that error appears in the above-identified patent and that said Letters Patent is hereby corrected as shown below:

<u>Title page,</u>
Item [63], Related U.S. Application Data, delete "filed as application No. PCT/US99/02293" and insert -- which is a CIP of application No. PCT/US99/02293 --.

<u>Column 292,</u>
Line 64, delete "ATCG" and insert -- ATCC --.

Signed and Sealed this

Fifteenth Day of November, 2005

JON W. DUDAS
*Director of the United States Patent and Trademark Office*

SEQUENCE LISTING

<160> NUMBER OF SEQ ID NOS: 172

<210> SEQ ID NO 1
<211> LENGTH: 733
<212> TYPE: DNA
<213> ORGANISM: Homo sapiens

<400> SEQUENCE: 1

```
gggatccgga gcccaaatct tctgacaaaa ctcacacatg cccaccgtgc ccagcacctg      60
aattcgaggg tgcaccgtca gtcttcctct tccccccaaa acccaaggac accctcatga     120
tctcccggac tcctgaggtc acatgcgtgg tggtggacgt aagccacgaa gaccctgagg     180
tcaagttcaa ctggtacgtg gacggcgtgg aggtgcataa tgccaagaca aagccgcggg     240
aggagcagta caacagcacg taccgtgtgg tcagcgtcct caccgtcctg caccaggact     300
```

-continued

```
ggctgaatgg caaggagtac aagtgcaagg tctccaacaa agccctccca accccccatcg    360 agaaaaccat ctccaaagcc aaagggcagc cccgagaacc acaggtgtac accctgcccc    420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                      733
```

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally ocurring
      L-amino acids

<400> SEQUENCE: 2

Trp Ser Xaa Trp Ser
 1               5

<210> SEQ ID NO 3
<211> LENGTH: 86
<212> TYPE: DNA
<213> ORGANISM: Homo sapiens

<400> SEQUENCE: 3

```
gcgcctcgag atttccccga aatctagatt tccccgaaat gatttccccg aaatgatttc    60
cccgaaatat ctgccatctc aattag                                         86
```

<210> SEQ ID NO 4
<211> LENGTH: 27
<212> TYPE: DNA
<213> ORGANISM: Homo sapiens

<400> SEQUENCE: 4

```
gcggcaagct ttttgcaaag cctaggc                                        27
```

<210> SEQ ID NO 5
<211> LENGTH: 271
<212> TYPE: DNA
<213> ORGANISM: Homo sapiens

<400> SEQUENCE: 5

```
ctcgagattt ccccgaaatc tagatttccc cgaaatgatt tccccgaaat gatttccccg    60
aaatatctgc catctcaatt agtcagcaac catagtcccg cccctaactc cgcccatccc   120
gcccctaact ccgcccagtt ccgcccattc tccgcccat ggctgactaa ttttttttat   180
ttatgcagag gccgaggccg cctcggcctc tgagctattc cagaagtagt gaggaggctt   240
ttttggaggc ctaggctttt gcaaaaagct t                                   271
```

<210> SEQ ID NO 6
<211> LENGTH: 32
<212> TYPE: DNA
<213> ORGANISM: Homo sapiens

```
<400> SEQUENCE: 6
gcgctcgagg gatgacagcg atagaacccc gg                              32

<210> SEQ ID NO 7
<211> LENGTH: 31
<212> TYPE: DNA
<213> ORGANISM: Homo sapiens

<400> SEQUENCE: 7
gcgaagcttc gcgactcccc ggatccgcct c                               31

<210> SEQ ID NO 8
<211> LENGTH: 12
<212> TYPE: DNA
<213> ORGANISM: Homo sapiens

<400> SEQUENCE: 8
ggggactttc cc                                                    12

<210> SEQ ID NO 9
<211> LENGTH: 73
<212> TYPE: DNA
<213> ORGANISM: Homo sapiens

<400> SEQUENCE: 9
gcggcctcga ggggactttc cgggggactt tccggggact ttccggggact ttccatcctg    60 ccatctcaat tag                                                   73

<210> SEQ ID NO 10
<211> LENGTH: 256
<212> TYPE: DNA
<213> ORGANISM: Homo sapiens

<400> SEQUENCE: 10
ctcgagggga ctttcccggg gactttccgg gactttccg ggactttcca tctgccatct     60
caattagtca gcaaccatag tcccgcccct aactccgccc atcccgcccc taactccgcc   120
cagttccgcc cattctccgc cccatggctg actaattttt tttatttatg cagaggccga   180
ggccgcctcg gcctctgagc tattccagaa gtagtgagga ggcttttttg gaggcctagg   240
cttttgcaaa aagctt                                               256

<210> SEQ ID NO 11
<211> LENGTH: 1810
<212> TYPE: DNA
<213> ORGANISM: Homo sapiens

<400> SEQUENCE: 11
aattcggcag agccatcttg ctctaagtga aagtgaaaga aaagtcggca gcagagggaa     60
cagggaagaa acctaaaggc tgcaggctgc caggtgtgct ggagagccc ccttcttccg    120 ccgggcctcg caagcagcgt aggactgtgg agaagggcgg tgggcaagga gggaactcga   180
gagcagcctc catgggcaca caggagggct ggtgcctgct gctctgcctg gctctatctg   240
gagcagcaga aaccaagccc cacccagcag agggcagtg gcgggcagtg gacgtggtcc    300
tagactgctt cctggcgaag gacgtgcgc accgtgagc tctcgccagc agtgaggaca    360
gggcaagggc ctcccttgtg ctgaagcagg tgccagtgct ggacgatggc tccctggagg   420
acttcaccga tttccaaggg gcacactggg cccaagatga cccacctatt atctttgagg   480
cctcagtgga cctggtccag attccccagg ccgaggcctt gctccatgct gactgcagtg   540
```

```
ggaaggaggt gacctgtgag atctcccgct actttctcca gatgacagag accactgtta    600
agacagcagc ttggttcatg ccaacatgc aggtctctgg aggggacct agcatctcct      660 tggtgatgaa gactcccagg gtcrccaaga atgaggcgct ctggcacccg acgctgaact    720
tgccactgag cccccagggg actgtgcgaa ctgcagtgga gttccaggtg atgacacaga    780
cccaatccct gagcttcctg ctggggtcct cagcctcctt ggactgtggc ttctccatgg    840
caccgggctt ggacctcatc agtgtggagt ggcgactgca gcacaagggc agggtcagt    900 tggtgtacag ctggaccgca ggcaggggca rgctgtgcgg aagggcgcta ccctggagcc    960
tgcacaactg ggcatggcca gggatgcctc cctcaccctg cccggcctca ctatacagga   1020 cgagggggacc tacatttgcc agatcaccac ctctctgtac cgagctcagc agatcatcca   1080
gctcaacatc caagcttccc ctaaagtacg actgagcttg gcaaacgaag ctctgctgcc   1140
caccctcatc tgcgacattg ctggctatta ccctctggat gtggtggtga cgtggacccg   1200
agaggagctg ggtggatccc cagcccaagt ctctggtgcc tccttctcca gcctcaggca   1260
aagcgtggca ggcacctaca gcatctcctc ctctctcacc gcagaacctg gctctgcagg   1320
tgccacttac acctgccagg tcacacacat ctctctggag gagccccttg gggccagcac   1380
ccaggttgtc ccaccagagc ggagaacagc cttgggagtc atctttgcca gcagtctctt   1440
ccttcttgca ctgatgttcc tggggcttca gagacggcaa gcacctacag gacttgggct   1500
gcttcaggct gaacgctggg agaccacttc ctgtgctgac acacagagct cccatctcca   1560
tgaagaccgc acagcgcgtg taagccagcc cagctgacct aaagcgacat gagactacta   1620
gaaagaaacg acaccettcc ccaagccccc acagctactc caacccaaac aacaaccaag   1680
ccagtttaat ggtaggaatt tgtattttttt gcctttgttc agaatacatg acattggtaa   1740
atatgccaca aaaaaaaaaa aaaaaaaaaa aaaaaaaaa aaaaaaaaaa aaaaaaaaa     1800 gggcggccgc                                                           1810
```

<210> SEQ ID NO 12
<211> LENGTH: 2353
<212> TYPE: DNA
<213> ORGANISM: Homo sapiens
<220> FEATURE:
<221> NAME/KEY: SITE
<222> LOCATION: (229)
<223> OTHER INFORMATION: n equals a,t,g, or c
<221> NAME/KEY: SITE
<222> LOCATION: (1759)
<223> OTHER INFORMATION: n equals a,t,g, or c
<221> NAME/KEY: SITE
<222> LOCATION: (1908)
<223> OTHER INFORMATION: n equals a,t,g, or c

<400> SEQUENCE: 12

```
gagctccggg ggccgctgca gccgcccaag cgcccgccat gcgcgctgcc cgcgccgcgc    60
cgctgctcca gctgctgctc ctgctggggc cgtggctgga ggctgcgggc gttgcggagt   120
cgccgctgcc cgccgtggtc cttgccatcc tggcccgcaa tgccgaacac tcgctgcccc   180
actacctggg cgctctggag cggctggact accccgggc caggatggnc ctctggtgtg   240
ccacggacca caatgtggac aacaccacag agatgctgca ggagtggctg gcggctgtgg   300
gcgatgacta tgctgctgtg gtctggaggc ctgagggcga gcccaggttc tacccagatg   360
aagagggtcc caagcactgg accaaagaaa ggcaccagtt tctgatggag ctgaagcagg   420
aagccctcac ctttgccagg aactgggggg ccgactatat cctgtttgca gacacagaca   480
```

| | |
|---|---|
| acattctgac caacaatcag actctgcggc ttctcatggg gcaggggctt ccagtggtgg | 540 |
| ccccaatgct ggactcccag acctactact ccaacttctg tgtgggatc accccccagg | 600 |
| gctactaccg ccgcacagcc gagtacttcc ccaccaagaa ccgccagcgc cggggctgct | 660 |
| tccgtgtccc catggtccac tccaccttcc ttgcatccct gcgggctgaa ggggcagacc | 720 |
| agcttgcttt ctacccgcca catcccaact cacttggcc tttcgacgac atcatcgtct | 780 |
| tcgcctatgc ctgccaggct gctggggtct ccgtccacgt gtgcaatgag caccgttatg | 840 |
| ggtacatgaa tgtgccggtg aaatcccacc aggggctgga agacgagagg gtcaacttca | 900 |
| tccacctgat cttagaagca ctagtggacg ccccccgcat gcaggcctca gctcatgtga | 960 |
| ctcggccctc taagaggccc agcaagatag ggtttgacga ggtctttgtc atcagcctgg | 1020 |
| ctcgcaggcc tgaccgtcgg gaacgcatgc tcgcctcgct ctgggagatg gagatctctg | 1080 |
| ggagggtggt ggacgctgtg gatggctgga tgctcaacag cagtgccatc aggaacctcg | 1140 |
| gcgtagacct gctcccgggc taccaggacc cttactcggg ccgcactctg accaagggcg | 1200 |
| aggtgggctg cttcctcagc cattactcca tctgggaaga ggtggttgcc aggggcctgg | 1260 |
| cccgggtcct ggtgtttgag gatgacgtgc gctttgagag caacttcagg gggcggctgg | 1320 |
| agcggctgat ggaggatgtg gaggcagaga aactgtcttg ggacctgatc tacctcggac | 1380 |
| ggaarcaggt gaaccctgag aaggagacgc cgtggaggg gctgccgggc ctggtggtgg | 1440 |
| ctgggtactc ctactggacg ctggcctatg ccctgcgtct ggcgggtgcc cgcaagctgc | 1500 |
| tggcctcaca gcctctgcgc cgcatgctgc ccgtggacga gttcctgccc atcatgttcg | 1560 |
| accagcaccc caacgagcag tacaaggcac acttctggcc acgggacctg gtggccttct | 1620 |
| ccgcccagcc cctgctcgct gcccctaccc actatgccgg ggacgccgag tggctcagtg | 1680 |
| acacggagac atcctctcca tgggatgatg acagcggccg cctcatcagc tggagcggct | 1740 |
| cccaaaagac cctgcgcganc cccgcctgga cctgactggc agcagcgggc acagctccaa | 1800 |
| ccccagcccc gagatgagct ctaggtccag gtgatgactg caaagcakkg tccaggagca | 1860 |
| ggccactact gcccagagag cagaggagga ggttgttggc agggactnca gatcctgtca | 1920 |
| gacctggcca ccaccttggg catggccact ctgccctctg gacctgtctt tcatcgggag | 1980 |
| aaaccactca gagatggatc ccattcccta aaggtctcac agcaaaggag caggactccc | 2040 |
| aggcccctgt accctgcctg gcctgattca gggccttgtg gcccccagct tctgtttcaa | 2100 |
| gctgggcaga ccccaggatc ccttccctcc ctaaggactc agctgagggg cccctctgcc | 2160 |
| cccttctacc tccacctcag caccctcccc cagcttgatg tttgggtctc cccagcaccc | 2220 |
| tcctcccctgg ccggtgcaaa gtacagggag gtaaagcagg acccttgcag acmtgttgcc | 2280 |
| cagcacacag taggccctca ataaaagcca tttgcacttt aaatataaaa aaaaaaaaa | 2340 |
| aaaaaaaaaa ata | 2353 |

<210> SEQ ID NO 13
<211> LENGTH: 928
<212> TYPE: DNA
<213> ORGANISM: Homo sapiens

<400> SEQUENCE: 13

| | |
|---|---|
| gaggagcatc gctacttcaa ggccaatgac acgctgggct tcatgcttat gttggctgtg | 60 |
| ctcatggcag ctacccatgc tgtctacggc aagctgctcc tcttcgagta tcgtcaccgc | 120 |
| aagatgaagc cagtgcagat ggtgccagcc atcagccaga actggacatt ccatggtccc | 180 |
| ggggccaccg gccaggctgc tgccaactgg atcgccggct ttggccgtgg gcccatgcca | 240 |

```
ccaaccctgc tgggtatccg gcagaatggg catgcagcca gccggcggct actgggcatg    300
gacgaggtca aggtgaaaa gcagctgggc cgcatgttct acgcgatcac actgctcttt    360
ctgctcctct ggtcacccta catcgtggcc tgctactggc gagtgtttgt gaaagcctgt    420
gctgtgcccc accgctacct ggccactgct gtttggatga gcttcgccca ggctgccgtc    480
aacccaattg tctgcttcct gctcaacaag gacctcaaga agtgcctgag gactcatgcc    540
ccctgctggg gcacaggagg tgccccggct cccagagaac cctactgtgt catgtgaagc    600
aggctggtag gcagacaggc agagagaagg tcatggccac cgtgatgggg ccaacagcaa    660
gggaggggta ggggcccata caggagtcct cctttctgag ctccagcccc agcccctcga    720
accacctgta atctaggcac ctttgccaac acctcccaag gatggaggac tgggcgaggg    780
actgggaaag aggcatattt agttttgtgg ggcctgtctc cgctgcctcc ttctccactt    840
ctacaatctc attctctctc tctctctctc tgtctctctc tctctctctc tctctcagaa    900
gtgacaattc aaaaaaaaaa aaaaaaaa                                       928

<210> SEQ ID NO 14
<211> LENGTH: 1590
<212> TYPE: DNA
<213> ORGANISM: Homo sapiens

<400> SEQUENCE: 14
tttttttttt tttgtttaaa tgatacaact taatttatt aggacagacg ctggcggcca     60
ccagaagttt gagcctcttt ggtagcagga ggctggaaga aaggacagaa gtagctctgg    120
ctgtgatggg gatcttactg ggcctgctac tcctgggca cctaacagtg gacacttatg    180
gccgtcccat cctggaagtg ccagagagtg taacaggacc ttggaaaggg gatgtgaatc    240
ttccctgcac ctatgacccc ctgcaaggct cacccaagt cttggtgaag tggctggtac    300
aacgtggctc agaccctgtc accatctttc tacgtgactc ttctggagac catatccagc    360
aggcaaagta ccagggccgc ctgcatgtga gccacaaggt tccaggagat gtatccctcc    420
aattgagcac cctggagatg gatgaccgga gccactacac gtgtgaagtc acctggcaga    480
ctcctgatgg caaccaagtc gtgagagata agattactga gctccgtgtc cagaaacact    540
cctcaaagct actcaagacc aagactgagg cacctacaac catgacatac cccttgaaag    600
caacatctac agtgaagcag tcctgggact ggaccactga catggatggc taccttggag    660
agaccagtgc tgggccagga aagagcctgc ctgtctttgc catcatcctc atcatctcct    720
tgtgctgtat ggtggttttt accatggcct atatcatgct ctgtcggaag acatcccaac    780
aagagcatgt ctacgaagca gccagggcac atgccagaga ggccaacgac tctggagaaa    840
ccatgagggt ggccatcttc gcaagtggct gctccagtga tgagccaact tcccagaatc    900
tgggcaacaa ctactctgat gagccctgca taggacagga gtaccagatc atcgcccaga    960
tcaatggcaa ctacgcccgc ctgctggaca cagttcctct ggattatgag tttctggcca   1020
ctgagggcaa aagtgtctgt taaaatgcc ccattaggcc aggatctgct gacataattg    1080
cctagtcagt ccttgccttc tgcatggcct tcttccctgc tacctctctt cctggatagc   1140
ccaaagtgtc cgcctaccaa cactggagcc gctgggagtc actggctttg ccctggaatt   1200
tgccagatgc atctcaagta agccagctgc tggatttggc tctgggccct tctagtatct   1260
ctgccggggg cttctggtac tcctctctaa ataccagagg gaagatgccc atagcactag   1320
gacttggtca tcatgcctac agacactatt caactttggc atcttgccac cagaagaccc   1380
```

| | |
|---|---|
| gagggaggct cagctctgcc agctcagagg accagctata tccaggatca tttctctttc | 1440 |
| ttcagggcca gacagctttt aattgaaatt gttatttcac aggccagggt tcagttctgc | 1500 |
| tcctccacta taagtctaat gttctgactc tctcctggtg ctcaataaat atctaatcat | 1560 |
| aacagcaaaa aaaaaaaaaa aaaactcgag | 1590 |

<210> SEQ ID NO 15
<211> LENGTH: 815
<212> TYPE: DNA
<213> ORGANISM: Homo sapiens
<220> FEATURE:
<221> NAME/KEY: SITE
<222> LOCATION: (406)
<223> OTHER INFORMATION: n equals a,t,g, or c
<221> NAME/KEY: SITE
<222> LOCATION: (794)
<223> OTHER INFORMATION: n equals a,t,g, or c

<400> SEQUENCE: 15

| | |
|---|---|
| ggcacgagcg gcacgagcgg cacgagatgg aatgttcatt ttatggcagt tgttttaagt | 60 |
| tktaaawtac acagaggaaa mtattgtgga aggacctctt tgttgctttc ccttctaagt | 120 |
| tgtcttcttc ttcttcttct tcttcttctt cttcttcttt ggtccttaag tgaaataaag | 180 |
| actctaaaac taatttgtat attatcagcc agagatgcgg atggcagtcg agccaaatcg | 240 |
| catggctttc agatcaggta ttctgcacat tcattccaag gtcatagatt tttaaaagga | 300 |
| cctggatttg aagagatggc aaatgrtgag ccatcagaaa acttaatttg gaaaacatgt | 360 |
| atgtagccag tgtggatatt gtggcctctc tcaagacaca ttgacnactg tagacytcat | 420 |
| tcagtccagt gtgagtattt tggagtaggt tggatgtaga ttttgttttt atcgttgatt | 480 |
| tgtaccgaca gaaatagaca tttcatcatg taaaattcct gttattctgg aaaaacctat | 540 |
| tgttttgatc cttcttgttt tcctgacttg gaagtatcct ttcaaaaaaa ctcttaagat | 600 |
| atctaggtct aaaagcact tcatgagatg ctaaagctga cccactggtt gaaaatgttg | 660 |
| accctatcct gttatttaaa tgtgaacatt tattgtacat tcagtgagtt atagtgttaa | 720 |
| tagtcttgtg ctatgcagca ggtgtaaaaa ttaataaata tatttttaa taaaaaaaaa | 780 |
| aaaaaaaaaa attnctgcgg tccgcaaggg aattc | 815 |

<210> SEQ ID NO 16
<211> LENGTH: 990
<212> TYPE: DNA
<213> ORGANISM: Homo sapiens

<400> SEQUENCE: 16

| | |
|---|---|
| gcatgccagt gcctactctg tgcctgctgt gggccctggc aatggtgacc cggcctgcct | 60 |
| cagcggcccc catggscggc ccagaactgg cacagcatga ggagctgacc ctgctcttcc | 120 |
| acgggaccct gcagctgggc caggccctca acggtgtgta caggaccacg gagggacggc | 180 |
| tgacaaaggc caggaacagc ctgggtctct atggccgcac aatagaactc ctggggcagg | 240 |
| aggtcagccg gggccgggat gcagcccagg aacttcgggc aagcctgttg gagactcaga | 300 |
| tggaggagga tattctgcag ctgcaggcag aggccacagc tgaggtgctg ggggaggtgg | 360 |
| cccaggcaca gaaggtgcta cgggacagcg tkcagcggct agaagtccag ytragragcg | 420 |
| cctggctggg ccctgcctac cgagaatttg aggtcttaaa ggctcacgct gacaagcaag | 480 |
| agcccacatc ctatgcccct cacaggccac gtcagcggca gaggcgggag atggtggcac | 540 |
| agcagcatcg gctgcgacag atccaggaga ggtgagcctg cagggggttt ggcaggcagg | 600 |

```
gcagttggat gggggcgca cagggcagct ggaaagggc cccctcacct gggctgagcc      660
acatctccct ccccagactc cacacagcgg cgctcccagc ctgaatctgc ctggatggaa    720
ctgaggacca atcatgctgc aaggaacact tccacgcccc gtgaggcccc tgtgcaggga    780
ggagctgcst gttcactggg aymagccagg gcgccgggcc ccacttctga gcacagagca   840
gagacagacg caggcgggga caaaggcaga ggatgtagtc cccattgggg aggggtggag    900
gaaggacatg taccctttca tgcctacaca cccctcatta aagcagagtc gtggcatctc    960
aaaaaaaaaa aaaaaaaaa aaaactcgta                                      990
```

<210> SEQ ID NO 17
<211> LENGTH: 1188
<212> TYPE: DNA
<213> ORGANISM: Homo sapiens
<220> FEATURE:
<221> NAME/KEY: SITE
<222> LOCATION: (892)
<223> OTHER INFORMATION: n equals a,t,g, or c

<400> SEQUENCE: 17

```
gacggagcgg gcgccttccg agcgccgatc agggagcccg gagtcccgc gtccccgcag     60 ccccagaac ccggacaact gttgcggcgg cggcaggggc atcgcggggg cgtgggcagc    120
ccccgcaccc cagcaggcgg ctcccgcggg cgccggctcc cggctacgaa gcaggaacg    180 agcgggcggc gggcacgagg cagctctgga cggatcaatg caagccagac gatgaccagt   240
tgtggccagc agtccttgaa cgtgctcgcc gtcctcttct cattgctgtt ttctgcagtc    300
ttgtctgcac atttccgggt ctgtgaacca tacacagacc acaaaggccg ctaccacttt   360
ggcttccact gccccggct ctcggacaac aagaccttca tcctctgttg tcaccataac    420
aacacggtct tcaaatactg ctgcaacgag acggagttcc aggcggtgat gcaggcgaac    480
ctcacggcca gytccgaggg ttacatgcac aacaattaca ccgccctgtt gggagtgtgg    540
atctatggat ttttcgtgtt gatgctgctg gttctggacc twwwgtatwa mtcggcaatg    600
aactacgaca tctgcaaggt ctacctggca cggtggggca tccaaggacg atggatgaaa    660 caggacccc ggcggtgggg gaacccgct cgggcccctc ggccgggtca gcgggcccca    720
cagccgcagc ctcccccagg cccgctgcca caagccccac aggccgtgca cacattgcgg    780
ggagatgctc acagcccacc gctgatgacy ttccagagtt cgtctgcctg aaaacgcttt    840
tgctgtgcct caggatgggg gagatgagat ctgaagcacc cggtgcagcc tncgagaaga    900
acaacttcta cagagatgcc agggacagcc gaggtagcgg cgrtggcaca ggaggaaatg    960
ctgcctgtgc ccaaagcccc cttccacgga cttctaagat taggagcaaa ctcagggta   1020 ggggctgggg gtgcagggga ggggattctg agccacctgt ccgcaagcaa tagtcctatt  1080
ttgggctggt ggcttctgag aggtgactca ttgtggactc aggatgacca agacaaaggt  1140
cgacgcggcc gcgaattccc gggtcgacga gctcactagt cggcggcc              1188
```

<210> SEQ ID NO 18
<211> LENGTH: 1605
<212> TYPE: DNA
<213> ORGANISM: Homo sapiens

<400> SEQUENCE: 18

```
gcgtccatgt actagtataa cagcttgggt ttgttagaat ttgggcaaca ttttgattat     60
aatgacaact tcattttcac atgttactca gttccctaat aggatggtgc tcttttgttg    120
aacctgtatt gattttttt ttttttaacta tattgattcg tttactagaa cagtctaatt     180
```

| | |
|---|---|
| ggggcattga ggaaatgaag actggatact tctgtatctg tgaagttggc acaggtaaca | 240 |
| tttggacatg ttcatcttat tcttaggaag gaaaaaatca cttgccaaaa taatacatac | 300 |
| ttcatagacc actgagttct agtttttatt cacactacaa cattctcttt aacgatgttg | 360 |
| caggtattct caatttcctt ttaagaaaaa tgaaatgtga ggagaattct ggttgtaata | 420 |
| gatgacagta catatgatct gcaggtttgg gcatatgctt tcatcattaa attatctgat | 480 |
| aaagttacaa gtcacaaagg agaatgagaa cttaatgatt ctattggatt taatatatta | 540 |
| gcaagaaaac atactattta catatgtgta gcttagtaag gcattaacat aagtacaaaa | 600 |
| actatgaaac agatgcatat ttcctcaaca tactgtgtca ggtatactgt tttataattt | 660 |
| ggttgtttta gccttattgc acaccaactc ccaaaatata ggttactctt gttcaaaagg | 720 |
| aaaaaaaaaa ttgtgatttt ctttgagtgg tatatgttat taattaccat tagcatttgc | 780 |
| tcttataaag ggcaatgatt atagtagaca atattgtaac tcagtagact tgttgaatat | 840 |
| gcaaacttac tgtcaagtga cctcaaaaaa aaaatgaaaa gatagaatac actagtagtt | 900 |
| cttatcctct tttgtaggaa accaataata gccattgtgg caataattca tcagttgatt | 960 |
| ttaaagcttc atgttatgca aaaagaatc ctgctgttat acatgtgaca gtgactttgt | 1020 |
| gctgaaattt cagctattcc agataaacat tgtatatctt gtaaattaat gtttaaaggt | 1080 |
| agttttgttc ttacagaaag tgttgattgc caggttgctt atagcacttt aagttattct | 1140 |
| aaaaatgaaa ttataagcca aatatttggc ttaagtagat ttagttgtat agcacttaca | 1200 |
| tatttagttc ttttgaaagt ttagataatt atttaaagaa agcataatgc taatggaaaa | 1260 |
| gaaaatctga tgttctatta taatatgcta ttgctgaata tgaatagaaa tacagggcat | 1320 |
| catttccttg tctcattata agttagtaac aatatataga ttaaatgttt acaatatagg | 1380 |
| gaattgtaaa taaatatatc agtttttty cccttcggtc ttccacagca gtattattgt | 1440 |
| ctttgtggag ttgactaatg ataatttaaa aatcctgtaa tggatttcta ctaaaataag | 1500 |
| gtcatagtgg catataccaa ataaaatcaa atacagaaat acaaaaaaaa aaaaaaaaa | 1560 |
| aactcgaggg ggggcccgta cccaatcgcc ctaatgatga atcgt | 1605 |

<210> SEQ ID NO 19
<211> LENGTH: 2089
<212> TYPE: DNA
<213> ORGANISM: Homo sapiens
<220> FEATURE:
<221> NAME/KEY: SITE
<222> LOCATION: (774)
<223> OTHER INFORMATION: n equals a,t,g, or c

<400> SEQUENCE: 19

| | |
|---|---|
| ggcacgagcc cggaggccta cgtcggaccc ggaggccctg aatgccccat gcgcacccca | 60 |
| cagctcgcgc tcctgcaagt gttctttctg gtgttccccg atggcgtccg gcctcagccc | 120 |
| tcttcctccc catcaggggc agtgcccacg tctttggagc tgcagcgagg gacggatggc | 180 |
| ggaaccctcc agtccccttc agaggcgact gcaactcgcc cggccgtgcc tggactccct | 240 |
| acagtggtcc ctactctcgt gactccctcg gcccctggga ataggactgt ggacctcttc | 300 |
| ccagtcttac cgatctgtgt ctgtgacttg actcctggag cctgcgatat aaattgctgc | 360 |
| tgcgacaggg actgctatct tctccatccg aggacagttt tctccttctg ccttccaggc | 420 |
| agcgtaaggt cttcaagctg ggtttgtgta gacaactctg ttatcttcag gagtaattcc | 480 |
| ccgtttcctt caagagtttt catggattct aatggaatca ggcagttttg tgtccatgtg | 540 |

-continued

| | |
|---|---|
| aacaactcaa acttaaacta tttccagaag cttcaaaagg tcaatgcaac caacttccag | 600 |
| gccctggctg cagagtttgg aggcgaatca ttcacttcaa cattccaaac wcaatcacca | 660 |
| ccatcttttt acagggctgg ggaccccatt cttacttact tccccaagtg gtctgtaata | 720 |
| agcttgctga dacaacctgc aggagttgga gctgggggac tctgtgctga aagnaatcct | 780 |
| gcaggtttcc tagagagtaa aagtacaact tgcactcgtt ttttcaagaa cctggctagt | 840 |
| agctgtacct tggattcagc cctcaatgct gcctcttact ataacttcac agtcttaaag | 900 |
| gttccaagaa gcatgactga tccacagaat atggagttcc aggttcctgt aatacttacc | 960 |
| tcacaggcta atgctcctct gttggctgga aacacttgtc agaatgtagt ttctcaggtc | 1020 |
| acctatgaga tagagaccaa tgggactttt ggaatccaga agtttctgt cagtttggga | 1080 |
| caaaccaacc tgactgttga gccaggcgct tccttacagc aacacttcat ccttcgcttc | 1140 |
| agggcttttc aacagagcac agctgcttct ctcaccagtc ctagaagtgg gaatcctggc | 1200 |
| tatatagttg ggaagccact cttggctctg actgatgata taagttactc aatgaccctc | 1260 |
| ttacagagcc agggtaatgg aagttgctct gttaaaagac atgaagtgca gtttggagtg | 1320 |
| aatgcaatat ctggatgcaa gctcaggttg aagaaggcag actgcagcca cttgcagcag | 1380 |
| gagatttatc agactcttca tggaaggccc agaccagagt atgttgccat ctttggtaat | 1440 |
| gctgacccag cccagaaagg agggtggacc aggatcctca acaggcactg cagcatttca | 1500 |
| gctataaact gtacttcctg ctgtctcata ccagtttccc tggagatcca ggtattgtgg | 1560 |
| gcatatgtag gtctcctgtc caacccgcaa gctcatgtat caggagttcg attcctatac | 1620 |
| cagtgccagt ctatacagga ttctcagcaa gttacagaag tatctttgac aactcttgtg | 1680 |
| aactttgtgg acattaccca gaagccacag cctccaaggg gccaacccaa aatggactgg | 1740 |
| aaatggccat tcgacttctt tcccttcaaa gtggcattca gcagaggagt attctctcaa | 1800 |
| aaatgctcag tctctcccat ccttatcctg tgcctcttac tacttggagt tctcaaccta | 1860 |
| gagactatgt gaagaaaaga aaataatcag atttcagttt tccctatgag aaactctgag | 1920 |
| gcagccactt atcttggcta aatagaacct cacctgctca tgaccagaga gcatttagga | 1980 |
| taatagagga cctaactgaa ggaatccttg tatatgaaag gagttatttt agaaaagcaa | 2040 |
| taaaaatatt ttattcatma aaaaaaaaaa aaaaaaaaa aaaaaaaa | 2089 |

<210> SEQ ID NO 20
<211> LENGTH: 1281
<212> TYPE: DNA
<213> ORGANISM: Homo sapiens

<400> SEQUENCE: 20

| | |
|---|---|
| agcgtcactg accagaagga cctgtggcag attccagaaa aggtctccct ataagaagct | 60 |
| gctgtcctcc ctataactta tggcactgcg atttttgctc ttgagcattg ggcccgtacc | 120 |
| cagcctgggt aatatagctg ctgctggaag tgacgagaag tgcaagctgg cgatgcagag | 180 |
| gggtgcgcag tccagcgtga actacagtca gggcagcctg aaggatgcag catcagcatc | 240 |
| aacgagaaca gcaagtgggt gggtgaaaag gaatagaagc agagaaaatc aggaaatgct | 300 |
| tatatatagc aaaaacaaaa tacccatctg gaaaatatcc aaaaaatgac tgcagactct | 360 |
| cttagttggc aatgccaaat gctttagaaa ttattcatgt gttaaattca gttatgccag | 420 |
| ttctcactaa ctactttata tccatgtctg tggggaattc ttgcagaggg cattgttcag | 480 |
| ctattagaat tactggggtg gcagttcccc ttttcccagt tcattgtgga ccaaactaca | 540 |
| ggctcttctg atcttactgc tttctgaagc agccagcagc gtagataatt ccttgacttg | 600 |

```
ttttatttaa aaaatatcac tggagattta gtaggagtgt tgtatcacac caattctcat    660
tctgttttca accaaggatt ctggagtact ctgatagcat tggtttcatt tctcatgtcg    720
tcctggcaag cataattttg tagtttatct cagtttcagg tagaagctgc agaagcagag    780
agcagcctac ccacaaaagg ggtccagttg ttctctagc ccctgagctg agtggcaggc    840
agtctatatg tttgctcatc tctgcactgt gcctggtgct gtgcttagag gagaagcaaa    900
ggaaggagcg tgtagtccaa gtggaaagcc aggatagaca gctggtaaaa ctcgcccatc    960
tcttgccttc cttcttgcct tctggataat tgtgttttg caatagcttc tcatttccct   1020
tctaaagaag aaaagcaaaa agcaaaagcc aaacaaatat acacatattt tatatcaaag   1080
atgtttgcaa aagttgtttc tgtaactcat tgcttagcaa tggtaccgta ggggaattt    1140 catactgggc tacagaatac ttatgcattt ttgtagttta tttaaaattc tctaaagagg   1200
caatgtgtta aaggaatcct aaagtaagtc tttgtataaa gcaaatggtc cttccctcaa   1260
aaaaaaaaaa aaaaactcga g                                             1281
```

<210> SEQ ID NO 21
<211> LENGTH: 1761
<212> TYPE: DNA
<213> ORGANISM: Homo sapiens
<220> FEATURE:
<221> NAME/KEY: SITE
<222> LOCATION: (1207)
<223> OTHER INFORMATION: n equals a,t,g, or c

<400> SEQUENCE: 21

```
gctcgtgcat tcatacagga gatgttatga ttttscctgt actttcttgc ttcacaagat     60
ttatggctgg tttgatcttt gtactccaca gttgttttag attcatcact tttgtttgtc    120
ccacatcctc tgatcccctg aggacctgcg cagtcctgct atgtgttggt tatcaggacc    180
ttccaaatcc agttttccga tatttgcaga gtgtgaatga attgttgagc actttgctca    240
actctgactc accccagcag gttttacagt ttgtgccaat ggaggtactc cttaagggg     300 ccctgcttga ttttttgtgg gatttgaatg ctgccattgc taaaaggcat ttgcatttca    360
ttattcaaag agagagagaa gaaattatca acagccttca gttacaaaac tgaacatatg    420
ctttctgaga ttcaacttta tgatttctta aatttgccc agtatttgca tcctgttgct    480
ctattaattt aaaaaccttt tattttgggg aaaggccaac atttgcatca ttcaaagtct    540
cattaattct ggaaaaccat ccattctgat ctctagggta tatacaccca caggcataga    600
gctcttccac gtggtggaat ctatgcaatg atagatattc acactctaaa tatgaggtgt    660
gtgtatgtgt atgggtggcc acagccatgc ttacctatgc catttagttg gtcttactta    720
atctgcttaa gatttgcatc tgtgtacctt tgttcagatt agtttttttt ttccagccga    780
tttcctctta gtggctaatg ctgttagtga attttccaac taatttcctc tcattggtta    840
atgttgttaa tgaattgaga gaggtaattg aggaaaggaa atgagtaaat cactgttcag    900
caacactgat ttccgttaac acatcagtta tgaatttcag ggaattcatc tcgccagatt    960
cttgataaca tgccattcat tgcccttagg tgattgaccc tattttctta catggctcaa   1020
ataaaactag tatgctgttg tatgaatctt ttactgacca caccatccaa ctataaaaat   1080
ataacgggac agctttaaac caaagatcat gcttagaaca atgaaaaatt atttgttgta   1140
tctaatacac gcctgtattg tgaaaagctt catttagcaa tgatgtaata attttttaact   1200 tccaggnaaa taatctgtga atggaaagat tttttaagat tttgagatag tgtttagtct   1260
```

-continued

```
catgttggga acacatgaat gtgatgaaca tagtgaatac taaagaaaac gcttcagact    1320
ttcagatgat ggttcagaat ttaaaatttt taatcttttc taatttcttt ttttcagtgt    1380
gaaaatagca ctttaccaaa agattagcca tgaaatggtt attttgccag ttacatttga    1440
tttcttttgt atctgcaatg taatgagtta ttttatttct tctgtatttg cagtgtaatg    1500 agttttgtg gcaaagtgta ttaagcaatt tttcattatc ttgaagttcc acaaagtgga     1560
gaatatttat attctcacat gcattttagg cacttttgat atgtgaaaat agatgtattt    1620
tctgatgcat ttggttaata aatattaatc tgaacatttt catgttcttt gctattttga    1680
attccattat agattcatga ataaagtcat tactagagaa aaaaaaaaa aaaaaaaaa      1740 aaaaaaaaa aaaactcgta g                                               1761
```

<210> SEQ ID NO 22
<211> LENGTH: 1189
<212> TYPE: DNA
<213> ORGANISM: Homo sapiens

<400> SEQUENCE: 22

```
ggtagacatc tggtagcctc tcagaagcgt gtccttagag acagacgtgt ccagacaggc    60
atatggagtg accaattgta ttctcagcgg ccttgggctc cagtgacttg gcctgatcac    120 tgggggtgt gtgtgtgtgt gtatgtatgt atgtgtgtgt ggggtgtgtg tgtgtgtgtg     180
gtggccaggg tgtgtgtgtg gctggggcta gcagagctat ttcggggaag ggttagggac    240 tgtgaaaaa taactcattt tcccacgtat ctcctttatt ggactttgaa aaataataat     300
aaacatcaag ttaagttcct aaaccatgta ttgtgtgtgt gtgtgtgtgt gtgtgtgtgt    360
gtatgtatat gtaaatgtat atgtatatgt atgctacttt atttccaggt caacaattac    420
attgaggatt gtatcgccca aaagcactcg ttgatcaagg tgttaagact agtttgcctc    480
caatccgtgt gtaatagtgg gctcaaacaa aaagttttgg attattacaa aagagagatt    540
ctccaggtga gtatatttt aaattattaa tttgccaagg gggacagcat cttttttaaa     600
aatacttcat gggccgggca cagtggctta cgcctgtaat cccagcactt tgggaggcca    660
aagcaggtgg atcacttgag gttaggagtt tgagaccagc ctggccaaca tggtgaaacc    720
cccatctcta ttaaaaatac aaaaattagc caggcatggt agcatgcacc tgtagtccca    780
gctatttgag aggatcaggc aggagaatcg cttgaacgca ggaggcggag gttacagtgt    840
gtcaagatca tgcccctgca ctccagcctg ggcaacagag tgagactctg tctcaaaaaa    900
taataataaa aaatttaaaa ttaaaaaaaa taaaaattac aaagctgcca ttttggtatc    960
ttgtaacgac tgttgtataa attttttaac acctagagga attggtcttg gtagccatca    1020
ctgtttattg tatttgtgtg ataataatag ctaacaggct gggcacagtk gctcacctct    1080
gttatctcaa tattttgtgg ggctgaggcg ggaggatcgc tggaggccaa gaccagcctg    1140
gcaacatggc aagaccctgt ctctacaaaa aaaaaaaaa agggcggcc                 1189
```

<210> SEQ ID NO 23
<211> LENGTH: 1492
<212> TYPE: DNA
<213> ORGANISM: Homo sapiens

<400> SEQUENCE: 23

```
gccttcccac actccattcc ctgtcaagtt atggctgtcc cctcaccccca gctgctccta   60 gagaggcccct tkttacctgt gtcattcatg tttctaacaa gccaccctcc accccgtctt    120
gtgtgcccca tgcacctgtg catctgtgct gtgtgggtgt tggtggccct tttgcgcatg    180
```

```
catggggcat ccccctgccca gaccagcggg acaaggagcg ggaacggcgg ctgcaggagg    240
cacggggccg gccaggggag gggcgcggca acacagccac tgagaccacc acgaggcaca    300
gccagcgggc agctgatggc tctgctgtca gcactgttac caagactgag cggctcgtcc    360
actccaatga tggcacacgg acggcccgca ccaccacagt ggagtcgagt ttcgtgaggc    420
gctcggagaa tggcagtggc agcaccatga tgcaaaccaa gaccttctcc tcttcctcct    480
catccaagaa gatgggcagc atcttcgacc gcgargacca ggccagccca cgggccggca    540
gcctggcggc gctcgagaaa cggcaggccg agaagaagaa agagctgatg aaggcgcaga    600
gtctgcccaa gacctcagcc tcccaggcgc gcaaggccat gattgaraag ctggagaagg    660
agggcgcggc cggcagccct ggcggacccc gcgcagccgt gcagcgatcc accagcttcg    720 ggtccccaa cgccaacagc atcaagcaga tgctgctgga ctggtgtcga gccaagactc    780
gcggctacga gcacgtcgac atccagaact ctcctccag ctggagtgat gggatggcct    840
tctgtgccct ggtgcacaac ttcttccctg aggccttcga ctatgggcag cttagccctc    900
agaaccgacg ccagaacttc gaggtggcct tctcatctgc ggagacccat gcggactgcc    960
cgcagctcct ggatacagag gacatggtgc ggcttcgaga gcctgactgg aagtgcgtgt   1020
acacgtacat ccaggaattc taccgctgtc tggtccagaa ggggctggta aaaaccaaaa   1080
agtcctaamc cctgctcggg gccccacgga tgctggtgga ctgtgtgccc ctggtggagg   1140
tggacgacat gatgatcatg ggcaagaagc ctgaccccaa gtgtgtcttc acctatgtgc   1200
agtcgctcta caaccacctg cgacgccacg aactgcgcct cgcggcaag aatgtctagc   1260 ctgcccgccc gcatggccag ccagtggcaa gctgccgccc ccactctccg ggcaccgtct   1320
cctgcctgtg cgtccgccca ccgctgccct gtctgttgcg acaccctccc ccacatac   1380 acacgcagcg ttttgataaa ttattggttt tcaamraaaa aaaaaaaaaa aaaaaaaaa   1440 aaaaaaaaa aaaaaaaaaa aaaaaaaaa aaaaaaaaa aaaaaaaaa ag              1492
```

<210> SEQ ID NO 24
<211> LENGTH: 1608
<212> TYPE: DNA
<213> ORGANISM: Homo sapiens

<400> SEQUENCE: 24

```
gctttggggc ccaggcataa gtcccttcct ccaggacctt tcctatttat atgtccctat     60
acaaaatcca tctgctttta tacgtagctg ttttatcatc tgtagcttca tcctatccgg    120
aggcacagca catgagccct ggacaggtcc caaagttcca agcagtcctt tccgtaaaag    180
caggggtttg catgtgctac caacacatga tacggggaag acccacccag ggagcggttt    240
cagtggcgca acaaagcacc acttttactg ttgcctactt ctgaccaaga agaaaaagga    300
ccttagtatt tagcataaaa ttccagcgct ggatgaatgc agatctagtt tggtctgtgg    360
ctagtttaaa tatgtttcta accacagagr atttcatata tatatacata tatatataca    420
catacatata tatatatata tatgtatgta taaaatttca cagggatatg cttttttttt    480
taaagactga atgtgttcac satttagcct gtagatttat ttccattttc caaattccag    540
cacacagaga tcccagcccc tatgagtagg gtgtttgtgg actacctaat ggaatatttt    600
tgaggcctgg atgaactttg ccatatgggt agaggttaca gagggaggtg atattttcag    660
ctaaaaaaaa aaacggggtgg agtttggact gatcaacttg agatttaaaa actgctattc    720
cttttgttct ytctagcatc yctccccacc ctctgagagc tcctcaggct tagatagtga    780
```

-continued

```
agtgatcaaa tgccagtgtc attttgtact taagttccaa agtaggaaca ttttatactt       840
ttttctgtat tgtaataggt agttttgtat gaaatctttt ctcctctccc gttgtaccgc       900
attctttcca gcattgtgct ttttccctgg gcttatttga aaattttact gttttataca       960 agctcgttm syacwttktt ctatgttyta ccacaagtta caatttgaaa agaaaactat      1020
tttttttaaa tattccattg ttaactgaat gttactgttt ccactccagc aactacatgt      1080
cctcccttca actgcctgcc ttttggggaa agaccacctt ttgtgtgttt gttttttctc      1140
tctctttctt tccctttctc tttctatctc tctttatttt tctttctttt tctttgtttt      1200
tgagttttct ataggaaata aatagctttc tatatatgag ttgctgggga ccttcacatt      1260
ctcttttaga aagctgtggc atgcagtctc attgcaggac tcctgaata ttgtctggtt      1320 cttggtattt actgtatgta agcaacaact tgaaaggtgg caatatggtg tcgatttgga      1380
ctatgaatca aaagaccttt ttcaggttct ttcactattg tctgggggac tcagaacaag      1440
attgttctct gtatttattg tttgtccatt taggtaacat ctgtcttacc ttcctcayag      1500
actttgtaca gaccaaagca acaaatattt attgccatgt atagcagaaa atgaaacatg      1560
caacaaaagc actttgaaaa atawawaagg aattgttgag cctgtctg                   1608

<210> SEQ ID NO 25
<211> LENGTH: 1964
<212> TYPE: DNA
<213> ORGANISM: Homo sapiens

<400> SEQUENCE: 25
actgcaggtc gacactagtg gatccaaaga attcggcaca ggccctctgt aggagktaat        60
tttcatggca gttcgtttga ttaaaccggc ggtattcgca gtgctcgccg ggttttctgt       120
gttgtggctc agccctgcaa gcctggcggc cagttttgac tgtgaccggg cgaagcgcct       180
gacgagaaaa ccatctgtgc cacgcgctcc ctcaatgatc aggacgtgac catggcgctg       240
ctttatgacc tgaaccggca cttcatggcc atgggcgggc gcggttcgtt gatggatgat       300
caggctgtgt ggctcaagca acggcatacg tgcggcgccc aagtcagttg cctgagcaaa       360
gcctatacgg agcgtattgc gatgttgcgt attttattga tgagcgggtg atgacgaagg       420
ggccgttctg aagcagttac agatcttgta atagttttgc attgtaggaa attcttgttt       480
cgcctgtacg attcaagtcc ttttcccaca acaggaccta catgaacacc ctctcggagc       540
ctcccagtcg tctttcccca agacatgcac tgtcgccgtt cccgctgatc gcctgcctcc       600
gggccaagca tcccgtcttc cgattgccta ccttamccgg tccctcgacc gtgcgttgcc       660
gtgcccggca ttctgaaaaa cttgaagagr tactgaaaaa tggaatggtt agcggatcca       720
acggcctggc tcggcctgtt gactttgatt gtgctgragc tggtgctggg catcgacaac       780
ctggtgttta tykygatcmt ggcgmccaag ttgccgccgg agcagcgtga ccgtgcgcgg       840
ctgatcggtt tgtccctggc gttgctgatg cgtctgggcc tgttggcaag tatttcctgg       900
ttggtgaccc tgacccaacc gctgttcgag gtgttcgaca agagtttctc gggccgtgac       960
ttgatcatgc tgtttggtgg tgtgttcctg ttgttcaagg ccaccatgga attgcatgag      1020
cgccttgagg ggcatgtggc tcagcgcact ggcaacgtgg cttatgcgat gttctggccg      1080
atcgttgcgc agattgtggt gctggatgcg tgttctcccc tggatgcagt gattactgcc      1140
gtgggcatgg tggatgagct ggcggtgatg atgatcgcgr tgatcatttc catcggcctg      1200
atgatcgttg ccagcaagcc gctgacccgt ttcgtcaacg cccacccgac ggtgatcatg      1260
ctgtgcctgg gcttcctgat gatgatcggt tttgccctga ccgcagaggg cctgggctty      1320
```

```
cacattccca aaggctatct gtacgcggcc atcggcttct cgatcctgat cgagctgttc    1380
aaccagatcg cccggtcgcg ccgcaagaag tcggcccagg gcacgctgcc gaggcgtgag    1440
cgtacggccc acgcggtgat gcgtttgctc ggcgggcgga atctggcagt ggaggaggtg    1500
ggtgaagagg tcgccgacct gctggataac cctgatgcca acggcgggcc gctgttcgac    1560
cggcgcgagc gggtgatgat cagtggcgtg ctgcaactgg ctgaacgccc gatccgtacg    1620
ctgatgacgc ctcgggcgaa ggtggactct atagatctgt cggacgatcc cgasacyatc    1680
cgcctgaaac tgagmattcg tcttactcgc gcctgccctt gatccgcaac ggtaatgtcg    1740
acgagccatt gggctttgtg cacaagaagg agttgctcaa ggaatacctg gccggtaacg    1800
agccgaacct ggagcacctg gcgcgccggg cggtcaactt gctggagagc ttttcgattc    1860
tcaatgcctt ggagcagatg cgtgaggagt cgactcacat tgccttcgtg atcaacgaat    1920
ttggcgactt tatcggggtg ttgagcatga ccgacatcct cgag                    1964
```

<210> SEQ ID NO 26
<211> LENGTH: 933
<212> TYPE: DNA
<213> ORGANISM: Homo sapiens

<400> SEQUENCE: 26

```
ggcacgaggt gcttccctcc cagatggctg tgtatgtatt ttctttttctt ttttgctttc     60 ttcttctttc cgttgttttg ttattgtttt aactataata agagggccag aggcagtcaa    120
gccctggcca ggtcctggcg gcccatgggg gttctgggga gggggagggg ggaagtcagt    180
gggggtcaga ggtggagggt gaagaatgag aaagttgggg agttaggctt agctcaggaa    240
ccatgtgtcc ctgcccactc ccctccttcc ttgcccctcc ctacctccct gcctctacat    300
ggcttctctc cacccctccc agagtcctac gggacaggac cctgctccag tggtatccaa    360
ctcctccctg cccactcttc ctcatgggcc acctcacctc ccactttcga tgtctcgcct    420
cccgtggcca ccctgcaatt agctttccaa gcccctccc gtggccgtcc cctcccaaga    480
cctctcaccc atgtagcaat ccctacatgg ctgcctgtca tgtccctact ctctaagccc    540
tcctgcccac tgttcctccc tcccgacat gctgasacca agtggtggaa accacccctc    600
agccccagcc tgccctgtgc agarttcagc tktgtgttga atgaggggga garggacaag    660
tgagggcgga gagagagttc aggaggaggc aggatgcgca gggagcagag agtgagggag    720
ggagataccg aacagataga cagaaaacgt tgtacgaaaa agttgttttt tcttattttt    780
tttccgggag aacccgctta cacagctctg tttgtaattt ttttcttcat gctaaaatca    840
cacggcctat ttgttgatgt aagttgcctg aattccgtgg tatgctatct tcttttttaa    900
aaacaaaagc aaaaaaaaaa aaaaaaact cga                                  933
```

<210> SEQ ID NO 27
<211> LENGTH: 1237
<212> TYPE: DNA
<213> ORGANISM: Homo sapiens
<220> FEATURE:
<221> NAME/KEY: SITE
<222> LOCATION: (556)
<223> OTHER INFORMATION: n equals a,t,g, or c
<221> NAME/KEY: SITE
<222> LOCATION: (619)
<223> OTHER INFORMATION: n equals a,t,g, or c
<221> NAME/KEY: SITE
<222> LOCATION: (672)
<223> OTHER INFORMATION: n equals a,t,g, or c

```
<400> SEQUENCE: 27
tgacgtctgg ggggcgcctc aaatcttcca ctccagcatc ggatcccgga aaggcagcgt      60
cggagatgga cccaaaactc ttcctgttct gcctgcagag ttgagcccg tccgggtcct     120
ggacccgcgt agtactgacc ctggatccct gttcactgcg ttctcgctcc ccgcgctccc    180
tgctggaccc cgggatgccg ggcatctccg cccgaggcct ctctcatgag gggaggaagc    240
agctagctgt taacctcacc cgtgtcctgg cactctaccg ttccatcttg gatgcctaca    300
tcatcgtaca ggtcagtgtg gccactcacc ctgctggccc tgaagtccac ggcgtgtgcc    360
ctggcctta cccggatgcc tggctttcag acccctcag aattcctgga gaacccagc       420
cagagctccc gactaacagc tccattccgg aaacatgtca gcccaagaa gcagcatgag     480
atccggaggc tgggagagtt ggtgaagaag ccgagtgatt tcacaggctg cacccaggtt    540
gtagacgtgg gctcangcca ggggcatctc tcccgcttca tggctcttgg cctggggttg    600
atgtgaagaa gcatcgaang ggatcagaga ctggtggaga garcccagcg cctgaccag     660
gagcttctgc angctctgga gaaagaggag aagaggaacc cgcagatatg tgcagcgggg    720
gctacagcga gtggggctag atccccagct gccactgaat ctggctgccc ttcaggccca    780
cctggcccag gagaaccgtg tggtggcctt cttcagcctg gctctactgc ttgccccact    840
ggtggagacg cttattctac tggaccggct gctgtaccct caggaacagg gttccatgc     900
tgagctcctg cccatcttca gtcctgaact ctctcccaga aacctggttc tggtggccac    960
caagatgccc ctgggtcagg ctctttctgt tctggagact gaagacagct gatgcagcct   1020
gaggasacat ctcagacccc atcatctgaa agtgcccaga gagcacagtg gcagagtaca   1080
tctcatccag agaaacagca tcctgcatcc tccagagtcc tggttccttc agtttcatcc   1140
cctttctctc cttccatgga ttatgtaata cattgtaaag ttttaattaa ttaaaaattg   1200
gatatctgaa aaaaaaaaaa aaaaaaattg ctcggtc                            1237

<210> SEQ ID NO 28
<211> LENGTH: 960
<212> TYPE: DNA
<213> ORGANISM: Homo sapiens

<400> SEQUENCE: 28
ggcacgagca tttctgctcc tgatctgccc tgtcgatttc taaccatcag ggcttttca      60
tgttattact gatgcttgtg aacacgtctg ctgtagcctg cactcacgga ggcagagggc    120
cgtgggggaa ctctgcagcc caagcttgcg ccgcgctcgc ccgtggccc aggcaggacc     180
cttccgcggc ctcccagtgg cagccacagg tgctggttgg tttgctgagc tatcacgggt    240
ggggtgggca gcgtctgagt ccttgcccga gaagcatctg ctgtgtgtcc acgaggcacc    300
tggaggggc cagatccaag gcacagggcc ctgctgcatg gctccacatg gaagttcgag     360
tccccgtgt ccagccgccg gccctgcagg tgccagcag ctctgacaaa gcggggcagg      420
gccgctgggg tgtccctgga cagcggggcc tggtgggcag gggaggaggc tgcaaggtga    480
cacccagttt gccttgcaga cgtacggagc gcaagaggac ggcagcgtcg gcgaaggtga    540
cctgtcctgc atcctcaaga cggccctggg ggtggcagag ctcaccgtga ccgacctatt    600
ccgagccatt gaccaagagg agaagggaa gatcacattc ggtgagcccg caggagtggg    660
gtcgtcctcg cgaccttgg gcggggctg gcagagtgt gggcgagtc ccgtgggag         720
cccaggacag gagtggagtc cccgccatgc ctccattcac caggctgccc tgtgtaacaa   780
agaaacccct gagaaggaag gttctggaga cctggcaggg ttcgtaggga gctttccaat   840
```

| ctgatttgtt ttggcgattt atacaaccaa actccaagcc cagttccgaa gctctgagcc | 900 |
| ttccatggcc tcaggctggg attcaggtgc ctggaggtgg gggatacccg cacccagccc | 960 |

<210> SEQ ID NO 29
<211> LENGTH: 1067
<212> TYPE: DNA
<213> ORGANISM: Homo sapiens

<400> SEQUENCE: 29

| ggcagagaat agttatgcac aaaaataatt tattttttgtg tgtattattc aggttattat | 60 |
| tcaggtgttc gtgttttaat ttgttaaact tcccacaaac atatgctgtt ggaaagggcc | 120 |
| aggcagggaa agatcagtgc tcaagctaaa agaatgaawg cttaatgtgg acttttaggc | 180 |
| actaatacct ggatagaaga ggtatttgga ggcagagatg ttttcttggt gttcctcaaa | 240 |
| ccacrgcata caagtaaccc ttataacact ccctaatcta gcaataaatt gtgcctagac | 300 |
| atgaatcctc ctctgacttg aagaactact gctctgggaa ggaactaaat aatccaaatc | 360 |
| ttagcactkg atcatacagc ccatatggag ttctttatac gatgactgct tcattgtata | 420 |
| aatcctctct ccccactcaa gccttaaact cttcgagcgc agaaatttta ttkgtcctca | 480 |
| ttgtacacca acaatgtta aatactcagt aaatacctgg cagactgaat tgaggcagta | 540 |
| cggcttatag gaaaawtcta cctgaacaca catgagactc aaawtacttc ttgaatttac | 600 |
| atcatgacca accatccact tttactgcaa agagaacttt tcatacagat tatttccaaa | 660 |
| acccaatggt tcccagtcat cacagcttgt ccctgaccca gttctccttc tcaacctgat | 720 |
| tgcaatctaa ctccctcctc ccttccctcg tcttttcaag atgcaccacg ctggtgcatc | 780 |
| ttgaaccgtg ccaggaacgg tacctcatct ttcccttaa aatattttc atttgcaact | 840 |
| gcattaataa agacgacagg cagcctctgg agagaaytct gaatacctgc ccgacccacc | 900 |
| tcagggagtg ccactcggcg taccgagcct cacaggagaa atgtggccca gcccaagccg | 960 |
| cccatgttcc tcagagttgg gaaggaggaa gacatttcta cgtgaaagtt tgattgcttt | 1020 |
| aagggacaaa acccaaaatt tgcaatcgtt ttcaaaacaa actcgag | 1067 |

<210> SEQ ID NO 30
<211> LENGTH: 1063
<212> TYPE: DNA
<213> ORGANISM: Homo sapiens
<220> FEATURE:
<221> NAME/KEY: SITE
<222> LOCATION: (965)
<223> OTHER INFORMATION: n equals a,t,g, or c

<400> SEQUENCE: 30

| ggcagaggca taactctgct tatttaaggt ggtttggttt gtgccaagct aaaggaggga | 60 |
| atattgattg aattacttt ttaaaatgca attaatttt atttaattgt tttccctgga | 120 |
| gttgtggggt tgaggtattg cagtttaaag cagtttggat gtgctgataa tttttttctg | 180 |
| attatcttca agtctccatg gacagtgtca ctgcaggtct attcatgctt tcgttcctcc | 240 |
| tttacctgcc ttcatctgct ttctctgggc attggtaccc atacccaggt gtggtcagtt | 300 |
| ggagtaactc ctgccttgct gggcttaact gtggtgtttc tgggcctaag gcaattggaa | 360 |
| catctgtagt ttatttccta atcccaattt tgtggaggtt tgtgttctag cttttgattca | 420 |
| attactccta agtagtggcc cgtattaagt agaggctgtg tgagacaaga cacttaatgt | 480 |
| agccccttgg agctgctggg tcctttcat cagaatttgg ctaatgatgc ctctctcttt | 540 |

-continued

| | | |
|---|---|---|
| tttacacact aagcctaata taactagtaa tgaacctcat taataatttg tattggcaga | 600 |
| tgtgaggtgt cacacattaa aactgttttta caccatgagc attgacttca ttcggtcagt | 660 |
| gagggaggat gcaaccacct ttgccaaaat aggaaggaag agaagaccca gagttttcag | 720 |
| ggaacggaat taaatagcac tttaacaagc ttggcggagg cagtggggtg aggagaggaa | 780 |
| gttaataggc ctagggagga gagtatctca ctggtttctc caagctgatt cttctgggtg | 840 |
| ccaagagagc tgtggaaacc cacagaggaa tgccccggtt cctttccttc cttctttctg | 900 |
| gtaagggttt agatctattt atttgatggt cagccttcca gttttatcag caccggtctc | 960 |
| tttgnacaac ttcccaaatg tacaaactcc agacagatga gtacagttgg tgttttccgg | 1020 |
| ggagggtgtt gctccctgtg gtctgtcaca gccagagagc agg | 1063 |

<210> SEQ ID NO 31
<211> LENGTH: 1430
<212> TYPE: DNA
<213> ORGANISM: Homo sapiens

<400> SEQUENCE: 31

| | | |
|---|---|---|
| ggcacgagca cttatgtgtt tggcattctc cgtcatcatt ctggccgggg cgggcagttc | 60 |
| taggagttgg aactcagtcc tggtggaaaa ggaagtcgtg gagggagggc tagggccgtg | 120 |
| ggggaactgc tctgctgagc ctcttcctca cctgctgctt cctaggacta acctgaaagg | 180 |
| ctaaggtacc aggctgaagt cagtgctcag aaaaccaatc gtcattcttt gggttttttt | 240 |
| ttcttgaaga gccactttct ctttaccttg ttctagcctg ttggaggtag ggtttctgca | 300 |
| attccaaagg ccgtacacag cctctcacca tcagaccact ttttaaggct cttcgttcat | 360 |
| acctagctcg aagattcact tcctcaggaa gccattttag ttacaaatct gggaaaactt | 420 |
| aaaatgcttt cattgtgcca tgttttctgt tgcagcttca gtaccgtacc tagtggtcag | 480 |
| gcatacttac aagtttcttt ttacagtaac cccttgtgga catctaataa atggtcatta | 540 |
| ttttttagta ctagtttgtt ttcctgaaca ctgtaagatc tgtgactgac gtttgatacc | 600 |
| ttaaagcagt gccatataat aactacccac tatttgttct ttatttctgt cagataaaaa | 660 |
| tgttctatgt agtgtctaca gtcattttttt ttttaactag aatttagatt tggaagtagt | 720 |
| ttttctatta gttgatttgc atgaaataca aattaggaa aaggcttatt ccacctcaac | 780 |
| ctagttgaac tattaatgat tttttttttt ttttgaggat ttgggctctt tctagataga | 840 |
| aaatcaccct gaacttctag ctttgcattg tgaagtgagc atcatgaaga tgagaaaatg | 900 |
| ttgggagatc attttttgcaa agggcataat agtcggcatt cagatatgag ttaactgcag | 960 |
| agggaaaatt gcaagctgtc atgttggcct tgttcctctc aaccttctgg taacctaaca | 1020 |
| agctcctaca ggttgtatgt gaaattgcaa gatgattata tagcccctgtt gaatttacaa | 1080 |
| ccagatcttg ctttcaaacc attattagcc aagggtttga ttccacacct gtgttcatgg | 1140 |
| atttttttggt attagacatt gctgtaactc tgttttcact ttttcatctg ttatcttggc | 1200 |
| tcacttaagg gagaaggtat cagcagccta ggaccacttg gtttctgttt ttatgtttca | 1260 |
| tagttcatgg ctgataaaaa ttacctgtcc ttaggccgag tgcagtgcct cacacctgta | 1320 |
| atcccagcac tttgggaggc cgaggtgagt agatcacctg agatcaggag ttcgagacca | 1380 |
| gcctggacaa caagagcaaa actccatctc caaaaaaaa aaaaaaaaaa | 1430 |

<210> SEQ ID NO 32
<211> LENGTH: 1382
<212> TYPE: DNA
<213> ORGANISM: Homo sapiens

```
<220> FEATURE:
<221> NAME/KEY: SITE
<222> LOCATION: (1339)
<223> OTHER INFORMATION: n equals a,t,g, or c

<400> SEQUENCE: 32
gctttgttga tgtgccattt tagtgctctg tcgttcacat tttgtgtttt gccactggct      60
ttttcgtttc tccagaaaca ttgttacttc actcacaaat ttggtcaaaa tgtgcaatac     120
tcacatttca gagttagttt tcaatggaag aaatgagcaa aggtttttat tttagttaat     180
atagaaattt gaataattca gagtacagaa aggaacacat tcatgaaca tggtgggaat      240 ttttcactta atgtattata ttccaccaat atacaaatat ttgtatyatt ttagggcagt     300
tagaatagaa aatacatttt cagtagaatc gttaataaat gaatagaaaa atgagaactc     360
attggtgagg tagagagcaa acacacacta agggagtgac ttgtaattga gcagaaattt     420
cctttgagtt tcctaatagc caaagcaaaa gaaaaaaaaa aaaggaagga aacaaactta     480
caaactctta ccatctaaaa aagaaatcat accatttttt aggtggtaca aacatttttc     540
tattatcaaa ctagaggtgg cttttaccat gtgaatattt ttataaaggc tgtggaatga     600
taatgtgaaa attccagggg ggaaagtaag caagaaagta aagctgcaga gctgcatgtt     660
gggagtcagg tgacagaggt gaggagttgg ataggttggt gtctcaggta cttgaatytc     720
tggggtggtt ttcttctgcc tagaaaggct tttgggaaag taaatgtgaa gtcacaagta     780
gagaaaggaa acatcagaag agagacagcc tgagagtttg cagagctaag atctcaggtt     840
aatggttatc tgccccaggg acaaaggatg ttgtacccett ttccttagga ttttcttag      900 gcatttaact aatgttccct tgttttacct agccttgtgt cctaccaaac tgacatttca     960
aagagcagca agtgcctctt ggagaacact gggtggctta acaggatgc aataataata     1020 ctcttaaacg gtgtacattt tttaaaatgt cttttgtat ataakwwaaa tataagagct     1080
gtagcttagc tcactaattg ccttcctttt tgcagaaaat gtgttggtgt attcagaagc     1140
agatctttct tacaaggaca gattgtttaa agctaactag tattgtagtc aacgcttacc     1200
caagggcaga atagagctga tcagaagcaa atcttgaatt caattcgtat ttatattttc     1260
aggaactcta aaattaattg atctttctgt tctgcccttc tgtcgtaact gccacagctc     1320
cagctctggg cgacagagnc aagactccgt ctcaaaaaaa aaaaaaaaaa aagggcggcc    1380
gc                                                                  1382

<210> SEQ ID NO 33
<211> LENGTH: 1502
<212> TYPE: DNA
<213> ORGANISM: Homo sapiens

<400> SEQUENCE: 33
gctgattacc tttatgttgg tttctcttat tatttgtctc ttgctagatc tgctaaacca      60
acccagcttg ctcagagatc tcatattgaa gcaacataca ggcaatccac atctttcttt     120
ccctttgaag tatagtcatt ggatgggatg agggacaggg cctgttgggt tcacagggcc     180
ttgcactgca tgggcacata cttaaaagct cttgtgcatg gaatccctgt ctgttagcca     240
caggcctctt tagctctata cattcaaaat aactactgta gtagaaaata gataagcttc     300
agctgagttg gcttttgata gtggaaaaaa acaaaatttt gacttttat ggccaaaatt      360 ccttgttgac agctgtgatg ttctaatatg atttgggaat atgtcagtct acagaacctg     420
catcctgtaa aaacaccttt ggggtagacg ataaaagtca ttttaaggc aaatacttac      480
```

```
catgtgactt tttattacca aatgcatcag tagtggagct ggtatgttgt ttcataggat      540
ggaaacatta gaagtccaga gaaaaataaa ttttaaaaaa aggtggaaaa gttacggcaa      600
acctgagatt tcagcataaa atctttagta tgaagtgaga gaaagaagag ggaggctggt      660
tctgttgctc gtatcaatag gttatctgtg tccctcatct tggtgttaca gtgttatttc      720
tgtcagtatt atgaatatgt ggttgaccca tcctgtcaaa tgtaccaaca ttttcgaaag      780
aattcattca aatctcttat gccaacagaa aagttccttc ttgtttaata tctctttacc      840
tcagtcctac attttgattc tctggaggag attttagctt gtcttaaaaa gccaaatttg      900
gagtcatcaa gcctgctgaa cctgatgggg cagcttttg aacagctttc tggaagtaag      960
aacttcagtt gaaaagccct tgatcgctt cagcccggga catgcccttc agatggctta      1020
ttctcagtaa agctttatgt agactgtgac actgtatatg tgtgactcgt acaactttga      1080
cgtgtttctg aagtggttta atcgtatttg ttattagctt ctttgtggaa atgcaatttt      1140
tatactaaaa acattgctta tttgcaatgc aatatgttat aaatttgttg tttatattac      1200
tggtattagt cttagcctaa tgaacctaat tattttctt tctgtattct ttgcttcctc       1260
aaatagcatc tgcagcaatt ggaatgagaa atccagatat gtgtttcaag tagtacattg      1320
cctgaatcac aaatcacttg atcacagtat tgtatataat ccctgatcct atttgtttca     1380
ttttattgta aattcccatt tgcatcaaaa cctaatgata gtgattggta agtaaaaaca      1440
aatggtgtat tgcttttcat aaaaaaaaaa aaaaaaaaaa aaaaaaaaaa aaaaaactcg      1500
ag                                                                   1502

<210> SEQ ID NO 34
<211> LENGTH: 727
<212> TYPE: DNA
<213> ORGANISM: Homo sapiens

<400> SEQUENCE: 34
gctggtatct ccagtgtttg ggtttagctc caacttacag gttaggacca gcttttctgc       60
aggtgttgac cagcaatttc ctgcggcatt tacttcttga taacaagagt gagaagatag      120
agacagggca gatagacact taagagtaaa atgtattaac acaaaggctc tggccgcccc      180
cctacaaagg aggccatgga accgatggaa ctgatggagg aaatgctggg actgtgggtc      240
agtgctgaca cacccatggc catacgtttg gtcttcttgg ccttggctgg gctggtggat      300
gggaagccag tatggatcac cttgtggatg gatgcaaaga gaccaaactt ggcgggcact      360
ggaagtacct ggggaagcag gagagactca cactgctgtc atggcccac agcctggagc      420 ctcccctgcc tcctctgcct cttcagagcc cagcagaaag acagagaaag aagcctcctt      480
ggggttccat tacccacact ccaaggtgga aatctttcag atggttagat gatgaaggta      540
gtagaaggca aggatgattg ggagtagaag gaagagtgac aggctagcat gagctgtgca      600
gcagcaagat tccatatgag caaagttcag aaagtgrgmm aaaaggacca agttggatct      660
cctcctaacc ctgacctgca tgatatgggt gtgagaagct tcaactgaga aagctgctga      720
gaaagta                                                              727

<210> SEQ ID NO 35
<211> LENGTH: 1991
<212> TYPE: DNA
<213> ORGANISM: Homo sapiens
<220> FEATURE:
<221> NAME/KEY: SITE
<222> LOCATION: (300)
<223> OTHER INFORMATION: n equals a,t,g, or c
```

<221> NAME/KEY: SITE
<222> LOCATION: (353)
<223> OTHER INFORMATION: n equals a,t,g, or c

<400> SEQUENCE: 35

```
gcgacgctcg gcccgaagat ggcggccgaa tggggcggag gagtgggtta ctcgggctca      60
ggcccggccg gagccggtgg cgctggagcg ggtctgtgtg ggtccgaagc gttttactcc     120
tgttgggcgg gctccgggcc agcgccacat ctactcccgt ctccttgggc agttcccctc     180
cctgccggca ccacgtcccc tctgacactg aggtcataaa taaagttcat cttaaggcaa     240
atcatgtggt caagagagat gttgatgagc atttaagaat caagactgtc tatgataaan     300
tgktgaasag ttgctccctg agaaaaagaa tcttgtaaag aacaagcttc tcncacawgc     360
gatttcttat ttagagaaga cttttcaggt ccgtcgacct gcgggcacta tcttacttag     420
cagacaatgt gcaacaaacc aatacctccg gaaggaaaac gatcctcaca ggtactgcac     480
cggggagtgt gccgcacaca caaagtgcgg ccccgttatt gttcctgagg aacatctcca     540
gcaatgccgg gtctaccgtg ggggtaagtg gcctcatgga gcagtgggtg tgccagacca     600
agaaggcatc tcagatgcag actttgttct ttacgttggt gctctggcca ccgagagatg     660
cagccatgaa acatcatctc cttatgcagc ctattgtcag caggaagcaa acatggacag     720
gccaatagca ggatatgcta acctgtgtcc aaatatgatc tctacccagc tcaggagtt      780
tgttgggatg ctgtccacag tgaaacatga ggttattcat gccctgggtt tctctgctgg     840
gctgtttgca ttctaccatg ataaagatgg aaatcctctc acttcaagat ttgcagatgg     900
cctyccacct tttaattata gtctgggatt atatcaatgg agtgataaag tagttcgaaa     960
agtgragaga ttatgggatg ttcgagataa taagatagtt cgtcacactg tgtatctcct    1020
ggtaacgcct cgtgttgttg aggaagcacg aaaacatttt gattgtccag ttctagaggg    1080
aatgaacttt gaaaatcaag gtggtgtggg cactgagctc aaccattggg aaaaaaggtt    1140
attagagaat gaagcgatga ctggttctca cactcagaat cgagtactct ctcgaatcac    1200
tctggcatta atggaggaca ctggctggta taaagcaaat tacagcatgg ctgagaagtt    1260
agactggggc cgaggaatgg gctgtgactt tgtcaggaag agctgtaaat tctggattga    1320
tcagcagaga caaagagac agatgctgag cccttactgt gacacgctca gaagtaaccc     1380
actgcagcta acttgcagac aggaccagag agcagttgcc gtgtgtaatt tgcagaagtt    1440
ccctaagcct ttaccacagg aataccagta ctttgatgaa ctcagtggaa tacctgcaga    1500
agatttgcct tattatggtg gctccgtgga aattgctgac tactgscctt tcagtcagga    1560
attcagttgg catttaagtg gtgaatatca gcgcagctca gattgtagaa tattggaaaa    1620
tcaaccagaa attttttaaga actatggcgc tgaaaagtat ggacctcatt ccgtttgtct    1680
aattcagaaa tcagcattcg ttatggagaa gtgtgagagg aagctgagtt acccagactg    1740
gggaagcgga tgctatcagg tttcttgttc tcctcaaggt ctgaaagttt gggtccaaga    1800
tacttcatat ttgtgtagtc gggctgggca ggtcctccct gtcagtatcc agatgaatgg    1860
ctggattcac gatggaaacc tgctctgccc atcatgttgg gacttctgtg agctctgtcc    1920
tccagaaaca gatcctccag ccactaacct gacccgagct ctgccacttg atctttgttc    1980
ctgttcctcg a                                                         1991
```

<210> SEQ ID NO 36
<211> LENGTH: 2321
<212> TYPE: DNA
<213> ORGANISM: Homo sapiens
<220> FEATURE:
<221> NAME/KEY: SITE
<222> LOCATION: (787)
<223> OTHER INFORMATION: n equals a,t,g, or c
<221> NAME/KEY: SITE
<222> LOCATION: (880)
<223> OTHER INFORMATION: n equals a,t,g, or c

<400> SEQUENCE: 36

```
gtgaaagtgg gccttggaaa aakttctgaa ttaaagaaaa gctgcatgtg cacggaatgc      60
agtgtgatac attctctaaa gcaacatgtt gtaaaatttt actgctttct tgttgtgttt     120
tatatcttgt tttctccagg cttcgtggac tcgaccagaa aagcaagagg tatagcttac     180
ctgaccacta gccagtcttt agttttgaaa gcattacagt ttaactcacc attgcagttt     240
aataaccaga catgctaaac taattagtaa tttagctaaa gaataggtcg atagtggtag     300
acattactta gcaatagtat catttaggat gagcaagcaa gctgtgttgg gagtggatga     360
acaaatccat attatttcct aaaactggat cttattctct tgctggtgct ggtaaaatca     420
catccaggta attacaccaa tagaaataaa ttgcccccaa ttcccaggcc aggcattttg     480
aaatggtgaa agttttttga ctcacatggt tgatgtggct ctggaccata aagtcacaga     540
gttagtgatc taaaaaccca ctcctccctt tcctttccag ctcaactcat cttgttgctc     600
acttatttta taatgatcag tcttggtaaa ttatcacatc acgtttcatc tcaaaagcaa     660
tgcaaatgac atctctcgtt ggttttccca aattgctaaa cgtatctctg ttacttttat     720
agagcatyaa atttatgaga ttagaatgat gtggtacaaa tggttttatg ttttttaaag     780
tcagtancat ttaacctttg aaatttctct gactcattgc ttcagtttgg ataatgtggg     840
acttartttg aaaactgaar ttaagtatta atctttaggn tttgattgcc acatctcaag     900
amcctactta tgatcatgam tataatttttt tacccgattt atatgaagta acatatagtg     960
aaaatgaaac cagtggactt cagatgagat tcaaggatct aatctctaag gactttttta    1020
aagttgcctt tgccttttat ccagatgggg ctttgatcgt gtaatgctat aaatgcagaa    1080
catcatgatc ctatagattc tgtatttttaa tttggtaaat ctatccctta gtctttcmga    1140
aatgataayt attcagaacg tataactcaa gtgttcaggt caaggytata catatttata    1200
tgctgtttaa tatttaaaag ttgactgcct gtccccaggc actgatctta gtttctgcmc    1260
atgaacaggc tgccattgtc maattcartt cmttataaac ttccygtgtw taagactgtc    1320
ctcccygtca ttgggatgac tgttaagtgc acagcctcac tgagaggctt cccscctgtg    1380
gcacaggaat cacttagtgc tgtcacaggt tgggtgcttt attgtccaaa agtcatggac    1440
ccactgggat tggggaagag agagaagggt taattatcag ccaytcttaa gcagctacag    1500
atctcattct gcttgccttc atacaacttt ccttgtcatt ctcatttaga gctggttgag    1560
gaggagctga gatttatcag ggagcattaa ggagatgtta agagaattat tattgtaagt    1620
ggaagtaata ggtttactcc catgaaagca gacacctcac tctgttttc agaagtgtcc    1680
ttatcatgag tgtcttactt tggacgtaat tgactttcaa gtgaatgctg ccctagggc     1740
tcagaagttc cattctctcc tgtttgtctc atttggagat gaagaccata agtccagatg    1800
agtgcaaaag aaggctcagg ttatggccaa tttcattttg taagttctaa aagcattagc    1860
acttttacct ggaaggaggg agacaaaaac attttgatga gaagaataat tatcattaac    1920
cttcatattt tgggggaaaa aaggagtttt cttgccatca atatcttttc atacttgccc    1980
agagctcatc tcctccttct gctgcagcct gggtggtcag catgacttt tgtctggatg     2040
gctggtaggt ggcacaccct gaagttgtgc aggagccata gtaaaagcat ttcaggggaa    2100
```

-continued

| | |
|---|---|
| gatagtctaa tgacactgga gtctatctgt gtatcctcaa agggagaact gggcatctgg | 2160 |
| cagataattc catcatcaaa tctgtagtga gcctactgca aaataagaat tctctttaga | 2220 |
| aggctggtct gtggacatca ttaaacagga gaaatttcca catggagaaa tttcctgaaa | 2280 |
| gaaactagat aggaattaaa aaaaaaaaaa aaaaactcgt a | 2321 |

<210> SEQ ID NO 37
<211> LENGTH: 1558
<212> TYPE: DNA
<213> ORGANISM: Homo sapiens

<400> SEQUENCE: 37

| | |
|---|---|
| ggttttggag tatatatatt gtatgccatg aactatattt ttctgcttat ggctttgcct | 60 |
| catttaattg ccatagcact tacatggggc aggtattcat tttcctgctt agcaaataag | 120 |
| gaaactgaat ttcagagatg tcaggtaacc tgcctacttc acacactagg agttttgatg | 180 |
| tttaattttg aactaagatc tatctggctt gaaagctctt tgcattaaac aaccttgaac | 240 |
| aatatacttg gaacgtaggt gtgttttttgg cacagaacat ggcatgtgtg tgagggattg | 300 |
| aacacagact tgcccagatt caaacttacc aatcttctgt ttcatgtgcc cagaagaaac | 360 |
| agcctgtttc tcagcctcaa acccaaactt ctagttgtct tgattggttc agcctgactg | 420 |
| tccaactctg atttatagct gtgattgggg gagctgagat tacacagtgt aggcaggcag | 480 |
| aagggcccca ggcctattga tatgggtgag acaatactc acgcactccc ttcacttact | 540 |
| cactcttcca aggtcttggc ttgaacccaa ttttttttga gagaataaac caggctttt | 600 |
| gttctccact tggcctgact ccatttctgg cattccagcc atgtatttag ctgttatcag | 660 |
| cttttcagatt tagascaaag ccttgtttcc aataagcttg tttctctgaa gtaattgtta | 720 |
| aaatataatt ttcagaaaaa ggttaaatca tgactcatac aaatataaaa atgaacatgt | 780 |
| gctaaagatt tttatttcac tcatgtgata tgaagtaacc agacagaagt tataaccagt | 840 |
| acatatggaa agtcaaaaag cacaaattca tatgtagtaa aggaattgga ttgcaaatga | 900 |
| aggcaaaact gtttttycta cagggtggag ggaagataat caaaatgcta gaaccagaat | 960 |
| ttscatgcct gtcacttagc ttcaatttac aaaagcccag aataactcaa aggcaaattc | 1020 |
| tagccctgca aatatcagcc ctaaagctgt gctgtggcca gtgcatagtt ttctattgaa | 1080 |
| gtacaatttt ttccccaaat acattatctc tcagagggag tccaaattgc ttcccttttca | 1140 |
| ctcagcagat ctgttcagtc aacagatgtt aaatagctac agcgtatcag gcacaaataa | 1200 |
| ttctttataa aataaagtaa caaactatat gttgtttcaa agttccagtt aaggccagcc | 1260 |
| gtggtagctc acccttataa tcccaacact gggaggccga ggcaggcgga tcacttgggc | 1320 |
| taggagttcc ataccagcat ggccaacatg gtgaaaccct gctctactag aatgcaaaga | 1380 |
| ttagccaggt gtggtggcgc atgccggtag tccaggctac tcaggtggct gaggcacagg | 1440 |
| aatggcttga gcctgggagg cggaggttgc agtgagccga gattgcgwcc gctgcactcc | 1500 |
| agcctgggca acactgtgag actcctgtct acaaaaaaaa aaaaaaaaa aactcgta | 1558 |

<210> SEQ ID NO 38
<211> LENGTH: 1701
<212> TYPE: DNA
<213> ORGANISM: Homo sapiens

<400> SEQUENCE: 38

| | |
|---|---|
| aaatgtataa actatacatt tggagtgttt gcatataatt ctttataacc tccacttaaa | 60 |

```
gctgtcagac attggtattt tatcagtcca cattgttgaa taaaactaat gttcttagga       120
atccagcttg tacacactgt ttaaaaaccc tcagggacag tttacacact cttctcactc       180
aattcaggta ctttgatgct attcttaaac ctaacagtga cttgtatttt tctgttttgc       240
ttttatttca acgtgctggt agcacatctg atgaatgtca acttaaaaaa ctcagttcag       300
ttatccaggt ataactcagc caaacagatt ttaaagctgc atataactct ccagcacatg       360
gtgcctcaca ctcttatagt ggcattctat atattcagtt attactactg agcagataat       420 atggggttc ctgttaacag tgtatttttt aaaaaagcg cataaatgta tagccagcac         480
actacacaca cacacacaaa catgcacagt taaactatat attttaaat gccactaata        540 gccagcacaa ctaaaacaaa agacattcct aactgctctg taagctgtka acagatgcag       600
ttccttcttg atgtggctct tgcttcttca cgataactac tactaaattc aagcactggt       660
ccttgggtgt ctgacctcta cattctagtt tatgcaatgt ctttagagaa ttttgtgcac       720
tggccactgt gatggaacca ttgggccagg agtgctttga gtttatcagt agtgattctg       780
ccaaagttgg tgttgtaaca tgagtatgta aaatgtcaaa aaaattagca gaggtctagg       840
tctgcatatc agcagacagt tttgtccgta tattttgtag ccttgaagtt ctcagtgaca       900
agttttttct gatgcgaagt tctaattcca gtgttttagt cctttgcatc tttaatgtta       960
agacttgcct ctttaaaatt gcttttgttt tctgcagtac tatctgtggt taacaaaata      1020
gattatttct ctgctttaat atttgatatc ttacatctaa ataaattct ctccacatat       1080 aaaacccata gcctttggag atatggaaaa tggtatcttt cagatttcta gaagttcaag      1140
tgtcatacaa caaaacagga accccctta ctcttatgga cctcatttca atatactgtt       1200
tacagtttga tggaattgta taatttaata tttctcttgt actgtagttt atatttattt      1260
acagattttt ttgtactgtg tgatttgaac tttttgttcc ttgctatgat caatgtttat      1320
gtagtagagc acttatgatc acaaattaag tttttggtt tgattgcact acattaaatt      1380
ttttaatgca gttctgattt tgactggac taaaactgtg tcttaatgta tgtgatgagt       1440
acttaaaatt ttaatccatg tggtccccccc ccttttttt tttttgcatt gtatgtcaaa     1500
agcgcttgtt ctttcgtgca tgtgtaagat ttaatggttc cattgtatta tttgaccatg     1560
acattttgga gaaacattcc cagctgtaat gttgtgtatg gtagttctca ctggatgcta     1620
gagttttcaa aaccactatt cttctaataa attttgttgt gaaaaactga aaaaaaaaa      1680 aaaaaaaaaa aaactcgtag g                                               1701
```

<210> SEQ ID NO 39
<211> LENGTH: 1903
<212> TYPE: DNA
<213> ORGANISM: Homo sapiens

<400> SEQUENCE: 39

```
saacaaagcc ttctacttga gcagttttc catcactgat atgtgcagga aatgaagaca        60
ttgcctgcca tgcttggaac tgggaaatta ttttgggtct tcttcttaat cccatatctg      120
gacatctgga acatccatgg gaaagaatca tgtgatgtac agctttatat aaagagacaa      180
tctgaacact ccatcttagc aggagatccc tttgaactag aatgccctgt gaaatactgt      240
gctaacaggc tcatgtgac ttggtgcaag ctcaatggaa caacatgtgt aaaacttgaa       300
gatagacaaa caagttggaa ggaagagaag acatttcat ttttcattct acattttgaa       360
ccagtgcttc ctaatgacaa tgggtcatac cgctgttctg caaattttca gtctaatctc      420
attgaaagcc actcaacaac tctttatgtg acaggtgagt tctcaacacc tagaccatct      480
```

-continued

```
gatattttc ttataatgtt tccaggaaga gggggttca gtttctcaag tgattatgtt      540
agaaagccaa ctcctatagc acatctgaaa tctgctacac ctcacagatt gttatgtgcc    600
agtgtgtaca tatgtgtgtg tatgtgtgcg tttgaggtga gtgagataga ggagagtaga    660
gaaatagata gtaaaagtta ttgttttttga ctttagggat tataaaattt atttgataag   720
tccaaaagta gaccactgaa atattgaaaa aattataaag tgaataccta tagttgcgaa    780
tagctctgtg attgcttgtc cttctttgtt gttttttttt tctcttttc ccattttct      840 cttctttact tttgttcatt acaatttctt gaagttatgt ttgtggtgct taggcaatta    900
aacacttctt aatagttcac agtttgttta gaggaaaaac agcaaacaac taactgactt    960
cctagtgatt ttctgggaat attcagagct tcatctctct tccctgttcc ccgaaagagg    1020
cctttaatat gctttgacaa ctgaggaagg acagatagaa gttaagcttg gggaaaccaa    1080
gctgaataaa acatgaaaaa atacataggg ggggagtagg taagagtaaa aaatacttgg    1140
tttataaaaa ttttatagcc aacatcatat tcaatggtga aaggcttaga gctttccccc    1200
taagaacagg aacaagacat ggatccttgc ttttgccatt tccatttaac attaaactga    1260
aaattctagc cagagcaaac aggcaagaac aagaaataaa agatatctaa cttagaaaaa    1320
aagaagtaaa actttattca cagatggcat gaacttatgt gtagaaaaat tcttaaaaat    1380
ttgtttaaaa ctattaaagc taatacatga atttagcaat tccacatgat acaggatcaa    1440
cacacaaaaa tcagtgatat ttctatacac tagcaataaa caatccacaa agaaaattaa    1500
ggaaacagtt ccatttacaa tagcatcaaa atgaataaaa tatttaagta caaatttaac    1560
caaagaggta taagagttgt acactgaaca aagaaagcat ggctgaaaga aattcaagaa    1620 tatgtaaaata aatgcaaaga cattctgtat tcatggactg aaagatgtaa tattgtaaag    1680
atagcaatat tccccaaggt gatctacaga ttcaatgcag ttccactaaa atcctaacag    1740 cttttttgttg ctattgcaga aataaaaaag ctgatcctaa aattcacatt gagttgcaac    1800
agacccagaa ttgccaaaac aatcttgaaa aagaacaaaa ctgaagctaa gacttcccta    1860
tttcaaaact tactacaaaa tgacagttaa aaaaaaaaa aaa                       1903
```

<210> SEQ ID NO 40
<211> LENGTH: 1280
<212> TYPE: DNA
<213> ORGANISM: Homo sapiens

<400> SEQUENCE: 40

```
gggcagactt aactgctgtc tgctcagcat ggaagccagg agccaaacca gtgggcttga    60
tgacagtgag ctatttctgg tggctcaggg ttggggcttg ggccgaagat gtggaggccc    120
tggcttccct tcctgaggac agactgaggt ggaaccttt ggctctgcca gcttctccat    180
gtgcagtcac agcactggtg gcaaggcata ggagagctgg gctacaaaga agcattcagt    240
gtctcctggg gcggcaggga ggtgggggtt gtaattgtga actcaccaaa ccccaggtgg    300
gcagtaagtg ggtgggtcat aggaagaaaa gtgatcttca gtcaggagac ttgggttctg    360
ggctctgtct gatgactggc tctgtgatgt gagccaggtg acttctctaa ccctgagttg    420
cctcatctgt aaagataatt ccagtcttgg aggattttta tggasyaaaa aggacagagc    480
ggtcctgtgt atcccctgca aatggttaga cgttatccat ttacagcccc tgccaagcca    540
ccactagctt cttcagagaa cttttgaacc ctgcctccct aaagtagttc taaaacattt    600
ttcactgtgt tacccatcaa gggaaacaaa atgtttctac aaaccatagt aaataggatc    660
```

-continued

```
gtttttgtat tgtgtttcaa ggaggaaaag ctgaccagca agaagaacgt cggagacaaa        720
agcagatgaa ggttctgaag aaggagctgc gccacctgct gtcccagcca ctgtttacgg        780
agagccagaa aaccaagtat cccactcagt ctggcaagcc gccccctgctt gtgtctgccc       840 caagtaagag cgagtctgct ttgagctgtc tctccaagca gaagaagaag aagacaaaga        900
agccgaagga gccacagccg aacagccac agccaagtac aagtgcaaat taactggtca         960
agtgtgtcag tgactgcaca ttggtttctg ttctctggct atttgcaaaa cctctcccac       1020
ccttgtgttt cactccacca ccaaccccag gtaaaaaagt ctccctctct tccactcaca       1080
cccatagcgg gagagacctc atgcagattt gcattgtttt ggagtaagaa ttcaatgcag       1140
cagcttaatt tttctgtatt gcagtgttta taggcttctt gtgtgttaaa cttgatttca       1200
taaattaaaa acaatggtca gaaaaaaaaa aaaaaaaaa aaaaaaaaaa aaaammmag         1260 ggsggcccgg gaaccaattt                                                   1280

<210> SEQ ID NO 41
<211> LENGTH: 1918
<212> TYPE: DNA
<213> ORGANISM: Homo sapiens

<400> SEQUENCE: 41
gaattcggca cgaggtagga tgagagagaa agaagaatag gagatggtta aggttggggc         60
ctggagagct gtacagatat tgatgctatt cgccaatcca ggacatgcag aaggagcatg        120
catcagcccc gggcccgcag gaaagaggga gccactcaaa ctaggataat gcacagaggg        180
tgttttcaca aaggtgtgag cgtggtgtcg gataaaggca ggactaatgc agtaacctag        240
agccagtagc agtggagtga aggagcttct cccatcaccc agccagaaga ccaggaggag        300
aacagctacc tggaccagaa ggagaggtct tgtagagaag ctcccttgag aggatcccct        360
tctgccaagg gacagccaac ctaggtggtc ttgctgggag catgacagag gagttaattc        420
cccggtttca tgttcctcct ttcctccact cctctgaggg ttactagcca aatccaccga        480
aggcagccac caagacatcc tcacagatca gcctcccagg acacacagca gggcaaagaa        540
ggtggagatg gatgggaggg gagcaaggag cagatttgga ggagtgcagc atggtcctag        600
gagagcgcca tccctgctgc ccctagctgt gtggccttgg ccaggttacc taacttctct        660
aatcctcaga gagaggttgg ggctgaatac tcaggagtct tcagtggaaa ggtggatgcc        720
atgggtgtgc tgcgatttcc tggagaaggt gtagcttaga ggggaactgg ggcaggctga        780
agagtgagag tcagggtacg aggctgggga ggagccacca cacagtcagc agtagcttcc        840
tcctctggga tcctctagca tttctctttt aacttctcac agaagacttt acagatttta       900
ttgccactgc ttccgtgtgc ctcccatcag agtgtgagca cctttgttcc tcagtccctc        960
aaggccgatg catggtcagc ccttgttagt tgagtgaatg aacaaacaac actgaagaag       1020
ctgcccttga aaaccgggg catcgttaag ggctttgagc agaggataga agacagtgga       1080
gggggaggct cakgaggaag tgggatgtca agctgtgggg cagctgcaag accttgcatg       1140
catttggtgg aaatttcyta ggggctacca ggggcaggc tgtgcttggg actagaggct        1200
agagaggtgg ggaaggctca gtctctgtgc tcaagagaca gccctctgga cagagcacgg       1260
cagctcctcc atgacacagc tgtccacaag cttcggagca cagctccttg ttagtgagtg       1320
gtggtgttag gcaggtgggg aggtggggga agttgaaagg tatcctgggg atgagcaaag       1380
tctgatttgg gggtgaaggg gaacatgcaa caatgaaccc agttcaatgt ttagggcaaa       1440
cgtttaatgc aggaagcagt gagaggtaag actggagcca taagcaggca gaagctcgtg       1500
```

```
gagacccaag tgcccagatg tggactttc cttataggca gtggagctcc ctgaagggtt    1560
ctgaagcaga gaagagcata catagtcagg tgtgcttctt acctggacta ctgctgaggg    1620
atatttagga tgcagcatcc tctggatggt tgctataata ataactattg tgacaaagct    1680
tcttcctgtg gagctgttgt gtttgcaaat cggaccaagg tcccaggcat ccaggccatg    1740
gagctaagtt cctagcccag gtctctggtc agggcataag tcattcagtg tgccaaacct    1800
ctgaaaggta gcccggcccc tttatttacc atactacaca cagccagttc accttctcct    1860
cctgagcacc tgctcgtgcc gaattcgata tcaagcttat cgataccgtc gacctcga      1918
```

<210> SEQ ID NO 42
<211> LENGTH: 1268
<212> TYPE: DNA
<213> ORGANISM: Homo sapiens
<220> FEATURE:
<221> NAME/KEY: SITE
<222> LOCATION: (2)
<223> OTHER INFORMATION: n equals a,t,g, or c
<221> NAME/KEY: SITE
<222> LOCATION: (15)
<223> OTHER INFORMATION: n equals a,t,g, or c
<221> NAME/KEY: SITE
<222> LOCATION: (23)
<223> OTHER INFORMATION: n equals a,t,g, or c
<221> NAME/KEY: SITE
<222> LOCATION: (368)
<223> OTHER INFORMATION: n equals a,t,g, or c
<221> NAME/KEY: SITE
<222> LOCATION: (479)
<223> OTHER INFORMATION: n equals a,t,g, or c

<400> SEQUENCE: 42

```
gnaggaccgc tctanaatat ggntcccccg gcgcagattc gcacgagcaa taatgcgggt     60
ccaccttcca taccatcttg caaccaatta tcagaaagag aaggcctgag caggggatg    120 tgcattttgc tttctttcgg cgtacatctc atgctagatt tttatctggg ggcctttgaa    180
gagccagccg gcacagaagc atggtggcaa cgctgtgcct ggaaaactca tcagtgtcac    240
tctggtttat tttcctctcc tctttgagct cttttcccatg gtgtgggct ctcagtgaca    300 actggccaag cggcggggcg gttgctcgtt gtcattctgg taggcgctgg tttccggagg    360
gctccgantg cttgtgatat cgcattgttt ctgagagcgg gagcacgttg gcactggtcc    420
catttcggat gaagaaactg aggctctggg gattaagatc gtgaactgtg gggatggang    480
aggcayagct ggagtgaatt gggtgtccag ggttctgttt cgtctcacag aggatgtgcg    540
agggtgtatg tgtgcatttg agaatgtgtg aggttgtgtg tgtttaagaa aatgagaatg    600
aggctgggca cagtggctca tgcctgtaat cccaacactt tgagaggctg agctgggtgg    660
atgacttgag cccaggagtt caagaccaga ctggggaaca tggtgatgaa accctgtctc    720
tacaaaaaaa tacaaaaaat tagcagggca tggcaatcca tgcctgtagt cccagctact    780
tgggargctg argtgggarg attgcttgaa cccaggagat aaaggctgca gtgagccatg    840
atcgcaccac tgcactccag cctgggcaac agagtgagac cctgtctcca aaaaagaaa    900 gaaagaaaat aaaaaggaga gaggttagaa aagggggctg ggcgcggtgc tcacgcctgt    960
aatcccagca ctttgggagg ccgaggcggg cggatcacga ggtcaggaga tcgagaccat    1020
cctggctaac acggtgaaac cccgtctcta ctaaaaaaaa atacaaaaaa ttagccgggc    1080
gtggtagcgg gcgcctgtag tcccagctac tcgggaggct gaggcaggag aatggcgtga    1140
gcccgggagg cggagcttgc agtgagccga gatcgcgcca ctgcactcca gcctgggcga    1200
```

```
cagagcaaga ctccgtctca aaaaaaaaaa aaaaaaaaaa aaaaaaaaaa aaaaaaaaaa    1260
aactcgta                                                             1268

<210> SEQ ID NO 43
<211> LENGTH: 1201
<212> TYPE: DNA
<213> ORGANISM: Homo sapiens
<220> FEATURE:
<221> NAME/KEY: SITE
<222> LOCATION: (1192)
<223> OTHER INFORMATION: n equals a,t,g, or c
<221> NAME/KEY: SITE
<222> LOCATION: (1197)
<223> OTHER INFORMATION: n equals a,t,g, or c

<400> SEQUENCE: 43
acccacgcgt ccgaagtaca agtactggtt tagctttatg gttaaaagca ttggctctag      60
agcagataac acaggctcaa accctagttc tgccgtttac tggttgtgtt accttgggta     120
ggttacttga cctttttgag cttcagattt ctaatcttta tttaatgagt tttaataata     180
gaataatagg attgctttga ggatcaaata agttaataaa ccacttagaa cagtgttcaa     240
taggctggat ttttgtttgt ttgtttgttt gttgctattc ttttgtgtt atgttttgta      300 tccagcagaa gtggttattt agcttcctat tttatgaggt aggactgatg ggaattgaca    360
gtcttaggaa aaagtacaac tgtaagtcag tggaagtttt tcctagtcaa gatgtcaaat    420
gccagaggtc ggattcatgt ggcaggatgg ggtccaaact gtacaaaagc ttggagatga    480
atgaggtgag acagctaagc ttaagacaaa aaacaatgtg aagttatgtc cttgggcagt    540
gtttgcagta gtatagtgcc gctttggaaa acttagaaga tgatcctcaa ctgtgtccac    600
tcaaaataga ttgtgcatct caatgtcata gagtcagaaa tttctaccac tatctgttta    660
aatcatcgtt tatttatatt ccttaaatat tcataccttt cacataagtg agatacatta    720
tttttaaaaa cgcagttttc cttcttgatt ttttcatatt gtcccattat tctgagaaga    780
gtttatttta tgagaattaa gttattatct tacagaataa atckgattac ygactagata    840
caagataacc acatatttt cctagaataa tttaattcca attttactta tttgkacctt     900
atatgactta ttttcaggtt agaaaaatgt ggtcctacag ttttgttttg aagtttgcct    960
gggccatgtg aagccaccat tatcatttac gtcaaaatg aaggttatct gttgcccaag    1020
agaaaaatac agcattctga atttaaaaca ctaaaatagt gagggtttca taagctgttt    1080
cagtgatttc tgaccttggg ttggaaagct ctcatgtctc agttacctca gtgggtatag    1140
tgacattgtc ccagtctgca ttaccaaatt gtttcaaatc actttaatta anaaaantaa    1200
a                                                                    1201

<210> SEQ ID NO 44
<211> LENGTH: 819
<212> TYPE: DNA
<213> ORGANISM: Homo sapiens

<400> SEQUENCE: 44
aattccgaac atatccctac aaggtaagac agatataggc tgatgmgtmt ttttmacctt      60
tctcatttgc tgattttcac aggaagaaga attgtgtaac atttatttct aacagtaaat     120
ggcaaaactt atgtattacc agatactatg tctagtagtg ttttgttggc tcattcactc    180
attcattcat ttattcaaca aacatttttt gattgccttt tatgtgccag gccctgccat    240
agatgctagg gactcagcag tgagcacaac agataaagaa ttctgtcatt gcggagttta    300
```

```
cattttagtg gcaggtgaca gataataagc taaattaaat aagcmaaata tacagtatgt    360
ttaatagcaa taatttctat ggcaaaaaat aaagcaggaa agagtaataa taagtgtttg    420
gaatgatggt cagatagttc tgaatatcac ctgtgcatca ttcttttaag aggctgtgtt    480
gttttaagtg tattgatata ataattatac tgaaacattg tgggattcaa ttatttaaaa    540
aaggtctata cactgtgaaa gctgatacac tcactaacag tggacgtggt taaatgttga    600
cataaacaaa aaataaacga aggagtagag taatagatct aagacaagtt tggggaaatc    660
tgtgaatctt aagctttttct ttttttctga gacaggttct tgctctgtca cctaggctgg    720
agtgcattgg cacgatcatg gctcacttca gcctctacct ctccaactca gtaatccgg    780 aattcgatat caagcttatc gataccgtcg acctcgagg                           819
```

```
<210> SEQ ID NO 45
<211> LENGTH: 1566
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<221> NAME/KEY: SITE
<222> LOCATION: (12)
<223> OTHER INFORMATION: n equals a,t,g, or c
<221> NAME/KEY: SITE
<222> LOCATION: (16)
<223> OTHER INFORMATION: n equals a,t,g, or c
<221> NAME/KEY: SITE
<222> LOCATION: (170)
<223> OTHER INFORMATION: n equals a,t,g, or c
<221> NAME/KEY: SITE
<222> LOCATION: (184)
<223> OTHER INFORMATION: n equals a,t,g, or c
<221> NAME/KEY: SITE
<222> LOCATION: (728)
<223> OTHER INFORMATION: n equals a,t,g, or c

<400> SEQUENCE: 45
tgctntggcc antggntggt tggggctcgg gttggcgtgg tgtgcaggct gcattgcttt    60
ggccagggaa gcaggctgaa gcgtgtccca gccctcccgt ggctccacga gcttgcttc    120 cccgttcccc ctgtgaacaa cctgggccac cagctcggtg gtggccaggn ccactcacca    180
cctntttcct ccccacagtg gcatttctgt taacatccag gacttggccc cgtcctgcgc    240
cggctttctg tttggtgtgg ccaacacagc cggggccttg gcaggtgtcg tgggtgtgtg    300
tctaggcggc tacttgatgg agaccacggg ctcctggact tgcctgttca accttgtggc    360
catcatcagc aacctggggc tgtgcacctt cctggtgttt ggacaggctc agagggtgga    420
cctgagctct acccatgagg acctctagct cccaaccca cagcctctcc aaggacccag    480
gcgccagcag ccccrggaca caggggactc agtgtgtggg acttggtcac tccatgtcag    540
acacacgagc agagaggaac acaaaccact gtggagcctg aagctcctta agaagagtcc    600
acaacagctg gtgggagggt ggggtgggcc tgggtccaga ccaggctcgc tgctctctgg    660
gcctcagttt ccccacctgc cagcgggctc ggccctgtcc tcctcacagg ctggtgtggc    720
cgtcaggntg ggtggggtta ttgttagtag gcgcactcat tcccaccacg atctgttccg    780
cgtggttccc gccaaacctc cctcggtcgc cgtgttctcc gcaagcctcc tgcagcgccc    840
gcctgccaat gtgaggctgg caccaggctg cagctcccca atcccagccc actttgctgt    900
gtctctggcg ggctgtcctc cttggtggga gctgtcctgc acactgtagg atgcttaaag    960
gtatccctgg cctccaccca yccctagcca gcagctccca gtcagacaac agccagaaat    1020
```

```
gtctccagac tctgcccagc ctccccaggt agccaccctc gagacaygac ctcagagtct    1080
ctgtgtctcc tagaagcctg acagagaccc ccagggcagt gggtgggtgg cgggctagag    1140
acccttgcct gtgtccggga ccctggcgcc gctctcccct cctgtggatc cctccgcact    1200
aacagtgttc tcagtgggca gacgcctggg caccccttgg gccctgccca gcatggccat    1260
ggcgcaggct ctcgaacccg catggctttc ccaggcctgg tgattctgct ctccagggac    1320
ggttggcacc ttcctcgggg gcgggcccca cgcaccccag aacacacaga cccacctttc    1380
tggcgttctt tctacctccc ttttcgttgc ctgaggagct ggtggtttca tgagttaatg    1440
atacatcttg caaggtgtac acatagagaa aaaaacctaa aaatgtggaa aagcacgcca    1500
aagccttatt taaataataa ctattaaact attcaaaaag aaaaaaaaaa aaaaaaaac    1560 tcgtag                                                              1566

<210> SEQ ID NO 46
<211> LENGTH: 2094
<212> TYPE: DNA
<213> ORGANISM: Homo sapiens

<400> SEQUENCE: 46
gccaccccct tgatcctgta actctatagg tgccctgcct tctgggtgtt tctcatcagg     60
gctgtagatc atgaaggctc agatgctctt aagcctggcc tggccccttc ccctgagcac    120
agctaacagc tgcctaccgc agtttccaag gggattgtat tctgctcact actgtcccag    180
ttgtttgctt tccttggagg ctctaagtta aggaagcact gggtggcaaa cttagagttt    240
cctaagcatc cttcagtatt cttgctaagt tgtgttctca aaggcaggcc ctcccaggtg    300
cctttggctc agtgggagag gagaactgga ggagctgact ctgtctccaa caagctccgg    360
ggctgtgagc aagccctgcc cttccctgaa agtgcagaat cccctgtct gcactccaca    420 gccacccttt ttagatggga aggaaaggga tttgccaaag ttcagttgat gtggartggc    480
gctgggactc acatcctaat tttctgacac ttaagccaat agtctttctt cgtgaaaatg    540
taccttgtgt ttagaggctc tctgatgttc attctggttg gtttcagggg tgtctgaktg    600
catcatcatg ggaatcccaa tgaacattgg aaccgggctc ttcaagctgc ttcacaaggc    660
tgmcagggac ccgaaccctc ccaagaggcc cctgatcttc gacacaaatg aattccacat    720
cccccttgtc acatagtcca aagaaagagg ggaccatgcc tgaccttgac tccttgtcct    780
gtctccagct gatgtataaa gagttttgtg ctccctggga cggggtcct gaggtcccca    840 cctatgccag caatcagaga agccctcttg gcatccccag gagcagcttc tcctctgata    900
gggtgcagct cacaccagtg accctgactg tgccacgctg ctcgggagag ctgagggttt    960
tattgtttgc ttgcttgaaa cctaatctat agacggcccc acagctcstg cacacactgc   1020
ttccctggac ttaaagccca gccaggtgtc atggtccatc ccagctcact gcatacatcc   1080
atcggctccc catggtgtct tcacacctga cgatgagcca ggcctgagcc ccacacaggc   1140
cagggcacat tcttggattt tccattcctt ggtcatgctg gaatctctca atgtgacata   1200
cttatgtaaa tattgttact attatttatt tgttccattt gagggatttg gaattttttgt   1260 tattttagtt ttattttttga aaccaagcat ctatagaaac caagaaagtc agcatgtaag   1320
cgtcactgga aaaactggtt taagcaaata gagccgtctg ggatttgtaa ctgaggtgca   1380
actgtcatga ggcccaggca gctctgtaac atcttctata gatgcccctg gctaccctgt   1440
tgttttcatc tacctcagac ccctatcatg gggctctacc ctgtgacaag agccaaaccc   1500
attctccatg gcctatggaa gcctcactgg agtttggggc ctgctgcaat ggggatgaga   1560
```

-continued

```
tggtttttg tagaattata cttacgttcc ttggatgatc tctagttgat tttttaagtt    1620
ctgagttgat gctgttaagg tacccggggt agccattggt tcttggatct gtgttagaat    1680
gagtgctttc ccttcctact gatgtgattg tggattagga attcgtgacc gagtgatttt    1740
tggccagtgg ttgggtttaa aattctatta aaatttgtag tttgggctgg gtgctgtggc    1800
tcatacctat aatcccagca ctttgggagg ccgagggggg cagatcactt gagcccagga    1860
gttcgagagc agcctgggca acatgacgaa accccgtctc tactaaaaaa aatataaaaa    1920
ttagctgggc acggtggcag gcacctgtaa tcccagctac tcgggaggct gaggcaggag    1980
aatctcttga acctgggagg cagaggttgc agtgagccga gattgcacca ctgcactcta    2040
gcctgagcaa cagagcagga tccgtctcaa aaaaaaaaa aaaaaaact cgag            2094
```

<210> SEQ ID NO 47
<211> LENGTH: 956
<212> TYPE: DNA
<213> ORGANISM: Homo sapiens
<220> FEATURE:
<221> NAME/KEY: SITE
<222> LOCATION: (319)
<223> OTHER INFORMATION: n equals a,t,g, or c

<400> SEQUENCE: 47

```
gtgagaatga aagaagacac aaataactat taagccagga caagagattc ctgataaatc     60
aggaaatatg gtcatactac tttgaatgta gttatctatt aaatgtgtct cttgtcattc    120
aactgtaaag ctgtgttaag tttgagcctt atttctctta gcttcctttg ttgcctggaa    180
ttgtgtctgg cacgttgtgg tggcagaaga aatgttagtg ccccttaaa aatgttcatt     240 atttaaacat atactatatt gatgtagaac tcataccatc ccatttgggg cctttatga     300 gccattttct cagtatacna awgtagaaca atgagcttaa ttatakgctt gtgtaatgat    360
aataactagc ttttaccagc acagcctgtt ccaaggctaa ggctaacgat tttacttgag    420
ttctcttata tatttctcac aacagacctc acaggtaggt aatattattg gtcttattaa    480
actagaagaa aagataggtt tagaaaaaac tttgtttaga gtcacctaac taattatgca    540
gcagaatttk gatttgaact ccagactctg actccgtaca ccagtctcct aaatgttaga    600
agaactgcta taaattttg gaaagaggga tttaaaaac attaatagtg gctgggcacg      660
gtggctcccg cctgtaatcc cagcgctttg ggaggctggg gcggcggat cacctgaggt    720 caggagttca agaccagcct ggccgacatg gtgaaaccct gtctctacta aaaatacaaa    780
aattagccag gcgtggtggt gggcgcctgt aatcccagct actcaggagg ctgaaggagg   840
agagaatcac ttgaactcag gagaggaaga ttgcagtgag ccaagattgc accactgcac   900
tccagcctgt gtgacagagc gagacgctct ctcaaaaaaa aaaaaaaaa actcga         956
```

<210> SEQ ID NO 48
<211> LENGTH: 1859
<212> TYPE: DNA
<213> ORGANISM: Homo sapiens

<400> SEQUENCE: 48

```
gggcggcggc cagaggsctg cccggctccc ggaagcaggc tgtgaggggc gggagcgctg     60
ctggaacccg agccggagcc ggagccacag cggggagggt ggcctggcgg cctggagccg    120
gacgtgtccg gggcgtcccc gcagaccggg gcagcaggtc gtccggggc ccaccatgct     180 ggtgactgcc taccttgctt ttgtaggcct cctggcctcc tgcctggggc tggaactgtc    240
```

| | |
|---|---|
| aagatgccgg gctaaacccc ctggaagggc ctgcagcaat ccctccttcc ttcggtttca | 300 |
| actggacttc tatcaggtct acttcctggc cctggcagct gattggcttc aggcccccta | 360 |
| cctctataaa ctctaccagc attactactt cctggaaggt caaattgcca tcctctatgt | 420 |
| ctgtggcctt gcctctacag tcctctttgg cctagtggcc tcctcccttg tggattggct | 480 |
| gggtcgcaag aattcttgtg tcctcttctc cctgacttac tcactatgct gcttaaccaa | 540 |
| actctctcaa gactactttg tgctgctagt ggggcgagca cttggtgggc tgtccacagc | 600 |
| cctgctcttc tcagccttcg aggcctggta tatccatgag cacgtggaac ggcatgactt | 660 |
| ccctgctgag tggatcccag ctacctttgc tcgagctgcc ttctggaacc atgtgctggc | 720 |
| tgtagtggca ggtgtggcag ctgaggctgt agccagctgg ataggctggg gcctgtagc | 780 |
| gcccttttgtg gctgccatcc ctcctcctggc tctggcaggg gccttggccc ttcgaaactg | 840 |
| gggggagaac tatgaccggc agcgtgcctt ctcaaggacc tgtgctggag gcctgcgctg | 900 |
| cctcctgtcg gaccgccgcg tgctgctgct gggcaccata caagctctat ttgagagtgt | 960 |
| catcttcatc tttgtcttcc tctggacacc tgtgctggac ccacacgggg cccctctggg | 1020 |
| cattatcttc tccagcttca tggcagccag cctgcttggc tcttccctgt accgtatcgc | 1080 |
| cacctccaag aggtaccacc ttcagcccat gcacctgctg tcccttgctg tgctcatcgt | 1140 |
| cgtcttctct ctcttcatgt tgactttctc taccagccca ggccaggaga gtccggtgga | 1200 |
| gtccttcata gcctttctac ttattgagtt ggcttgtgga ttatactttc ccagcatgag | 1260 |
| cttcctacgg agaaaggtga tccctgagac agagcaggct ggtgtactca actggttccg | 1320 |
| ggtacctctg cactcactgg cttgcctagg gctccttgtc ctccatgaca gtgatcgaaa | 1380 |
| aacaggcact cggaatatgt tcagcatttg ctctgctgtc atggtgatgg ctctgctggc | 1440 |
| agtggtggga ctcttcaccg tggtaaggca tgatgctgag ctgcgggtac cttcacctac | 1500 |
| tgaggagccc tatgcccctg agctgtaacc ccactccagg acaagatagc tgggacagac | 1560 |
| tcttgaattc cagctatccg ggattgtaca gatctctctg tgactgactt tgtgactgtc | 1620 |
| ctgtggtttc tcctgccatt gctttgtgtt tgggaggaca tgatgggggt gatggactgg | 1680 |
| aaagaaggtg ccaaaagttc cctctgtgtt actcccattt agaaaataaa cacttttaaa | 1740 |
| tgatcaaaaa aaaaaaaaaa aagggcggcc gctctagagg atccctcgag gggcccaagc | 1800 |
| ttacgcgtgc atgcgacgtc atagctctct ccctatagtg agtcgtatta taagctagg | 1859 |

<210> SEQ ID NO 49
<211> LENGTH: 1461
<212> TYPE: DNA
<213> ORGANISM: Homo sapiens

<400> SEQUENCE: 49

| | |
|---|---|
| aattcggcac gagttttgct ctgtttacat agctttatac cttttttatat actaaattga | 60 |
| aatggatagg tagaagcaat attttcagaa ttggtcattg tcctgaataa aatgagccac | 120 |
| tgtgttctct caggcaccat gcaagctcac ccaatattca tataccacaa aagggtgttt | 180 |
| ttcctgctta agtttatatt ctatatcata ttctgttttt tttttctgga tatttccact | 240 |
| ttatattgtt ctcttcaac attttgtaag aagtagtatt cctattctct gctgttacaa | 300 |
| agactatgaa aatacatgca actcatttaa agaaacaggt ggatgtctgg aagttttctc | 360 |
| tacctaacac tttcacatat aaaatttatg atgkttggkt tctatggtaw ttaacattgg | 420 |
| caagaaaaaa taactcccaa tgaagtaact aagaccactg gttcyagtyc ttcctgtagt | 480 |
| ggaaagagrt agagaagagt gatagtaaca aagtattctc attactctag aacagagatt | 540 |

-continued

```
gscaaacatt tttctgtaaa ggsccagatg gwatatactt ttggcttcgt ggsccatagg      600
gtctctgtta aaactgctca actctgtctt tggggtggga aagcagcagt agacactttg      660
taaatgaatg ggaatggctg tgttccaata aactttatt tacaaaaata ggctgtgggc      720
agcatttagc ctgtgttctg tagtttgccc atccctgctc tataaaaaga gtaggaaact      780
atgccccagg gccaaatcca gcctgaagcc tgttttttgtt tggtcacaga gctaggaatg    840
gtttatttgt tttcaaagag ttgttaaagg aggagaggga agaggagagg aaggaaaagg      900
tagaagagga gaggaaggga gagaaatagg aagaggaaga agaggaagaa aaccttatgt      960
ggcccacaaa gcgtaaaagt tgaccatttg gacctctatg gaaaaagtct gttagatctt     1020
gctctgagag attgtttact tgtaacttcc ttgataattt caacttatgg atttgatttt     1080
gtgctcattt tctattttcc tatgcttata gtcttcgtaa tatgaagcaa gtaagtttat     1140
tagtcagata aaatacagaa tttaaaattt tggtaatgta ttggctatca gaaaaaatac     1200
tgattgcttt ctatgtcact ttattctttt gaaatttgag atttttataag aaattttgaa   1260 aatgtatatt attctcttgt cttgaaaatg tttttaagtg ggaatataag aaacaaggat    1320
gtgttgctgc ttaattctgt gcctgaactt tggagtcttc tgatctgtgt ttgggacaga    1380
gaatgctcta gctatgctaa aaccttttca ataattgtaa cgttgtttga tgttagcaaa    1440
aaaaaaaaaa aaaaactcgt a                                               1461
```

<210> SEQ ID NO 50
<211> LENGTH: 1238
<212> TYPE: DNA
<213> ORGANISM: Homo sapiens

<400> SEQUENCE: 50

```
ccctcacatc agggaaaatg accttcactg ctgttaacag taatgkgtcc ctttcatttt      60
ctggatcaag ccttctcagc ggtgggtctg gatgtgggta aactaaggta aaggggatga     120
tattccacaa actaattatg cacacagaaa atctgtggag cctatcagac cccaagtgtc     180
ttgaaatgtt tgtagaaacc cactaaaatg ccccttctct gggtgtgggc ccttattgca     240
gctgtctcac agcctgagct gtggtacaga gaaatggggg ttctccttttt attttcatttt   300 tttttcccca atggcagctt ttctcccgtt gttttacctt cctatttccc aaacagttcc    360 tcttatttg tcttttgcac cagtttctgg aggcccttgt catttcaaaa aggatagtct     420
cttttcttac tctggcaaac ctgtgagtga ttccacaaag atacagtatt acttagctaw    480
ctgaattatg atagaaaagg tcctagttag gttcctatat aaagcatttg gaagatgacc    540 tgttgccct tgaaacttga aaatagggat tctggggtga ggatacaaag acattgtctt     600
gcatatccat aagcaggtct tagagcatta ttccaaactc tagctgtttc agtagttcta    660
tgaggattgc aagtcatagg tgtgtgtggc atatcagtcc atctccctca tctccattct    720
cagtttcttc cccacaaaat ttggaatcaa gcttttatg acgtttgcca attgcagaac    780
ttcttcagct aaggttaatt tgacgctatg ataaaactga gagatgtcaa aaagcctctt    840
agaaatttta atcttgaaag acttttcagg gtatctcatt ttttaggtgg gggtggcagg   900
tgtatttctt ttttaacaaa taaaaggcat ttaagtaaaa ctaaaatgaa aaaagtaggc    960
cttctgacat tgtgtacttg gtggttctgt ccctctgcct gtaacaaatc tcattttttgt  1020 taccaagaac tgtatgaaag aagtaaatcc accccgattc tgtatgatta attccatctg   1080
tgtttgtcat ttctgactgg aaaacttctt actccatacc ttgttcgata tggaggacaa    1140
```

```
ataattggat tgtctgataa gtctgccaat aaactatcca gaaatagcaa gtgtaaaaaa    1200
aaaaaaaaaa aaaaaaaaaa aaaaaaaaaa gggcggcc                           1238

<210> SEQ ID NO 51
<211> LENGTH: 2581
<212> TYPE: DNA
<213> ORGANISM: Homo sapiens

<400> SEQUENCE: 51
gctgacattg atacaggtca aaatgcgtag atgcttttg gtgttggaaa taagtgtctg     60
tcttatggtc atcattgtct tcttagattt ttgggtaggg ggggccaggta ggggagact   120 cagaaataaa agcgttcccc agataacttc aatctggaaa gaattttttg tatagagtcc   180
atctctccct caagactgac cacaggtttc atgagaaggt ccctgaaaac atcacatttc   240
tctgaagaac catcaacttg tcttttcttg aaccacagga atggttctac agaccctact   300
ataattcttc acatttcaga acccatgttt aatggaggga agagagaaat gcatgggaa    360 aagaacacct cctttctcc tttctcttaa attcaaagac gtttgctttg ggaatgccct    420
cacttctccc tattcacagg cttctaaaat cattaattta ctcaaggcac atgtgccttc   480
tttgccccaa atgcatcact ttcctttag ttatggctga ttttgggtgt gtgtgtgtaa    540
gacatgcagt caacaaygag atgaaggcca ttgcatagat ctcatgcaga tagtgatgga   600
ttcagaaagt aggttccagt ggcgtcacta ccttcttgta agccagtata cactggctat   660
ttgtggaaat ctctttggga gatcaaatag agtattatgc cactgtgagt gtttataaac   720
tggaaggaac aagtacctgt gtttcttggg acacaaagca ctcagatcct gagtggatgc   780
agacatgaga gtaaatgtca gcccaaatta ggcccctcga cctacagaca tttcatgggt   840
tttatttaat cacaccccat ggtttggggc tacatgagga agttggtaat gagctgaatt   900
tcttattcag tggaaaaaac tgaaactgtc taaaaacacg ggatatattt tagaggcaat   960
tgtggaagcg gagagaatga gatgatggtg ttcagaggga ccagcttctt tttcagttgt  1020
ctttagaact caagaataat caataattta gtgccccttc aacagccata ctcagcaaga  1080
agaatcagaa gcttgatcct ctaacagaaa tagaagaggg tagctttgcc cattgccact  1140
gtctttactg cccttctgc ccctccaccc acatccacat tcagcatcac tccaaggatg   1200
tgtcagcatc ttgcccatgc aggtagaaat ttgtgagtag gcctccatac ttcctcgggg  1260
gaagaaagag aaactagtgc tggttttaag aatgtagctg gcttttcatc agaacccta   1320 tgctaacctg accacacttg ctctcgggga gttcaagcc tgtgatgtgc ataaactcca   1380
acaagcctgg ctttggtgtt cagcatgcac attccataaa tatctcttgc aggcataccc  1440
cacagctaga ctgcaggatt aaaataactt ccaaaaggtg ctggattgga gtttgttcaa  1500
atttctcatt aaccactaat gttaattcat accaaatgca agtattcta aaccagctga   1560 tgctgtcagt gttcaagttt taagtgactt caaacacaat ggaagtgttt caatgggagc  1620
cagatctcat gagtaaaaat ccattttata atagctctgt gatatatcag tgggagatga  1680
ttcatagggg agagatttga acaagcagaa ttaagtgtta gcaaaaatgc tgcattgctt  1740
tgattcatgt ttaaagacct aaatttctat gcacaaggaa taagggcct acttaccaag   1800 tgtaaatcac aacataggct accaaaatat ttcttatttg ctaggagaac aaagctgtca  1860
cggtgcatga tagttggaca gagatggcta aaaagaggc aaattcgat ttggaaacag    1920 ggtggcctct tcattatta ttgccaagat ctgaaaatct tcaacatctt ataagacaac   1980
aatgaagtag cccctgaaca gcatggagtt gctgtgagtt tgttcgttgc agacctttgt  2040
```

```
gttgggtcct gggaatctga gctttgttcc ctgtgcatgg tggataattg aaaccaagag    2100
gacatgggat agaccttgtg acagaccaat tctgtgaccc ctgtcttctg ggtcacatta    2160
ttcattgttg atttaaatac aggactacca aacagtacaa atctatcatg agtctggtag    2220
aaaagtaaaa gtaaaagctg cacacgttac atactgttta ttgttctaat gtacaactaa    2280
ctatttgcat ataatgtgat ttaatttatt gctgttttgt gtagaaaagg agaactaatg    2340
actgtggata taacccatgt tttgtataat atattttatt tcttgtgcga actggtcatt    2400
taaaatatct acttcatttg atgtttggat ataaatgtgt atgtgtcctt gtaaatgttt    2460
ctatcaagca agaatgccac gtactcagag tataacaatg tgttctcatt aaaaaataca    2520
tcccaaaaaa aaaaaaaaaa aaaaaaaaaa aaaaaaaaa aaaaaaaaaa agggcggccg    2580
c                                                                   2581
```

<210> SEQ ID NO 52
<211> LENGTH: 991
<212> TYPE: DNA
<213> ORGANISM: Homo sapiens

<400> SEQUENCE: 52

```
gaaactttgt attttggtag cactacatag aaaatgtgtt ttagatttat gatgatcata      60
tttctcacca atgtaatttc agtctcagca gtgattttca aacttaggga aagggacagc     120
attagatttt tttttttttt cattttttta aaatgatatc ttacctgaaa ctacaaacga     180
caaaagagaa ttagaaatgt tgaattaaa gtgaagaagg gttgggggag atgggcctga     240
acccacttcc tgtctcaatc catgctaccc caaacactcc agggaacctc tgaggtttta     300
ttgggtgcac tttgaaaatt tctcttctat agtgtgtttg tttgatttta aatcacagag     360
aaaactgggt tttactctta gagaaacatt ttcatccagt tttttagttt gcttcatttg     420
acttcctaaa tcatttttga gttcacaagg atttggtact tttctgttta gctttctctc     480
tctaagcttt atctaccttta aaaacaaagt ccttttttta atggccagtc caaccaattg     540
atttctcaaa ctgaagtgcc caggtgtgga ctcatcaatt tccgttagaa tagggacatc     600
ctacttaaga gttggtgcag ctccaaggag ctgacttgtc cttgcttggg gttttttttt     660 tttttttcttt caccttctca agtttccatg gcctttgtgt gttcttttta tgttgattta     720
aattcatatg gttttccaca aatcccttct ttggctacat tgtctcctta ttcaatggat     780
tatccctttg tggggctgc ttatttttaaa gatgttgggg gggaaacaaa cccaaatcta     840
cgagcagtag ttgcacatag ttgccagttt taccttctta gtcattagat ttccaaacca     900
tgttgcagtt ttttggtcca gatatagtat ttctttctaa taaagttttta tgttgctgct     960 ctaaaaaaaa aaaaaaaaa aaaactcgta g                                    991
```

<210> SEQ ID NO 53
<211> LENGTH: 2422
<212> TYPE: DNA
<213> ORGANISM: Homo sapiens
<220> FEATURE:
<221> NAME/KEY: SITE
<222> LOCATION: (388)
<223> OTHER INFORMATION: n equals a,t,g, or c

<400> SEQUENCE: 53

```
 aggcccttct ggaacacagc agggcctaca acgaggggcc tttgcaatgg gctgtgagga      60
tgggggtggt gggaagaatt ggccacgttg gagaccccat gccaccccac catggtgagt     120
```

-continued

```
gctctgtgcc tcctgctcac ctgtggtgag ctgggcgagc tgggcgagct gggcgagctg      180
ggctggggag agcctgtgag gaccgagagg agaaatgaga agaaggaaca aaaatattat      240
ttctatgtaa tttatatttt acttatgcca aattatttat gataatttgc cattgctata      300
ctgtaccagt gtcaaatgct gcagcctgcc aagctgtgat tttgtgaggc ttgtccctat      360
gtaggatgca ccgcaggccc ctggcacntg aaagagtgtg cagtggactg tgggtctccc      420
atatgcggtg ccgcccaaag gtggcttttgc ctcaagcaac ctaccctgat gttttactca      480
ttggaatgtt tttccccgat gtgtgatgac ttcttttctg atggagagag tccaggaggg      540
atggaaaack cctggattta agctcagcat cccccacatg ggcttttcga tcatcttcag      600
gcctgaagct gcacgacctg aagttcgcct gcatttatca gccctctttg tgctgctcct      660
tgccaccttg gggttcctgc tggggaccat gtgtggttgt ggcatgtgtg agcagaaggg      720
aggatgagga aaagagaag aaaccccggt actgacaagc tgttttgag tgccactgtt      780 tgccatcatc taagccactg aatcaagtgt atttcaggct tatttcaaca ttccaatgcc      840
ctggttttcc tgcttgaatc tgttcgtggt caaaggtttg ggggaatttg tgaccctgga      900
acatccccag agtgaaagat ggagctgggc cacatcagaa taaggccttg gccccatcct      960
ctcacagcct aggtgctctg caggcatgct gactgtcctg attgcgatcc agcccgaaat     1020
tccctcctct gctttcaaaa gtcaaatccc ccattcttag gccacactgg tgtcacaagc     1080
tcctgtcagg gagctggggt ttgggaatgt gctttgtgaa ctctgcttta aagtgagggg     1140
ccgaggaaaa cttagaaaca ggcagagttg gaagcagcca aatcacagtg ggtgttgtgt     1200
gtgtgtgcgt gtgtgcatgc gtgcgtgtat gcgtgtgtga aagcaggtgg accattccac     1260
tttttagctc ctattgatgc accaaaccaa gtgcctcatt tctgtgccaa atgtttgcct     1320
tggtcgttgt ggacctcctt tctctaacttg cggtggcatg actgtcagga ggtgctggca     1380
ttttcagcag atcctcatgt gttgaccctg atgtctttag cagaggcctc tagcatctcg     1440 gttttttcatc cactgcagga atgtggccac agggagcaga ggtttgtact tccccaaga     1500 ggtcctcatc ctgagacggt ctctacccat gtttaaccca aagagtgcag gccaggttcc     1560
ttatccttct gatgaaggat gagagagctc atttagaagt cagagcaaac tagggtctca     1620
gtattgagaa acgcagcctg ccagggaatc acagagacat cggggtgccc gcgatggccc     1680
tcatgaagcc atgcctcgac ggcattcagg aagccctgca aacgtgcttt ttgaactcat     1740
tggccaggtg tgatttttac acaaggtaaa cgtggtcaag ggcatcgggg aatttgctcc     1800
aagcagatag ctccctctga ggaaccaaag gaagcaagtt tccacgattt ctgaagagct     1860
ggtataggaa gtttctttct tccttttgtg ttacatgtgc attaaacaga acaagctgtg     1920
tgtcatcaca gattgtactg tgggctcaga accgtgaga gagcccccac cgtggacacc      1980
ggctctaggg ccacaggaaa aggaacgttt ccaggcattt tgtctccagg ctcccgctg      2040 gacaggcacg tactgccctg gggagtaaat gcggagagtt cacgaactgt gcccaacgca     2100
tgttatagcc agggtcctac taactactca gtaaagaac gtattgttgt attcctccag      2160
tgttaagcta tagccatgtt aaagtcact gtgcatttat tctcagcatc aaataccttg      2220
taacgtcttc tctgccttgt tagtgcatat ttttactttt ctgatactgt aagaatata      2280 tccagtatgt aaatgaatgt tctataaatc ttttgtatag tcattttctc tgctccttaa     2340
atatcatctc tattcagagt ataataaaat tatgaacttg gtaaaaaaaa aaaaaaaaa      2400 aaaaaaaaa  aaaaaaactc ga                                              2422
```

<210> SEQ ID NO 54
<211> LENGTH: 985
<212> TYPE: DNA
<213> ORGANISM: Homo sapiens

<400> SEQUENCE: 54

| | | | | | |
|---|---|---|---|---|---|
| gtcggcacga | gtaataaaat | ctaacacctg | cttagagacc | attcttgtag | tggacacaaa | 60 |
| gtgccagcct | ctaatactcc | ttccttactc | ttcatggaaa | ccttgaagag | tgattaaaaa | 120 |
| tagtactgtt | tatgtctctg | accacagagc | cagtcatttt | cagcacttaa | ctgaaattgc | 180 |
| tcatgatagt | gtttctaaca | atggccacat | aagtggcaaa | tcccttaaga | attttgccct | 240 |
| ctcagcaggt | ggcaatctgc | cacctttatc | tgatcatttc | tctcctcctt | tggcattgta | 300 |
| gacaccattt | tttcctggtt | atgaccctac | ttctctttat | cttctttgtc | gattgctttt | 360 |
| ccactccagg | gagttctgtg | tttgacacac | aggaggtgtg | ggtagttgtt | tactctgtaa | 420 |
| ataagttgtt | agccgtgcag | cactgccaag | gaattgcacc | aaatgtgtat | gcattagcag | 480 |
| ttaagaagag | cgtgtgcaat | gttagtgaat | ggagtctggt | catttgtcat | ccaatgccta | 540 |
| tttagcacct | gttatgtgac | agataacagg | ccggcactcg | gatcataacc | cggagcaaca | 600 |
| tagtcagaaa | caaacacaat | ttctctcctt | ggtaagcctg | gtctgttggg | aggtttgata | 660 |
| agtaaaaaga | agactgagar | gccgggagcg | gtgctcasgc | ctgtaatccc | agtactttgg | 720 |
| gaggccgarg | tgggtggawc | acctgaggtc | aggarttcaa | gaccagcctg | gccaacatga | 780 |
| taaaaccccg | tctctactaa | aaatmcaaaa | cctagccarg | catggtggca | ggcgcctata | 840 |
| atcccagcta | ctcgggggct | gaggcagaag | aatcgcttga | acccgggagg | cagaggttgc | 900 |
| agtaagccga | gatagcacca | tcgcactcca | gcctagggga | caagagcaag | acttcatctc | 960 |
| aaaaaaaaaa | aaaaaaaaac | tcgag | | | | 985 |

<210> SEQ ID NO 55
<211> LENGTH: 932
<212> TYPE: DNA
<213> ORGANISM: Homo sapiens
<220> FEATURE:
<221> NAME/KEY: SITE
<222> LOCATION: (888)
<223> OTHER INFORMATION: n equals a,t,g, or c
<221> NAME/KEY: SITE
<222> LOCATION: (890)
<223> OTHER INFORMATION: n equals a,t,g, or c
<221> NAME/KEY: SITE
<222> LOCATION: (892)
<223> OTHER INFORMATION: n equals a,t,g, or c

<400> SEQUENCE: 55

| | | | | | |
|---|---|---|---|---|---|
| aattcggcac | gaggagcatc | gctacttcaa | ggccaatgac | acgctgggct | tcatgcttat | 60 |
| gttggctgtg | ctcatggcag | ctacccatgc | tgtctacggc | aagctgctcc | tcttcgagta | 120 |
| tcgtcaccgc | aagatgaagc | cagtgcagat | ggtgccagcc | atcagccaga | actggacatt | 180 |
| ccatggtccc | ggggccaccg | gccaggctgc | tgccaactgg | atcgccggct | ttggccgtgg | 240 |
| gccatgccac | caaccctgct | gggtatccgg | cagaatgggc | atgcagccag | ccggcggcta | 300 |
| ctgggcatgg | acgaggtcaa | gggtgaaaag | cagctgggcc | gcatgttcta | cgcgatcaca | 360 |
| ctgctctttc | tgctcctctg | gtcacccta | catcgtggcct | gctactggcg | agtgtttgtr | 420 |
| aaagcctgtg | ctgtgcccca | ccgctacctg | gccactgctg | tttggatgag | cttcgcccag | 480 |
| gctgccgtca | acccaattgt | ctgcttcctg | ctcaacaagg | acctcaagaa | gtgcctgagg | 540 |
| actcaygccc | cctgctgggg | cacaggaggt | gccggctccc | agagaaccct | actgtgtcat | 600 |

```
gtgaagcagg ctggtaggca gacaggcaga gagaaggtca tggccaccgt gatggggcca    660
acagcaaggg aggggtaggg gcccatacag gagtcctcct ttctgagctc agccccagcc    720
cctcgaacca cctgtaatct aggcaccttt gccaacacct yccaaggatg gaggactggg    780
cgagggactg ggaaagaggc atatttagtt ttgtggggcc tgtctccgct gcctccttct    840
ccacttctac aatctcattc tctctctctc tctctctgtc tctctctntn tntctgtgtc    900
tcagaagtga caattcaaaa aaaaaaaaaa aa                                  932

<210> SEQ ID NO 56
<211> LENGTH: 957
<212> TYPE: DNA
<213> ORGANISM: Homo sapiens

<400> SEQUENCE: 56
gcatttctgc tcctgatctg ccctgtcgat ttctaaccat cagggctttt tcatgttatt     60
actgatgctt gtraacacgt ctgctgtagc ctgcactcac ggaggcagag ggccgtgggg    120
gaactctgca gcccaagctt gcgccgcgct cgcccgtggc ccaggcagga cccttccgcg    180
gcctcccagt ggcagccaca ggtgctggtt ggtttgctga rctatacgg gtggggtggg     240 cagcgtctga gtccttgccc gagaagcatc tgctgtgtgt ccacgaggca cctggagggg    300
gccagatcca aggcacaggg ccctgctgca tggctccaca tggaagttcg agtccccgt     360 gtccagccgc cggccctgca ggtgcccagc agctctgaca aagcggggca gggccgctgg    420
ggtgtccctg gacagcgggg cctggtgggc aggggaggag gctgcaaggt gacacccagt    480
ttgccttgca gacgtacgga gcgcaagagg acggcagcgt cggcgaaggt gacctgtcct    540
gcatcctcaa gacggccctg ggggtggcag agctcaccgt gaccgaccta ttccgagcca    600
ttgaccaaga ggagaagggg aagatcacat tcggtgagcc cgcaggagtg gggtcgtcct    660 cgcgacccctt gggcggggc tgggcagagt gtggggcgag tctccgtggg agcccaggac    720
aggagtggag tccccgccat gcctccattc accaggctgc cctgtgtaac aaagaaaccc    780
ctgagaagga aggttctgga gacctggcag ggttcgtagg gagctttcca atctgatttg    840
ttttggcgat ttatacaacc aaactccaag cccagttccg aagctctgag ccttccatgg    900
cctcaggctg ggattcaggt gcctggaggt gggggatacc cgcacccagc cctcgag      957

<210> SEQ ID NO 57
<211> LENGTH: 1433
<212> TYPE: DNA
<213> ORGANISM: Homo sapiens

<400> SEQUENCE: 57
ggcagagcac ttatgtkttt ggcattctcc gtcatcattc tggccggggc gggcagttct     60
aggagttgga actcagtcct ggtggaaaag gaagtcgtgg agggagggct agggccgtgg    120
gggaactgct ctgctgagcc tcttcctcac ctgctgcttc ctaggactaa cctgaaggct    180
aaggtaccag gctgaagtca gtgctcagaa accaatcgt cattctttgg ggttttttt      240 cttgaagagc cactttctct ttaccttgtt ctagcctgtt ggaggtaggg tttctgcaat    300
tccaaaggcc gtacacagcc tctcaccatc agaccacttt ttaaggctct tcgttcatac    360
ctagctcgaa gattcacttc ctcaggaagc catttagtt acaaatctgg gaaaacttaa     420
aatgctttca ttgtgccatg ttttctgttg cagcttcagt accgtaccta gtggtcaggc    480
atacttacaa gtttctttt acagtaaccc cttgtggaca tctaataaat ggtcattatt    540
ttttagtact agtttgtttt cctgaacact gtaagatctg tgactgacgt ttgataccctt   600
```

```
aaagcagtgc catataataa ctacccacta tttgttcttt atttctgtca gataaaaatg    660
ttctatgtag tgtctacagt catttttttt ttaactagaa tttagatttg gaagtagttt    720
ttctattagt tgatttgcat gaaatacaaa attaggaaaa ggcttattcc acctcaacct    780
agttgaacta ttaatgattt tttttttttt ttgaggattt gggctctttc tagatagaaa    840
atcaccctga acttctagct ttgcattgtg aagtgagcat catgaagatg agaaaatgtt    900
gggagatcat ttttgcaaag gcataatag tcggcattca gatatgagtt aactgcagag    960
ggaaaattgc aagctgtcat gttggccttg ttcctctcaa ccttctggta acctaacaag   1020
ctcctacagg ttgtatgtga aattgcaaga tgattatata gccctgttga atttacaacc   1080
agatcttgct ttcaaaccat tattagccaa gggtttgatt ccacacctgt gttcatggat   1140 ttttggtat tagacattgc tgtaactctg ttttcacttt ttcatctgtt atcttggctc     1200
acttaaggga gaaggtatca gcagcctagg accacttggt ttctgttttt atgtttcata   1260
gttcatggct gataaaaatt acctgtcctt aggccgagtg cagtgcctca cacctgtaat   1320
cccagcactt tgggaggccg aggtgagtag atcacctgag atcaggagtt cgagaccagc   1380
ctggacaaca agagcaaaac tccatctcca aaaaaaaaa aaaaaaact cga            1433
```

<210> SEQ ID NO 58
<211> LENGTH: 1940
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<221> NAME/KEY: SITE
<222> LOCATION: (1573)
<223> OTHER INFORMATION: n equals a,t,g, or c

<400> SEQUENCE: 58

```
tcganccacg cgtccgcgga cgctgggcgc aacaaagcct tctacttgag cagttttttcc    60 atcactgata tgtgcaggaa atgaagacat tgcctgccat gcttggaact gggaaaattat   120 tttgggtctt cttcttaatc ccatatctgg acatctggaa catccatggg aaagaatcat    180
gtgatgtaca gctttatata aagagacaat ctgaacactc catcttagca ggagatccct    240
ttgaactaga atgccctgtg aaatactgtg ctaacaggcc tcatgtgact tggtgcaagc    300
tcaatggaac aacatgtgta aaacttgaag atagacaaac aagttggaag aagagaagaa    360
catttcattt ttcatctacr yttttgaacca gtgcttccta atgacaatgg gtcataccgc    420
tgttctgcaa attttcagtc taatctcatt gaaagccact caacaactct ttatgtgaca    480
ggtgagttct caacacctag accatctgat attttttctta taatgtttcc aggaagaggg    540
gggttcagtt tctcaagtga ttatgttaga aagccaactc ctatagcaca tctgaaatct    600
gctacacctc acagattgtt atgtgccagt gtgtacatat gtgtgtgtat gtgtgcgttt    660
gargtgagtg agatagagga gagtagakaa atagatagta aaagttattg ttttttgactt    720 tagggattat aaaatttatt tgataagtcc aaaagtagac cactgaaata ttgaaaaaat    780
tataaagtga ataccttatag ttgcgaatag ctctgtgatt gcttgtcctt ctttgttgtt    840 tttttttct cttttccca ttttttctctt ctttactttt gttcattaca atttcttgaa    900
gttatgtttg tggtgcttag gcaattaaac acttcttaat agttcacagt tgtttagag    960 gaaaacagc aaacaactaa ctgacttcct agtgattttc tgggaatatt cagagyttca   1020
tctytyttcc ctgttccccg aaagaggcct ttaatatgct ttgacaactg aggaaggaca   1080
```

-continued

```
gatagaagtt aagcttgggg aaaccaagct gaataaaaca tgaaaaaata catagggggg    1140
gagtaggtaa gagtaaaaaa tacttggttt ataaaaattt tatagccaac atcatattca    1200
atggtgaaag gcttagagct ttccccctaa gaacaggaac aagacatgga tccttgcttt    1260
tgccatttcc atttaacatt aaactgaaaa ttctagccag agcaaacagg caagaacaag    1320
aaataaaaga tatctaactt agaaaaaaag aagtaaaact ttattcacag atggcatgaa    1380
cttatgtgta gaaaaattct taaaaatttg tttaaaacta ttaaagctaa tacatgaatt    1440
tagcaattcc acatgataca ggatcaacac acmaaaatca gtgatatttc tatacactag    1500
caataaacaa tccacaaaga aaattaagga aacagttcca tttacaatag catcaaaatg    1560
aataaaatat ttnagtacaa atttaaccaa agaggtataa gagttgtaca ctgaacaaag    1620
aaagcatggc tgaaagaaat tcaagaatat gtaaataaat gcaagacat  tctgtattca    1680 tggactgaaa gatgtaatat tgtaaagata gcaatattcc ccaaggtgat ctacagattc    1740
aatgcagttc cactaaaatc ctaacagctt tttgttgcta ttgcagaaat aaaaaagctg    1800
atcctaaaat tcacattgag ttgcaacaga cccagaattg ccaaaacaat cttgaaaaag    1860
aacaaaactg aagctaagac ttccctattt caaaacttac tacaaaatga cagttaaaaa    1920
aaaaaaaaaa gggcggccgc                                                1940
```

<210> SEQ ID NO 59
<211> LENGTH: 1715
<212> TYPE: DNA
<213> ORGANISM: Homo sapiens

<400> SEQUENCE: 59

```
gggagttggc agcggggttg ggtggagctg ccatctgctt aagacagccc cttgaccgtg      60
ctgcccgaag atggatatgg ctctgactcc cacctctctt cccaggtcgt ccggggggccc    120 accatgctgg tgactgccta ccttgctttt gtaggcctcc tggcctcctg cctggggctg    180
gaactgtcaa gatgccgggc taaaccccct ggaagggcct gcagcaatcc ctccttcctt    240
cggtttcaac tggacttcta tcaggtctac ttcctggccc tggcagctga ttggcttcag    300 gcccccctacc tctataaact ctaccagcat tactacttcc tggaaggtca aattgccatc    360
ctctatgtct gtggccttgc ctctacagtc tctttggcc tagtggcctc ctcccttgtg    420
gattggctgg gtcgcaagaa ttcttgtgtc ctcttctccc tgacttactc actatgctgc    480
ttaaccaaac tctctcaaga ctactttgtg ctgctagtgg ggcgagcact tggtgggctg    540
tccacagctg ctcttctcag ccttcgaggc ctggtatatc catgagcacg tggaacggca    600
tgacttccct gctgagtgga tcccagctac ctttgctcga gctgccttct ggaaccatgt    660
gctggctgta gtggcaggtg tggcagctga ggctgtagcc agctggatag gctggggct    720 gtagcgccct ttgtggctgc catccctctc ctggctctgg caggggcctt gccttcgaaa    780 ctgggggggag aactatgacc ggcagcgtgc cttctcaagg acctgtgctg gaggcctgcg    840
ctgcctcctg tcggaccgcc gcgtgctgct gytgggcacc atacaagctc tatttgagag    900
tgtcatcttc atctttgtct tcctctggac acctgtgctg acccacacg gggcccctct    960 ggcattatc ttctccagct tcatggcagc cagcctgctt ggctcttccc tgtaccgtat   1020
cgccacctcc aagaggtacc accttcagcc catgcacctg ctgtcccttg ctgtgctcat   1080
cgtcgtcttc tctctcttca tgttgacttt ctctaccagc ccaggccagg agagtccggt   1140
ggagtccttc atagcctttc tacttattga gttggcttgt ggattatact ttcccagcat   1200
```

-continued

```
gagcttccta cggagaaagg tgatccctga cacagagcag gctggtgtac tcaactggtt    1260
ccgggtacct ctgcactcac tggcttgcct agggctcctt gtcctccatg acagtgatcg    1320
aaaaacaggc actcggaata tgttcagcat ttgctctgct gtcatggtga tggctctgct    1380
ggcagtggtg ggactcttca ccgtggtaag gcatgatgct gagctgcggg taccttcacc    1440
tactgaggag ccctatgccc ctgagctgta accccactcc aggacaagat agctgggaca    1500
gactcttgaa ttccagctat ccgggattgt acagatctct ctgtgactga ctttgtgact    1560
gtcctgtggt ttctcctgcc attgctttgt gtttgggagg acatgatggg ggtgatggac    1620
tggaaagaag gtgccaaaag ttccctctgt gttactccca tttagaaaat aaacactttt    1680
aaatgatcaa aaaaaaaaaa aaaagggcg gccgc                                1715
```

<210> SEQ ID NO 60
<211> LENGTH: 308
<212> TYPE: PRT
<213> ORGANISM: Homo sapiens
<220> FEATURE:
<221> NAME/KEY: SITE
<222> LOCATION: (165)
<223> OTHER INFORMATION: Xaa equals any of the naturally occurring L-amino acids
<221> NAME/KEY: SITE
<222> LOCATION: (247)
<223> OTHER INFORMATION: Xaa equals any of the naturally occurring L-amino acids
<221> NAME/KEY: SITE
<222> LOCATION: (308)
<223> OTHER INFORMATION: Xaa equals stop translation

<400> SEQUENCE: 60

```
Met Gly Thr Gln Glu Gly Trp Cys Leu Leu Cys Leu Ala Leu Ser
 1               5                  10                  15

Gly Ala Ala Glu Thr Lys Pro His Pro Ala Glu Gly Gln Trp Arg Ala
                20                  25                  30

Val Asp Val Val Leu Asp Cys Phe Leu Ala Lys Asp Gly Ala His Arg
            35                  40                  45

Gly Ala Leu Ala Ser Ser Glu Asp Arg Ala Arg Ala Ser Leu Val Leu
        50                  55                  60

Lys Gln Val Pro Val Leu Asp Asp Gly Ser Leu Glu Asp Phe Thr Asp
 65                  70                  75                  80

Phe Gln Gly Gly Thr Leu Ala Gln Asp Asp Pro Ile Ile Phe Glu
                85                  90                  95

Ala Ser Val Asp Leu Val Gln Ile Pro Gln Ala Glu Ala Leu Leu His
            100                 105                 110

Ala Asp Cys Ser Gly Lys Glu Val Thr Cys Glu Ile Ser Arg Tyr Phe
        115                 120                 125

Leu Gln Met Thr Glu Thr Thr Val Lys Thr Ala Ala Trp Phe Met Ala
    130                 135                 140

Asn Met Gln Val Ser Gly Gly Pro Ser Ile Ser Leu Val Met Lys
145                 150                 155                 160

Thr Pro Arg Val Xaa Lys Asn Glu Ala Leu Trp His Pro Thr Leu Asn
                165                 170                 175

Leu Pro Leu Ser Pro Gln Gly Thr Val Arg Thr Ala Val Glu Phe Gln
            180                 185                 190

Val Met Thr Gln Thr Gln Ser Leu Ser Phe Leu Gly Ser Ser Ala
        195                 200                 205

Ser Leu Asp Cys Gly Phe Ser Met Ala Pro Gly Leu Asp Leu Ile Ser
    210                 215                 220
```

```
Val Glu Trp Arg Leu Gln His Lys Gly Arg Gly Gln Leu Val Tyr Ser
225                 230                 235                 240

Trp Thr Ala Gly Arg Gly Xaa Leu Cys Gly Arg Ala Leu Pro Trp Ser
            245                 250                 255

Leu His Asn Trp Ala Trp Pro Gly Met Pro Pro Ser Pro Cys Pro Ala
            260                 265                 270

Ser Leu Tyr Arg Thr Arg Gly Pro Thr Phe Ala Arg Ser Pro Pro Leu
            275                 280                 285

Cys Thr Glu Leu Ser Arg Ser Ser Ser Thr Ser Lys Leu Pro Leu
            290                 295                 300

Lys Tyr Asp Xaa
305

<210> SEQ ID NO 61
<211> LENGTH: 579
<212> TYPE: PRT
<213> ORGANISM: Homo sapiens
<220> FEATURE:
<221> NAME/KEY: SITE
<222> LOCATION: (64)
<223> OTHER INFORMATION: Xaa equals any of the naturally occurring L-
      amino acids
<221> NAME/KEY: SITE
<222> LOCATION: (574)
<223> OTHER INFORMATION: Xaa equals any of the naturally occurring L-
      amino acids
<221> NAME/KEY: SITE
<222> LOCATION: (579)
<223> OTHER INFORMATION: Xaa equals stop translation

<400> SEQUENCE: 61

Met Arg Ala Ala Arg Ala Ala Pro Leu Leu Gln Leu Leu Leu Leu Leu
  1               5                  10                  15

Gly Pro Trp Leu Glu Ala Ala Gly Val Ala Glu Ser Pro Leu Pro Ala
             20                  25                  30

Val Val Leu Ala Ile Leu Ala Arg Asn Ala Glu His Ser Leu Pro His
         35                  40                  45

Tyr Leu Gly Ala Leu Glu Arg Leu Asp Tyr Pro Arg Ala Arg Met Xaa
     50                  55                  60

Leu Trp Cys Ala Thr Asp His Asn Val Asp Asn Thr Thr Glu Met Leu
 65                  70                  75                  80

Gln Glu Trp Leu Ala Ala Val Gly Asp Tyr Ala Ala Val Val Trp
                 85                  90                  95

Arg Pro Glu Gly Glu Pro Arg Phe Tyr Pro Asp Glu Gly Pro Lys
            100                 105                 110

His Trp Thr Lys Glu Arg His Gln Phe Leu Met Glu Leu Lys Gln Glu
            115                 120                 125

Ala Leu Thr Phe Ala Arg Asn Trp Gly Ala Asp Tyr Ile Leu Phe Ala
            130                 135                 140

Asp Thr Asp Asn Ile Leu Thr Asn Asn Gln Thr Leu Arg Leu Leu Met
145                 150                 155                 160

Gly Gln Gly Leu Pro Val Val Ala Pro Met Leu Asp Ser Gln Thr Tyr
                165                 170                 175

Tyr Ser Asn Phe Trp Cys Gly Ile Thr Pro Gln Gly Tyr Tyr Arg Arg
            180                 185                 190

Thr Ala Glu Tyr Phe Pro Thr Lys Asn Arg Gln Arg Arg Gly Cys Phe
            195                 200                 205

Arg Val Pro Met Val His Ser Thr Phe Leu Ala Ser Leu Arg Ala Glu
```

```
                210                 215                 220
Gly Ala Asp Gln Leu Ala Phe Tyr Pro Pro His Pro Asn Tyr Thr Trp
225                 230                 235                 240

Pro Phe Asp Asp Ile Ile Val Phe Ala Tyr Ala Cys Gln Ala Ala Gly
                245                 250                 255

Val Ser Val His Val Cys Asn Glu His Arg Tyr Gly Tyr Met Asn Val
                260                 265                 270

Pro Val Lys Ser His Gln Gly Leu Glu Asp Glu Arg Val Asn Phe Ile
                275                 280                 285

His Leu Ile Leu Glu Ala Leu Val Asp Gly Pro Arg Met Gln Ala Ser
290                 295                 300

Ala His Val Thr Arg Pro Ser Lys Arg Pro Lys Ile Gly Phe Asp
305                 310                 315                 320

Glu Val Phe Val Ile Ser Leu Ala Arg Arg Pro Asp Arg Arg Glu Arg
                325                 330                 335

Met Leu Ala Ser Leu Trp Glu Met Glu Ile Ser Gly Arg Val Val Asp
                340                 345                 350

Ala Val Asp Gly Trp Met Leu Asn Ser Ser Ala Ile Arg Asn Leu Gly
                355                 360                 365

Val Asp Leu Leu Pro Gly Tyr Gln Asp Pro Tyr Ser Gly Arg Thr Leu
                370                 375                 380

Thr Lys Gly Glu Val Gly Cys Phe Leu Ser His Tyr Ser Ile Trp Glu
385                 390                 395                 400

Glu Val Val Ala Arg Gly Leu Ala Arg Val Leu Phe Glu Asp Asp
                405                 410                 415

Val Arg Phe Glu Ser Asn Phe Arg Gly Arg Leu Glu Arg Leu Met Glu
                420                 425                 430

Asp Val Glu Ala Glu Lys Leu Ser Trp Asp Leu Ile Tyr Leu Gly Arg
                435                 440                 445

Lys Gln Val Asn Pro Glu Lys Glu Thr Ala Val Glu Gly Leu Pro Gly
                450                 455                 460

Leu Val Val Ala Gly Tyr Ser Tyr Trp Thr Leu Ala Tyr Ala Leu Arg
465                 470                 475                 480

Leu Ala Gly Ala Arg Lys Leu Leu Ala Ser Gln Pro Leu Arg Arg Met
                485                 490                 495

Leu Pro Val Asp Glu Phe Leu Pro Ile Met Phe Asp Gln His Pro Asn
                500                 505                 510

Glu Gln Tyr Lys Ala His Phe Trp Pro Arg Asp Leu Val Ala Phe Ser
                515                 520                 525

Ala Gln Pro Leu Leu Ala Ala Pro Thr His Tyr Ala Gly Asp Ala Glu
                530                 535                 540

Trp Leu Ser Asp Thr Glu Thr Ser Ser Pro Trp Asp Asp Ser Gly
545                 550                 555                 560

Arg Leu Ile Ser Trp Ser Gly Ser Gln Lys Thr Leu Arg Xaa Pro Ala
                565                 570                 575

Trp Thr Xaa

<210> SEQ ID NO 62
<211> LENGTH: 184
<212> TYPE: PRT
<213> ORGANISM: Homo sapiens

<400> SEQUENCE: 62

Met Leu Met Leu Ala Val Leu Met Ala Ala Thr His Ala Val Tyr Gly
```

-continued

```
              1               5              10              15
Lys Leu Leu Leu Phe Glu Tyr Arg His Arg Lys Met Lys Pro Val Gln
                 20                  25                  30

Met Val Pro Ala Ile Ser Gln Asn Trp Thr Phe His Gly Pro Gly Ala
                 35                  40                  45

Thr Gly Gln Ala Ala Ala Asn Trp Ile Ala Gly Phe Gly Arg Gly Pro
                 50                  55                  60

Met Pro Pro Thr Leu Leu Gly Ile Arg Gln Asn Gly His Ala Ala Ser
 65                  70                  75                  80

Arg Arg Leu Leu Gly Met Asp Glu Val Lys Gly Glu Lys Gln Leu Gly
                 85                  90                  95

Arg Met Phe Tyr Ala Ile Thr Leu Leu Phe Leu Leu Leu Trp Ser Pro
                100                 105                 110

Tyr Ile Val Ala Cys Tyr Trp Arg Val Phe Val Lys Ala Cys Ala Val
                115                 120                 125

Pro His Arg Tyr Leu Ala Thr Ala Val Trp Met Ser Phe Ala Gln Ala
                130                 135                 140

Ala Val Asn Pro Ile Val Cys Phe Leu Leu Asn Lys Asp Leu Lys Lys
145                 150                 155                 160

Cys Leu Arg Thr His Ala Pro Cys Trp Gly Thr Gly Gly Ala Pro Ala
                165                 170                 175

Pro Arg Glu Pro Tyr Cys Val Met
                180
```

<210> SEQ ID NO 63
<211> LENGTH: 306
<212> TYPE: PRT
<213> ORGANISM: Homo sapiens
<220> FEATURE:
<221> NAME/KEY: SITE
<222> LOCATION: (306)
<223> OTHER INFORMATION: Xaa equals stop translation

<400> SEQUENCE: 63

```
Met Gly Ile Leu Leu Gly Leu Leu Leu Gly His Leu Thr Val Asp
 1               5              10              15

Thr Tyr Gly Arg Pro Ile Leu Glu Val Pro Glu Ser Val Thr Gly Pro
                 20                  25                  30

Trp Lys Gly Asp Val Asn Leu Pro Cys Thr Tyr Asp Pro Leu Gln Gly
                 35                  40                  45

Tyr Thr Gln Val Leu Val Lys Trp Leu Val Gln Arg Gly Ser Asp Pro
 50                  55                  60

Val Thr Ile Phe Leu Arg Asp Ser Ser Gly Asp His Ile Gln Gln Ala
 65                  70                  75                  80

Lys Tyr Gln Gly Arg Leu His Val Ser His Lys Val Pro Gly Asp Val
                 85                  90                  95

Ser Leu Gln Leu Ser Thr Leu Glu Met Asp Asp Arg Ser His Tyr Thr
                100                 105                 110

Cys Glu Val Thr Trp Gln Thr Pro Asp Gly Asn Gln Val Val Arg Asp
                115                 120                 125

Lys Ile Thr Glu Leu Arg Val Gln Lys His Ser Ser Lys Leu Leu Lys
                130                 135                 140

Thr Lys Thr Glu Ala Pro Thr Thr Met Thr Tyr Pro Leu Lys Ala Thr
145                 150                 155                 160

Ser Thr Val Lys Gln Ser Trp Asp Trp Thr Thr Asp Met Asp Gly Tyr
                165                 170                 175
```

-continued

```
Leu Gly Glu Thr Ser Ala Gly Pro Gly Lys Ser Leu Pro Val Phe Ala
            180                 185                 190
Ile Ile Leu Ile Ile Ser Leu Cys Cys Met Val Val Phe Thr Met Ala
        195                 200                 205
Tyr Ile Met Leu Cys Arg Lys Thr Ser Gln Gln Glu His Val Tyr Glu
    210                 215                 220
Ala Ala Arg Ala His Ala Arg Glu Ala Asn Asp Ser Gly Glu Thr Met
225                 230                 235                 240
Arg Val Ala Ile Phe Ala Ser Gly Cys Ser Ser Asp Glu Pro Thr Ser
                245                 250                 255
Gln Asn Leu Gly Asn Asn Tyr Ser Asp Glu Pro Cys Ile Gly Gln Glu
            260                 265                 270
Tyr Gln Ile Ile Ala Gln Ile Asn Gly Asn Tyr Ala Arg Leu Leu Asp
        275                 280                 285
Thr Val Pro Leu Asp Tyr Glu Phe Leu Ala Thr Glu Gly Lys Ser Val
    290                 295                 300
Cys Xaa
305

<210> SEQ ID NO 64
<211> LENGTH: 108
<212> TYPE: PRT
<213> ORGANISM: Homo sapiens
<220> FEATURE:
<221> NAME/KEY: SITE
<222> LOCATION: (7)
<223> OTHER INFORMATION: Xaa equals any of the naturally occurring L-
      amino acids
<221> NAME/KEY: SITE
<222> LOCATION: (9)
<223> OTHER INFORMATION: Xaa equals any of the naturally occurring L-
      amino acids
<221> NAME/KEY: SITE
<222> LOCATION: (13)
<223> OTHER INFORMATION: Xaa equals any of the naturally occurring L-
      amino acids
<221> NAME/KEY: SITE
<222> LOCATION: (95)
<223> OTHER INFORMATION: Xaa equals any of the naturally occurring L-
      amino acids
<221> NAME/KEY: SITE
<222> LOCATION: (108)
<223> OTHER INFORMATION: Xaa equals stop translation

<400> SEQUENCE: 64

Met Ala Val Val Leu Ser Xaa Lys Xaa His Arg Gly Xaa Tyr Cys Gly
 1               5                  10                  15
Arg Thr Ser Leu Leu Leu Ser Leu Leu Ser Cys Leu Leu Leu Leu Leu
            20                  25                  30
Leu Leu Leu Leu Leu Leu Leu Trp Ser Leu Ser Glu Ile Lys Thr Leu
        35                  40                  45
Lys Leu Ile Cys Ile Leu Ser Ala Arg Asp Ala Asp Gly Ser Arg Ala
    50                  55                  60
Lys Ser His Gly Phe Gln Ile Arg Tyr Ser Ala His Ser Phe Gln Gly
65                  70                  75                  80
His Arg Phe Leu Lys Gly Pro Gly Phe Glu Glu Met Ala Asn Xaa Glu
                85                  90                  95
Pro Ser Glu Asn Leu Ile Trp Lys Thr Cys Met Xaa
            100                 105

<210> SEQ ID NO 65
```

```
<211> LENGTH: 191
<212> TYPE: PRT
<213> ORGANISM: Homo sapiens
<220> FEATURE:
<221> NAME/KEY: SITE
<222> LOCATION: (25)
<223> OTHER INFORMATION: Xaa equals any of the naturally occurring L-
      amino acids
<221> NAME/KEY: SITE
<222> LOCATION: (191)
<223> OTHER INFORMATION: Xaa equals stop translation

<400> SEQUENCE: 65
```

Met Pro Val Pro Thr Leu Cys Leu Leu Trp Ala Leu Ala Met Val Thr
1               5                   10                  15

Arg Pro Ala Ser Ala Ala Pro Met Xaa Gly Pro Glu Leu Ala Gln His
            20                  25                  30

Glu Glu Leu Thr Leu Leu Phe His Gly Thr Leu Gln Leu Gly Gln Ala
        35                  40                  45

Leu Asn Gly Val Tyr Arg Thr Thr Glu Gly Arg Leu Thr Lys Ala Arg
    50                  55                  60

Asn Ser Leu Gly Leu Tyr Gly Arg Thr Ile Glu Leu Leu Gly Gln Glu
65                  70                  75                  80

Val Ser Arg Gly Arg Asp Ala Ala Gln Glu Leu Arg Ala Ser Leu Leu
                85                  90                  95

Glu Thr Gln Met Glu Glu Asp Ile Leu Gln Leu Gln Ala Glu Ala Thr
            100                 105                 110

Ala Glu Val Leu Gly Glu Val Ala Gln Ala Gln Lys Val Leu Arg Asp
        115                 120                 125

Ser Val Gln Arg Leu Glu Val Gln Leu Arg Ser Ala Trp Leu Gly Pro
    130                 135                 140

Ala Tyr Arg Glu Phe Glu Val Leu Lys Ala His Ala Asp Lys Gln Glu
145                 150                 155                 160

Pro Thr Ser Tyr Gly Pro His Arg Pro Arg Gln Arg Arg Glu
                165                 170                 175

Met Val Ala Gln Gln His Arg Leu Arg Gln Ile Gln Glu Arg Xaa
            180                 185                 190

```
<210> SEQ ID NO 66
<211> LENGTH: 200
<212> TYPE: PRT
<213> ORGANISM: Homo sapiens
<220> FEATURE:
<221> NAME/KEY: SITE
<222> LOCATION: (118)
<223> OTHER INFORMATION: Xaa equals any of the naturally occurring L-
      amino acids
<221> NAME/KEY: SITE
<222> LOCATION: (120)
<223> OTHER INFORMATION: Xaa equals any of the naturally occurring L-
      amino acids
<221> NAME/KEY: SITE
<222> LOCATION: (200)
<223> OTHER INFORMATION: Xaa equals stop translation

<400> SEQUENCE: 66
```

Met Thr Ser Cys Gly Gln Gln Ser Leu Asn Val Leu Ala Val Leu Phe
1               5                   10                  15

Ser Leu Leu Phe Ser Ala Val Leu Ser Ala His Phe Arg Val Cys Glu
            20                  25                  30

Pro Tyr Thr Asp His Lys Gly Arg Tyr His Phe Gly Phe His Cys Pro
        35                  40                  45

-continued

```
Arg Leu Ser Asp Asn Lys Thr Phe Ile Leu Cys Cys His His Asn Asn
         50                  55                  60

Thr Val Phe Lys Tyr Cys Cys Asn Glu Thr Glu Phe Gln Ala Val Met
 65                  70                  75                  80

Gln Ala Asn Leu Thr Ala Ser Ser Glu Gly Tyr Met His Asn Asn Tyr
                 85                  90                  95

Thr Ala Leu Leu Gly Val Trp Ile Tyr Gly Phe Phe Val Leu Met Leu
            100                 105                 110

Leu Val Leu Asp Leu Xaa Tyr Xaa Ser Ala Met Asn Tyr Asp Ile Cys
            115                 120                 125

Lys Val Tyr Leu Ala Arg Trp Gly Ile Gln Gly Arg Trp Met Lys Gln
130                 135                 140

Asp Pro Arg Arg Trp Gly Asn Pro Ala Arg Ala Pro Arg Pro Gly Gln
145                 150                 155                 160

Arg Ala Pro Gln Pro Gln Pro Pro Gly Pro Leu Pro Gln Ala Pro
                165                 170                 175

Gln Ala Val His Thr Leu Arg Gly Asp Ala His Ser Pro Pro Leu Met
            180                 185                 190

Thr Phe Gln Ser Ser Ser Ala Xaa
            195                 200
```

<210> SEQ ID NO 67
<211> LENGTH: 62
<212> TYPE: PRT
<213> ORGANISM: Homo sapiens
<220> FEATURE:
<221> NAME/KEY: SITE
<222> LOCATION: (62)
<223> OTHER INFORMATION: Xaa equals stop translation

<400> SEQUENCE: 67

```
Met Leu Leu Ser Ser Leu Ile Gly Trp Cys Ser Phe Val Glu Pro Val
 1               5                  10                  15

Leu Ile Phe Phe Phe Leu Thr Ile Leu Ile Arg Leu Leu Glu Gln Ser
                20                  25                  30

Asn Trp Gly Ile Glu Glu Met Lys Thr Gly Tyr Phe Cys Ile Cys Glu
            35                  40                  45

Val Gly Thr Gly Asn Ile Trp Thr Cys Ser Ser Tyr Ser Xaa
         50                  55                  60
```

<210> SEQ ID NO 68
<211> LENGTH: 608
<212> TYPE: PRT
<213> ORGANISM: Homo sapiens
<220> FEATURE:
<221> NAME/KEY: SITE
<222> LOCATION: (242)
<223> OTHER INFORMATION: Xaa equals any of the naturally occurring L-
      amino acids
<221> NAME/KEY: SITE
<222> LOCATION: (608)
<223> OTHER INFORMATION: Xaa equals stop translation

<400> SEQUENCE: 68

```
Met Arg Thr Pro Gln Leu Ala Leu Leu Gln Val Phe Phe Leu Val Phe
 1               5                  10                  15

Pro Asp Gly Val Arg Pro Gln Pro Ser Ser Pro Ser Gly Ala Val
                20                  25                  30

Pro Thr Ser Leu Glu Leu Gln Arg Gly Thr Asp Gly Gly Thr Leu Gln
            35                  40                  45
```

-continued

```
Ser Pro Ser Glu Ala Thr Ala Thr Arg Pro Ala Val Pro Gly Leu Pro
     50                  55                  60
Thr Val Val Pro Thr Leu Val Thr Pro Ser Ala Pro Gly Asn Arg Thr
 65                  70                  75                  80
Val Asp Leu Phe Pro Val Leu Pro Ile Cys Val Cys Asp Leu Thr Pro
                 85                  90                  95
Gly Ala Cys Asp Ile Asn Cys Cys Asp Arg Asp Cys Tyr Leu Leu
                100                 105                 110
His Pro Arg Thr Val Phe Ser Phe Cys Leu Pro Gly Ser Val Arg Ser
            115                 120                 125
Ser Ser Trp Val Cys Val Asp Asn Ser Val Ile Phe Arg Ser Asn Ser
130                 135                 140
Pro Phe Pro Ser Arg Val Phe Met Asp Ser Asn Gly Ile Arg Gln Phe
145                 150                 155                 160
Cys Val His Val Asn Asn Ser Asn Leu Asn Tyr Phe Gln Lys Leu Gln
                165                 170                 175
Lys Val Asn Ala Thr Asn Phe Gln Ala Leu Ala Ala Glu Phe Gly Gly
                180                 185                 190
Glu Ser Phe Thr Ser Thr Phe Gln Thr Gln Ser Pro Pro Ser Phe Tyr
            195                 200                 205
Arg Ala Gly Asp Pro Ile Leu Thr Tyr Phe Pro Lys Trp Ser Val Ile
210                 215                 220
Ser Leu Leu Arg Gln Pro Ala Gly Val Gly Ala Gly Gly Leu Cys Ala
225                 230                 235                 240
Glu Xaa Asn Pro Ala Gly Phe Leu Glu Ser Lys Ser Thr Thr Cys Thr
                245                 250                 255
Arg Phe Phe Lys Asn Leu Ala Ser Ser Cys Thr Leu Asp Ser Ala Leu
                260                 265                 270
Asn Ala Ala Ser Tyr Tyr Asn Phe Thr Val Leu Lys Val Pro Arg Ser
            275                 280                 285
Met Thr Asp Pro Gln Asn Met Glu Phe Gln Val Pro Val Ile Leu Thr
290                 295                 300
Ser Gln Ala Asn Ala Pro Leu Leu Ala Gly Asn Thr Cys Gln Asn Val
305                 310                 315                 320
Val Ser Gln Val Thr Tyr Glu Ile Glu Thr Asn Gly Thr Phe Gly Ile
                325                 330                 335
Gln Lys Val Ser Val Ser Leu Gly Gln Thr Asn Leu Thr Val Glu Pro
                340                 345                 350
Gly Ala Ser Leu Gln Gln His Phe Ile Leu Arg Phe Arg Ala Phe Gln
            355                 360                 365
Gln Ser Thr Ala Ala Ser Leu Thr Ser Pro Arg Ser Gly Asn Pro Gly
370                 375                 380
Tyr Ile Val Gly Lys Pro Leu Leu Ala Leu Thr Asp Asp Ile Ser Tyr
385                 390                 395                 400
Ser Met Thr Leu Leu Gln Ser Gln Gly Asn Gly Ser Cys Ser Val Lys
                405                 410                 415
Arg His Glu Val Gln Phe Gly Val Asn Ala Ile Ser Gly Cys Lys Leu
                420                 425                 430
Arg Leu Lys Lys Ala Asp Cys Ser His Leu Gln Gln Glu Ile Tyr Gln
            435                 440                 445
Thr Leu His Gly Arg Pro Arg Pro Glu Tyr Val Ala Ile Phe Gly Asn
450                 455                 460
Ala Asp Pro Ala Gln Lys Gly Gly Trp Thr Arg Ile Leu Asn Arg His
```

```
                465                 470                 475                 480
        Cys Ser Ile Ser Ala Ile Asn Cys Thr Ser Cys Cys Leu Ile Pro Val
                        485                 490                 495
        Ser Leu Glu Ile Gln Val Leu Trp Ala Tyr Val Gly Leu Leu Ser Asn
                        500                 505                 510
        Pro Gln Ala His Val Ser Gly Val Arg Phe Leu Tyr Gln Cys Gln Ser
                        515                 520                 525
        Ile Gln Asp Ser Gln Gln Val Thr Glu Val Ser Leu Thr Thr Leu Val
                        530                 535                 540
        Asn Phe Val Asp Ile Thr Gln Lys Pro Gln Pro Pro Arg Gly Gln Pro
        545                 550                 555                 560
        Lys Met Asp Trp Lys Trp Pro Phe Asp Phe Phe Pro Phe Lys Val Ala
                        565                 570                 575
        Phe Ser Arg Gly Val Phe Ser Gln Lys Cys Ser Val Ser Pro Ile Leu
                        580                 585                 590
        Ile Leu Cys Leu Leu Leu Leu Gly Val Leu Asn Leu Glu Thr Met Xaa
                        595                 600                 605
```

<210> SEQ ID NO 69
<211> LENGTH: 90
<212> TYPE: PRT
<213> ORGANISM: Homo sapiens
<220> FEATURE:
<221> NAME/KEY: SITE
<222> LOCATION: (90)
<223> OTHER INFORMATION: Xaa equals stop translation

<400> SEQUENCE: 69

```
        Met Ala Leu Arg Phe Leu Leu Leu Ser Ile Gly Pro Val Pro Ser Leu
        1                   5                   10                  15
        Gly Asn Ile Ala Ala Ala Gly Ser Asp Glu Lys Cys Lys Leu Ala Met
                        20                  25                  30
        Gln Arg Gly Ala Gln Ser Ser Val Asn Tyr Ser Gln Gly Ser Leu Lys
                        35                  40                  45
        Asp Ala Ala Ser Ala Ser Thr Arg Thr Ala Ser Gly Trp Val Lys Arg
                        50                  55                  60
        Asn Arg Ser Arg Glu Asn Gln Glu Met Leu Ile Tyr Ser Lys Asn Lys
        65                  70                  75                  80
        Ile Pro Ile Trp Lys Ile Ser Lys Lys Xaa
                        85                  90
```

<210> SEQ ID NO 70
<211> LENGTH: 117
<212> TYPE: PRT
<213> ORGANISM: Homo sapiens
<220> FEATURE:
<221> NAME/KEY: SITE
<222> LOCATION: (117)
<223> OTHER INFORMATION: Xaa equals stop translation

<400> SEQUENCE: 70

```
        Met Ala Gly Leu Ile Phe Val Leu His Ser Cys Phe Arg Phe Ile Thr
        1                   5                   10                  15
        Phe Val Cys Pro Thr Ser Ser Asp Pro Leu Arg Thr Cys Ala Val Leu
                        20                  25                  30
        Leu Cys Val Gly Tyr Gln Asp Leu Pro Asn Pro Val Phe Arg Tyr Leu
                        35                  40                  45
        Gln Ser Val Asn Glu Leu Leu Ser Thr Leu Leu Asn Ser Asp Ser Pro
                        50                  55                  60
```

```
Gln Gln Val Leu Gln Phe Val Pro Met Glu Val Leu Lys Gly Ala
 65                  70                  75                  80

Leu Leu Asp Phe Leu Trp Asp Leu Asn Ala Ala Ile Ala Lys Arg His
                 85                  90                  95

Leu His Phe Ile Ile Gln Arg Glu Arg Glu Ile Ile Asn Ser Leu
            100                 105                 110

Gln Leu Gln Asn Xaa
        115

<210> SEQ ID NO 71
<211> LENGTH: 140
<212> TYPE: PRT
<213> ORGANISM: Homo sapiens
<220> FEATURE:
<221> NAME/KEY: SITE
<222> LOCATION: (140)
<223> OTHER INFORMATION: Xaa equals stop translation

<400> SEQUENCE: 71

Met Cys Val Trp Gly Val Cys Val Val Ala Arg Val Cys Val
 1               5                  10                  15

Trp Leu Gly Leu Ala Glu Leu Phe Arg Gly Arg Val Arg Asp Cys Gly
                 20                  25                  30

Lys Ile Thr His Phe Pro Thr Tyr Leu Leu Tyr Trp Thr Leu Lys Asn
             35                  40                  45

Asn Asn Lys His Gln Val Lys Phe Leu Asn His Val Leu Cys Val Cys
         50                  55                  60

Val Cys Val Cys Val Cys Val Cys Ile Cys Lys Cys Ile Cys Ile Cys
 65                  70                  75                  80

Met Leu Leu Tyr Phe Gln Val Asn Asn Tyr Ile Glu Asp Cys Ile Ala
                 85                  90                  95

Gln Lys His Ser Leu Ile Lys Val Leu Arg Leu Val Cys Leu Gln Ser
            100                 105                 110

Val Cys Asn Ser Gly Leu Lys Gln Lys Val Leu Asp Tyr Tyr Lys Arg
        115                 120                 125

Glu Ile Leu Gln Val Ser Ile Phe Leu Asn Tyr Xaa
    130                 135                 140

<210> SEQ ID NO 72
<211> LENGTH: 96
<212> TYPE: PRT
<213> ORGANISM: Homo sapiens
<220> FEATURE:
<221> NAME/KEY: SITE
<222> LOCATION: (96)
<223> OTHER INFORMATION: Xaa equals stop translation

<400> SEQUENCE: 72

Met His Leu Cys Ile Cys Ala Val Trp Val Leu Val Ala Leu Leu Arg
 1               5                  10                  15

Met His Gly Ala Ser Pro Ala Gln Thr Ser Gly Thr Arg Ser Gly Asn
                 20                  25                  30

Gly Gly Cys Arg Arg His Gly Ala Gly Gln Gly Arg Gly Ala Ala Thr
             35                  40                  45

Gln Pro Leu Arg Pro Pro Arg Gly Thr Ala Ser Gly Gln Leu Met Ala
         50                  55                  60

Leu Leu Ser Ala Leu Leu Pro Arg Leu Ser Gly Ser Ser Thr Pro Met
 65                  70                  75                  80
```

```
Met Ala His Gly Arg Pro Ala Pro Pro Gln Trp Ser Arg Val Ser Xaa
                85                  90                  95
```

```
<210> SEQ ID NO 73
<211> LENGTH: 78
<212> TYPE: PRT
<213> ORGANISM: Homo sapiens
<220> FEATURE:
<221> NAME/KEY: SITE
<222> LOCATION: (78)
<223> OTHER INFORMATION: Xaa equals stop translation

<400> SEQUENCE: 73
```

```
Met Ser Leu Tyr Lys Ile His Leu Leu Leu Tyr Val Ala Val Leu Ser
 1               5                  10                  15

Ser Val Ala Ser Ser Tyr Pro Glu Ala Gln His Met Ser Pro Gly Gln
                20                  25                  30

Val Pro Lys Phe Gln Ala Val Leu Ser Val Lys Ala Gly Val Cys Met
            35                  40                  45

Cys Tyr Gln His Met Ile Arg Gly Arg Pro Thr Gln Gly Ala Val Ser
        50                  55                  60

Val Ala Gln Gln Ser Thr Thr Phe Thr Val Ala Tyr Phe Xaa
 65                  70                  75
```

```
<210> SEQ ID NO 74
<211> LENGTH: 55
<212> TYPE: PRT
<213> ORGANISM: Homo sapiens
<220> FEATURE:
<221> NAME/KEY: SITE
<222> LOCATION: (55)
<223> OTHER INFORMATION: Xaa equals stop translation

<400> SEQUENCE: 74
```

```
Met Ala Val Arg Leu Ile Lys Pro Ala Val Phe Ala Val Leu Ala Gly
 1               5                  10                  15

Phe Ser Val Leu Trp Leu Ser Pro Ala Ser Leu Ala Ala Ser Phe Asp
                20                  25                  30

Cys Asp Arg Ala Lys Arg Leu Thr Arg Lys Pro Ser Val Pro Arg Ala
            35                  40                  45

Pro Ser Met Ile Arg Thr Xaa
        50                  55
```

```
<210> SEQ ID NO 75
<211> LENGTH: 210
<212> TYPE: PRT
<213> ORGANISM: Homo sapiens
<220> FEATURE:
<221> NAME/KEY: SITE
<222> LOCATION: (181)
<223> OTHER INFORMATION: Xaa equals any of the naturally occurring L-
      amino acids
<221> NAME/KEY: SITE
<222> LOCATION: (200)
<223> OTHER INFORMATION: Xaa equals any of the naturally occurring L-
      amino acids
<221> NAME/KEY: SITE
<222> LOCATION: (207)
<223> OTHER INFORMATION: Xaa equals any of the naturally occurring L-
      amino acids
<221> NAME/KEY: SITE
<222> LOCATION: (210)
<223> OTHER INFORMATION: Xaa equals stop translation

<400> SEQUENCE: 75
```

```
Met Tyr Phe Leu Phe Phe Phe Ala Phe Phe Phe Phe Pro Leu Phe Cys
```

-continued

```
                1               5              10              15
Tyr Cys Phe Asn Tyr Asn Lys Arg Ala Arg Gly Ser Gln Ala Leu Ala
                       20                  25                  30

Arg Ser Trp Arg Pro Met Gly Val Leu Gly Arg Gly Arg Gly Glu Val
               35                  40                  45

Ser Gly Gly Gln Arg Trp Arg Val Lys Asn Glu Lys Val Gly Glu Leu
     50                  55                  60

Gly Leu Ala Gln Glu Pro Cys Val Pro Ala His Ser Pro Pro Ser Leu
 65                  70                  75                  80

Pro Leu Pro Thr Ser Leu Pro Leu His Gly Phe Ser Pro Pro Leu Pro
                     85                  90                  95

Glu Ser Tyr Gly Thr Gly Pro Cys Ser Ser Gly Ile Gln Leu Leu Pro
                100                 105                 110

Ala His Ser Ser Ser Trp Ala Thr Ser Pro Pro Thr Phe Asp Val Ser
            115                 120                 125

Pro Pro Val Ala Thr Leu Gln Leu Ala Phe Gln Ala Pro Ser Arg Gly
        130                 135                 140

Arg Pro Leu Pro Arg Pro Leu Thr His Val Ala Ile Pro Thr Trp Leu
145                 150                 155                 160

Pro Val Met Ser Leu Leu Ser Lys Pro Ser Cys Pro Leu Phe Leu Pro
                165                 170                 175

Pro Arg His Ala Xaa Thr Lys Trp Trp Lys Pro Pro Leu Ser Pro Ser
                180                 185                 190

Leu Pro Cys Ala Glu Phe Ser Xaa Val Leu Asn Glu Gly Glu Xaa Asp
            195                 200                 205

Lys Xaa
    210

<210> SEQ ID NO 76
<211> LENGTH: 105
<212> TYPE: PRT
<213> ORGANISM: Homo sapiens
<220> FEATURE:
<221> NAME/KEY: SITE
<222> LOCATION: (89)
<223> OTHER INFORMATION: Xaa equals any of the naturally occurring L-
      amino acids
<221> NAME/KEY: SITE
<222> LOCATION: (105)
<223> OTHER INFORMATION: Xaa equals stop translation

<400> SEQUENCE: 76

Met Pro Thr Ser Ser Tyr Arg Ser Val Trp Pro Leu Thr Leu Leu Ala
  1               5                  10                  15

Leu Lys Ser Thr Ala Cys Ala Leu Ala Phe Thr Arg Met Pro Gly Phe
             20                  25                  30

Gln Thr Pro Ser Glu Phe Leu Glu Asn Pro Ser Gln Ser Ser Arg Leu
         35                  40                  45

Thr Ala Pro Phe Arg Lys His Val Arg Pro Lys Lys Gln His Glu Ile
     50                  55                  60

Arg Arg Leu Gly Glu Leu Val Lys Lys Pro Ser Asp Phe Thr Gly Cys
 65                  70                  75                  80

Thr Gln Val Val Asp Val Gly Ser Xaa Gln Gly His Leu Ser Arg Phe
                 85                  90                  95

Met Ala Leu Gly Leu Gly Leu Met Xaa
            100                 105
```

<210> SEQ ID NO 77
<211> LENGTH: 176
<212> TYPE: PRT
<213> ORGANISM: Homo sapiens

<400> SEQUENCE: 77

Met Leu Leu Leu Met Leu Val Asn Thr Ser Ala Val Ala Cys Thr His
 1               5                  10                  15

Gly Gly Arg Gly Pro Trp Gly Asn Ser Ala Ala Gln Ala Cys Ala Ala
            20                  25                  30

Leu Ala Pro Trp Pro Arg Gln Asp Pro Ser Ala Ala Ser Gln Trp Gln
        35                  40                  45

Pro Gln Val Leu Val Gly Leu Leu Ser Tyr His Gly Trp Gly Gly Gln
    50                  55                  60

Arg Leu Ser Pro Cys Pro Arg Ser Ile Cys Cys Val Ser Thr Arg His
65                  70                  75                  80

Leu Glu Gly Ala Arg Ser Lys Ala Gln Gly Pro Ala Ala Trp Leu His
                85                  90                  95

Met Glu Val Arg Val Pro Arg Val Gln Pro Pro Ala Leu Gln Val Pro
            100                 105                 110

Ser Ser Ser Asp Lys Ala Gly Gln Gly Arg Trp Gly Val Pro Gly Gln
        115                 120                 125

Arg Gly Leu Val Gly Arg Gly Gly Cys Lys Val Thr Pro Ser Leu
    130                 135                 140

Pro Cys Arg Arg Thr Glu Arg Lys Arg Thr Ala Ala Ser Ala Lys Val
145                 150                 155                 160

Thr Cys Pro Ala Ser Ser Arg Arg Pro Trp Gly Trp Gln Ser Ser Pro
                165                 170                 175

<210> SEQ ID NO 78
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 78

Met His Lys Asn Asn Leu Phe Leu Cys Val Leu Phe Arg Leu Leu Phe
 1               5                  10                  15

Arg Cys Ser Cys Phe Asn Leu Leu Asn Phe Pro Gln Thr Tyr Ala Val
            20                  25                  30

Gly Lys Gly Gln Ala Gly Lys Asp Gln Cys Ser Ser Xaa
        35                  40                  45

<210> SEQ ID NO 79
<211> LENGTH: 71
<212> TYPE: PRT
<213> ORGANISM: Homo sapiens
<220> FEATURE:
<221> NAME/KEY: SITE
<222> LOCATION: (71)
<223> OTHER INFORMATION: Xaa equals stop translation

<400> SEQUENCE: 79

Met Asp Ser Val Thr Ala Gly Leu Phe Met Leu Ser Phe Leu Leu Tyr
 1               5                  10                  15

Leu Pro Ser Ser Ala Phe Ser Gly His Trp Tyr Pro Tyr Pro Gly Val
            20                  25                  30

-continued

Val Ser Trp Ser Asn Ser Cys Leu Ala Gly Leu Asn Cys Gly Val Ser
         35                  40                  45

Gly Pro Lys Ala Ile Gly Thr Ser Val Val Tyr Phe Leu Ile Pro Ile
     50                  55                  60

Leu Trp Arg Phe Val Phe Xaa
 65                  70

<210> SEQ ID NO 80
<211> LENGTH: 56
<212> TYPE: PRT
<213> ORGANISM: Homo sapiens

<400> SEQUENCE: 80

Met Cys Leu Ala Phe Ser Val Ile Ile Leu Ala Gly Ala Gly Ser Ser
  1               5                  10                  15

Arg Ser Trp Asn Ser Val Leu Val Glu Lys Val Val Glu Gly Gly
             20                  25                  30

Leu Gly Pro Trp Gly Asn Cys Ser Ala Glu Pro Leu Pro His Leu Leu
         35                  40                  45

Leu Pro Arg Thr Asn Leu Lys Gly
     50                  55

<210> SEQ ID NO 81
<211> LENGTH: 49
<212> TYPE: PRT
<213> ORGANISM: Homo sapiens
<220> FEATURE:
<221> NAME/KEY: SITE
<222> LOCATION: (49)
<223> OTHER INFORMATION: Xaa equals stop translation

<400> SEQUENCE: 81

Met Cys His Phe Ser Ala Leu Ser Phe Thr Phe Cys Val Leu Pro Leu
  1               5                  10                  15

Ala Phe Ser Phe Leu Gln Lys His Cys Tyr Phe Thr His Lys Phe Gly
             20                  25                  30

Gln Asn Val Gln Tyr Ser His Phe Arg Val Ser Phe Gln Trp Lys Lys
         35                  40                  45

Xaa

<210> SEQ ID NO 82
<211> LENGTH: 46
<212> TYPE: PRT
<213> ORGANISM: Homo sapiens
<220> FEATURE:
<221> NAME/KEY: SITE
<222> LOCATION: (46)
<223> OTHER INFORMATION: Xaa equals stop translation

<400> SEQUENCE: 82

Met Leu Val Ser Leu Ile Ile Cys Leu Leu Asp Leu Leu Asn Gln
  1               5                  10                  15

Pro Ser Leu Leu Arg Asp Leu Ile Leu Lys Gln His Thr Gly Asn Pro
             20                  25                  30

His Leu Ser Phe Pro Leu Lys Tyr Ser His Trp Met Gly Xaa
         35                  40                  45

<210> SEQ ID NO 83
<211> LENGTH: 91
<212> TYPE: PRT
<213> ORGANISM: Homo sapiens
<220> FEATURE:

```
<221> NAME/KEY: SITE
<222> LOCATION: (91)
<223> OTHER INFORMATION: Xaa equals stop translation

<400> SEQUENCE: 83

Met Ala Ile Arg Leu Val Phe Leu Ala Leu Ala Gly Leu Val Asp Gly
 1               5                  10                  15

Lys Pro Val Trp Ile Thr Leu Trp Met Asp Ala Lys Arg Pro Asn Leu
            20                  25                  30

Ala Gly Thr Gly Ser Thr Trp Gly Ser Arg Arg Asp Ser His Cys Cys
        35                  40                  45

His Gly Pro Thr Ala Trp Ser Leu Pro Cys Leu Leu Cys Leu Phe Arg
    50                  55                  60

Ala Gln Gln Lys Asp Arg Glu Arg Ser Leu Leu Gly Val Pro Leu Pro
65                  70                  75                  80

Thr Leu Gln Gly Gly Asn Leu Ser Asp Gly Xaa
                85                  90

<210> SEQ ID NO 84
<211> LENGTH: 103
<212> TYPE: PRT
<213> ORGANISM: Homo sapiens
<220> FEATURE:
<221> NAME/KEY: SITE
<222> LOCATION: (91)
<223> OTHER INFORMATION: Xaa equals any of the naturally occurring L-
      amino acids
<221> NAME/KEY: SITE
<222> LOCATION: (92)
<223> OTHER INFORMATION: Xaa equals any of the naturally occurring L-
      amino acids
<221> NAME/KEY: SITE
<222> LOCATION: (93)
<223> OTHER INFORMATION: Xaa equals any of the naturally occurring L-
      amino acids
<221> NAME/KEY: SITE
<222> LOCATION: (103)
<223> OTHER INFORMATION: Xaa equals stop translation

<400> SEQUENCE: 84

Met Gly Arg Arg Ser Gly Leu Leu Gly Leu Arg Pro Gly Arg Ser Arg
 1               5                  10                  15

Trp Arg Trp Ser Gly Ser Val Trp Val Arg Ser Val Leu Leu Leu Leu
            20                  25                  30

Gly Gly Leu Arg Ala Ser Ala Thr Ser Thr Pro Val Ser Leu Gly Ser
        35                  40                  45

Ser Pro Pro Cys Arg His His Val Pro Ser Asp Thr Glu Val Ile Asn
    50                  55                  60

Lys Val His Leu Lys Ala Asn His Val Val Lys Arg Asp Val Asp Glu
65                  70                  75                  80

His Leu Arg Ile Lys Thr Val Tyr Asp Lys Xaa Xaa Xaa Ser Cys Ser
                85                  90                  95

Leu Arg Lys Arg Ile Leu Xaa
            100

<210> SEQ ID NO 85
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation
```

-continued

```
<400> SEQUENCE: 85

Met Gln Cys Asp Thr Phe Ser Lys Ala Thr Cys Cys Lys Ile Leu Leu
 1               5                  10                  15

Leu Ser Cys Cys Val Leu Tyr Leu Val Phe Ser Arg Leu Arg Gly Leu
                20                  25                  30

Asp Gln Arg Ser Lys Arg Tyr Ser Leu Pro Asp His Xaa
            35                  40                  45

<210> SEQ ID NO 86
<211> LENGTH: 67
<212> TYPE: PRT
<213> ORGANISM: Homo sapiens
<220> FEATURE:
<221> NAME/KEY: SITE
<222> LOCATION: (67)
<223> OTHER INFORMATION: Xaa equals stop translation

<400> SEQUENCE: 86

Met Asn Tyr Ile Phe Leu Leu Met Ala Leu Pro His Leu Ile Ala Ile
 1               5                  10                  15

Ala Leu Thr Trp Gly Arg Tyr Ser Phe Ser Cys Leu Ala Asn Lys Glu
                20                  25                  30

Thr Glu Phe Gln Arg Cys Gln Val Thr Cys Leu Leu His Thr Leu Gly
            35                  40                  45

Val Leu Met Phe Asn Phe Glu Leu Arg Ser Ile Trp Leu Glu Ser Ser
    50                  55                  60

Leu His Xaa
 65

<210> SEQ ID NO 87
<211> LENGTH: 72
<212> TYPE: PRT
<213> ORGANISM: Homo sapiens
<220> FEATURE:
<221> NAME/KEY: SITE
<222> LOCATION: (72)
<223> OTHER INFORMATION: Xaa equals stop translation

<400> SEQUENCE: 87

Met Leu Phe Leu Asn Leu Thr Val Thr Cys Ile Phe Leu Phe Cys Phe
 1               5                  10                  15

Tyr Phe Asn Val Leu Val Ala His Leu Met Asn Val Asn Leu Lys Asn
                20                  25                  30

Ser Val Gln Leu Ser Arg Tyr Asn Ser Ala Lys Gln Ile Leu Lys Leu
            35                  40                  45

His Ile Thr Leu Gln His Met Val Pro His Thr Leu Ile Val Ala Phe
    50                  55                  60

Tyr Ile Phe Ser Tyr Tyr Tyr Xaa
 65                  70

<210> SEQ ID NO 88
<211> LENGTH: 212
<212> TYPE: PRT
<213> ORGANISM: Homo sapiens

<400> SEQUENCE: 88

Met Lys Thr Leu Pro Ala Met Leu Gly Thr Gly Lys Leu Phe Trp Val
 1               5                  10                  15

Phe Phe Leu Ile Pro Tyr Leu Asp Ile Trp Asn Ile His Gly Lys Glu
                20                  25                  30
```

Ser Cys Asp Val Gln Leu Tyr Ile Lys Arg Gln Ser Glu His Ser Ile
         35                  40                  45

Leu Ala Gly Asp Pro Phe Glu Leu Glu Cys Pro Val Lys Tyr Cys Ala
         50                  55                  60

Asn Arg Pro His Val Thr Trp Cys Lys Leu Asn Gly Thr Thr Cys Val
 65                  70                  75                  80

Lys Leu Glu Asp Arg Gln Thr Ser Trp Lys Glu Lys Asn Ile Ser
                 85                  90                  95

Phe Phe Ile Leu His Phe Glu Pro Val Leu Pro Asn Asp Asn Gly Ser
                100                 105                 110

Tyr Arg Cys Ser Ala Asn Phe Gln Ser Asn Leu Ile Glu Ser His Ser
        115                 120                 125

Thr Thr Leu Tyr Val Thr Gly Glu Phe Ser Thr Pro Arg Pro Ser Asp
    130                 135                 140

Ile Phe Leu Ile Met Phe Pro Gly Arg Gly Phe Ser Phe Ser Ser
145                 150                 155                 160

Asp Tyr Val Arg Lys Pro Thr Pro Ile Ala His Leu Lys Ser Ala Thr
                165                 170                 175

Pro His Arg Leu Leu Cys Ala Ser Val Tyr Ile Cys Val Cys Met Cys
                180                 185                 190

Ala Phe Glu Val Ser Glu Ile Glu Glu Ser Arg Glu Ile Asp Ser Lys
        195                 200                 205

Ser Tyr Cys Phe
    210

<210> SEQ ID NO 89
<211> LENGTH: 111
<212> TYPE: PRT
<213> ORGANISM: Homo sapiens
<220> FEATURE:
<221> NAME/KEY: SITE
<222> LOCATION: (111)
<223> OTHER INFORMATION: Xaa equals stop translation

<400> SEQUENCE: 89

Met Thr Val Ser Tyr Phe Trp Trp Leu Arg Val Gly Ala Trp Ala Glu
 1               5                  10                  15

Asp Val Glu Ala Leu Ala Ser Leu Pro Glu Asp Arg Leu Arg Trp Asn
            20                  25                  30

Leu Leu Ala Leu Pro Ala Ser Pro Cys Ala Val Thr Ala Leu Val Ala
        35                  40                  45

Arg His Arg Arg Ala Gly Leu Gln Arg Ser Ile Gln Cys Leu Leu Gly
    50                  55                  60

Arg Gln Gly Gly Gly Cys Asn Cys Glu Leu Thr Lys Pro Gln Val
 65                  70                  75                  80

Gly Ser Lys Trp Val Gly His Arg Lys Lys Ser Asp Leu Gln Ser Gly
                85                  90                  95

Asp Leu Gly Ser Gly Leu Cys Leu Met Thr Gly Ser Val Met Xaa
                100                 105                 110

<210> SEQ ID NO 90
<211> LENGTH: 42
<212> TYPE: PRT
<213> ORGANISM: Homo sapiens
<220> FEATURE:
<221> NAME/KEY: SITE
<222> LOCATION: (42)
<223> OTHER INFORMATION: Xaa equals stop translation

```
<400> SEQUENCE: 90

Met Val Lys Val Gly Ala Trp Arg Ala Val Gln Ile Leu Met Leu Phe
 1               5                  10                  15

Ala Asn Pro Gly His Ala Glu Gly Ala Cys Ile Ser Pro Gly Pro Ala
            20                  25                  30

Gly Lys Arg Glu Pro Leu Lys Leu Gly Xaa
            35                  40

<210> SEQ ID NO 91
<211> LENGTH: 59
<212> TYPE: PRT
<213> ORGANISM: Homo sapiens
<220> FEATURE:
<221> NAME/KEY: SITE
<222> LOCATION: (56)
<223> OTHER INFORMATION: Xaa equals any of the naturally occurring L-
      amino acids
<221> NAME/KEY: SITE
<222> LOCATION: (59)
<223> OTHER INFORMATION: Xaa equals stop translation

<400> SEQUENCE: 91

Met Val Ala Thr Leu Cys Leu Glu Asn Ser Ser Val Ser Leu Trp Phe
 1               5                  10                  15

Ile Phe Leu Ser Ser Leu Ser Ser Phe Pro Trp Cys Gly Ala Leu Ser
            20                  25                  30

Asp Asn Trp Pro Ser Gly Gly Ala Val Ala Arg Cys His Ser Gly Arg
            35                  40                  45

Arg Trp Phe Pro Glu Gly Ser Xaa Cys Leu Xaa
 50                  55

<210> SEQ ID NO 92
<211> LENGTH: 77
<212> TYPE: PRT
<213> ORGANISM: Homo sapiens
<220> FEATURE:
<221> NAME/KEY: SITE
<222> LOCATION: (77)
<223> OTHER INFORMATION: Xaa equals stop translation

<400> SEQUENCE: 92

Met Phe Cys Ile Gln Gln Lys Trp Leu Phe Ser Phe Leu Phe Tyr Glu
 1               5                  10                  15

Val Gly Leu Met Gly Ile Asp Ser Leu Arg Lys Lys Tyr Asn Cys Lys
            20                  25                  30

Ser Val Glu Val Phe Pro Ser Gln Asp Val Lys Cys Gln Arg Ser Asp
            35                  40                  45

Ser Cys Gly Arg Met Gly Ser Lys Leu Tyr Lys Ser Leu Glu Met Asn
     50                  55                  60

Glu Val Arg Gln Leu Ser Leu Arg Gln Lys Thr Met Xaa
 65                  70                  75

<210> SEQ ID NO 93
<211> LENGTH: 69
<212> TYPE: PRT
<213> ORGANISM: Homo sapiens
<220> FEATURE:
<221> NAME/KEY: SITE
<222> LOCATION: (69)
<223> OTHER INFORMATION: Xaa equals stop translation

<400> SEQUENCE: 93

Met Ala Lys Leu Met Tyr Tyr Gln Ile Leu Cys Leu Val Val Phe Cys
```

```
                 1               5                  10                 15
Trp Leu Ile His Ser Phe Ile His Leu Phe Asn Lys His Phe Leu Ile
                    20                 25                 30

Ala Phe Tyr Val Pro Gly Pro Ala Ile Asp Ala Arg Asp Ser Ala Val
            35                 40                 45

Ser Thr Thr Asp Lys Glu Phe Cys His Cys Gly Val Tyr Ile Leu Val
        50                 55                 60

Ala Gly Asp Arg Xaa
 65
```

<210> SEQ ID NO 94
<211> LENGTH: 44
<212> TYPE: PRT
<213> ORGANISM: Homo sapiens
<220> FEATURE:
<221> NAME/KEY: SITE
<222> LOCATION: (44)
<223> OTHER INFORMATION: Xaa equals stop translation

<400> SEQUENCE: 94

```
Met Glu Thr Thr Gly Ser Trp Thr Cys Leu Phe Asn Leu Val Ala Ile
 1               5                  10                 15

Ile Ser Asn Leu Gly Leu Cys Thr Phe Leu Val Phe Gly Gln Ala Gln
                20                 25                 30

Arg Val Asp Leu Ser Ser Thr His Glu Asp Leu Xaa
            35                 40
```

<210> SEQ ID NO 95
<211> LENGTH: 47
<212> TYPE: PRT
<213> ORGANISM: Homo sapiens
<220> FEATURE:
<221> NAME/KEY: SITE
<222> LOCATION: (47)
<223> OTHER INFORMATION: Xaa equals stop translation

<400> SEQUENCE: 95

```
Met Lys Ala Gln Met Leu Leu Ser Leu Ala Trp Pro Leu Pro Leu Ser
 1               5                  10                 15

Thr Ala Asn Ser Cys Leu Pro Gln Phe Pro Arg Gly Leu Tyr Ser Ala
                20                 25                 30

His Tyr Cys Pro Ser Cys Leu Leu Phe Leu Glu Ala Leu Ser Xaa
            35                 40                 45
```

<210> SEQ ID NO 96
<211> LENGTH: 48
<212> TYPE: PRT
<213> ORGANISM: Homo sapiens
<220> FEATURE:
<221> NAME/KEY: SITE
<222> LOCATION: (48)
<223> OTHER INFORMATION: Xaa equals stop translation

<400> SEQUENCE: 96

```
Met Cys Leu Leu Ser Phe Asn Cys Lys Ala Val Leu Ser Leu Ser Leu
 1               5                  10                 15

Ile Ser Leu Ser Phe Leu Cys Cys Leu Glu Leu Cys Leu Ala Arg Cys
                20                 25                 30

Gly Gly Arg Arg Asn Val Ser Ala Pro Leu Lys Met Phe Ile Ile Xaa
            35                 40                 45
```

<210> SEQ ID NO 97

```
<211> LENGTH: 450
<212> TYPE: PRT
<213> ORGANISM: Homo sapiens

<400> SEQUENCE: 97

Met Leu Val Thr Ala Tyr Leu Ala Phe Val Gly Leu Leu Ala Ser Cys
 1               5                   10                  15

Leu Gly Leu Glu Leu Ser Arg Cys Arg Ala Lys Pro Pro Gly Arg Ala
            20                  25                  30

Cys Ser Asn Pro Ser Phe Leu Arg Phe Gln Leu Asp Phe Tyr Gln Val
        35                  40                  45

Tyr Phe Leu Ala Leu Ala Ala Asp Trp Leu Gln Ala Pro Tyr Leu Tyr
    50                  55                  60

Lys Leu Tyr Gln His Tyr Tyr Phe Leu Glu Gly Gln Ile Ala Ile Leu
65                  70                  75                  80

Tyr Val Cys Gly Leu Ala Ser Thr Val Leu Phe Gly Leu Val Ala Ser
                85                  90                  95

Ser Leu Val Asp Trp Leu Gly Arg Lys Asn Ser Cys Val Leu Phe Ser
            100                 105                 110

Leu Thr Tyr Ser Leu Cys Cys Leu Thr Lys Leu Ser Gln Asp Tyr Phe
        115                 120                 125

Val Leu Leu Val Gly Arg Ala Leu Gly Gly Leu Ser Thr Ala Leu Leu
    130                 135                 140

Phe Ser Ala Phe Glu Ala Trp Tyr Ile His Glu His Val Glu Arg His
145                 150                 155                 160

Asp Phe Pro Ala Glu Trp Ile Pro Ala Thr Phe Ala Arg Ala Ala Phe
                165                 170                 175

Trp Asn His Val Leu Ala Val Val Ala Gly Val Ala Ala Glu Ala Val
            180                 185                 190

Ala Ser Trp Ile Gly Leu Gly Pro Val Ala Pro Phe Val Ala Ala Ile
        195                 200                 205

Pro Leu Leu Ala Leu Ala Gly Ala Leu Ala Leu Arg Asn Trp Gly Glu
    210                 215                 220

Asn Tyr Asp Arg Gln Arg Ala Phe Ser Arg Thr Cys Ala Gly Gly Leu
225                 230                 235                 240

Arg Cys Leu Leu Ser Asp Arg Arg Val Leu Leu Leu Gly Thr Ile Gln
                245                 250                 255

Ala Leu Phe Glu Ser Val Ile Phe Ile Phe Val Phe Leu Trp Thr Pro
            260                 265                 270

Val Leu Asp Pro His Gly Ala Pro Leu Gly Ile Ile Phe Ser Ser Phe
        275                 280                 285

Met Ala Ala Ser Leu Leu Gly Ser Ser Leu Tyr Arg Ile Ala Thr Ser
    290                 295                 300

Lys Arg Tyr His Leu Gln Pro Met His Leu Leu Ser Leu Ala Val Leu
305                 310                 315                 320

Ile Val Val Phe Ser Leu Phe Met Leu Thr Phe Ser Thr Ser Pro Gly
                325                 330                 335

Gln Glu Ser Pro Val Glu Ser Phe Ile Ala Phe Leu Leu Ile Glu Leu
            340                 345                 350

Ala Cys Gly Leu Tyr Phe Pro Ser Met Ser Phe Leu Arg Arg Lys Val
        355                 360                 365

Ile Pro Glu Thr Glu Gln Ala Gly Val Leu Asn Trp Phe Arg Val Pro
    370                 375                 380

Leu His Ser Leu Ala Cys Leu Gly Leu Leu Val Leu His Asp Ser Asp
```

```
                385                 390                 395                 400
Arg Lys Thr Gly Thr Arg Asn Met Phe Ser Ile Cys Ser Ala Val Met
                    405                 410                 415

Val Met Ala Leu Leu Ala Val Val Gly Leu Phe Thr Val Val Arg His
                    420                 425                 430

Asp Ala Glu Leu Arg Val Pro Ser Pro Thr Glu Glu Pro Tyr Ala Pro
            435                 440                 445

Glu Leu
    450

<210> SEQ ID NO 98
<211> LENGTH: 46
<212> TYPE: PRT
<213> ORGANISM: Homo sapiens
<220> FEATURE:
<221> NAME/KEY: SITE
<222> LOCATION: (46)
<223> OTHER INFORMATION: Xaa equals stop translation

<400> SEQUENCE: 98

Met Gln Ala His Pro Ile Phe Ile Tyr His Lys Arg Val Phe Phe Leu
 1               5                  10                  15

Leu Lys Phe Ile Phe Tyr Ile Ile Phe Cys Phe Phe Phe Leu Asp Ile
             20                  25                  30

Ser Thr Leu Tyr Cys Ser Leu Ser Thr Phe Cys Lys Lys Xaa
         35                  40                  45

<210> SEQ ID NO 99
<211> LENGTH: 48
<212> TYPE: PRT
<213> ORGANISM: Homo sapiens
<220> FEATURE:
<221> NAME/KEY: SITE
<222> LOCATION: (48)
<223> OTHER INFORMATION: Xaa equals stop translation

<400> SEQUENCE: 99

Met Gly Val Leu Leu Phe Ser Phe Phe Pro Asn Gly Ser Phe
 1               5                  10                  15

Ser Pro Val Val Leu Pro Ser Tyr Phe Pro Asn Ser Ser Tyr Phe
             20                  25                  30

Val Phe Cys Thr Ser Phe Trp Arg Pro Leu Ser Phe Gln Lys Gly Xaa
         35                  40                  45

<210> SEQ ID NO 100
<211> LENGTH: 51
<212> TYPE: PRT
<213> ORGANISM: Homo sapiens
<220> FEATURE:
<221> NAME/KEY: SITE
<222> LOCATION: (51)
<223> OTHER INFORMATION: Xaa equals stop translation

<400> SEQUENCE: 100

Met Arg Arg Cys Phe Leu Val Leu Glu Ile Ser Val Cys Leu Met Val
 1               5                  10                  15

Ile Ile Val Phe Leu Asp Phe Trp Val Gly Pro Gly Arg Gly Arg
             20                  25                  30

Leu Arg Asn Lys Ser Val Pro Gln Ile Thr Ser Ile Trp Lys Glu Phe
         35                  40                  45

Phe Val Xaa
    50
```

```
<210> SEQ ID NO 101
<211> LENGTH: 41
<212> TYPE: PRT
<213> ORGANISM: Homo sapiens
<220> FEATURE:
<221> NAME/KEY: SITE
<222> LOCATION: (41)
<223> OTHER INFORMATION: Xaa equals stop translation

<400> SEQUENCE: 101

Met Cys Phe Arg Phe Met Met Ile Ile Phe Leu Thr Asn Val Ile Ser
 1               5                  10                  15

Val Ser Ala Val Ile Phe Lys Leu Arg Glu Arg Asp Ser Ile Arg Phe
            20                  25                  30

Phe Phe Phe Phe Ile Phe Leu Lys Xaa
        35                  40

<210> SEQ ID NO 102
<211> LENGTH: 50
<212> TYPE: PRT
<213> ORGANISM: Homo sapiens
<220> FEATURE:
<221> NAME/KEY: SITE
<222> LOCATION: (50)
<223> OTHER INFORMATION: Xaa equals stop translation

<400> SEQUENCE: 102

Met Gly Phe Ser Ile Ile Phe Arg Pro Glu Ala Ala Arg Pro Glu Val
 1               5                  10                  15

Arg Leu His Leu Ser Ala Leu Phe Val Leu Leu Ala Thr Leu Gly
            20                  25                  30

Phe Leu Leu Gly Thr Met Cys Gly Cys Gly Met Cys Glu Gln Lys Gly
        35                  40                  45

Gly Xaa
    50

<210> SEQ ID NO 103
<211> LENGTH: 75
<212> TYPE: PRT
<213> ORGANISM: Homo sapiens
<220> FEATURE:
<221> NAME/KEY: SITE
<222> LOCATION: (75)
<223> OTHER INFORMATION: Xaa equals stop translation

<400> SEQUENCE: 103

Met Thr Leu Leu Leu Phe Ile Phe Phe Val Asp Cys Phe Ser Thr Pro
 1               5                  10                  15

Gly Ser Ser Val Phe Asp Thr Gln Glu Val Trp Val Val Tyr Ser
            20                  25                  30

Val Asn Lys Leu Leu Ala Val Gln His Cys Gln Gly Ile Ala Pro Asn
        35                  40                  45

Val Tyr Ala Leu Ala Val Lys Lys Ser Val Cys Asn Val Ser Glu Trp
    50                  55                  60

Ser Leu Val Ile Cys His Pro Met Pro Ile Xaa
65                  70                  75

<210> SEQ ID NO 104
<211> LENGTH: 123
<212> TYPE: PRT
<213> ORGANISM: Homo sapiens
<220> FEATURE:
```

```
<221> NAME/KEY: SITE
<222> LOCATION: (123)
<223> OTHER INFORMATION: Xaa equals stop translation

<400> SEQUENCE: 104
```

Met Leu Met Leu Ala Val Leu Met Ala Ala Thr His Ala Val Tyr Gly
1               5                   10                  15

Lys Leu Leu Leu Phe Glu Tyr Arg His Arg Lys Met Lys Pro Val Gln
                20                  25                  30

Met Val Pro Ala Ile Ser Gln Asn Trp Thr Phe His Gly Pro Gly Ala
            35                  40                  45

Thr Gly Gln Ala Ala Ala Asn Trp Ile Ala Gly Phe Gly Arg Gly Pro
        50                  55                  60

Cys His Gln Pro Cys Trp Val Ser Gly Arg Met Gly Met Gln Pro Ala
65                  70                  75                  80

Gly Gly Tyr Trp Ala Trp Thr Arg Ser Arg Val Lys Ser Ser Trp Ala
                85                  90                  95

Ala Cys Ser Thr Arg Ser His Cys Ser Phe Cys Ser Ser Gly His Pro
                100                 105                 110

Thr Ser Trp Pro Ala Thr Gly Glu Cys Leu Xaa
            115                 120

```
<210> SEQ ID NO 105
<211> LENGTH: 56
<212> TYPE: PRT
<213> ORGANISM: Homo sapiens
<220> FEATURE:
<221> NAME/KEY: SITE
<222> LOCATION: (56)
<223> OTHER INFORMATION: Xaa equals stop translation

<400> SEQUENCE: 105
```

Met Leu Leu Leu Met Leu Val Asn Thr Ser Ala Val Ala Cys Thr His
1               5                   10                  15

Gly Gly Arg Gly Pro Trp Gly Asn Ser Ala Ala Gln Ala Cys Ala Ala
                20                  25                  30

Leu Ala Arg Gly Pro Gly Arg Thr Leu Pro Arg Pro Pro Ser Gly Ser
            35                  40                  45

His Arg Cys Trp Leu Val Cys Xaa
        50                  55

```
<210> SEQ ID NO 106
<211> LENGTH: 61
<212> TYPE: PRT
<213> ORGANISM: Homo sapiens
<220> FEATURE:
<221> NAME/KEY: SITE
<222> LOCATION: (2)
<223> OTHER INFORMATION: Xaa equals any of the naturally occurring L-
      amino acids
<221> NAME/KEY: SITE
<222> LOCATION: (61)
<223> OTHER INFORMATION: Xaa equals stop translation

<400> SEQUENCE: 106
```

Met Xaa Leu Ala Phe Ser Val Ile Ile Leu Ala Gly Ala Gly Ser Ser
1               5                   10                  15

Arg Ser Trp Asn Ser Val Leu Val Glu Lys Glu Val Val Glu Gly Gly
                20                  25                  30

Leu Gly Pro Trp Gly Asn Cys Ser Ala Glu Pro Leu Pro His Leu Leu
            35                  40                  45

-continued

Leu Pro Arg Thr Asn Leu Lys Ala Lys Val Pro Gly Xaa
            50                  55                  60

<210> SEQ ID NO 107
<211> LENGTH: 102
<212> TYPE: PRT
<213> ORGANISM: Homo sapiens
<220> FEATURE:
<221> NAME/KEY: SITE
<222> LOCATION: (101)
<223> OTHER INFORMATION: Xaa equals any of the naturally occurring L-
      amino acids
<221> NAME/KEY: SITE
<222> LOCATION: (102)
<223> OTHER INFORMATION: Xaa equals stop translation

<400> SEQUENCE: 107

Met Lys Thr Leu Pro Ala Met Leu Gly Thr Gly Lys Leu Phe Trp Val
 1               5                  10                  15

Phe Phe Leu Ile Pro Tyr Leu Asp Ile Trp Asn Ile His Gly Lys Glu
                20                  25                  30

Ser Cys Asp Val Gln Leu Tyr Ile Lys Arg Gln Ser Glu His Ser Ile
            35                  40                  45

Leu Ala Gly Asp Pro Phe Glu Leu Glu Cys Pro Val Lys Tyr Cys Ala
        50                  55                  60

Asn Arg Pro His Val Thr Trp Cys Lys Leu Asn Gly Thr Thr Cys Val
 65                  70                  75                  80

Lys Leu Glu Asp Arg Gln Thr Ser Trp Lys Lys Arg Thr Phe His
                85                  90                  95

Phe Ser Ser Thr Xaa Xaa
            100

<210> SEQ ID NO 108
<211> LENGTH: 154
<212> TYPE: PRT
<213> ORGANISM: Homo sapiens
<220> FEATURE:
<221> NAME/KEY: SITE
<222> LOCATION: (154)
<223> OTHER INFORMATION: Xaa equals stop translation

<400> SEQUENCE: 108

Met Leu Val Thr Ala Tyr Leu Ala Phe Val Gly Leu Leu Ala Ser Cys
 1               5                  10                  15

Leu Gly Leu Glu Leu Ser Arg Cys Arg Ala Lys Pro Pro Gly Arg Ala
                20                  25                  30

Cys Ser Asn Pro Ser Phe Leu Arg Phe Gln Leu Asp Phe Tyr Gln Val
            35                  40                  45

Tyr Phe Leu Ala Leu Ala Asp Trp Leu Gln Ala Pro Tyr Leu Tyr
        50                  55                  60

Lys Leu Tyr Gln His Tyr Tyr Phe Leu Glu Gly Gln Ile Ala Ile Leu
 65                  70                  75                  80

Tyr Val Cys Gly Leu Ala Ser Thr Val Leu Phe Gly Leu Val Ala Ser
                85                  90                  95

Ser Leu Val Asp Trp Leu Gly Arg Lys Asn Ser Cys Val Leu Phe Ser
            100                 105                 110

Leu Thr Tyr Ser Leu Cys Cys Leu Thr Lys Leu Ser Gln Asp Tyr Phe
        115                 120                 125

Val Leu Leu Val Gly Arg Ala Leu Gly Gly Leu Ser Thr Ala Ala Leu
130                 135                 140

Leu Ser Leu Arg Gly Leu Val Tyr Pro Xaa
145                 150

<210> SEQ ID NO 109
<211> LENGTH: 55
<212> TYPE: PRT
<213> ORGANISM: Homo sapiens

<400> SEQUENCE: 109

Val Lys Val Lys Glu Lys Ser Ala Ala Glu Gly Thr Gly Lys Lys Pro
1               5                   10                  15

Lys Gly Cys Arg Leu Pro Gly Val Leu Gly Glu Pro Pro Ser Ser Ala
            20                  25                  30

Gly Pro Arg Lys Gln Arg Thr Val Glu Lys Gly Gly Gln Gly
        35                  40                  45

Gly Asn Ser Arg Ala Ala Ser
    50                  55

<210> SEQ ID NO 110
<211> LENGTH: 14
<212> TYPE: PRT
<213> ORGANISM: Homo sapiens

<400> SEQUENCE: 110

Glu Glu His Arg Tyr Phe Lys Ala Asn Asp Thr Leu Gly Phe
1               5                   10

<210> SEQ ID NO 111
<211> LENGTH: 14
<212> TYPE: PRT
<213> ORGANISM: Homo sapiens

<400> SEQUENCE: 111

Gly Thr Ser Gly Thr Ser Gly Thr Arg Trp Asn Val His Phe
1               5                   10

<210> SEQ ID NO 112
<211> LENGTH: 77
<212> TYPE: PRT
<213> ORGANISM: Homo sapiens

<400> SEQUENCE: 112

Asp Gly Ala Gly Ala Phe Arg Ala Pro Ile Arg Glu Pro Gly Val Pro
1               5                   10                  15

Ala Ser Pro Gln Pro Pro Glu Pro Gly Gln Leu Leu Arg Arg Arg Gln
            20                  25                  30

Gly His Arg Gly Gly Val Gly Ser Pro Arg Thr Pro Ala Gly Gly Ser
        35                  40                  45

Arg Gly Arg Arg Leu Pro Ala Thr Lys Arg Gly Thr Ser Gly Arg Arg
    50                  55                  60

Ala Arg Gly Ser Ser Gly Arg Ile Asn Ala Ser Gln Thr
65                  70                  75

<210> SEQ ID NO 113
<211> LENGTH: 217
<212> TYPE: PRT
<213> ORGANISM: Homo sapiens
<220> FEATURE:
<221> NAME/KEY: SITE
<222> LOCATION: (25)
<223> OTHER INFORMATION: Xaa equals any of the naturally occurring L-
      amino acids
<221> NAME/KEY: SITE

```
<222> LOCATION: (55)
<223> OTHER INFORMATION: Xaa equals any of the naturally occurring L-
      amino acids
<221> NAME/KEY: SITE
<222> LOCATION: (57)
<223> OTHER INFORMATION: Xaa equals any of the naturally occurring L-
      amino acids
<221> NAME/KEY: SITE
<222> LOCATION: (58)
<223> OTHER INFORMATION: Xaa equals any of the naturally occurring L-
      amino acids
<221> NAME/KEY: SITE
<222> LOCATION: (131)
<223> OTHER INFORMATION: Xaa equals any of the naturally occurring L-
      amino acids
<221> NAME/KEY: SITE
<222> LOCATION: (158)
<223> OTHER INFORMATION: Xaa equals any of the naturally occurring L-
      amino acids
<221> NAME/KEY: SITE
<222> LOCATION: (175)
<223> OTHER INFORMATION: Xaa equals any of the naturally occurring L-
      amino acids

<400> SEQUENCE: 113

Gln His Gly Leu Gln Ile Leu Leu Gln Arg Asp Gly Val Pro Gly Gly
  1               5                  10                  15

Asp Ala Gly Glu Pro His Gly Gln Xaa Arg Gly Leu His Ala Gln Gln
             20                  25                  30

Leu His Arg Pro Val Gly Ser Val Asp Leu Trp Ile Phe Arg Val Asp
         35                  40                  45

Ala Ala Gly Ser Gly Pro Xaa Val Xaa Xaa Gly Asn Glu Leu Arg His
     50                  55                  60

Leu Gln Gly Leu Pro Gly Thr Val Gly His Pro Arg Thr Met Asp Glu
 65                  70                  75                  80

Thr Gly Pro Pro Ala Val Gly Glu Pro Arg Ser Gly Pro Ser Ala Gly
                 85                  90                  95

Ser Ala Gly Pro Thr Ala Ala Ser Pro Arg Pro Ala Ala Thr Ser
            100                 105                 110

Pro Thr Gly Arg Ala His Ile Ala Gly Arg Cys Ser Gln Pro Thr Ala
            115                 120                 125

Asp Asp Xaa Pro Glu Phe Val Cys Leu Lys Thr Leu Leu Leu Cys Leu
130                 135                 140

Arg Met Gly Glu Met Arg Ser Glu Ala Pro Gly Ala Ala Xaa Glu Lys
145                 150                 155                 160

Asn Asn Phe Tyr Arg Asp Ala Arg Asp Ser Arg Gly Ser Gly Xaa Gly
                165                 170                 175

Thr Gly Gly Asn Ala Ala Cys Ala Gln Ser Pro Leu Pro Arg Thr Ser
            180                 185                 190

Lys Ile Arg Ser Lys Leu Arg Gly Arg Gly Trp Gly Cys Arg Gly Gly
            195                 200                 205

Asp Ser Glu Pro Pro Val Arg Lys Gln
    210                 215

<210> SEQ ID NO 114
<211> LENGTH: 49
<212> TYPE: PRT
<213> ORGANISM: Homo sapiens
<220> FEATURE:
<221> NAME/KEY: SITE
<222> LOCATION: (25)
<223> OTHER INFORMATION: Xaa equals any of the naturally occurring L-
      amino acids
```

-continued

```
<400> SEQUENCE: 114

Gln His Gly Leu Gln Ile Leu Leu Gln Arg Asp Gly Val Pro Gly
1               5                   10                  15

Asp Ala Gly Glu Pro His Gly Gln Xaa Arg Gly Leu His Ala Gln Gln
            20                  25                  30

Leu His Arg Pro Val Gly Ser Val Asp Leu Trp Ile Phe Arg Val Asp
        35                  40                  45

Ala

<210> SEQ ID NO 115
<211> LENGTH: 48
<212> TYPE: PRT
<213> ORGANISM: Homo sapiens
<220> FEATURE:
<221> NAME/KEY: SITE
<222> LOCATION: (6)
<223> OTHER INFORMATION: Xaa equals any of the naturally occurring L-
      amino acids
<221> NAME/KEY: SITE
<222> LOCATION: (8)
<223> OTHER INFORMATION: Xaa equals any of the naturally occurring L-
      amino acids
<221> NAME/KEY: SITE
<222> LOCATION: (9)
<223> OTHER INFORMATION: Xaa equals any of the naturally occurring L-
      amino acids

<400> SEQUENCE: 115

Ala Gly Ser Gly Pro Xaa Val Xaa Xaa Gly Asn Glu Leu Arg His Leu
1               5                   10                  15

Gln Gly Leu Pro Gly Thr Val Gly His Pro Arg Thr Met Asp Glu Thr
            20                  25                  30

Gly Pro Pro Ala Val Gly Glu Pro Arg Ser Gly Pro Ser Ala Gly Ser
        35                  40                  45

<210> SEQ ID NO 116
<211> LENGTH: 48
<212> TYPE: PRT
<213> ORGANISM: Homo sapiens
<220> FEATURE:
<221> NAME/KEY: SITE
<222> LOCATION: (34)
<223> OTHER INFORMATION: Xaa equals any of the naturally occurring L-
      amino acids

<400> SEQUENCE: 116

Ala Gly Pro Thr Ala Ala Ser Pro Arg Pro Ala Ala Thr Ser Pro
1               5                   10                  15

Thr Gly Arg Ala His Ile Ala Gly Arg Cys Ser Gln Pro Thr Ala Asp
            20                  25                  30

Asp Xaa Pro Glu Phe Val Cys Leu Lys Thr Leu Leu Cys Leu Arg
        35                  40                  45

<210> SEQ ID NO 117
<211> LENGTH: 48
<212> TYPE: PRT
<213> ORGANISM: Homo sapiens
<220> FEATURE:
<221> NAME/KEY: SITE
<222> LOCATION: (13)
<223> OTHER INFORMATION: Xaa equals any of the naturally occurring L-
      amino acids
<221> NAME/KEY: SITE
<222> LOCATION: (30)
<223> OTHER INFORMATION: Xaa equals any of the naturally occurring L-
      amino acids
```

```
<400> SEQUENCE: 117

Met Gly Glu Met Arg Ser Glu Ala Pro Gly Ala Ala Xaa Glu Lys Asn
  1               5                  10                  15

Asn Phe Tyr Arg Asp Ala Arg Asp Ser Arg Gly Ser Gly Xaa Gly Thr
             20                  25                  30

Gly Gly Asn Ala Ala Cys Ala Gln Ser Pro Leu Pro Arg Thr Ser Lys
         35                  40                  45

<210> SEQ ID NO 118
<211> LENGTH: 24
<212> TYPE: PRT
<213> ORGANISM: Homo sapiens

<400> SEQUENCE: 118

Ile Arg Ser Lys Leu Arg Gly Arg Gly Trp Gly Cys Arg Gly Gly Asp
  1               5                  10                  15

Ser Glu Pro Pro Val Arg Lys Gln
             20

<210> SEQ ID NO 119
<211> LENGTH: 16
<212> TYPE: PRT
<213> ORGANISM: Homo sapiens

<400> SEQUENCE: 119

Gly Thr Ser Pro Glu Ala Tyr Val Gly Pro Gly Gly Pro Glu Cys Pro
  1               5                  10                  15

<210> SEQ ID NO 120
<211> LENGTH: 20
<212> TYPE: PRT
<213> ORGANISM: Homo sapiens
<220> FEATURE:
<221> NAME/KEY: SITE
<222> LOCATION: (11)
<223> OTHER INFORMATION: Xaa equals any of the naturally occurring L-
      amino acids

<400> SEQUENCE: 120

Ser Cys Ile His Thr Gly Asp Val Met Ile Xaa Pro Val Leu Ser Cys
  1               5                  10                  15

Phe Thr Arg Phe
             20

<210> SEQ ID NO 121
<211> LENGTH: 50
<212> TYPE: PRT
<213> ORGANISM: Homo sapiens

<400> SEQUENCE: 121

Gly Arg His Leu Val Ala Ser Gln Lys Arg Val Leu Arg Asp Arg Arg
  1               5                  10                  15

Val Gln Thr Gly Ile Trp Ser Asp Gln Leu Tyr Ser Gln Arg Pro Trp
             20                  25                  30

Ala Pro Val Thr Trp Pro Asp His Trp Gly Val Cys Val Cys Val Tyr
         35                  40                  45

Val Cys
     50

<210> SEQ ID NO 122
<211> LENGTH: 43
```

```
<212> TYPE: PRT
<213> ORGANISM: Homo sapiens
<220> FEATURE:
<221> NAME/KEY: SITE
<222> LOCATION: (24)
<223> OTHER INFORMATION: Xaa equals any of the naturally occurring L-
      amino acids

<400> SEQUENCE: 122

Ala Phe Pro His Ser Ile Pro Cys Gln Val Met Ala Val Pro Ser Pro
 1               5                  10                  15

Gln Leu Leu Leu Glu Arg Pro Xaa Leu Pro Val Ser Phe Met Phe Leu
             20                  25                  30

Thr Ser His Pro Pro Arg Leu Val Cys Pro
         35                  40

<210> SEQ ID NO 123
<211> LENGTH: 361
<212> TYPE: PRT
<213> ORGANISM: Homo sapiens
<220> FEATURE:
<221> NAME/KEY: SITE
<222> LOCATION: (24)
<223> OTHER INFORMATION: Xaa equals any of the naturally occurring L-
      amino acids

<400> SEQUENCE: 123

Leu Pro Thr Leu His Ser Leu Ser Ser Tyr Gly Cys Pro Leu Thr Pro
 1               5                  10                  15

Ala Ala Pro Arg Glu Ala Leu Xaa Thr Cys Val Ile His Val Ser Asn
             20                  25                  30

Lys Pro Pro Ser Thr Pro Ser Cys Val Pro His Ala Pro Val His Leu
         35                  40                  45

Cys Cys Val Gly Val Gly Gly Pro Phe Ala His Ala Trp Gly Ile Pro
     50                  55                  60

Cys Pro Asp Gln Arg Asp Lys Glu Arg Glu Arg Leu Gln Glu Ala
 65                  70                  75                  80

Arg Gly Arg Pro Gly Glu Gly Arg Gly Asn Thr Ala Thr Glu Thr Thr
                 85                  90                  95

Thr Arg His Ser Gln Arg Ala Ala Asp Gly Ser Ala Val Ser Thr Val
            100                 105                 110

Thr Lys Thr Glu Arg Leu Val His Ser Asn Asp Gly Thr Arg Thr Ala
        115                 120                 125

Arg Thr Thr Thr Val Glu Ser Ser Phe Val Arg Ser Glu Asn Gly
    130                 135                 140

Ser Gly Ser Thr Met Met Gln Thr Lys Thr Phe Ser Ser Ser Ser
145                 150                 155                 160

Ser Lys Lys Met Gly Ser Ile Phe Asp Arg Glu Asp Gln Ala Ser Pro
                165                 170                 175

Arg Ala Gly Ser Leu Ala Ala Leu Glu Lys Arg Gln Ala Glu Lys Lys
            180                 185                 190

Lys Glu Leu Met Lys Ala Gln Ser Leu Pro Lys Thr Ser Ala Ser Gln
        195                 200                 205

Ala Arg Lys Ala Met Ile Glu Lys Leu Glu Lys Glu Gly Ala Ala Gly
    210                 215                 220

Ser Pro Gly Gly Pro Arg Ala Ala Val Gln Arg Ser Thr Ser Phe Gly
225                 230                 235                 240

Val Pro Asn Ala Asn Ser Ile Lys Gln Met Leu Leu Asp Trp Cys Arg
                245                 250                 255
```

-continued

```
Ala Lys Thr Arg Gly Tyr Glu His Val Asp Ile Gln Asn Phe Ser Ser
            260                 265                 270

Ser Trp Ser Asp Gly Met Ala Phe Cys Ala Leu Val His Asn Phe Phe
        275                 280                 285

Pro Glu Ala Phe Asp Tyr Gly Gln Leu Ser Pro Gln Asn Arg Arg Gln
    290                 295                 300

Asn Phe Glu Val Ala Phe Ser Ser Ala Glu Thr His Ala Asp Cys Pro
305                 310                 315                 320

Gln Leu Leu Asp Thr Glu Asp Met Val Arg Leu Arg Glu Pro Asp Trp
                325                 330                 335

Lys Cys Val Tyr Thr Tyr Ile Gln Glu Phe Tyr Arg Cys Leu Val Gln
            340                 345                 350

Lys Gly Leu Val Lys Thr Lys Lys Ser
            355                 360

<210> SEQ ID NO 124
<211> LENGTH: 46
<212> TYPE: PRT
<213> ORGANISM: Homo sapiens
<220> FEATURE:
<221> NAME/KEY: SITE
<222> LOCATION: (24)
<223> OTHER INFORMATION: Xaa equals any of the naturally occurring L-
      amino acids

<400> SEQUENCE: 124

Leu Pro Thr Leu His Ser Leu Ser Ser Tyr Gly Cys Pro Leu Thr Pro
1               5                   10                  15

Ala Ala Pro Arg Glu Ala Leu Xaa Thr Cys Val Ile His Val Ser Asn
            20                  25                  30

Lys Pro Pro Ser Thr Pro Ser Cys Val Pro His Ala Pro Val
        35                  40                  45

<210> SEQ ID NO 125
<211> LENGTH: 46
<212> TYPE: PRT
<213> ORGANISM: Homo sapiens

<400> SEQUENCE: 125

His Leu Cys Cys Val Gly Val Gly Gly Pro Phe Ala His Ala Trp Gly
1               5                   10                  15

Ile Pro Cys Pro Asp Gln Arg Asp Lys Glu Arg Glu Arg Leu Gln
            20                  25                  30

Glu Ala Arg Gly Arg Pro Gly Glu Gly Arg Gly Asn Thr Ala
        35                  40                  45

<210> SEQ ID NO 126
<211> LENGTH: 46
<212> TYPE: PRT
<213> ORGANISM: Homo sapiens

<400> SEQUENCE: 126

Thr Glu Thr Thr Thr Arg His Ser Gln Arg Ala Ala Asp Gly Ser Ala
1               5                   10                  15

Val Ser Thr Val Thr Lys Thr Glu Arg Leu Val His Ser Asn Asp Gly
            20                  25                  30

Thr Arg Thr Ala Arg Thr Thr Thr Val Glu Ser Ser Phe Val
        35                  40                  45
```

<210> SEQ ID NO 127
<211> LENGTH: 46
<212> TYPE: PRT
<213> ORGANISM: Homo sapiens

<400> SEQUENCE: 127

Arg Arg Ser Glu Asn Gly Ser Gly Ser Thr Met Met Gln Thr Lys Thr
1               5                   10                  15

Phe Ser Ser Ser Ser Ser Lys Lys Met Gly Ser Ile Phe Asp Arg
            20                  25                  30

Glu Asp Gln Ala Ser Pro Arg Ala Gly Ser Leu Ala Ala Leu
        35                  40                  45

<210> SEQ ID NO 128
<211> LENGTH: 47
<212> TYPE: PRT
<213> ORGANISM: Homo sapiens

<400> SEQUENCE: 128

Glu Lys Arg Gln Ala Glu Lys Lys Glu Leu Met Lys Ala Gln Ser
1               5                   10                  15

Leu Pro Lys Thr Ser Ala Ser Gln Ala Arg Lys Ala Met Ile Glu Lys
            20                  25                  30

Leu Glu Lys Glu Gly Ala Ala Gly Ser Pro Gly Gly Pro Arg Ala
        35                  40                  45

<210> SEQ ID NO 129
<211> LENGTH: 47
<212> TYPE: PRT
<213> ORGANISM: Homo sapiens

<400> SEQUENCE: 129

Ala Val Gln Arg Ser Thr Ser Phe Gly Val Pro Asn Ala Asn Ser Ile
1               5                   10                  15

Lys Gln Met Leu Leu Asp Trp Cys Arg Ala Lys Thr Arg Gly Tyr Glu
            20                  25                  30

His Val Asp Ile Gln Asn Phe Ser Ser Trp Ser Asp Gly Met
        35                  40                  45

<210> SEQ ID NO 130
<211> LENGTH: 49
<212> TYPE: PRT
<213> ORGANISM: Homo sapiens

<400> SEQUENCE: 130

Ala Phe Cys Ala Leu Val His Asn Phe Phe Pro Glu Ala Phe Asp Tyr
1               5                   10                  15

Gly Gln Leu Ser Pro Gln Asn Arg Arg Gln Asn Phe Glu Val Ala Phe
            20                  25                  30

Ser Ser Ala Glu Thr His Ala Asp Cys Pro Gln Leu Leu Asp Thr Glu
        35                  40                  45

Asp

<210> SEQ ID NO 131
<211> LENGTH: 34
<212> TYPE: PRT
<213> ORGANISM: Homo sapiens

<400> SEQUENCE: 131

Met Val Arg Leu Arg Glu Pro Asp Trp Lys Cys Val Tyr Thr Tyr Ile
1               5                   10                  15

```
Gln Glu Phe Tyr Arg Cys Leu Val Gln Lys Gly Leu Val Lys Thr Lys
            20                  25                  30

Lys Ser
```

```
<210> SEQ ID NO 132
<211> LENGTH: 341
<212> TYPE: PRT
<213> ORGANISM: Homo sapiens
<220> FEATURE:
<221> NAME/KEY: SITE
<222> LOCATION: (21)
<223> OTHER INFORMATION: Xaa equals any of the naturally occurring L-
      amino acids
<221> NAME/KEY: SITE
<222> LOCATION: (33)
<223> OTHER INFORMATION: Xaa equals any of the naturally occurring L-
      amino acids
<221> NAME/KEY: SITE
<222> LOCATION: (35)
<223> OTHER INFORMATION: Xaa equals any of the naturally occurring L-
      amino acids
<221> NAME/KEY: SITE
<222> LOCATION: (37)
<223> OTHER INFORMATION: Xaa equals any of the naturally occurring L-
      amino acids
<221> NAME/KEY: SITE
<222> LOCATION: (162)
<223> OTHER INFORMATION: Xaa equals any of the naturally occurring L-
      amino acids
<221> NAME/KEY: SITE
<222> LOCATION: (326)
<223> OTHER INFORMATION: Xaa equals any of the naturally occurring L-
      amino acids
<221> NAME/KEY: SITE
<222> LOCATION: (333)
<223> OTHER INFORMATION: Xaa equals any of the naturally occurring L-
      amino acids

<400> SEQUENCE: 132
```

```
Lys Met Glu Trp Leu Ala Asp Pro Thr Ala Trp Leu Gly Leu Leu Thr
  1               5                  10                  15

Leu Ile Val Leu Xaa Leu Val Leu Gly Ile Asp Asn Leu Val Phe Ile
                 20                  25                  30

Xaa Ile Xaa Ala Xaa Lys Leu Pro Pro Glu Gln Arg Asp Arg Ala Arg
             35                  40                  45

Leu Ile Gly Leu Ser Leu Ala Leu Leu Met Arg Leu Gly Leu Leu Ala
         50                  55                  60

Ser Ile Ser Trp Leu Val Thr Leu Thr Gln Pro Leu Phe Glu Val Phe
 65                  70                  75                  80

Asp Lys Ser Phe Ser Gly Arg Asp Leu Ile Met Leu Phe Gly Gly Val
                 85                  90                  95

Phe Leu Leu Phe Lys Ala Thr Met Glu Leu His Glu Arg Leu Glu Gly
            100                 105                 110

His Val Ala Gln Arg Thr Gly Asn Val Ala Tyr Ala Met Phe Trp Pro
        115                 120                 125

Ile Val Ala Gln Ile Val Val Leu Asp Ala Val Phe Ser Leu Asp Ala
    130                 135                 140

Val Ile Thr Ala Val Gly Met Val Asp Glu Leu Ala Val Met Met Ile
145                 150                 155                 160

Ala Xaa Ile Ile Ser Ile Gly Leu Met Ile Val Ala Ser Lys Pro Leu
                165                 170                 175

Thr Arg Phe Val Asn Ala His Pro Thr Val Ile Met Leu Cys Leu Gly
            180                 185                 190
```

```
Phe Leu Met Met Ile Gly Phe Ala Leu Thr Ala Glu Gly Leu Gly Phe
            195                 200                 205

His Ile Pro Lys Gly Tyr Leu Tyr Ala Ala Ile Gly Phe Ser Ile Leu
        210                 215                 220

Ile Glu Leu Phe Asn Gln Ile Ala Arg Ser Arg Arg Lys Lys Ser Ala
225                 230                 235                 240

Gln Gly Thr Leu Pro Arg Arg Glu Arg Thr Ala His Ala Val Met Arg
                245                 250                 255

Leu Leu Gly Gly Arg Asn Leu Ala Val Glu Glu Val Gly Glu Glu Val
            260                 265                 270

Ala Asp Leu Leu Asp Asn Pro Asp Ala Asn Gly Gly Pro Leu Phe Asp
        275                 280                 285

Arg Arg Glu Arg Val Met Ile Ser Gly Val Leu Gln Leu Ala Glu Arg
290                 295                 300

Pro Ile Arg Thr Leu Met Thr Pro Arg Ala Lys Val Asp Ser Ile Asp
305                 310                 315                 320

Leu Ser Asp Asp Pro Xaa Thr Ile Arg Leu Lys Leu Xaa Ile Arg Leu
                325                 330                 335

Thr Arg Ala Cys Pro
            340
```

<210> SEQ ID NO 133
<211> LENGTH: 48
<212> TYPE: PRT
<213> ORGANISM: Homo sapiens
<220> FEATURE:
<221> NAME/KEY: SITE
<222> LOCATION: (21)
<223> OTHER INFORMATION: Xaa equals any of the naturally occurring L-
      amino acids
<221> NAME/KEY: SITE
<222> LOCATION: (33)
<223> OTHER INFORMATION: Xaa equals any of the naturally occurring L-
      amino acids
<221> NAME/KEY: SITE
<222> LOCATION: (35)
<223> OTHER INFORMATION: Xaa equals any of the naturally occurring L-
      amino acids
<221> NAME/KEY: SITE
<222> LOCATION: (37)
<223> OTHER INFORMATION: Xaa equals any of the naturally occurring L-
      amino acids

<400> SEQUENCE: 133

```
Lys Met Glu Trp Leu Ala Asp Pro Thr Ala Trp Leu Gly Leu Leu Thr
  1               5                  10                  15

Leu Ile Val Leu Xaa Leu Val Leu Gly Ile Asp Asn Leu Val Phe Ile
                20                  25                  30

Xaa Ile Xaa Ala Xaa Lys Leu Pro Pro Glu Gln Arg Asp Arg Ala Arg
            35                  40                  45
```

<210> SEQ ID NO 134
<211> LENGTH: 49
<212> TYPE: PRT
<213> ORGANISM: Homo sapiens

<400> SEQUENCE: 134

```
Leu Ile Gly Leu Ser Leu Ala Leu Leu Met Arg Leu Gly Leu Leu Ala
  1               5                  10                  15

Ser Ile Ser Trp Leu Val Thr Leu Thr Gln Pro Leu Phe Glu Val Phe
                20                  25                  30

Asp Lys Ser Phe Ser Gly Arg Asp Leu Ile Met Leu Phe Gly Gly Val
```

```
              35                  40                  45
Phe

<210> SEQ ID NO 135
<211> LENGTH: 47
<212> TYPE: PRT
<213> ORGANISM: Homo sapiens

<400> SEQUENCE: 135

Leu Leu Phe Lys Ala Thr Met Glu Leu His Glu Arg Leu Glu Gly His
 1               5                  10                  15

Val Ala Gln Arg Thr Gly Asn Val Ala Tyr Ala Met Phe Trp Pro Ile
             20                  25                  30

Val Ala Gln Ile Val Val Leu Asp Ala Val Phe Ser Leu Asp Ala
         35                  40                  45

<210> SEQ ID NO 136
<211> LENGTH: 49
<212> TYPE: PRT
<213> ORGANISM: Homo sapiens
<220> FEATURE:
<221> NAME/KEY: SITE
<222> LOCATION: (18)
<223> OTHER INFORMATION: Xaa equals any of the naturally occurring L-
      amino acids

<400> SEQUENCE: 136

Val Ile Thr Ala Val Gly Met Val Asp Glu Leu Ala Val Met Met Ile
 1               5                  10                  15

Ala Xaa Ile Ile Ser Ile Gly Leu Met Ile Val Ala Ser Lys Pro Leu
             20                  25                  30

Thr Arg Phe Val Asn Ala His Pro Thr Val Ile Met Leu Cys Leu Gly
         35                  40                  45

Phe

<210> SEQ ID NO 137
<211> LENGTH: 50
<212> TYPE: PRT
<213> ORGANISM: Homo sapiens

<400> SEQUENCE: 137

Leu Met Met Ile Gly Phe Ala Leu Thr Ala Glu Gly Leu Gly Phe His
 1               5                  10                  15

Ile Pro Lys Gly Tyr Leu Tyr Ala Ala Ile Gly Phe Ser Ile Leu Ile
             20                  25                  30

Glu Leu Phe Asn Gln Ile Ala Arg Ser Arg Lys Lys Ser Ala Gln
         35                  40                  45

Gly Thr
     50

<210> SEQ ID NO 138
<211> LENGTH: 48
<212> TYPE: PRT
<213> ORGANISM: Homo sapiens

<400> SEQUENCE: 138

Leu Pro Arg Arg Glu Arg Thr Ala His Ala Val Met Arg Leu Leu Gly
 1               5                  10                  15

Gly Arg Asn Leu Ala Val Glu Glu Val Gly Glu Glu Val Ala Asp Leu
             20                  25                  30
```

Leu Asp Asn Pro Asp Ala Asn Gly Gly Pro Leu Phe Asp Arg Arg Glu
            35                  40                  45

<210> SEQ ID NO 139
<211> LENGTH: 50
<212> TYPE: PRT
<213> ORGANISM: Homo sapiens
<220> FEATURE:
<221> NAME/KEY: SITE
<222> LOCATION: (35)
<223> OTHER INFORMATION: Xaa equals any of the naturally occurring L-
      amino acids
<221> NAME/KEY: SITE
<222> LOCATION: (42)
<223> OTHER INFORMATION: Xaa equals any of the naturally occurring L-
      amino acids

<400> SEQUENCE: 139

Arg Val Met Ile Ser Gly Val Leu Gln Leu Ala Glu Arg Pro Ile Arg
 1               5                  10                  15

Thr Leu Met Thr Pro Arg Ala Lys Val Asp Ser Ile Asp Leu Ser Asp
            20                  25                  30

Asp Pro Xaa Thr Ile Arg Leu Lys Leu Xaa Ile Arg Leu Thr Arg Ala
            35                  40                  45

Cys Pro
    50

<210> SEQ ID NO 140
<211> LENGTH: 15
<212> TYPE: PRT
<213> ORGANISM: Homo sapiens

<400> SEQUENCE: 140

Leu Leu Thr Ser Pro Val Ser Trp His Ser Thr Val Pro Ser Trp
 1               5                  10                  15

<210> SEQ ID NO 141
<211> LENGTH: 12
<212> TYPE: PRT
<213> ORGANISM: Homo sapiens

<400> SEQUENCE: 141

Ser Ala Leu Ser Ile Ser Asn His Gln Gly Phe Phe
 1               5                  10

<210> SEQ ID NO 142
<211> LENGTH: 32
<212> TYPE: PRT
<213> ORGANISM: Homo sapiens

<400> SEQUENCE: 142

His Lys Gly Ser Gly Arg Pro Pro Thr Lys Glu Ala Met Glu Pro Met
 1               5                  10                  15

Glu Leu Met Glu Glu Met Leu Gly Leu Trp Val Ser Ala Asp Thr Pro
            20                  25                  30

<210> SEQ ID NO 143
<211> LENGTH: 10
<212> TYPE: PRT
<213> ORGANISM: Homo sapiens

<400> SEQUENCE: 143

Thr Val Lys His Glu Val Ile His Ala Leu
 1               5                  10

-continued

```
<210> SEQ ID NO 144
<211> LENGTH: 562
<212> TYPE: PRT
<213> ORGANISM: Homo sapiens
<220> FEATURE:
<221> NAME/KEY: SITE
<222> LOCATION: (2)
<223> OTHER INFORMATION: Xaa equals any of the naturally occurring L-
      amino acids
<221> NAME/KEY: SITE
<222> LOCATION: (17)
<223> OTHER INFORMATION: Xaa equals any of the naturally occurring L-
      amino acids
<221> NAME/KEY: SITE
<222> LOCATION: (18)
<223> OTHER INFORMATION: Xaa equals any of the naturally occurring L-
      amino acids
<221> NAME/KEY: SITE
<222> LOCATION: (221)
<223> OTHER INFORMATION: Xaa equals any of the naturally occurring L-
      amino acids
<221> NAME/KEY: SITE
<222> LOCATION: (414)
<223> OTHER INFORMATION: Xaa equals any of the naturally occurring L-
      amino acids

<400> SEQUENCE: 144

Glu Xaa Leu Leu Pro Glu Lys Lys Asn Leu Val Lys Asn Lys Leu Leu
 1               5                  10                  15

Xaa Xaa Ala Ile Ser Tyr Leu Glu Lys Thr Phe Gln Val Arg Arg Pro
                20                  25                  30

Ala Gly Thr Ile Leu Leu Ser Arg Gln Cys Ala Thr Asn Gln Tyr Leu
            35                  40                  45

Arg Lys Glu Asn Asp Pro His Arg Tyr Cys Thr Gly Glu Cys Ala Ala
    50                  55                  60

His Thr Lys Cys Gly Pro Val Ile Val Pro Glu Glu His Leu Gln Gln
 65                  70                  75                  80

Cys Arg Val Tyr Arg Gly Gly Lys Trp Pro His Gly Ala Val Gly Val
                85                  90                  95

Pro Asp Gln Glu Gly Ile Ser Asp Ala Asp Phe Val Leu Tyr Val Gly
                100                 105                 110

Ala Leu Ala Thr Glu Arg Cys Ser His Glu Asn Ile Ile Ser Tyr Ala
            115                 120                 125

Ala Tyr Cys Gln Gln Glu Ala Asn Met Asp Arg Pro Ile Ala Gly Tyr
    130                 135                 140

Ala Asn Leu Cys Pro Asn Met Ile Ser Thr Gln Pro Gln Glu Phe Val
145                 150                 155                 160

Gly Met Leu Ser Thr Val Lys His Glu Val Ile His Ala Leu Gly Phe
                165                 170                 175

Ser Ala Gly Leu Phe Ala Phe Tyr His Asp Lys Asp Gly Asn Pro Leu
            180                 185                 190

Thr Ser Arg Phe Ala Asp Gly Leu Pro Pro Phe Asn Tyr Ser Leu Gly
    195                 200                 205

Leu Tyr Gln Trp Ser Asp Lys Val Val Arg Lys Val Xaa Arg Leu Trp
210                 215                 220

Asp Val Arg Asp Asn Lys Ile Val Arg His Thr Val Tyr Leu Leu Val
225                 230                 235                 240

Thr Pro Arg Val Val Glu Ala Arg Lys His Phe Asp Cys Pro Val
                245                 250                 255

Leu Glu Gly Met Glu Leu Glu Asn Gln Gly Val Gly Thr Glu Leu
                260                 265                 270
```

```
Asn His Trp Glu Lys Arg Leu Leu Glu Asn Glu Ala Met Thr Gly Ser
            275                 280                 285

His Thr Gln Asn Arg Val Leu Ser Arg Ile Thr Leu Ala Leu Met Glu
        290                 295                 300

Asp Thr Gly Trp Tyr Lys Ala Asn Tyr Ser Met Ala Glu Lys Leu Asp
305                 310                 315                 320

Trp Gly Arg Gly Met Gly Cys Asp Phe Val Arg Lys Ser Cys Lys Phe
                325                 330                 335

Trp Ile Asp Gln Gln Arg Gln Lys Arg Gln Met Leu Ser Pro Tyr Cys
            340                 345                 350

Asp Thr Leu Arg Ser Asn Pro Leu Gln Leu Thr Cys Arg Gln Asp Gln
        355                 360                 365

Arg Ala Val Ala Val Cys Asn Leu Gln Lys Phe Pro Lys Pro Leu Pro
370                 375                 380

Gln Glu Tyr Gln Tyr Phe Asp Glu Leu Ser Gly Ile Pro Ala Glu Asp
385                 390                 395                 400

Leu Pro Tyr Tyr Gly Gly Ser Val Glu Ile Ala Asp Tyr Xaa Pro Phe
                405                 410                 415

Ser Gln Glu Phe Ser Trp His Leu Ser Gly Glu Tyr Gln Arg Ser Ser
            420                 425                 430

Asp Cys Arg Ile Leu Glu Asn Gln Pro Glu Ile Phe Lys Asn Tyr Gly
        435                 440                 445

Ala Glu Lys Tyr Gly Pro His Ser Val Cys Leu Ile Gln Lys Ser Ala
450                 455                 460

Phe Val Met Glu Lys Cys Glu Arg Lys Leu Ser Tyr Pro Asp Trp Gly
465                 470                 475                 480

Ser Gly Cys Tyr Gln Val Ser Cys Ser Pro Gln Gly Leu Lys Val Trp
                485                 490                 495

Val Gln Asp Thr Ser Tyr Leu Cys Ser Arg Ala Gly Gln Val Leu Pro
            500                 505                 510

Val Ser Ile Gln Met Asn Gly Trp Ile His Asp Gly Asn Leu Leu Cys
        515                 520                 525

Pro Ser Cys Trp Asp Phe Cys Glu Leu Cys Pro Pro Glu Thr Asp Pro
530                 535                 540

Pro Ala Thr Asn Leu Thr Arg Ala Leu Pro Leu Asp Leu Cys Ser Cys
545                 550                 555                 560

Ser Ser
```

<210> SEQ ID NO 145
<211> LENGTH: 47
<212> TYPE: PRT
<213> ORGANISM: Homo sapiens
<220> FEATURE:
<221> NAME/KEY: SITE
<222> LOCATION: (2)
<223> OTHER INFORMATION: Xaa equals any of the naturally occurring L-
    amino acids
<221> NAME/KEY: SITE
<222> LOCATION: (17)
<223> OTHER INFORMATION: Xaa equals any of the naturally occurring L-
    amino acids
<221> NAME/KEY: SITE
<222> LOCATION: (18)
<223> OTHER INFORMATION: Xaa equals any of the naturally occurring L-
    amino acids

<400> SEQUENCE: 145

Glu Xaa Leu Leu Pro Glu Lys Lys Asn Leu Val Lys Asn Lys Leu Leu

-continued

```
                1               5                  10                  15
Xaa Xaa Ala Ile Ser Tyr Leu Glu Lys Thr Phe Gln Val Arg Arg Pro
                    20                  25                  30
Ala Gly Thr Ile Leu Leu Ser Arg Gln Cys Ala Thr Asn Gln Tyr
            35                  40                  45

<210> SEQ ID NO 146
<211> LENGTH: 45
<212> TYPE: PRT
<213> ORGANISM: Homo sapiens

<400> SEQUENCE: 146

Leu Arg Lys Glu Asn Asp Pro His Arg Tyr Cys Thr Gly Glu Cys Ala
 1               5                  10                  15
Ala His Thr Lys Cys Gly Pro Val Ile Val Pro Glu Glu His Leu Gln
                20                  25                  30
Gln Cys Arg Val Tyr Arg Gly Gly Lys Trp Pro His Gly
            35                  40                  45

<210> SEQ ID NO 147
<211> LENGTH: 45
<212> TYPE: PRT
<213> ORGANISM: Homo sapiens

<400> SEQUENCE: 147

Ala Val Gly Val Pro Asp Gln Glu Gly Ile Ser Asp Ala Asp Phe Val
 1               5                  10                  15
Leu Tyr Val Gly Ala Leu Ala Thr Glu Arg Cys Ser His Glu Asn Ile
                20                  25                  30
Ile Ser Tyr Ala Ala Tyr Cys Gln Gln Glu Ala Asn Met
            35                  40                  45

<210> SEQ ID NO 148
<211> LENGTH: 46
<212> TYPE: PRT
<213> ORGANISM: Homo sapiens

<400> SEQUENCE: 148

Asp Arg Pro Ile Ala Gly Tyr Ala Asn Leu Cys Pro Asn Met Ile Ser
 1               5                  10                  15
Thr Gln Pro Gln Glu Phe Val Gly Met Leu Ser Thr Val Lys His Glu
                20                  25                  30
Val Ile His Ala Leu Gly Phe Ser Ala Gly Leu Phe Ala Phe
            35                  40                  45

<210> SEQ ID NO 149
<211> LENGTH: 45
<212> TYPE: PRT
<213> ORGANISM: Homo sapiens
<220> FEATURE:
<221> NAME/KEY: SITE
<222> LOCATION: (38)
<223> OTHER INFORMATION: Xaa equals any of the naturally occurring L-
      amino acids

<400> SEQUENCE: 149

Tyr His Asp Lys Asp Gly Asn Pro Leu Thr Ser Arg Phe Ala Asp Gly
 1               5                  10                  15
Leu Pro Pro Phe Asn Tyr Ser Leu Gly Leu Tyr Gln Trp Ser Asp Lys
                20                  25                  30
Val Val Arg Lys Val Xaa Arg Leu Trp Asp Val Arg Asp
            35                  40                  45
```

35                  40                  45

<210> SEQ ID NO 150
<211> LENGTH: 46
<212> TYPE: PRT
<213> ORGANISM: Homo sapiens

<400> SEQUENCE: 150

Asn Lys Ile Val Arg His Thr Val Tyr Leu Leu Val Thr Pro Arg Val
 1               5                  10                  15

Val Glu Glu Ala Arg Lys His Phe Asp Cys Pro Val Leu Glu Gly Met
            20                  25                  30

Glu Leu Glu Asn Gln Gly Gly Val Gly Thr Glu Leu Asn His
        35                  40                  45

<210> SEQ ID NO 151
<211> LENGTH: 45
<212> TYPE: PRT
<213> ORGANISM: Homo sapiens

<400> SEQUENCE: 151

Trp Glu Lys Arg Leu Leu Glu Asn Glu Ala Met Thr Gly Ser His Thr
 1               5                  10                  15

Gln Asn Arg Val Leu Ser Arg Ile Thr Leu Ala Leu Met Glu Asp Thr
            20                  25                  30

Gly Trp Tyr Lys Ala Asn Tyr Ser Met Ala Glu Lys Leu
        35                  40                  45

<210> SEQ ID NO 152
<211> LENGTH: 45
<212> TYPE: PRT
<213> ORGANISM: Homo sapiens

<400> SEQUENCE: 152

Asp Trp Gly Arg Gly Met Gly Cys Asp Phe Val Arg Lys Ser Cys Lys
 1               5                  10                  15

Phe Trp Ile Asp Gln Gln Arg Gln Lys Arg Gln Met Leu Ser Pro Tyr
            20                  25                  30

Cys Asp Thr Leu Arg Ser Asn Pro Leu Gln Leu Thr Cys
        35                  40                  45

<210> SEQ ID NO 153
<211> LENGTH: 47
<212> TYPE: PRT
<213> ORGANISM: Homo sapiens

<400> SEQUENCE: 153

Arg Gln Asp Gln Arg Ala Val Ala Val Cys Asn Leu Gln Lys Phe Pro
 1               5                  10                  15

Lys Pro Leu Pro Gln Glu Tyr Gln Tyr Phe Asp Glu Leu Ser Gly Ile
            20                  25                  30

Pro Ala Glu Asp Leu Pro Tyr Tyr Gly Gly Ser Val Glu Ile Ala
        35                  40                  45

<210> SEQ ID NO 154
<211> LENGTH: 48
<212> TYPE: PRT
<213> ORGANISM: Homo sapiens
<220> FEATURE:
<221> NAME/KEY: SITE
<222> LOCATION: (3)
<223> OTHER INFORMATION: Xaa equals any of the naturally occurring L- amino acids

<400> SEQUENCE: 154

Asp Tyr Xaa Pro Phe Ser Gln Glu Phe Ser Trp His Leu Ser Gly Glu
1               5                   10                  15

Tyr Gln Arg Ser Ser Asp Cys Arg Ile Leu Glu Asn Gln Pro Glu Ile
            20                  25                  30

Phe Lys Asn Tyr Gly Ala Glu Lys Tyr Gly Pro His Ser Val Cys Leu
        35                  40                  45

<210> SEQ ID NO 155
<211> LENGTH: 46
<212> TYPE: PRT
<213> ORGANISM: Homo sapiens

<400> SEQUENCE: 155

Ile Gln Lys Ser Ala Phe Val Met Glu Lys Cys Glu Arg Lys Leu Ser
1               5                   10                  15

Tyr Pro Asp Trp Gly Ser Gly Cys Tyr Gln Val Ser Cys Ser Pro Gln
            20                  25                  30

Gly Leu Lys Val Trp Val Gln Asp Thr Ser Tyr Leu Cys Ser
        35                  40                  45

<210> SEQ ID NO 156
<211> LENGTH: 57
<212> TYPE: PRT
<213> ORGANISM: Homo sapiens

<400> SEQUENCE: 156

Arg Ala Gly Gln Val Leu Pro Val Ser Ile Gln Met Asn Gly Trp Ile
1               5                   10                  15

His Asp Gly Asn Leu Leu Cys Pro Ser Cys Trp Asp Phe Cys Glu Leu
            20                  25                  30

Cys Pro Pro Glu Thr Asp Pro Pro Ala Thr Asn Leu Thr Arg Ala Leu
        35                  40                  45

Pro Leu Asp Leu Cys Ser Cys Ser Ser
    50                  55

<210> SEQ ID NO 157
<211> LENGTH: 9
<212> TYPE: PRT
<213> ORGANISM: Homo sapiens

<400> SEQUENCE: 157

Ile Lys Glu Lys Leu His Val His Gly
1               5

<210> SEQ ID NO 158
<211> LENGTH: 9
<212> TYPE: PRT
<213> ORGANISM: Homo sapiens

<400> SEQUENCE: 158

Gly Phe Gly Val Tyr Ile Leu Tyr Ala
1               5

<210> SEQ ID NO 159
<211> LENGTH: 17
<212> TYPE: PRT
<213> ORGANISM: Homo sapiens

<400> SEQUENCE: 159

```
Lys Pro Ser Gly Thr Val Tyr Thr Leu Phe Ser Leu Asn Ser Gly Thr
 1               5                  10                  15
Leu

<210> SEQ ID NO 160
<211> LENGTH: 19
<212> TYPE: PRT
<213> ORGANISM: Homo sapiens

<400> SEQUENCE: 160

Ala Asp Leu Thr Ala Val Cys Ser Ala Trp Lys Pro Gly Ala Lys Pro
 1               5                  10                  15
Val Gly Leu

<210> SEQ ID NO 161
<211> LENGTH: 19
<212> TYPE: PRT
<213> ORGANISM: Homo sapiens

<400> SEQUENCE: 161

Ala Asp Leu Thr Ala Val Cys Ser Ala Trp Lys Pro Gly Ala Lys Pro
 1               5                  10                  15
Val Gly Leu

<210> SEQ ID NO 162
<211> LENGTH: 106
<212> TYPE: PRT
<213> ORGANISM: Homo sapiens

<400> SEQUENCE: 162

Gly Ser Asn Lys Leu Ile Asn His Leu Glu Gln Cys Ser Ile Gly Trp
 1               5                  10                  15

Ile Phe Val Cys Leu Phe Val Cys Cys Tyr Ser Phe Cys Val Met Phe
                20                  25                  30

Cys Ile Gln Gln Lys Trp Leu Phe Ser Phe Leu Phe Tyr Glu Val Gly
            35                  40                  45

Leu Met Gly Ile Asp Ser Leu Arg Lys Lys Tyr Asn Cys Lys Ser Val
    50                  55                  60

Glu Val Phe Pro Ser Gln Asp Val Lys Cys Gln Arg Ser Asp Ser Cys
65                  70                  75                  80

Gly Arg Met Gly Ser Lys Leu Tyr Lys Ser Leu Glu Met Asn Glu Val
                85                  90                  95

Arg Gln Leu Ser Leu Arg Gln Lys Thr Met
            100                 105

<210> SEQ ID NO 163
<211> LENGTH: 60
<212> TYPE: PRT
<213> ORGANISM: Homo sapiens
<220> FEATURE:
<221> NAME/KEY: SITE
<222> LOCATION: (12)
<223> OTHER INFORMATION: Xaa equals any of the naturally occurring L-
      amino acids

<400> SEQUENCE: 163

Thr Thr Trp Ala Thr Ser Ser Val Val Ala Arg Xaa Thr His His Leu
 1               5                  10                  15

Phe Pro Pro His Ser Gly Ile Ser Val Asn Ile Gln Asp Leu Ala Pro
                20                  25                  30
```

```
Ser Cys Ala Gly Phe Leu Phe Gly Val Ala Asn Thr Ala Gly Ala Leu
        35                  40                  45

Ala Gly Val Val Gly Val Cys Leu Gly Gly Tyr Leu
    50                  55                  60

<210> SEQ ID NO 164
<211> LENGTH: 103
<212> TYPE: PRT
<213> ORGANISM: Homo sapiens
<220> FEATURE:
<221> NAME/KEY: SITE
<222> LOCATION: (12)
<223> OTHER INFORMATION: Xaa equals any of the naturally occurring L-
      amino acids

<400> SEQUENCE: 164

Thr Thr Trp Ala Thr Ser Ser Val Val Ala Arg Xaa Thr His His Leu
  1               5                  10                  15

Phe Pro Pro His Ser Gly Ile Ser Val Asn Ile Gln Asp Leu Ala Pro
                 20                  25                  30

Ser Cys Ala Gly Phe Leu Phe Gly Val Ala Asn Thr Ala Gly Ala Leu
        35                  40                  45

Ala Gly Val Val Gly Val Cys Leu Gly Gly Tyr Leu Met Glu Thr Thr
    50                  55                  60

Gly Ser Trp Thr Cys Leu Phe Asn Leu Val Ala Ile Ile Ser Asn Leu
 65                  70                  75                  80

Gly Leu Cys Thr Phe Leu Val Phe Gly Gln Ala Gln Arg Val Asp Leu
                85                  90                  95

Ser Ser Thr His Glu Asp Leu
            100

<210> SEQ ID NO 165
<211> LENGTH: 27
<212> TYPE: PRT
<213> ORGANISM: Homo sapiens

<400> SEQUENCE: 165

Asp Ser Pro Leu Thr Val Leu Pro Glu Asp Gly Tyr Gly Ser Asp Ser
  1               5                  10                  15

His Leu Ser Ser Gln Val Val Arg Gly Pro Thr
                 20                  25

<210> SEQ ID NO 166
<211> LENGTH: 153
<212> TYPE: PRT
<213> ORGANISM: Homo sapiens

<400> SEQUENCE: 166

Met Leu Val Thr Ala Tyr Leu Ala Phe Val Gly Leu Leu Ala Ser Cys
  1               5                  10                  15

Leu Gly Leu Glu Leu Ser Arg Cys Arg Ala Lys Pro Pro Gly Arg Ala
                 20                  25                  30

Cys Ser Asn Pro Ser Phe Leu Arg Phe Gln Leu Asp Phe Tyr Gln Val
        35                  40                  45

Tyr Phe Leu Ala Leu Ala Ala Asp Trp Leu Gln Ala Pro Tyr Leu Tyr
    50                  55                  60

Lys Leu Tyr Gln His Tyr Tyr Phe Leu Glu Gly Gln Ile Ala Ile Leu
 65                  70                  75                  80

Tyr Val Cys Gly Leu Ala Ser Thr Val Leu Phe Gly Leu Val Ala Ser
```

|   |   | 85 |   |   |   | 90 |   |   |   | 95 |   |
|---|---|---|---|---|---|---|---|---|---|---|---|

Ser Leu Val Asp Trp Leu Gly Arg Lys Asn Ser Cys Val Leu Phe Ser
                100                    105                   110

Leu Thr Tyr Ser Leu Cys Cys Leu Thr Lys Leu Ser Gln Asp Tyr Phe
        115                    120                   125

Val Leu Val Gly Arg Ala Leu Gly Gly Leu Ser Thr Ala Ala Leu
130                  135                  140

Leu Ser Leu Arg Gly Leu Val Tyr Pro
145                  150

<210> SEQ ID NO 167
<211> LENGTH: 508
<212> TYPE: PRT
<213> ORGANISM: Homo sapiens
<220> FEATURE:
<221> NAME/KEY: SITE
<222> LOCATION: (6)
<223> OTHER INFORMATION: Xaa equals any of the naturally occurring L-
     amino acids

<400> SEQUENCE: 167

Gly Gly Gly Gln Arg Xaa Ala Arg Leu Pro Glu Ala Gly Cys Glu Gly
1               5                   10                15

Arg Glu Arg Cys Trp Asn Pro Ser Arg Ser Arg Ser His Ser Gly Glu
          20                    25                  30

Gly Gly Leu Ala Ala Trp Ser Arg Thr Cys Pro Gly Arg Pro Arg Arg
        35                  40                  45

Pro Gly Gln Gln Val Val Arg Gly Pro Thr Met Leu Val Thr Ala Tyr
50                  55                  60

Leu Ala Phe Val Gly Leu Leu Ala Ser Cys Leu Gly Leu Glu Leu Ser
65                  70                  75                80

Arg Cys Arg Ala Lys Pro Pro Gly Arg Ala Cys Ser Asn Pro Ser Phe
          85                    90                  95

Leu Arg Phe Gln Leu Asp Phe Tyr Gln Val Tyr Phe Leu Ala Leu Ala
        100                   105                110

Ala Asp Trp Leu Gln Ala Pro Tyr Leu Tyr Lys Leu Tyr Gln His Tyr
        115                   120                125

Tyr Phe Leu Glu Gly Gln Ile Ala Ile Leu Tyr Val Cys Gly Leu Ala
130                  135                  140

Ser Thr Val Leu Phe Gly Leu Val Ala Ser Ser Leu Val Asp Trp Leu
145                  150                  155                160

Gly Arg Lys Asn Ser Cys Val Leu Phe Ser Leu Thr Tyr Ser Leu Cys
                165                   170                175

Cys Leu Thr Lys Leu Ser Gln Asp Tyr Phe Val Leu Leu Val Gly Arg
        180                   185                190

Ala Leu Gly Gly Leu Ser Thr Ala Leu Leu Phe Ser Ala Phe Glu Ala
        195                   200                205

Trp Tyr Ile His Glu His Val Glu Arg His Asp Phe Pro Ala Glu Trp
210                  215                  220

Ile Pro Ala Thr Phe Ala Arg Ala Phe Trp Asn His Val Leu Ala
225                  230                  235                240

Val Val Ala Gly Val Ala Ala Glu Ala Val Ala Ser Trp Ile Gly Leu
        245                   250                255

Gly Pro Val Ala Pro Phe Val Ala Ala Ile Pro Leu Leu Ala Leu Ala
        260                   265                270

Gly Ala Leu Ala Leu Arg Asn Trp Gly Glu Asn Tyr Asp Arg Gln Arg

-continued

```
                275                 280                 285
Ala Phe Ser Arg Thr Cys Ala Gly Gly Leu Arg Cys Leu Leu Ser Asp
            290                 295                 300

Arg Arg Val Leu Leu Leu Gly Thr Ile Gln Ala Leu Phe Glu Ser Val
305                 310                 315                 320

Ile Phe Ile Phe Val Phe Leu Trp Thr Pro Val Leu Asp Pro His Gly
                325                 330                 335

Ala Pro Leu Gly Ile Ile Phe Ser Ser Phe Met Ala Ala Ser Leu Leu
            340                 345                 350

Gly Ser Ser Leu Tyr Arg Ile Ala Thr Ser Lys Arg Tyr His Leu Gln
            355                 360                 365

Pro Met His Leu Leu Ser Leu Ala Val Leu Ile Val Val Phe Ser Leu
        370                 375                 380

Phe Met Leu Thr Phe Ser Thr Ser Pro Gly Gln Glu Ser Pro Val Glu
385                 390                 395                 400

Ser Phe Ile Ala Phe Leu Leu Ile Glu Leu Ala Cys Gly Leu Tyr Phe
                405                 410                 415

Pro Ser Met Ser Phe Leu Arg Arg Lys Val Ile Pro Glu Thr Glu Gln
            420                 425                 430

Ala Gly Val Leu Asn Trp Phe Arg Val Pro Leu His Ser Leu Ala Cys
            435                 440                 445

Leu Gly Leu Leu Val Leu His Asp Ser Asp Arg Lys Thr Gly Thr Arg
        450                 455                 460

Asn Met Phe Ser Ile Cys Ser Ala Val Met Val Met Ala Leu Leu Ala
465                 470                 475                 480

Val Val Gly Leu Phe Thr Val Val Arg His Asp Ala Glu Leu Arg Val
                485                 490                 495

Pro Ser Pro Thr Glu Glu Pro Tyr Ala Pro Glu Leu
            500                 505

<210> SEQ ID NO 168
<211> LENGTH: 23
<212> TYPE: PRT
<213> ORGANISM: Homo sapiens

<400> SEQUENCE: 168

Val Glu Ala Ile Phe Ser Glu Leu Val Ile Val Leu Asn Lys Met Ser
1               5                   10                  15

His Cys Val Leu Ser Gly Thr
            20

<210> SEQ ID NO 169
<211> LENGTH: 68
<212> TYPE: PRT
<213> ORGANISM: Homo sapiens

<400> SEQUENCE: 169

Val Glu Ala Ile Phe Ser Glu Leu Val Ile Val Leu Asn Lys Met Ser
1               5                   10                  15

His Cys Val Leu Ser Gly Thr Met Gln Ala His Pro Ile Phe Ile Tyr
            20                  25                  30

His Lys Arg Val Phe Phe Leu Leu Lys Phe Ile Phe Tyr Ile Ile Phe
        35                  40                  45

Cys Phe Phe Phe Leu Asp Ile Ser Thr Leu Tyr Cys Ser Leu Ser Thr
    50                  55                  60

Phe Cys Lys Lys
```

```
<210> SEQ ID NO 170
<211> LENGTH: 26
<212> TYPE: PRT
<213> ORGANISM: Homo sapiens

<400> SEQUENCE: 170

Lys Pro Thr Lys Met Pro Leu Leu Trp Val Trp Ala Leu Ile Ala Ala
 1               5                  10                  15

Val Ser Gln Pro Glu Leu Trp Tyr Arg Glu
            20                  25

<210> SEQ ID NO 171
<211> LENGTH: 73
<212> TYPE: PRT
<213> ORGANISM: Homo sapiens

<400> SEQUENCE: 171

Lys Pro Thr Lys Met Pro Leu Leu Trp Val Trp Ala Leu Ile Ala Ala
 1               5                  10                  15

Val Ser Gln Pro Glu Leu Trp Tyr Arg Glu Met Gly Val Leu Leu Leu
            20                  25                  30

Phe Ser Phe Phe Phe Pro Asn Gly Ser Phe Ser Pro Val Val Leu Pro
        35                  40                  45

Ser Tyr Phe Pro Asn Ser Ser Ser Tyr Phe Val Phe Cys Thr Ser Phe
    50                  55                  60

Trp Arg Pro Leu Ser Phe Gln Lys Gly
 65                  70

<210> SEQ ID NO 172
<211> LENGTH: 85
<212> TYPE: PRT
<213> ORGANISM: Homo sapiens

<400> SEQUENCE: 172

Cys Phe Thr His Trp Asn Val Phe Pro Arg Leu Trp Met Thr Ser Phe
 1               5                  10                  15

Leu Met Glu Arg Val Gln Glu Gly Trp Lys Thr Pro Gly Phe Lys Leu
            20                  25                  30

Ser Ile Pro His Met Gly Phe Ser Ile Ile Phe Arg Pro Glu Ala Ala
        35                  40                  45

Arg Pro Glu Val Arg Leu His Leu Ser Ala Leu Phe Val Leu Leu Leu
    50                  55                  60

Ala Thr Leu Gly Phe Leu Leu Gly Thr Met Cys Gly Cys Gly Met Cys
 65                  70                  75                  80

Glu Gln Lys Gly Gly
                85
```